US011077130B2

(12) United States Patent
Haynes et al.

(10) Patent No.: US 11,077,130 B2
(45) Date of Patent: Aug. 3, 2021

(54) METHODS FOR REDUCING HIV-1 MOTHER-TO-CHILD TRANSMISSION BY INDUCING V3-SPECIFIC OR CD4 BINDING SITE-SPECIFIC ANTIBODIES

(71) Applicant: DUKE UNIVERSITY, Durham, NC (US)

(72) Inventors: Barton F. Haynes, Durham, NC (US); Sallie Permar, Durham, NC (US); M. Anthony Moody, Durham, NC (US); Feng Gao, Durham, NC (US); Hua-Xin Liao, Durham, NC (US); Georgia Tomaras, Durham, NC (US); David C. Montefiori, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 15/025,031

(22) PCT Filed: Sep. 26, 2014

(86) PCT No.: PCT/US2014/057809
§ 371 (c)(1),
(2) Date: Mar. 25, 2016

(87) PCT Pub. No.: WO2015/048512
PCT Pub. Date: Apr. 2, 2015

(65) Prior Publication Data
US 2016/0339051 A1 Nov. 24, 2016

Related U.S. Application Data

(60) Provisional application No. 61/968,560, filed on Mar. 21, 2014, provisional application No. 61/354,340, filed on Mar. 17, 2014, provisional application No. 61/884,024, filed on Sep. 28, 2013, provisional application No. 61/883,220, filed on Sep. 27, 2013.

(51) Int. Cl.
| A61K 39/21 | (2006.01) |
| A61K 31/7088 | (2006.01) |
| G01N 33/569 | (2006.01) |
| A61K 39/395 | (2006.01) |
| C07K 14/16 | (2006.01) |
| C07K 14/005 | (2006.01) |

(52) U.S. Cl.
CPC .......... *A61K 31/7088* (2013.01); *A61K 39/21* (2013.01); *A61K 39/395* (2013.01); *C07K 14/005* (2013.01); *C07K 14/162* (2013.01); *G01N 33/56988* (2013.01); *C12N 2740/16111* (2013.01); *C12N 2770/00041* (2013.01); *G01N 2800/50* (2013.01)

(58) Field of Classification Search
CPC .. C07K 14/162; C07K 16/1063; A61K 39/21; C12N 2740/16111
See application file for complete search history.

(56) References Cited

U.S. PATENT DOCUMENTS

| 2008/0009579 A1 | 4/2008 | Zolla-Pazner et al. |
| 2013/0022619 A1 | 1/2013 | Rawlin et al. |
| 2013/0273103 A1* | 10/2013 | Liao ........................ A61K 39/21 424/208.1 |
| 2014/0248301 A1* | 9/2014 | Haynes .............. A61K 39/0005 424/188.1 |

FOREIGN PATENT DOCUMENTS

| WO | 2011/106100 | 1/2011 |
| WO | 2012/047267 | 4/2012 |
| WO | 2013/006688 | 1/2013 |

OTHER PUBLICATIONS

Daniels, R. S., et al., Oct. 1991, Molecular characterization of biologically diverse envelope variants of human immunodeficiency virus type 1 derived from an individual, J. Virol. 65(10):5574-5578.*
Gerhardt, M., et al., Jul. 2005, In-depth, longitudinal analysis of viral quasispecies from an individual triply infected with late-stage human immunodeficiency virus type 1, using a multiple PCR primr approach, J. Virol. 79(13):8249-8261.*
Chailion, A., et al., Oct. 2012, The breadth and titer of maternal HIV-1-specific heterologous neutralizing antibodies are not associated with a lower rate of mother-to-child transmission of HIV-1, J. Virol. 86(19):10540-10546.*
Baan, E., et al., Jul. 2013, HIV-1 autologous antibody neutralization associates with mother to child transmission, PLOS One 8(7): e69274, pp. 1-13.*
Albert et al. "Rapid development of isolate-specific neutralizing antibodies after primary HIV-1 infection and consequent emergence of virus variants which resist neutralization by autologous sera." Aids 4.2 (1990): 107-112.
Broliden et al. "Diagnostic implication of specific immunoglobulin G patterns of children born to HIV-infected mothers." Aids 3.9 (1989): 577-582.
Fong, Y et al 2013, Fred Hutchison Technical Report, http://works.bepress.com/yfong/I/.
Gray, Glenda E., and Lawrence Corey. "Reevaluating HIV vaccine clinical trials policy for infants." (2014): 501-503.
Harris and Liddament. "Retroviral restriction by APOBEC proteins." Nature Reviews Immunology 4.11 (2004): 868-877.

(Continued)

*Primary Examiner* — Jeffrey S Parkin
(74) *Attorney, Agent, or Firm* — Baker Donelson

(57) ABSTRACT

The invention provides compositions and methods to induce and boost antibody response, including but not limited to IgG responses binding to HIV-1 in a subject in need thereof, wherein the induced/boosted plasma level of the antibody responses, for example V3 and/or CD4 binding site antibody responses, is over a threshold level and is associated with reduced risk of maternal-to-child-transmission (MTCT) of HIV-1.

17 Claims, 47 Drawing Sheets

Figures 1A, 1B:
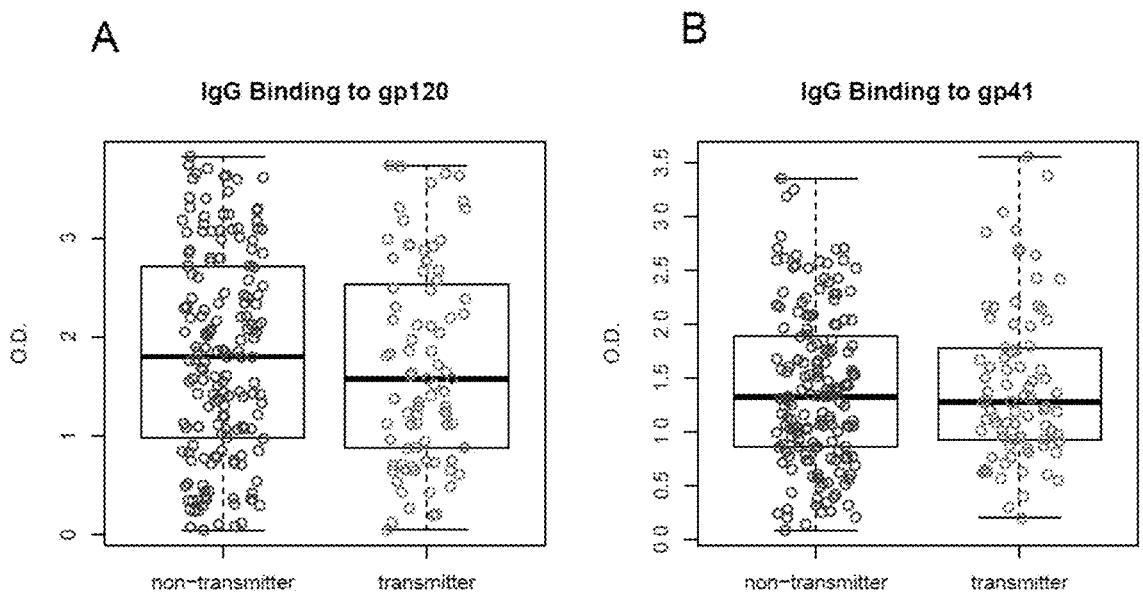
Figures 1C, 1D:
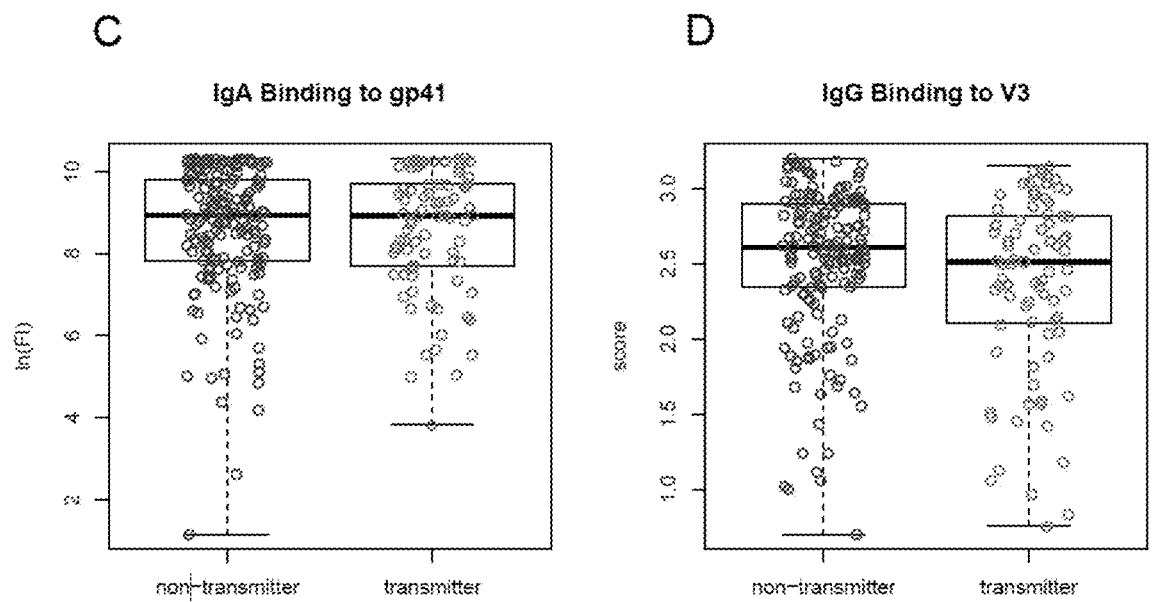

Specification includes a Sequence Listing.

(56) References Cited

OTHER PUBLICATIONS

Haynes, BF et al. "HIV Type 1 V3 Region Primer-Induced Antibody Suppression Is Overcome by Administration of C4-V3 Peptides as a Polyvalent Immunogen" AIDS Res. Hum. Retrovirol. 1 1 : 211, 1995.

Malek et al. "Evolution of maternofetal transport of immunoglobulins during human pregnancy." American Journal of Reproductive Immunology 36.5 (1996): 248-255.

Markham et al. "Maternal IgG1 and IgA antibody to V3 loop consensus sequence and maternal-infant HIV-1 transmission." The Lancet 343.8894 (1994): 390-391.

Mascola and Montefiori. "The role of antibodies in HIV vaccines." Annual review of immunology 28 (2009): 413-444.

Montefiori. "Evaluating neutralizing antibodies against HIV, SIV, and SHIV in luciferase reporter gene assays." Current protocols in immunology (2005): 12-11.

S. M. Rainwater et al., "Cloning and characterization of functional subtype A HIV-1 envelope variants transmitted through breastfeeding" Curr HIV Res 5, 189 (Mar. 2007).

Scarlatti et al. "Neutralizing antibodies and viral characteristics in mother-to-child transmission of HIV-1." Nov. 1993;7 Suppl 2:S45-8.

Liao et al., "Co-evolution of a broadly neutralizing HIV-1 antibody and founder virus" Nature. Apr. 25, 2013;496 (7446):469-76. doi: 10.1038/nature12053. Epub Apr. 3, 2013.

Bonsignori et al., "Analysis of a clonal lineage of HIV-1 envelope V2/V3 conformational epitope-specific broadly neutralizing antibodies and their inferred unmutated common ancestors" J Virol. Oct. 2011;85(19):9998-10009. doi: 10.1128/JVI.05045-11. Epub Jul. 27, 2011.

Wu et al., "Focused evolution of HIV-1 neutralizing antibodies revealed by structures and deep sequencing" Science. Sep. 16, 2011;333(6049)1593-602. doi: 101126/science.1207532. Epub Aug. 11, 2011.

Alam et al. "Human immunodeficiency virus type 1 gp41 antibodies that mask membrane proximal region epitopes: antibody binding kinetics, induction, and potential for regulation in acute infection." Journal of virology 82.1 (2008): 115-125.

Baan et al. "HIV-1 autologous antibody neutralization associates with mother to child transmission." PloS one 8.7 (2013): e69274.

Balla-Jhagjhoorsingh et al. "Characterization of neutralizing profiles in HIV-1 infected patients from whom the HJ16, HGN194 and HK20 mAbs were obtained." PloS one 6.10 (2011): e25488.

Balla-Jhagjhoorsingh et al. "The N276 glycosylation site is required for HIV-1 neutralization by the CD4 binding site specific HJ16 monoclonal antibody." PLoS One 8.7 (2013): e68863.

Bar et al. "Early low-titer neutralizing antibodies impede HIV-1 replication and select for virus escape." PLoS Pathog 8.5 (2012): e1002721.

Bartlett et al. "Safety and immunogenicity of an HLA-based HIV envelope polyvalent synthetic peptide immunogen." Aids 12.11 (1998): 1291-1300.

Berry et al. "The evolutionary rate dynamically tracks changes in HIV-1 epidemics: application of a simple method for optimizing the evolutionary rate in phylogenetic trees with longitudinal data." Epidemics 1.4 (2009): 230-239.

Berry et al. "Unequal evolutionary rates in the human immunodeficiency virus type 1 (HIV-1) pandemic: the evolutionary rate of HIV-1 slows down when the epidemic rate increases." Journal of virology 81.19 (2007): 10625-10635.

Bonsignori et al. "Antibody-dependent cellular cytotoxicity-mediating antibodies from an HIV-1 vaccine efficacy trial target multiple epitopes and preferentially use the VH1 gene family." Journal of virology 86.21 (2012): 11521-11532.

Bonsignori et al. "Two distinct broadly neutralizing antibody specificities of different clonal lineages in a single HIV-1-infected donor: implications for vaccine design." Journal of virology 86.8 (2012): 4688-4692.

Chaillon et al. "The breadth and titer of maternal HIV-1-specific heterologous neutralizing antibodies are not associated with a lower rate of mother-to-child transmission of HIV-1." Journal of virology 86.19 (2012): 10540-10546.

Chasela et al. "Maternal or infant antiretroviral drugs to reduce HIV-1 transmission." New England Journal of Medicine 362.24 (2010): 2271-2281.

Corti et al. "Analysis of memory B cell responses and isolation of novel monoclonal antibodies with neutralizing breadth from HIV-1-infected individuals." PloS one 5.1 (2010): e8805.

Dickover et al. "Role of maternal autologous neutralizing antibody in selective perinatal transmission of human immunodeficiency virus type 1 escape variants." Journal of virology 80.13 (2006): 6525-6533.

Diomede et al. "Passively Transmitted gp41 Antibodies in Babies Born from HIV-1 Subtype C-Seropositive Women: Correlation between Fine Specificity and Protection." Journal of Virology. 2012;86(8):4129-4138.

Ewing and Green. "Base-calling of automated sequencer traces using phred. II. Error probabilities." Genome research 8.3 (1998): 186-194.

Ewing et al. "Base-calling of automated sequencer traces using Phred. I. Accuracy assessment." Genome research 8.3 (1998): 175-185.

Fouda et al. "Infant HIV type 1 gp120 vaccination elicits robust and durable anti-V1V2 immunoglobulin G responses and only rare envelope-specific immunoglobulin A responses." Journal of Infectious Diseases 211.4 (2015): 508-517.

Frost et al. "Neutralizing antibody responses drive the evolution of human immunodeficiency virus type 1 envelope during recent HIV infection." Proceedings of the National Academy of Sciences of the United States of America 102.51 (2005): 18514-18519.

Gao et al. "Cooperation of B cell lineages in induction of HIV-1-broadly neutralizing antibodies." Cell 158.3 (2014): 481-491.

Gilbert et al. "Magnitude and Breadth of a Non-Protective Neutralizing Antibody Response in an Efficacy Trial of a Candidate HIV-1 gp120 Vaccine (AIDSVAXTM BIB)." The Journal of infectious diseases 202.4 (2010): 595-605. PMC. Web. Jun. 4, 2016.

Gorny et al. "Human monoclonal antibodies to the V3 loop of HIV-1 with intra-and interclade cross-reactivity." The Journal of Immunology 159.10 (1997): 5114-5122.

Gorny et al. "Preferential use of the VH5-51 gene segment by the human immune response to code for antibodies against the V3 domain of HIV-1." Molecular immunology 46.5 (2009): 917-926.

Gottardo et al. "Plasma IgG to linear epitopes in the V2 and V3 regions of HIV-1 gp120 correlate with a reduced risk of infection in the RV144 vaccine efficacy trial." PLoS One 8.9 (2013): e75665.

Gray et al. "Antibody specificities associated with neutralization breadth in plasma from human immunodeficiency virus type 1 subtype C-infected blood donors." Journal of virology 83.17 (2009): 8925-8937.

Gray et al. "Isolation of a monoclonal antibody that targets the alpha-2 helix of gp120 and represents the initial autologous neutralizing-antibody response in an HIV-1 subtype C-infected individual." Journal of virology 85.15 (2011): 7719-7729.

Gray et al. "The neutralization breadth of HIV-1 develops incrementally over four years and is associated with CD4+ T cell decline and high viral load during acute infection." Journal of virology 85.10 (2011): 4828-4840.

Guevara et al. "Maternal HIV-1 antibody and vertical transmission in subtype C virus infection" J Acquir Immune Defic Syndr. Apr. 15, 2002;29(5):435-40.

Guindon and Gascuel. "A simple, fast, and accurate algorithm to estimate large phylogenies by maximum likelihood." Systematic biology 52.5 (2003): 696-704.

Haim et al. "Contribution of intrinsic reactivity of the HIV-1 envelope glycoproteins to CD4-independent infection and global inhibitor sensitivity." PLoS Pathog 7.6 (2011): e1002101.

Haim et al. "Modeling virus-and antibody-specific factors to predict human immunodeficiency virus neutralization efficiency." Cell host & microbe 14.5 (2013): 547-558.

(56) References Cited

OTHER PUBLICATIONS

Hammer et al. "Efficacy trial of a DNA/rAd5 HIV-1 preventive vaccine." New England Journal of Medicine 369.22 (2013):2083-2092.
Haynes et al. "Immune-correlates analysis of an HIV-1 vaccine efficacy trial." New England Journal of Medicine 366.14 (2012):1275-1286.
Hraber et al. "Prevalence of broadly neutralizing antibody responses during chronic HIV-1 infection." AIDS (London, England) 28.2 (2014): 163-169.
Igarashi et al. "Emergence of a highly pathogenic simian/human immunodeficiency virus in a rhesus macaque treated with anti-CD8 mAb during a primary infection with a nonpathogenic virus." Proceedings of the National Academy of Sciences 96.24 (1999): 14049-14054.
Jeffs et al. "Characterization of human monoclonal antibodies selected with a hypervariable loop-deleted recombinant HIV-1 IIIB gp120." Immunology letters 79.3 (2001): 209-213.
Jiang et al. "Primary infection by a human immunodeficiency virus with atypical coreceptor tropism." Journal of virology 85.20 (2011): 10669-10681.
Keele et al. "Identification and characterization of transmitted and early founder virus envelopes in primary HIV-1 infection." Proceedings of the National Academy of Sciences 105.21 (2008): 7552-7557.
Kepler et al. "Chiropteran types I and II interferon genes inferred from genome sequencing traces by a statistical gene-family assembler." BMC genomics 11.1 (2010): 1.
Kirchherr et al. "High throughput functional analysis of HIV-1 env genes without cloning." Journal of virological methods 143.1 (2007): 104-111.
Kwong et al. "Structures of HIV-1 gp120 envelope glycoproteins from laboratory-adapted and primary isolates." Structure 8.12 (2000): 1329-1339.
Laird et al. "Importance of the V1/V2 loop region of simian-human immunodeficiency virus envelope glycoprotein gp120 in determining the strain specificity of the neutralizing antibody response." Journal of virology 82.22 (2008): 11054-11065.
Liao et al. "A group M consensus envelope glycoprotein induces antibodies that neutralize subsets of subtype B and C HIV-1 primary viruses." Virology 353.2 (2006): 268-282.
Liao et al. "Antigenicity and immunogenicity of transmitted/founder, consensus, and chronic envelope glycoproteins of human immunodeficiency virus type 1." Journal of virology 87.8 (2013): 4185-4201.
Liao et al. "High-throughput isolation of immunoglobulin genes from single human B cells and expression as monoclonal antibodies." Journal of virological methods 158.1 (2009): 171-179.
Liao et al. "Vaccine induction of antibodies against a structurally heterogeneous site of immune pressure within HIV-1 envelope protein variable regions 1 and 2." Immunity 38.1 (2013): 176-186.
Lynch et al. "The breadth and potency of passively acquired human immunodeficiency virus type 1-specific neutralizing antibodies do not correlate with the risk of infant infection." Journal of virology 85.11 (2011): 5252-5261.
Mascola and Haynes. "HIV-1 neutralizing antibodies: understanding nature's pathways." Immunological reviews 254.1 (2013):225-244.
Montefiori et al. "Magnitude and breadth of the neutralizing antibody response in the RV144 and Vax003 HIV-1 vaccine efficacy trials." Journal of Infectious Diseases 206.3 (2012): 431-441.
Montefiori et al. "Viremia control despite escape from a rapid and potent autologous neutralizing antibody response after therapy cessation in an HIV-1-infected individual." The Journal of Immunology 170.7 (2003): 3906-3914.
Moody et al. "Antibody lineages with evidence of somatic hypermutation persisting for> 4 years in a South African subject with broad neutralizing activity." Retrovirology 9.Suppl 2 (2012): P85.
Moody et al. "H3N2 influenza infection elicits more cross-reactive and less clonally expanded anti-hemagglutinin antibodies than influenza vaccination." PloS one 6.10 (2011): e25797.
Moody et al. "HIV-1 gp120 vaccine induces affinity maturation in both new and persistent antibody clonal lineages." Journal of virology 86.14 (2012): 7496-7507.
Moore et al. "Evolution of an HIV glycan-dependent broadly neutralizing antibody epitope through immune escape." Nature medicine 18.11 (2012): 1688-1692.
Moore et al. "Multiple pathways of escape from HIV broadly cross-neutralizing V2-dependent antibodies." Journal of virology 87.9 (2013): 4882-4894.
Moore et al. "Probing the structure of the human immunodeficiency virus surface glycoprotein gp120 with a panel of monoclonal antibodies." Journal of virology 68.1 (1994): 469-484.
Moore et al. "Specificity of the autologous neutralizing antibody response." Current opinion in HIV and AIDS 4.5 (2009): 358.
Moore et al. "The c3-v4 region is a major target of autologous neutralizing antibodies in human immunodeficiency virus type 1 subtype C infection." Journal of virology 82.4 (2008): 1860-1869.
Morris et al. "Isolation of a human anti-HIV gp41 membrane proximal region neutralizing antibody by antigen-specific single B cell sorting." PloS one 6.9 (2011): e23532.
Vickie et al. "HIV-specific probabilistic models of protein evolution." PLoS One 2.6 (2007): e503.
Pancino et al. "Apparent enhancement of perinatal transmission of human immunodeficiency virus type 1 by high maternal anti-gp160 antibody titer." Journal of Infectious Diseases 177.6 (1998): 1737-1741.
Pantophlet et al. "Neutralizing activity of antibodies to the V3 loop region of HIV-1 gp120 relative to their epitope fine specificity." Virology 381.2 (2008): 251-260.
Pitisuttithum et al. "Randomized, double-blind, placebo-controlled efficacy trial of a bivalent recombinant glycoprotein 120 HIV-1 vaccine among injection drug users in Bangkok, Thailand." Journal of Infectious Diseases 194.12 (2006): 1661-1671.
Plotkin, "Vaccines: correlates of vaccine-induced immunity." Clin Infect Dis 47, 401 (Aug. 1, 2008).
Posner et al. "An IgG human monoclonal antibody that reacts with HIV-1/GP120, inhibits virus binding to cells, and neutralizes infection." The Journal of immunology 146.12 (1991): 4325-4332.
Rerks-Ngarm et al. "Vaccination with ALVAC and AIDSVAX to prevent HIV-1 infection in Thailand." New England Journal of Medicine 361.23 (2009): 2209-2220.
Rich et al. "Maternal and infant factors predicting disease progression in human immunodeficiency virus type 1-infected infants." Pediatrics 105.1 (2000): e8-e8.
Richman et al. "Rapid evolution of the neutralizing antibody response to HIV type 1 infection." Proceedings of the National Academy of Sciences 100.7 (2003): 4144-4149.
Rose and Korber. "Detecting hypermutations in viral sequences with an emphasis on G? A hypermutation." Bioinformatics 16.4 (2000): 400-401.
Rossi, et al. "Presence of maternal antibodies to human immunodeficiency virus 1 envelope glycoprotein gp120 epitopes correlates with the uninfected status of children born to seropositive mothers." Proceedings of the National Academy of Sciences 86.20 (1989): 8055-8058.
Ruelas and Greene. "An integrated overview of HIV-1 latency." Cell 155.3 (2013): 519-529.
Russell et al. "The genetic bottleneck in vertical transmission of subtype C HIV-1 is not driven by selection of especially neutralization-resistant virus from the maternal viral population." Journal of virology 85.16 (2011): 8252-8262.
Salazar-Gonzalez et al. "Genetic identity, biological phenotype, and evolutionary pathways of transmitted/founder viruses in acute and early HIV-1 infection." The Journal of experimental medicine 206.6 (2009): 1273-1289.
Seaman et al. "Tiered categorization of a diverse panel of HIV-1 Env pseudoviruses for assessment of neutralizing antibodies." Journal of virology 84.3 (2010): 1439-1452.
Smith and Waterman. "Identification of common molecular subsequences." Journal of molecular biology 147.1 (1981): 195-197.

(56) References Cited

OTHER PUBLICATIONS

Swetnam et al. "Comparative magnitude of cross-strain conservation of HIV variable loop neutralization epitopes." PloS one 5.12 (2010): e15994.
Tang et al. "Epitopes immediately below the base of the V3 loop of gp120 as targets for the initial autologous neutralizing antibody response in two HIV-1 subtype B-infected individuals." Journal of virology 85.18 (2011): 9286-9299.
Thenin et al. "Envelope glycoproteins of Human Immunodeficiency Virus type 1 variants issued from mother-infant pairs display a wide spectrum of biological properties." Virology 426.1 (2012): 12-21.
Tomaras et al. "Initial B-cell responses to transmitted human immunodeficiency virus type 1: virion-binding immunoglobulin M (IgM) and IgG antibodies followed by plasma anti-gp41 antibodies with ineffective control of initial viremia." Journal of virology 82.24 (2008): 12449-12463.
Tomaras et al. "Polyclonal B cell responses to conserved neutralization epitopes in a subset of HIV-1-infected individuals." Journal of virology 85.21 (2011): 11502-11519.
Tomaras et al. "Vaccine-induced plasma IgA specific for the C1 region of the HIV-1 envelope blocks binding and effector function of IgG." Proceedings of the National Academy of Sciences 110.22 (2013): 9019-9024.
Ugen et al. "Vertical transmission of human immunodeficiency virus (HIV) infection. Reactivity of maternal sera with glycoprotein 120 and 41 peptides from HIV type 1." Journal of Clinical Investigation 89.6 (1992): 1923.
Volpe et al. "SoDa: implementation of a 3D alignment algorithm for inference of antigen receptor recombinations." Bioinformatics 22.4 (2006): 438-444.
Wei et al. "Antibody neutralization and escape by HIV-1." Nature 422.6929 (2003): 307-312.
Wettstein et al. "Missed opportunities to prevent mother-to-child-transmission in sub-Saharan Africa: systematic review and meta-analysis." AIDS (London, England) 26.18 (2012): 2361.
Whittle et al. "Broadly neutralizing human antibody that recognizes the receptor-binding pocket of influenza virus hemagglutinin." Proceedings of the National Academy of Sciences 108.34 (2011): 14216-14221.
Wibmer et al. "Viral escape from HIV-1 neutralizing antibodies drives increased plasma neutralization breadth through sequential recognition of multiple epitopes and immunotypes." PLoS Pathog 9.10 (2013): e1003738.
Wrammert et al. "Rapid cloning of high-affinity human monoclonal antibodies against influenza virus." Nature 453.7195 (2008): 667-671.
Wright et al. "Immunization with envelope MN rgp120 vaccine in human immunodeficiency virus-infected pregnant women." Journal of Infectious Diseases 180.4 (1999): 1080-1088.
Wu et al. "Neutralization escape variants of human immunodeficiency virus type 1 are transmitted from mother to infant" Journal of virology 80.2 (2006): 835-844.
International Search Report for International Application No. PCT/US2014/057809 (Applicant Duke University), dated Jan. 13, 2015.
Written Opinion of the International Searching Authority for International Application No. PCT/US2014/057809 (Applicant Duke University), dated Jan. 12, 2015.
Extended European Search Report for European Patent Application 14849379.4 (Applicant Duke University), dated May 15, 2017.
GenBank Accession No. EU123924, HIV-1 isolate SF162 from USA envelope glycoprotein (env) gene, complete coding sequence, Oct. 2007.
GenBank Accession No. JN944948, HIV-1 isolate pWITO.c from USA gag protein (gag) gene, complete cds; pol protein (pol) gene, partial cds; and vif protein (vif), vpr protein (vpr), tat protein (tat), rev protein (rev), vpu protein (vpu), envelope glycoprotein (env), and nef protein (nef) genes, complete cds, Feb. 22, 2012.

* cited by examiner

|                      | DH290 | DH291 | DH292 | DH293 | DH294 | DH295 | DH296 | DH298 | DH299 | HIVIG-C |
|----------------------|-------|-------|-------|-------|-------|-------|-------|-------|-------|---------|
| 5426.31              | >50   | >50   | >50   | >50   | >50   | >50   | >50   | >50   | >50   |         |
| 5426.31.V200I        | >50   | >50   | >50   | >50   | >50   | >50   | >50   | >50   | >50   |         |
| 5426.31.N188S        | >50   | >50   | >50   | >50   | >50   | >50   | 35.2  | 37.2  | >50   |         |
| 5426.31.V200I-N188S  | >50   |       | 24    |       | 39.5  | 40.9  |       |       | >50   |         |

Figure 2B

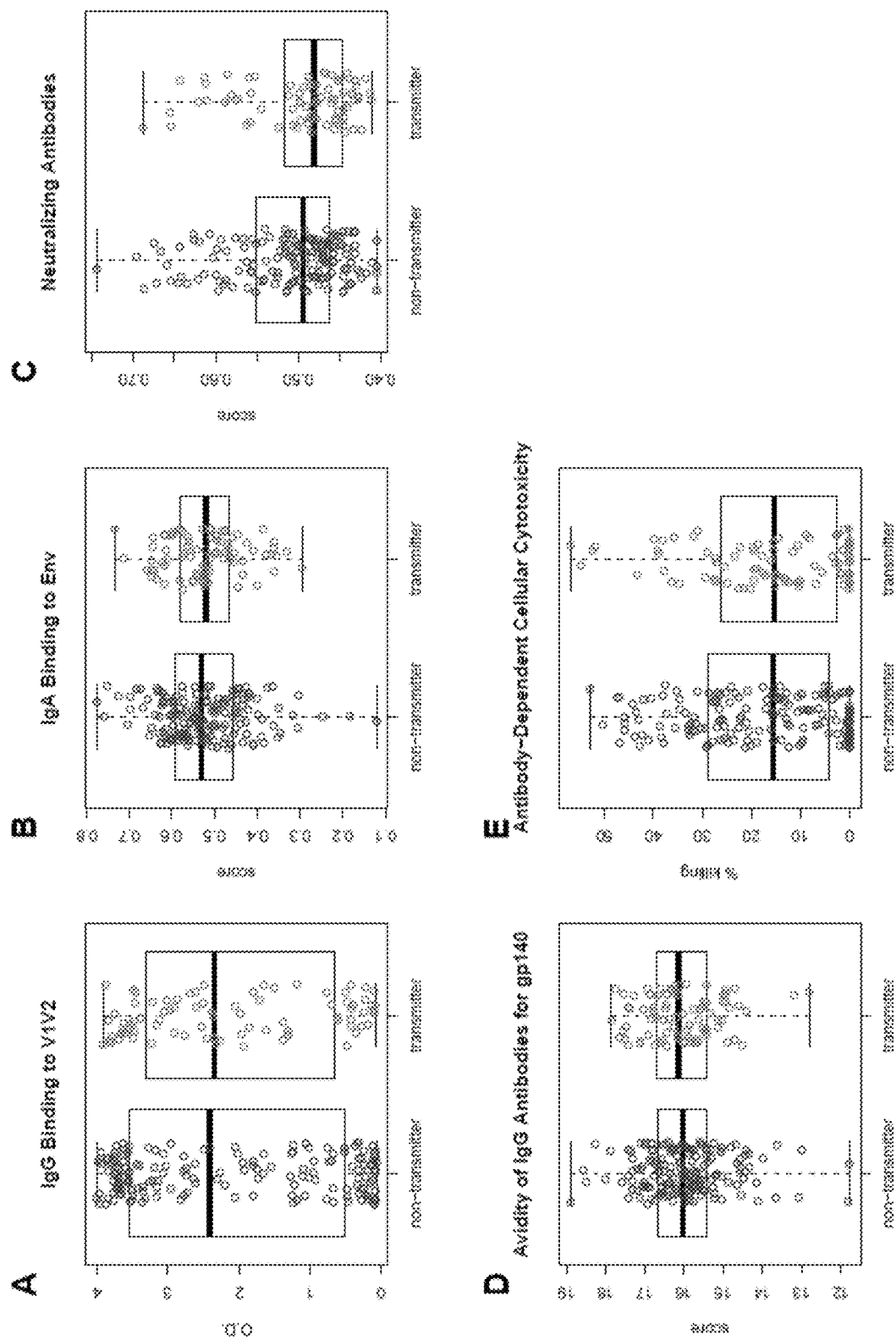
Figure 3 A.-E.

| | Tier 1 mAbs | | | | | | | nAbs | | | |
|---|---|---|---|---|---|---|---|---|---|---|---|
| | gp120 V3 mAbs | | CD4bs-directed mAbs | | | | | | | | |
| | | | Lineage CH13 | | | | | Lineage CH27 | | | |
| | CH14 | CH48 | CH13 | CH16 | CH17 | CH18 | CH45 | CH27 | CH28 | CH44 | HIVIG-C |
| w0.57c | 23 | >50 | >50 | >50 | >50 | >50 | >50 | >50 | >50 | >50 | 96 |
| w0.16c | 28 | >50 | >50 | >50 | 31 | >50 | >50 | >50 | >50 | >50 | 103 |
| w0.39c | 8.4 | 27 | >50 | >50 | >50 | >50 | >50 | >50 | >50 | >50 | 104 |
| w0.47c | 18 | 41 | >50 | >50 | >50 | >50 | >50 | >50 | >50 | >50 | 63 |
| w0.46c | >50 | >50 | >50 | >50 | >50 | >50 | >50 | >50 | >50 | >50 | 146 |
| w0.8c | 40 | >50 | >50 | >50 | >50 | >50 | >50 | >50 | >50 | >50 | 85 |
| w0.28c | 17 | 18 | >50 | >50 | >50 | >50 | >50 | >50 | >50 | >50 | 58 |
| w0.34c | 12 | 27 | >50 | >50 | >50 | >50 | >50 | >50 | >50 | >50 | 70 |
| w0.10c | 4.4 | 15 | 45 | >50 | >50 | 25 | 26 | >50 | >50 | >50 | 38 |
| w0.31c | 16 | >50 | >50 | >50 | >50 | >50 | >50 | >50 | >50 | >50 | 83 |
| w0.25c | 42 | 37 | >50 | >50 | >50 | >50 | >50 | >50 | >50 | >50 | 66 |
| w0.17c | 18 | 34 | >50 | >50 | >50 | >50 | >50 | >50 | >50 | >50 | 40 |
| w0.42c | >50 | >50 | >50 | >50 | >50 | >50 | >50 | >50 | >50 | >50 | 104 |
| w0.9c | 17 | 32 | >50 | >50 | >50 | >50 | >50 | >50 | >50 | >50 | 81 |
| w0.51c | 7.1 | 18 | >50 | >50 | 46 | >50 | >50 | >50 | >50 | >50 | 63 |
| w0.45c | 15 | 49 | >50 | >50 | >50 | >50 | >50 | >50 | >50 | >50 | 157 |
| w0.18c | 15 | 12 | >50 | >50 | >50 | >50 | >50 | >50 | >50 | >50 | 68 |
| w0.27c | 14 | 28 | >50 | >50 | >50 | >50 | >50 | >50 | >50 | >50 | 73 |
| w0.22c | 21 | 21 | >50 | >50 | >50 | >50 | >50 | >50 | >50 | >50 | 41 |
| w0.5c | 7.1 | 7.7 | >50 | >50 | >50 | >50 | >50 | >50 | >50 | >50 | 24 |
| w0.4c | 45 | 38 | >50 | >50 | >50 | >50 | >50 | >50 | >50 | >50 | 43 |
| w0.24c | 10 | 24 | 28 | 18 | 8.7 | 22 | 38 | >50 | >50 | >50 | 48 |
| w0.15c | 12 | 35 | >50 | 21 | 30 | 17 | >50 | >50 | >50 | >50 | 32 |
| w0.53c | 2.8 | 25 | >50 | >50 | 28 | 49 | >50 | >50 | >50 | >50 | 131 |
| w0.11c | 7.2 | 18 | 28 | 21 | 20 | 16 | 11 | >50 | >50 | >50 | 81 |
| w0.56c | 12 | 14 | 37 | 39 | 10 | >50 | >50 | 28 | >50 | >50 | 43 |
| w0.2c | 11 | 13 | 40 | 13 | 19 | 10 | 13 | 8.8 | >50 | 49 | 48 |
| w0.54c | 11 | 25 | 48 | >50 | >50 | >50 | >50 | >50 | >50 | >50 | 81 |
| w0.50c | NT | NT | >50 | >50 | >50 | >50 | >50 | >50 | >50 | >50 | 59 |
| w0.55c | >50 | >50 | >50 | >50 | >50 | >50 | >50 | >50 | >50 | >50 | 142 |
| w0.3c | >50 | >50 | >50 | >50 | >50 | >50 | >50 | >50 | >50 | >50 | 80 |
| w0.14c | 39 | 28 | >50 | >50 | 44 | >50 | 42 | >50 | 35 | 24 | 110 |
| w0.29c | 36 | >50 | >50 | >50 | >50 | >50 | >50 | >50 | 8.8 | 9.5 | 42 |
| w0.35c | >50 | >50 | >50 | >50 | >50 | >50 | >50 | 3.1 | 0.1 | 0.3 | 31 |

Figure 21 Sequences of B 63521 gp120 env, CH505 gp120 env and CON-S

>HV130043.opt (B.63521 D11gp120)

aagcttgtcgacaccATGCGCGTGAAGGGCATCCGCAAGAACTACCAGCACCTGTGGCGCTGGGGC
ACCATGCTGCTGGGCATCCTGATGATCTGCTCCGCCGTGCCCGTGTGGAAGGAGGCCACCA
CCACCCTGTTCTGCGCCTCCGACGCCAAGGCCTACGACACCGAGGTGCACAACGTGTGGGC
CACCCACGCCTGCGTGCCCACCGACCCCAACCCCCAGGAGCTGGTGCTGGCCAACGTGACC
GAGAACTTCAACATGTGGAACAACACCATGGTGGAGCAGATGCACGAGGACATCATCTCC
CTGTGGGACCAGTCCCTGAAGCCCTGCGTGAAGCTGACCCCCCTGTGCGTGACCCTGAACT
GCACCGACGTGACCAACGCCACCAACATCAACGCCACCAACATCAACAACTCCTCCGGCG
GCGTGGAGTCCGGCGAGATCAAGAACTGCTCCTTCAACATCACCACCTCCGTGCGCGACAA
GGTGCAGAAGGAGTACGCCCTGTTCTACAAGCTGGACATCGTGCCCATCACCAACGAGTCC
TCCAAGTACCGCCTGATCTCCTGCAACACCTCCGTGCTGACCCAGGCCTGCCCCAAGGTGT
CCTTCGAGCCCATCCCCATCCACTACTGCGCCCCCGCCGGCTTCGCCATCCTGAAGTGCAAC
AACGAGACCTTCAACGGCAAGGGCCCCTGCATCAACGTGTCCACCGTGCAGTGCACCCACG
GCATCCGCCCCGTGGTGTCCACCCAGCTGCTGCTGAACGGCTCCCTGGCCGAGAAGGAGGT
GATCATCCGCTCCGACAACTTCTCCGACAACGCCAAGAACATCATCGTGCAGCTGAAGGAG
TACGTGAAGATCAACTGCACCCGCCCCAACAACAACACCCGCAAGTCCATCCACATCGGCC
CCGGCCGCGCCTTCTACGCCACCGGCGAGATCATCGGCAACATCCGCCAGGCCCACTGCAA
CATCTCCCGCTCCAAGTGGAACGACACCCTGAAGCAGATCGCCGCCAAGCTGGGCGAGCA
GTTCCGCAACAAGACCATCGTGTTCAACCCCTCCTCCGGCGGCGACCTGGAGATCGTGACC
CACTCCTTCAACTGCGGCGGCGAGTTCTTCTACTGCAACACCACCAAGCTGTTCAACTCCAC
CTGGATTCGCGAGGGCAACAACGGCACCTGGAACGGCACCATCGGCCTGAACGACACCGC
CGGCAACGACACCATCATCCTGCCCTGCAAGATCAAGCAGATCATCAACATGTGGCAGGA
GGTGGGCAAGGCCATGTACGCCCCCCCCATCCGCGGCCAGATCCGCTGCTCCTCCAACATC
ACCGGCCTGATCCTGACCCGCGACGGCGGCAAGGACGACTCCAACGGCTCCGAGATCCTG
GAGATCTTCCGCCCCGGCGGCGGCGACATGCGCGACAACTGGCGCTCCGAGCTGTACAAGT
ACAAGGTGGTGCGCATCGAGCCCCTGGGCGTGGCCCCCACCCGCGCCCGCGAGCGCGTGGT
GCAGAAGGAGAAGGAGTAGggatcctctaga_

>B.63521 D11gp120

MRVKGIRKNYQHLWRWGTMLLGILMICSAVPVWKEATTTLFCASDAKAYDTEVHNVWATHA
CVPTDPNPQELVLANVTENFNMWNNTMVEQMHEDIISLWDQSLKPCVKLTPLCVTLNCTDVT
NATNINATNINNSSGGVESGEIKNCSFNITTSVRDKVQKEYALFYKLDIVPITNESSKYRLISCNT
SVLTQACPKVSFEPIPIHYCAPAGFAILKCNNETFNGKGPCINVSTVQCTHGIRPVVSTQLLLNGS
LAEKEVIIRSDNFSDNAKNIIVQLKEYVKINCTRPNNNTRKSIHIGPGRAFYATGEIIGNIRQAHCN
ISRSKWNDTLKQIAAKLGEQFRNKTIVFNPSSGGDLEIVTHSFNCGGEFFYCNTTKLFNSTWIRE
GNNGTWNGTIGLNDTAGNDTIILPCKIKQIINMWQEVGKAMYAPPIRGQIRCSSNITGLILTRDG
GKDDSNGSEILEIFRPGGGDMRDNWRSELYKYKVVRIEPLGVAPTRARERVVQKEKE*

>HV130043_MutC.opt (B.63521 D11gp120mutC)

aagcttgtcgacaccATGCGCGTGAAGGGCATCCGCAAGAACTACCAGCACCTGTGGCGCTGGGGC
ACCATGCTGCTGGGCATCCTGATGATCTGCTCCGCCGTGCCCGTGTGGAAGGAGGCCACCA
CCACCCTGTTCTGCGCCTCCGACGCCAAGGCCTACGACACCGAGGTGCACAACGTGTGGGC
CACCCACGCCTGCGTGCCCACCGACCCCAACCCCCAGGAGCTGGTGCTGGCCAACGTGACC
GAGAACTTCAACATGTGGAACAACACCATGGTGGAGCAGATGCACGAGGACATCATCTCC
CTGTGGGACCAGTCCCTGAAGCCCTGCGTGAAGCTGACCCCCCTGTGCGTGACCCTGAACT
GCACCGACGTGACCAACGCCACCAACATCAACGCCACCAACATCAACAACTCCTCCGGCG
GCGTGGAGTCCGGCGAGATCAAGAACTGCTCCTTCAACATCACCACCTCCGTGCGCGACAA
GGTGCAGAAGGAGTACGCCCTGTTCTACAAGCTGGACATCGTGCCCATCACCAACGAGTCC
TCCAAGTACCGCCTGATCTCCTGCAACACCTCCGTGCTGACCCAGGCCTGCCCCAAGGTGT
CCTTCGAGCCCATCCCCATCCACTACTGCGCCCCCGCCGGCTTCGCCATCCTGAAGTGCAAC
AACGAGACCTTCAACGGCAAGGGCCCCTGCATCAACGTGTCCACCGTGCAGTGCACCCACG
GCATCCGCCCCGTGGTGTCCACCCAGCTGCTGCTGAACGGCTCCCTGGCCGAGAAGGAGGT
GATCATCCGCTCCGACAACTTCTCCGACAACGCCAAGAACATCATCGTGCAGCTGAAGGAG
TACGTGAAGATCAACTGCACCCGCCCCAACAACAACACCCGCAAGTCCATCCGCATCGGCC
CCGGCCAGACCTTCTACGCCACCGGCGAGATCATCGGCAACATCCGCCAGGCCCACTGCAA
CATCTCCCGCTCCAAGTGGAACGACACCCTGAAGCAGATCGCCGCCAAGCTGGGCGAGCA
GTTCCGCAACAAGACCATCGTGTTCAACCCCTCCTCCGGCGGCGACCTGGAGATCGTGACC
CACTCCTTCAACTGCGGCGGCGAGTTCTTCTACTGCAACACCACCAAGCTGTTCAACTCCAC
CTGGATTCGCGAGGGCAACAACGGCACCTGGAACGGCACCATCGGCCTGAACGACACCGC
CGGCAACGACACCATCATCCTGCCCTGCAAGATCAAGCAGATCATCAACATGTGGCAGGA
GGTGGGCAAGGCCATGTACGCCCCCCCCATCCGCGGCCAGATCCGCTGCTCCTCCAACATC
ACCGGCCTGATCCTGACCCGCGACGGCGGCAAGGACGACTCCAACGGCTCCGAGATCCTG
GAGATCTTCCGCCCCGGCGGCGGCGACATGCGCGACAACTGGCGCTCCGAGCTGTACAAGT
ACAAGGTGGTGCGCATCGAGCCCCTGGGCGTGGCCCCCACCCGCGCCCGCGAGCGCGTGGT
GCAGAAGGAGAAGGAGTAGggatcctctaga >HV130043_MutC (B.63521 D11gp120mutC)

MRVKGIRKNYQHLWRWGTMLLGILMICSAVPVWKEATTTLFCASDAKAYDTEVHNVWATHA
CVPTDPNPQELVLANVTENFNMWNNTMVEQMHEDIISLWDQSLKPCVKLTPLCVTLNCTDVTN
ATNINATNINNSSGGVESGEIKNCSFNITTSVRDKVQKEYALFYKLDIVPITNESSKYRLISCNTSV
LTQACPKVSFEPIPIHYCAPAGFAILKCNNETFNGKGPCINVSTVQCTHGIRPVVSTQLLLNGSLA
EKEVIIRSDNFSDNAKNIIVQLKEYVKINCTRPNNNTRKSIRIGPGQTFYATGEIIGNIRQAHCNISR
SKWNDTLKQIAAKLGEQFRNKTIVFNPSSGGDLEIVTHSFNCGGEFFYCNTTKLFNSTWIREGNN
GTWNGTIGLNDTAGNDTIILPCKIKQIINMWQEVGKAMYAPPIRGQIRCSSNITGLILTRDGGKDD
SNGSEILEIFRPGGGDMRDNWRSELYKYKVVRIEPLGVAPTRARERVVQKEKE

>HV1300218 (CH0505TFdelta8gp120)

aagcttgtcgacaccATGCGCGTGATGGGCATCCAGCGCAACTACCCCCAGTGGTGGATCTGGTCCA
TGCTGGGCTTCTGGATGCTGATGATCTGCAACGGCGTGCCCGTGTGGAAGGAGGCCAAGAC

FIG 21 CONT.

CACCCTGTTCTGCGCCTCCGACGCCAAGGCCTACGAGAAGGAGGTGCACAACGTGTGGGCC
ACCCACGCCTGCGTGCCCACCGACCCCAACCCCAGGAGATGGTGCTGAAGAACGTGACC
GAGAACTTCAACATGTGGAAGAACGACATGGTGGACCAGATGCACGAGGACGTGATCTCC
CTGTGGGACCAGTCCCTGAAGCCCTGCGTGAAGCTGACCCCCCTGTGCGTGACCCTGAACT
GCACCAACGCCACCGCCTCCAACTCCTCCATCATCGAGGGCATGAAGAACTGCTCCTTCAA
CATCACCACCGAGCTGCGCGACAAGCGCGAGAAGAAGAACGCCCTGTTCTACAAGCTGGA
CATCGTGCAGCTGGACGGCAACTCCTCCCAGTACCGCCTGATCAACTGCAACACCTCCGTG
ATCACCCAGGCCTGCCCCAAGGTGTCCTTCGACCCCATCCCCATCCACTACTGCGCCCCCGC
CGGCTACGCCATCCTGAAGTGCAACAACAAGACCTTCACCGGCACCGGCCCCTGCAACAAC
GTGTCCACCGTGCAGTGCACCCACGGCATCAAGCCCGTGGTGTCCACCCAGCTGCTGCTGA
ACGGCTCCCTGGCCGAGGGCGAGATCATCATCCGCTCCGAGAACATCACCAACAACGTGA
AGACCATCATCGTGCACCTGAACGAGTCCGTGAAGATCGAGTGCACCCGCCCCAACAACA
AGACCCGCACCTCCATCCGCATCGGCCCCGGCCAGGCCTTCTACGCCACCGGCCAGGTGAT
CGGCGACATCCGCGAGGCCTACTGCAACATCAACGAGTCCAAGTGGAACGAGACCCTGCA
GCGCGTGTCCAAGAAGCTGAAGGAGTACTTCCCCCACAAGAACATCACCTTCCAGCCCTCC
TCCGGCGGCGACCTGGAGATCACCACCCACTCCTTCAACTGCGGCGGCGAGTTCTTCTACT
GCAACACCTCCTCCCTGTTCAACCGCACCTACATGGCCAACTCCACCGACATGGCCAACTC
CACCGAGACCAACTCCACCCGCACCATCACCATCCACTGCCGCATCAAGCAGATCATCAAC
ATGTGGCAGGAGGTGGGCCGCGCCATGTACGCCCCCCCCATCGCCGGCAACATCACCTGCA
TCTCCAACATCACCGGCCTGCTGCTGACCCGCGACGGCGGCAAGAACAACACCGAGACCTT
CCGCCCCGGCGGCGGCAACATGAAGGACAACTGGCGCTCCGAGCTGTACAAGTACAAGGT
GGTGGAGGTGAAGCCCCTGGGCGTGGCCCCCACCAACGCCCGCGAGCGCGTGGTGGAGCG
CGAGAAGGAGtagggatcctctaga >CH0505TFdelta8gp120

MRVMGIQRNYPQWWIWSMLGFWMLMICNGVPVWKEAKTTLFCASDAKAYEKEVHNVWAT
HACVPTDPNPQEMVLKNVTENFNMWKNDMVDQMHEDVISLWDQSLKPCVKLTPLCVTLNCT
NATASNSSIIEGMKNCSFNITTELRDKREKKNALFYKLDIVQLDGNSSQYRLINCNTSVITQACP
KVSFDPIPIHYCAPAGYAILKCNNKTFTGTGPCNNVSTVQCTHGIKPVVSTQLLLNGSLAEGEII
RSENITNNVKTIIVHLNESVKIECTRPNNKTRTSIRIGPGQAFYATGQVIGDIREAYCNINESKWN
ETLQRVSKKLKEYFPHKNITFQPSSGGDLEITTHSFNCGGEFFYCNTSSLFNRTYMANSTDMANS
TETNSTRTITIHCRIKQIINMWQEVGRAMYAPPIAGNITCISNITGLLLTRDGGKNNTETFRPGGG
NMKDNWRSELYKYKVVEVKPLGVAPTNARERVVEREKE*

>HV1300239(CH505w53.e16.delta8gp120)

aagcttgtcgacaccATGCGCGTGATGGGCATCCAGCGCAACTACCCCCAGTGGTGGATCTGGTCCA
TGCTGGGCTTCTGGATGCTGATGATCTGCAACGGCGTGCCCGTGTGGAAGGAGGCCAAGAC
CACCCTGTTCTGCGCCTCCGACGCCAAGGCCTACGAGAAGGAGGTGCACAACGTGTGGGCC
ACCCACGCCTGCGTGCCCACCGACCCCAACCCCAGGAGATGGTGCTGAAGAACGTGACC
GAGAACTTCAACATGTGGAAGAACGACATGGTGGACCAGATGCACGAGGACGTGATCTCC
CTGTGGGACCAGTCCCTGAAGCCCTGCGTGAAGCTGACCCCCCTGTGCGTGACCCTGAACT
GCACCAACGCCAACGCCACCGCCTCCAACTCCTCCATCATCGAGGGCATGAACTCCTCCAT CATCGAGGGCATGAAGAACTGCTCCTTCAACATCACCACCGAGCTGCGCGACAAGCGCGA
GAAGAAGAACGCCCTGTTCTACAAGCTGGACATCGTGCAGCTGGACGGCAACTCCTCCCAG
TACCGCCTGATCAACTGCAACACCTCCGTGATCACCCAGGCCTGCCCCAAGGTGTCCTTCG
ACCCCATCCCCATCCACTACTGCGCCCCCGCCGGCTACGCCATCCTGAAGTGCAACAACAA
GACCTTCAACGGCACCGGCCCCTGCAACAACGTGTCCACCGTGCAGTGCACCCACGGCATC
AAGCCCGTGGTGTCCACCCAGCTGCTGCTGAACGGCTCCCTGGCCGAGGGCGAGATCATCA
TCCGCTCCGAGAACATCACCGACAACGGCAAGACCATCATCGTGCACCTGAACGAGTCCGT
GAAGATCGAGTGCACCCGCCCCTCCAACAACACCCGCACCTCCATCCGCATCGGCCCCGGC
CAGGCCTTCTACGCCACCGGCCAGGTGATCGGCGACATCCGCGAGGCCCACTGCAACATCT
CCGAGTCCAAGTGGAACGAGACCCTGCAGCGCGTGTCCGAGAAGCTGAAGGAGTACTTCC
CCCACAAGAACATCACCTTCCAGCCCTCCTCCGGCGGCGACCTGGAGATCACCACCCACTC
CTTCAACTGCGGCGGCGAGTTCTTCTACTGCAACACCTCCTCCCTGTTCAACCGCACCTACA
TGGCCACCTCCACCGACATGGCCAACTCCACCGAGACCAACTCCACCCGCATCATCACCAT
CCGCTGCCGCATCAAGCAGATCATCAACATGTGGCAGGAGGTGGGCCGCGCCATGTACGCC
CCCCCCATCGCCGGCAACATCACCTGCATCTCCAACATCACCGGCCTGCTGCTGACCCGCG
ACGGCGGCAAGAACAACACCGAGACCTTCGAGACCTTCCGCCCCGGCGGCGGCAACATGA
AGGACAACTGGCGCTCCGAGCTGTACAAGTACAAGGTGGTGGAGGTGAAGCCCCTGGGCG
TGGCCCCCACCAACGCCCGCGAGCGCGTGGTGGAGCGCGAGAAGGAGtagggatcctctaga >CH505w53.e16.delta8gp120

MRVMGIQRNYPQWWIWSMLGFWMLMICNGVPVWKEAKTTLFCASDAKAYEKEVHNVWAT
HACVPTDPNPQEMVLKNVTENFNMWKNDMVDQMHEDVISLWDQSLKPCVKLTPLCVTLNCT
NANATASNSSIIEGMNSSIIEGMKNCSFNITTELRDKREKKNALFYKLDIVQLDGNSSQYRLINC
NTSVITQACPKVSFDPIPIHYCAPAGYAILKCNNKTFNGTGPCNNVSTVQCTHGIKPVVSTQLLL
NGSLAEGEIIRSENITDNGKTIIVHLNESVKIECTRPSNNTRTSIRIGPGQAFYATGQVIGDIREAH
CNISESKWNETLQRVSEKLKEYFPHKNITFQPSSGGDLEITTHSFNCGGEFFYCNTSSLFNRTYM
ATSTDMANSTETNSTRIITIRCRIKQIINMWQEVGRAMYAPPIAGNITCISNITGLLLTRDGGKNN
TETFETFRPGGGNMKDNWRSELYKYKVVEVKPLGVAPTNARERVVEREKE

>HV1300240,( CH505w100.B6.delta8gp120)

aagcttgtcgacaccATGAAGGTGCGCGGCATCCAGCGCAACTACCCCCAGTGGTGGATCTGGTCCA
TGCTGGGCCTGTGGATGCTGATGATCTGCAACGGCGTGCCCGTGTGGAAGGAGGCCAAGAC
CACCCTGTTCTGCGCCTCCGACGCCAAGGCCTACGAGAAGGAGGTGCACAACGTGTGGGCC
ACCCACGCCTGCGTGCCCACCGACCCCAACCCCCAGGAGATGGTGCTGGAGAACGTGACC
GAGAACTTCAACATGTGGAAGAACGACATGGCCGACCAGATGCACGAGGACGTGATCTCC
CTGTGGGACCAGTCCCTGAAGCCCTGCGTGAAGCTGACCCCCCTGTGCGTGACCCTGAACT
GCACCGACGCCAACGCCACCGCCTCCAACACCAACGCCACCGCCTCCAACATCAACGCCAC
CGCCTCCAAGTCCTCCATCATCGAGGAGATGAAGAACTGCTCCTTCAACATCACCACCGAG
CTGCGCGACAAGCGCGAGAAGAAGTACGCCCTGTTCTACAAGCTGGACATCGTGCAGCTG
GACGGCAACTCCTCCCAGTACCGCCTGATCAACTGCAACACCTCCGTGATCACCCAGGCCT
GCCCCAAGGTGTCCTTCGACCCCATCCCCATCCACTACTGCGCCCCCGCCGGCTACGCCATC
CTGAAGTGCAACAACAAGACCTTCAACGGCACCGGCCCCTGCAACAACGTGTCCACCGTGC AGTGCACCCACGGCATCAAGCCCGTGGTGTCCACCCAGCTGCTGCTGAACGGCTCCCTGGC
CGAGGGCGAGATCATCATCCGCTCCGAGAACATCACCGACAACTCCAAGACCATCATCGTG
CACCTGAACGAGTCCGTGAAGATCGAGTGCACCCGCCCCTCCAACAACACCCGCACCTCCA
TCCGCATCGGCCCCGGCCAGGCCTTCTACGCCACCGGCCAGGTGATCGGCGACATCCGCGA
GGCCCACTGCAACATCTCCGAGTCCAAGTGGAACGAGACCCTGCAGCGCGTGTCCAAGAA
GCTGAAGGAGTACTTCCCCGACAAGAACATCACCTTCCAGCCCTCCTCCGGCGGCGACCCC
GAGATCACCACCCACTCCTTCAACTGCGGCGGCGAGTTCTTCTACTGCAACACCTCCTCCCT
GTTCAACCGCACCTACATGGCCAACTCCACCGAGACCAACTCCACCCGCACCATCACCCTG
CACTGCCGCATCAAGCAGATCATCAACATGTGGCAGGAGGTGGGCCGCGCCATGTACGCCC
CCCCCATCGCCGGCAACATCACCTGCATCTCCAACATCACCGGCCTGCTGCTGACCCGCGA
CGGCGGCGAGAACACCCGCGACGGCGGCAACAACAACACCGAGACCTTCCGCCCCGAGGG
CGGCAACATGAAGGACAACTGGCGCTCCGAGCTGTACAAGTACAAGGTGGTGGAGGTGAA
GCCCCTGGGCGTGGCCCCCACCAAGGCCCGCGAGCGCGTGGTGGAGCGCGAGAAGGAGtag
ggatcctctaga >CH505w100.B6. delta 8gp120

MKVRGIQRNYPQWWIWSMLGLWMLMICNGVPVWKEAKTTLFCASDAKAYEKEVHNVWATH
ACVPTDPNPQEMVLENVTENFNMWKNDMADQMHEDVISLWDQSLKPCVKLTPLCVTLNCTD
ANATASNTNATASNINATASKSSIIEEMKNCSFNITTELRDKREKKYALFYKLDIVQLDGNSSQY
RLINCNTSVITQACPKVSFDPIPIHYCAPAGYAILKCNNKTFNGTGPCNNVSTVQCTHGIKPVVST
QLLLNGSLAEGEIIIRSENITDNSKTIIVHLNESVKIECTRPSNNTRTSIRIGPGQAFYATGQVIGDIR
EAHCNISESKWNETLQRVSKKLKEYFPDKNITFQPSSGGDPEITTHSFNCGGEFFYCNTSSLFNRT
YMANSTETNSTRTITLHCRIKQIINMWQEVGRAMYAPPIAGNITCISNITGLLLTRDGGENTRDG
GNNNTETFRPEGGNMKDNWRSELYKYKVVEVKPLGVAPTKARERVVEREKE

>HV1300249 (CH505.w78.env33. delta 8gp120)

aagcttgtcgacaccATGCGCGTGACCGGCATCCAGCGCAACTACCCCCAGTGGTGGATCTGGTCCA
TGCTGGGCCTGTGGATGCTGATGATCTGCAACGGCGTGCCCGTGTGGAAGGAGGCCAAGAC
CACCCTGTTCTGCGCCTCCGACGCCAAGGCCTACGAGAAGGAGGTGCACAACGTGTGGGCC
ACCCACGCCTGCGTGCCCACCGACCCCAACCCCCAGGAGATGGTGCTGAAGAACGTGACC
GAGAACTTCAACATGTGGAAGAACGACATGGCCGACCAGATGCACGAGGACGTGATCTCC
CTGTGGGACCAGTCCCTGAAGCCCTGCGTGAAGCTGACCCCCCTGTGCGTGACCCTGAACT
GCATCGACGCCAACGCCACCGCCTCCAACGCCACCGCCTCCAACTCCTCCATCATCGAGGG
CATGAAGAACTGCTCCTTCAACATCACCACCGAGCTGCGCGACAAGATCGAGAAGAAGAA
CGCCCTGTTCTACAAGCTGGACATCGTGCAGCTGGACGGCAACTCCTCCCAGTACCGCCTG
ATCAACTGCAACACCTCCGTGATCACCCAGGCCTGCCCCAAGGTGTCCTTCGACCCCATCC
CCATCCACTACTGCGCCCCCGCCGGCTACGCCATCCTGAAGTGCAACAACAAGACCTTCAA
CGGCACCGGCCCCTGCAACAACGTGTCCACCGTGCAGTGCACCCACGGCATCAAGCCCGTG
GTGTCCACCCAGCTGCTGCTGAACGGCTCCCTGGCCGAGGGCGAGATCATCATCCGCTCCG
AGAACATCACCAACTCCGCCAAGACCATCATCGTGCACCTGAACGAGTCCGTGAAGATCGA
GTGCACCCGCCCCTCCAACAACACCCGCACCTCCATCCGCATCGGCCCCGGCCAGGCCTTC
TACGCCACCGGCCAGGTGATCGGCGACATCCGCAAGGCCCACTGCAACATCTCCGAGTCCA AGTGGAACGAGACCCTGCAGCGCGTGTCCAAGAAGCTGAAGGAGTACTTCCCCCACAAGA
ACATCACCTTCCAGCCCTCCTCCGGCGGCGACCTGGAGATCACCACCCACTCCTTCAACTGC
GGCGGCGAGTTCTTCTACTGCAACACCTCCTCCCTGTTCAACCGCACCTACATGGCCAACTC
CACCGAGACCAACTCCACCCGCACCATCACCCTGCACTGCCGCATCAAGCAGATCATCAAC
ATGTGGCAGGAGGTGGGCCGCGCCATGTACGCCCCCCCCATCGCCGGCAACATCACCTGCA
TCTCCAACATCACCGGCCTGCTGCTGACCCGCGACGGCGGCAACAACAACACCACCGAGAC
CTTCCGCCCCGGCGGCGGCAACATGAAGGACAACTGGCGCTCCGAGCTGTACAAGTACAA
GGTGGTGGAGATCAAGCCCCTGGGCGTGGCCCCCACCAACGCCCGCGAGCGCGTGGTGGA
GCGCGAGAAGGAGtagggatcctctaga >CH505.w78.env33. delta 8gp120

MRVTGIQRNYPQWWIWSMLGLWMLMICNGVPVWKEAKTTLFCASDAKAYEKEVHNVWATH
ACVPTDPNPQEMVLKNVTENFNMWKNDMADQMHEDVISLWDQSLKPCVKLTPLCVTLNCID
ANATASNATASNSSIIEGMKNCSFNITTELRDKIEKKNALFYKLDIVQLDGNSSQYRLINCNTSVI
TQACPKVSFDPIPIHYCAPAGYAILKCNNKTFNGTGPCNNVSTVQCTHGIKPVVSTQLLLNGSLA
EGEIIIRSENITNSAKTIIVHLNESVKIECTRPSNNTRTSIRIGPGQAFYATGQVIGDIRKAHCNISES
KWNETLQRVSKKLKEYFPHKNITFQPSSGGDLEITTHSFNCGGEFFYCNTSSLFNRTYMANSTET
NSTRTITLHCRIKQIINMWQEVGRAMYAPPIAGNITCISNITGLLLTRDGGNNNTTETFRPGGGN
MKDNWRSELYKYKVVEIKPLGVAPTNARERVVEREKE

>CON-S gp160.opt (codon-optimized)

gtcgacaagaaATGAGGGTCCGGGGAATCCAGCGCAACTGCCAGCACCTCTGGAGGTGGGGCAC
GCTGATCCTGGGGATGCTGATGATCTGCAGCGCGGCTGAGAACCTGTGGGTGACAGTGTAC
TACGGCGTGCCTGTGTGGAAGGAGGCCAACACCACCCTGTTCTGCGCCTCGGACGCCAAGG
CCTACGACACGGAGGTCCACAACGTGTGGGCTACCCACGCCTGCGTGCCCACCGACCCCAA
TCCTCAGGAGATCGTCCTGGAGAACGTGACCGAGAACTTCAACATGTGGAAGAACAACAT
GGTGGAGCAGATGCACGAGGACATCATCAGCCTGTGGGACCAGAGCCTGAAGCCCTGCGT
GAAGCTGACCCCCCTGTGCGTGACCCTGAACTGCACGAACGTGAACGTGACCAACACCACG
AACAACACGGAGGAGAAGGGGGAGATCAAGAACTGCAGCTTCAACATCACCACCGAGATC
CGGGACAAGAAGCAGAAGGTGTACGCCCTGTTCTACCGGCTGGACGTCGTGCCGATCGAC
GACAACAACAACAACTCCAGCAACTACAGGCTGATCAACTGCAACACCAGCGCGATCACC
CAGGCCTGCCCTAAGGTGTCGTTCGAGCCCATCCCCATCCACTACTGCGCGCCTGCCGGCTT
CGCCATCCTGAAGTGCAACGACAAGAAGTTCAACGGCACCGGCCCCTGCAAGAACGTCAG
CACCGTCCAGTGCACCCACGGCATCAAGCCTGTGGTGTCCACCCAGCTGCTCCTGAACGGC
AGCCTGGCCGAGGAGGAGATCATCATCAGGAGCGAGAACATCACCAACAACGCCAAGACG
ATCATCGTGCAGCTGAACGAGTCGGTGGAGATCAACTGCACCCGGCCCAACAACAACACG
CGGAAGAGCATCCGGATCGGCCTGGACAGGCGTTCTACGCCACGGGCGACATCATCGGC
GACATCAGGCAGGCCCACTGCAACATCTCGGGGACGAAGTGGAACAAGACCCTGCAGCAG
GTCGCGAAGAAGCTGAGGGAGCACTTCAACAACAAGACCATCATCTTCAAGCCGAGCAGC
GGCGGAGACCTGGAGATCACCACGCACTCGTTCAACTGCCGGGGCGAGTTCTTCTACTGTA
ACACGTCGGGCCTGTTCAACAGCACCTGGATCGGCAACGGCACGAAGAACAACAACAACA
CTAACGACACCATCACCCTGCCCTGCCGGATCAAGCAGATCATCAACATGTGGCAGGGCGT GGGCCAGGCTATGTACGCCCCTCCCATCGAGGGCAAGATCACGTGCAAGAGCAACATCAC
CGGCCTGCTGCTGACCAGGGACGGCGGGAACAACAACACGAACGAGACCGAGATCTTCAG
ACCTGGCGGCGGAGACATGAGAGACAACTGGCGGAGCGAGCTGTACAAGTACAAGGTCGT
GAAGATCGAGCCCTGGGCGTCGCACCCACCAAGGCCAAGCGCAGGGTGGTGGAGCGGGA
GAAGCGCGCGGTCGGCATCGGCGCCGTGTTCCTGGGCTTCCTGGGAGCAGCCGGCAGCACC
ATGGGAGCCGCCTCGATCACCCTGACCGTGCAGGCGAGGCAGCTGCTGTCCGGCATCGTGC
AGCAGCAGTCGAACCTGCTGAGGGCCATCGAGGCCCAGCAGCACCTGCTCCAGCTGACCGT
GTGGGGCATCAAGCAGCTCCAGGCCAGGGTGCTGGCCGTCGAGCGCTACCTGAAGGACCA
GCAGCTGCTCGGCATCTGGGGCTGCAGCGGCAAGCTGATCTGCACCACCACCGTGCCCTGG
AACAGCAGCTGGAGCAACAAGAGCCAGGACGAGATCTGGGACAACATGACCTGGATGGAG
TGGGAGCGGGAGATCAACAACTACACCGACATCATCTACAGCCTGATCGAGGAGAGCCAG
AACCAGCAGGAGAAGAACGAGCAGGAGCTGCTGGCGCTGGACAAGTGGGCGTCGCTGTGG
AACTGGTTCGACATCACCAACTGGCTGTGGTACATCAAGATCTTCATCATGATCGTCGGCG
GCCTGATCGGTCTGAGAATCGTCTTCGCCGTGCTGTCCATCGTGAACCGCGTGAGGCAGGG
CTACAGCCCCCTGAGCTTCCAGACCCTGATCCCTAACCCGAGAGGCCCCGACAGACCGGAG
GGCATCGAGGAGGAGGGAGGAGAGCAGGACAGGGACAGGTCCATCAGGCTCGTAAACGG
CTTCCTGGCACTCGCCTGGGACGACCTGAGGAGCCTGTGCCTGTTCAGCTACCACCGGCTG
CGCGACTTCATCCTGATCGCGGCCAGAACCGTCGAGCTGCTGGGCAGGAAGGGTCTCAGGC
GGGGCTGGGAGGCCCTGAAGTACCTGTGGAACCTGCTCCAGTACTGGGGTCAGGAGCTGA
AGAACAGCGCCATCTCCCTGCTGGACACGACGGCCATCGCGGTGGCCGAGGGAACCGACC
GCGTCATCGAGGTGGTGCAGAGGGCCTGCCGCGCGATCCTGAACATCCCCCGGAGAATCCG
CCAGGGCCTGGAGCGCGCCCTGCTCTGAtgaggatcc >CON-S gp160

MRVRGIQRNCQHLWRWGTLILGMLMICSAAENLWVTVYYGVPVWKEANTTLFCASDAKAYD
TEVHNVWATHACVPTDPNPQEIVLENVTENFNMWKNNMVEQMHEDIISLWDQSLKPCVKLTP
LCVTLNCTNVNVTNTTNNTEEKGEIKNCSFNITTEIRDKKQKVYALFYRLDVVPIDDNNNSSN
YRLINCNTSAITQACPKVSFEPIPIHYCAPAGFAILKCNDKKFNGTGPCKNVSTVQCTHGIKPVVS
TQLLLNGSLAEEEIIRSENITNNAKTIIVQLNESVEINCTRPNNNTRKSIRIGPGQAFYATGDIIGDI
RQAHCNISGTKWNKTLQQVAKKLREHFNNKTIIFKPSSGGDLEITTHSFNCRGEFFYCNTSGLFN
STWIGNGTKNNNNTNDTITLPCRIKQIINMWQGVGQAMYAPPIEGKITCKSNITGLLLTRDGGN
NNTNETEIFRPGGGDMRDNWRSELYKYKVVKIEPLGVAPTKAKRRVVEREKRAVGIGAVFLGF
LGAAGSTMGAASITLTVQARQLLSGIVQQQSNLLRAIEAQQHLLQLTVWGIKQLQARVLAVER
YLKDQQLLGIWGCSGKLICTTTVPWNSSWSNKSQDEIWDNMTWMEWEREINNYTDIIYSLIEES
QNQQEKNEQELLALDKWASLWNWFDITNWLWYIKIFIMIVGGLIGLRIVFAVLSIVNRVRQGYS
PLSFQTLIPNPRGPDRPEGIEEEGGEQDRDRSIRLVNGFLALAWDDLRSLCLFSYHRLRDFILIAA
RTVELLGRKGLRRGWEALKYLWNLLQYWGQELKNSAISLLDTTAIAVAEGTDRVIEVVQRAC
RAILNIPRRIRQGLERALL

>CON-S gp140C.opt aagcttgtcgacgaaATGAGGGTCAAGGAGACGCAGATGAACTGGCCGAACCTCTGGAAGTGGGGC
ACCCTGATCCTGGGCCTCGTGATCATCTGCTCCGCGAGCGACAACCTGTGGGTGACGGTGT
ACTACGGCGTGCCTGTGTGGAAGGAGGCCACCACCACCCTGTTCTGCGCCTCGGACGCCAA
GGCCTACGACACGGAGGTCCACAACGTGTGGGCTACCTACGCCTGTGTGCCCACCGATCCC
AACCCTCAGGAGGTCGTGCTGGGCAACGTGACCGAGAACTTCAACATGTGGAAGAACAAC
ATGGTGGAGCAGATGCACGAGGACATCATCAGCCTGTGGGACCAGAGCCTGAAGCCCTGC
GTGCGCCTGACCCCGCTGTGCGTGACCCTGAACTGCTCCAACGCCAACACCACGAACACCA
ACTCGACGGAGGAGATCAAGAACTGCAGCTTCAACATCACCACCAGCATCCGGGACAAGG
TGCAGAAGGAGTACGCCCTGTTCTACAAGCTGGACGTCGTGCCGATCGACAACGACAACAC
CAGCTACAGGCTGATCTCGTGCAACACCAGCGTCATCACCCAGGCCTGCCCCAAAGTTAGC
TTCGAGCCCATCCCCATCCACTACTGCGCGCCTGCCGGCTTCGCCATCCTGAAGTGCAAGG
ACAAGAAGTTCAACGGCACCGGCCCTGCACGAACGTCAGCACCGTCCAGTGCACCCACG
GCATCAGGCCTGTGGTGTCCACCCAGCTGCTCCTGAACGGCAGCCTGGCCGAGGAGGAGGT
CGTGATCAGGAGCGAGAACTTCACCAACAACGCCAAGACGATCATCGTGCACCTGAACAA
GTCGGTGGAGATCAACTGCACCCGGCCCAACAACAACACCCGGAAGAGCATCCACATCGG
CCCTGGACGGGCGTTCTACGCTACGGGGGAGATCATCGGCGACATCAGGCAGGCCCACTGC
AACATCTCGCGGGCCAAGTGGAACAACACCCTGAAGCAGATCGTGAAGAAGCTGAAGGAG
CAGTTCAACAAGACCATCATCTTCAACCAGAGCAGCGGCGGAGACCCGGAGATCACCACG
CACTCGTTCAACTGTGGTGGCGAGTTCTTCTACTGTAACACGTCCGGGCTGTTCAACAGCAC
CTGGAACTCGACCGCGACGCAGGAGTCTAACAACACCGAGCTGAACGGCAACATCACCCT
GCCGTGCCGGATCAAGCAGATCGTCAACATGTGGCAGGAGGTGGGCAAGGCTATGTACGC
CCCTCCCATCCGCGGCCAGATCCGGTGCAGCTCGAACATCACCGGCCTGATCCTGACCAGG
GACGGCGGCAACAACAACTCGACGAACGAGACCTTCAGACCTGGCGGCGGAGACATGCGG
GACAACTGGCGGAGCGAGCTGTACAAGTACAAGGTCGTGAAGATCGAGCCCCTGGGCGTC
GCACCCACCAAGGCCAAGGAGAGAGTGGTGCAGCGGGAGAAGGAGGCGGTGGGAACGAT
CGGCGCCATGTTCCTGGGCTTCCTGGGAGCGGCCGGAAGCACGATGGGAGCCGCCTCGCTG
ACCCTGACCGTGCAGGCGAGGCTCCTGCTGTCCGGCATCGTGCAGCAGCAGAACAACCTGC
TGAGGGCCATCGAGGCCCAGCAGCACCTGCTCCAGCTGACAGTGTGGGGCATCAAGCAGC
TCCAGGCGAGGGTGCTGGCCGTCGAGAGATACCTGAAGGACCAGCAACTGCTCGGCATCT
GGGGCTGTAGCGGCAAGCTGATCTGTACCACCACCGTGCCCTGGAACACCAGCTGGAGCA
ACAAGAGCCTCAACGAGATCTGGGACAACATGACCTGGATGGAGTGGGAGCGGGAGATCG
ACAACTACACAGGGCTCATCTACACGCTGCTGGAGGAGAGCCAGAACCAGCAGGAGAAGA
ACGAGCAGGAGCTGCTGGAGCTGGACAAGTGGGCGTCGCTGTGGAACTGGTTCGACATCA
CCAAGTGGCTGTGGTACATCAAGTGAggatcctctaga >CON-S gp140C MRVRGIQRNCQHLWRWGTLILGMLMICSAAENLWVTVYYGVPVWKEANTTLFCASDAKAYD
TEVHNVWATHACVPTDPNPQEIVLENVTENFNMWKNNMVEQMHEDIISLWDQSLKPCVKLTP
LCVTLNCTNVNVTNTTNNTEEKGEIKNCSFNITTEIRDKKQKVYALFYRLDVVPIDDNNNSSN
YRLINCNTSAITQACPKVSFEPIPIHYCAPAGFAILKCNDKKFNGTGPCKNVSTVQCTHGIKPVVS
TQLLLNGSLAEEEIIRSENITNNAKTIIVQLNESVEINCTRPNNNTRKSIRIGPGQAFYATGDIIGDI
RQAHCNISGTKWNKTLQQVAKKLREHFNNKTIIFKPSSGGDLEITTHSFNCRGEFFYCNTSGLFN STWIGNGTKNNNNTNDTITLPCRIKQIINMWQGVGQAMYAPPIEGKITCKSNITGLLLTRDGGN
NNTNETEIFRPGGGDMRDNWRSELYKYKVVKIEPLGVAPTKAKERVVEREKE >CON-S 140CFI.opt aagcttgtcgacgaaATGCGCGTGCGCGGCATCCAGCGCAACTGCCAGCACCTGTGGCGCTGGGGC
ACCCTGATCCTGGGCATGCTGATGATCTGCTCCGCCGCCGAGAACCTGTGGGTGACCGTGT
ACTACGGCGTGCCCGTGTGGAAGGAGGCCAACACCACCCTGTTCTGCGCCTCCGACGCCAA
GGCCTACGACACCGAGGTGCACAACGTGTGGGCCACCCACGCCTGCGTGCCCACCGACCCC
AACCCCCAGGAGATCGTGCTGGAGAACGTGACCGAGAACTTCAACATGTGGAAGAACAAC
ATGGTGGAGCAGATGCACGAGGACATCATCTCCCTGTGGGACCAGTCCCTGAAGCCCTGCG
TGAAGCTGACCCCCCTGTGCGTGACCCTGAACTGCACCAACGTGAACGTGACCAACACCAC
CAACAACACCGAGGAGAAGGGCGAGATCAAGAACTGCTCCTTCAACATCACCACCGAGAT
CCGCGACAAGAAGCAGAAGGTGTACGCCCTGTTCTACCGCCTGGACGTGGTGCCCATCGAC
GACAACAACAACAACTCCTCCAACTACCGCCTGATCAACTGCAACACCTCCGCCATCACCC
AGGCCTGCCCCAAGGTGTCCTTCGAGCCCATCCCCATCCACTACTGCGCCCCCGCCGGCTTC
GCCATCCTGAAGTGCAACGACAAGAAGTTCAACGGCACCGGCCCTGCAAGAACGTGTCC
ACCGTGCAGTGCACCCACGGCATCAAGCCCGTGGTGTCCACCCAGCTGCTGCTGAACGGCT
CCCTGGCCGAGGAGGAGATCATCATCCGCTCCGAGAACATCACCAACAACGCCAAGACCA
TCATCGTGCAGCTGAACGAGTCCGTGGAGATCAACTGCACCCGCCCCAACAACAACACCCG
CAAGTCCATCCGCATCGGCCCCGGCCAGGCCTTCTACGCCACCGGCGACATCATCGGCGAC
ATCCGCCAGGCCCACTGCAACATCTCCGGCACCAAGTGGAACAAGACCCTGCAGCAGGTG
GCCAAGAAGCTGCGCGAGCACTTCAACAACAAGACCATCATCTTCAAGCCCTCCTCCGGCG
GCGACCTGGAGATCACCACCCACTCCTTCAACTGCCGCGGCGAGTTCTTCTACTGCAACAC
CTCCGGCCTGTTCAACTCCACCTGGATCGGCAACGGCACCAAGAACAACAACAACACCAAC
GACACCATCACCCTGCCCTGCCGCATCAAGCAGATCATCAACATGTGGCAGGGCGTGGGCC
AGGCCATGTACGCCCCCCCCATCGAGGGCAAGATCACCTGCAAGTCCAACATCACCGGCCT
GCTGCTGACCCGCGACGGCGGCAACAACAACACCAACGAGACCGAGATCTTCCGCCCCGG
CGGCGGCGACATGCGCGACAACTGGCGCTCCGAGCTGTACAAGTACAAGGTGGTGAAGAT
CGAGCCCCTGGGCGTGGCCCCCACCAAGGCCAAGCTGACCGTGCAGGCCCGCCAGCTGCTG
TCCGGCATCGTGCAGCAGCAGTCCAACCTGCTGCGCGCCATCGAGGCCCAGCAGCACCTGC
TGCAGCTGACCGTGTGGGGCATCAAGCAGCTGCAGGCCCGCGTGCTGGCCGTGGAGCGCTA
CCTGAAGGACCAGCAGCTGGAGATCTGGGACAACATGACCTGGATGGAGTGGGAGCGCGA
GATCAACAACTACACCGACATCATCTACTCCCTGATCGAGGAGTCCCAGAACCAGCAGGAG
AAGAACGAGCAGGAGCTGCTGGCCCTGGACAAGTGGGCCTCCCTGTGGAACTGGTTCGAC
ATCACCAACTGGCTGTGGTGAggatcctctaga

>CON-S 140CFI

MRVRGIQRNCQHLWRWGTLILGMLMICSAAENLWVTVYYGVPVWKEANTTLFCASDAKAYD
TEVHNVWATHACVPTDPNPQEIVLENVTENFNMWKNNMVEQMHEDIISLWDQSLKPCVKLTP
LCVTLNCTNVNVTNTTNNTEEKGEIKNCSFNITTEIRDKKQKVYALFYRLDVVPIDDNNNNSSN
YRLINCNTSAITQACPKVSFEPIPIHYCAPAGFAILKCNDKKFNGTGPCKNVSTVQCTHGIKPVVS
TQLLLNGSLAEEEIIIRSENITNNAKTIIVQLNESVEINCTRPNNNTRKSIRIGPGQAFYATGDIIGDI

FIG 21 CONT.

RQAHCNISGTKWNKTLQQVAKKLREHFNNKTIIFKPSSGGDLEITTHSFNCRGEFFYCNTSGLFN
STWIGNGTKNNNNTNDTITLPCRIKQIINMWQGVGQAMYAPPIEGKITCKSNITGLLLTRDGGN
NNTNETEIFRPGGGDMRDNWRSELYKYKVVKIEPLGVAPTKAKLTVQARQLLSGIVQQQSNLL
RAIEAQQHLLQLTVWGIKQLQARVLAVERYLKDQQLEIWDNMTWMEWEREINNYTDIIYSLIE
ESQNQQEKNEQELLALDKWASLWNWFDITNWLW

>CON-S gp120.opt aagcttgtcgacgaaATGCGCGTGCGCGGCATCCAGCGCAACTGCCAGCACCTGTGGC

STWIGNGTKNNNNTNDTITLPCRIKQIINMWQGVGQAMYAPPIEGKITCKSNITGLLLTRDGGN
NNTNETEIFRPGGGDMRDNWRSELYKYKVVKIEPLGVAPTKAKERVVEREKE

SEQUENCE LISTING

<160> NUMBER OF SEQ ID NOS: 72

<210> SEQ ID NO 1
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Lys Lys Lys Asn Asn Thr Arg Lys Ser Ile His Ile Gly Pro Gly Arg
1               5                   10                  15

Ala Phe Tyr Ala Thr Gly Asp Ile Ile Gly Asp Ile Arg Gln Ala His
            20                  25                  30

Cys

<210> SEQ ID NO 2
<211> LENGTH: 33

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Bio

<400> SEQUENCE: 2

Lys Lys Lys Asn Asn Thr Arg Lys Ser Ile His Ile Gly Pro Gly Arg
1               5                   10                  15

Ala Phe Tyr Ala Thr Gly Asp Ile Ile Gly Asp Ile Arg Gln Ala His
            20                  25                  30

Cys

<210> SEQ ID NO 3
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Bio

<400> SEQUENCE: 3

Lys Lys Lys Asn Asn Thr Arg Lys Ser Ile His Ile Gly Pro Gly Gln
1               5                   10                  15

Ala Phe Tyr Ala Thr Gly Asp Ile Ile Gly Asp Ile Arg Gln Ala His
            20                  25                  30

Cys

<210> SEQ ID NO 4
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu
65                  70                  75

<210> SEQ ID NO 5
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Thr Arg Pro Asn Asn Asn Thr Arg Lys Ser Ile Arg Ile Gly Pro Gly
1               5                   10                  15
```

```
Gln Thr Phe Tyr Ala Thr Gly Asp Ile Ile Gly Asn Ile Arg Gln Ala
            20                  25                  30
His

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
actacttgaa gcactcaagg caagctttat tg                                    32

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcactcaagg caagctttat tgaggctta                                       29

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gggtttatta cagggacagc agag                                            24

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggcttaggca tctcctatgg caggaagaa                                       29

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctgccaatca gggaagtagc cttgtgt                                         27

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 11
caaattayaa aaattcaaaa ttttcgggtt tattacag                                    38

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgaagcactc aaggcaagct ttattgaggc                                             30

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgaggcttaa gcagtgggtt cc                                                     22

<210> SEQ ID NO 14
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Ile, Thr or Phe
<220> FEATURE:
<221> NAME/KEY: MOD_RES
<222> LOCATION: (17)..(17)
<223> OTHER INFORMATION: Val, Met or Thr
<220> FEATURE:
<221> NAME/KEY: MOD_RES
<222> LOCATION: (79)..(79)
<223> OTHER INFORMATION: Val or Ile

<400> SEQUENCE: 14

Cys Thr Asp Phe Gly Asn Asp Thr Asn Thr Asn Ser Ser Xaa Glu Arg
1               5                   10                  15

Xaa Gly Ile Met Glu Lys Gly Glu Ile Lys Asn Cys Ser Phe Asn Ile
                20                  25                  30

Thr Thr Gly Ile Arg Asp Lys Met Gln Lys Glu Tyr Ala Leu Phe Tyr
            35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Xaa Ser
65                  70                  75                  80

Phe Glu Pro Ile Pro Ile His Tyr Cys Ala Pro Ala Gly
                85                  90

<210> SEQ ID NO 15
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 15

Cys Thr Asp Phe Gly Asn Asp Thr Lys Thr Asn Ser Ser Ile Glu Arg
1               5                   10                  15

Val Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Val Ser
65                  70                  75                  80

Phe Glu Pro Ile Pro Ile His Tyr Cys Ala Pro Ala Gly
                85                  90

<210> SEQ ID NO 16
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Cys Thr Asp Phe Gly Asn Asp Thr Lys Thr Asn Ser Ser Ile Glu Arg
1               5                   10                  15

Val Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Val Ser
65                  70                  75                  80

Phe Glu Pro Ile Pro Ile His Tyr Cys Ala Pro Ala Gly
                85                  90

<210> SEQ ID NO 17
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Ile Ser
65                  70                  75                  80

Phe Glu Pro Ile Pro Ile His Tyr Cys Ala Pro Ala Gly
                85                  90

```
<210> SEQ ID NO 18
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Cys Thr Asp Phe Gly Asn Asp Thr Lys Thr Asn Ser Ser Ile Glu Arg
1               5                   10                  15

Val Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Val Ser
65                  70                  75                  80

Phe Glu Pro Ile Pro Ile His Tyr Cys Ala Pro Ala Gly
                85                  90

<210> SEQ ID NO 19
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Cys Thr Asp Phe Gly Asn Asp Thr Asn Thr Asn Ser Ser Thr Glu Gly
1               5                   10                  15

Met Arg Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Ile Ser
65                  70                  75                  80

Phe Glu Pro Ile Pro Ile His Tyr Cys Ala Pro Ala Gly
                85                  90

<210> SEQ ID NO 20
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Cys Thr Asp Phe Gly Asn Asp Thr Asn Thr Asp Ser Ser Phe Lys Arg
1               5                   10                  15

Thr Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
```

```
                    50                  55                  60
Ile Ser Cys Asn Thr Ser Val Ile Thr Gln Ala Cys Pro Lys Ile Ser
 65                  70                  75                  80

Phe Glu Pro Ile Pro Ile His Tyr Cys Ala Pro Ala Gly
                    85                  90
```

<210> SEQ ID NO 21
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Cys Thr Asp Phe Gly Ser Asp Thr Asn Thr Asn Ser Ser Phe Glu Arg
  1               5                  10                  15

Thr Gly Ile Met Glu Lys Gly Glu Ile Lys Asn Cys Ser Phe Asn Ile
                 20                  25                  30

Thr Thr Gly Ile Arg Asp Lys Met Gln Lys Glu Tyr Ala Leu Phe Tyr
             35                  40                  45

Lys Pro Asp Ile Val Gln Ile Glu Asn Thr Asn Thr Ser Tyr Arg Leu
         50                  55                  60

Ile Ser Cys Asn Thr Ser Val Ile Thr Gln Ala Cys Pro Lys Ile Ser
 65                  70                  75                  80

Phe Glu Pro Ile Pro Ile His Tyr Cys Ala Pro Ala Gly
                 85                  90
```

<210> SEQ ID NO 22
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Cys Thr Asp Phe Gly Asn Asp Thr Lys Thr Asn Ser Ser Ile Glu Arg
  1               5                  10                  15

Val Gly Ile Met Glu Lys Gly Glu Ile Lys Asn Cys Ser Phe Asn Ile
                 20                  25                  30

Thr Thr Gly Ile Arg Asp Lys Met Gln Lys Glu Tyr Ala Leu Phe Tyr
             35                  40                  45

Lys Pro Asp Ile Val Gln Ile Glu Asn Thr Asn Thr Ser Tyr Arg Leu
         50                  55                  60

Ile Ser Cys Asn Thr Ser Val Ile Thr Gln Ala Cys Pro Lys Val Ser
 65                  70                  75                  80

Phe Glu Pro Ile Pro Ile His Tyr Cys Ala Pro Ala Gly
                 85                  90
```

<210> SEQ ID NO 23
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Cys Thr Asp Phe Gly Asn Asp Thr Lys Thr Asn Ser Ser Thr Glu Gly
  1               5                  10                  15
```

```
Met Arg Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
50                  55                  60

Ile Ser Cys Asn Thr Ser Val Ile Thr Gln Ala Cys Pro Lys Ile Ser
65                  70                  75                  80

Phe Glu Pro Ile Pro Ile His Tyr Cys Ala Pro Ala Gly
                85                  90

<210> SEQ ID NO 24
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Cys Thr Asp Phe Gly Asn Asp Thr Lys Thr Asn Ser Ser Ile Glu Arg
1               5                   10                  15

Val Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
50                  55                  60

Ile Ser Cys Asn Thr Ser Val Ile Thr Gln Ala Cys Pro Lys Ile Ser
65                  70                  75                  80

Phe Glu Pro Ile Pro Ile His Tyr Cys Ala Pro Ala Gly
                85                  90

<210> SEQ ID NO 25
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Cys Thr Asp Phe Gly Asn Asp Thr Lys Thr Asn Ser Ser Ile Glu Arg
1               5                   10                  15

Val Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
50                  55                  60

Ile Ser Cys Asn Thr Ser Val Ile Thr Gln Ala Cys Pro Lys Val Ser
65                  70                  75                  80

Phe Glu Pro Ile Pro Ile His Tyr Cys Ala Pro Ala Gly
                85                  90

<210> SEQ ID NO 26
<211> LENGTH: 93
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 26

Cys Thr Asp Phe Gly Asn Asp Thr Asn Thr Asn Ser Ser Thr Glu Gly
1               5                   10                  15

Met Arg Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Ile Ser
65                  70                  75                  80

Phe Glu Pro Ile Pro Ile His Tyr Cys Ala Pro Ala Gly
                85                  90

<210> SEQ ID NO 27
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Cys Thr Asp Phe Gly Asn Asp Thr Lys Thr Asn Ser Ser Ile Glu Arg
1               5                   10                  15

Val Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Val Ser
65                  70                  75                  80

Phe Glu Pro Ile Pro Ile His Tyr Cys Ala Pro Ala Gly
                85                  90

<210> SEQ ID NO 28
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Cys Thr Asp Phe Gly Asn Asp Thr Lys Thr Asn Ser Ser Ile Glu Arg
1               5                   10                  15

Val Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Val Ser
65                  70                  75                  80
```

Phe Glu Pro Ile Pro Ile His Tyr Cys Ala Pro Ala Gly
                85                  90

<210> SEQ ID NO 29
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Cys Thr Asp Phe Gly Asn Asp Thr Lys Thr Asn Ser Ser Ile Glu Arg
1               5                   10                  15

Val Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Val Ser
65                  70                  75                  80

Phe Glu Pro Ile Pro Ile His Tyr Cys Ala Pro Ala Gly
                85                  90

<210> SEQ ID NO 30
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Cys Thr Asp Phe Gly Asn Asp Thr Lys Thr Asn Ser Ser Ile Glu Arg
1               5                   10                  15

Val Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Val Ser
65                  70                  75                  80

Phe Glu Pro Ile Pro Ile His Tyr Cys Ala Pro Ala Gly
                85                  90

<210> SEQ ID NO 31
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr

```
            35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Ile Ser
65                  70                  75                  80

Phe Glu Pro Ile Pro Ile His Tyr Cys Ala Pro Ala Gly
                85                  90

<210> SEQ ID NO 32
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Cys Thr Asp Phe Gly Asn Asp Thr Lys Thr Asn Ser Ser Ile Glu Arg
1               5                   10                  15

Val Gly Ile Met Glu Lys Gly Glu Ile Lys Asn Cys Ser Phe Asn Ile
                20                  25                  30

Thr Thr Gly Ile Arg Asp Lys Met Gln Lys Glu Tyr Ala Leu Phe Tyr
            35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Ile Ser
65                  70                  75                  80

Phe Glu Pro Ile Pro Ile His Tyr Cys Ala Pro Ala Gly
                85                  90

<210> SEQ ID NO 33
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Cys Thr Asp Phe Gly Asn Asp Thr Lys Thr Asn Ser Ser Ile Glu Arg
1               5                   10                  15

Val Gly Ile Met Glu Lys Gly Glu Ile Lys Asn Cys Ser Phe Asn Ile
                20                  25                  30

Thr Thr Gly Ile Arg Asp Lys Met Gln Lys Glu Tyr Ala Leu Phe Tyr
            35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Ile Ser
65                  70                  75                  80

Phe Glu Pro Ile Pro Ile His Tyr Cys Ala Pro Ala Gly
                85                  90

<210> SEQ ID NO 34
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34
```

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
                20                  25                  30

Thr Thr Gly Ile Arg Asp Lys Met Gln Lys Glu Tyr Ala Leu Phe Tyr
            35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Ile Ser
65                  70                  75                  80

Phe Glu Pro Ile Pro Ile His Tyr Cys Ala Pro Ala Gly
                85                  90

<210> SEQ ID NO 35
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
                20                  25                  30

Thr Thr Gly Ile Arg Asp Lys Met Gln Lys Glu Tyr Ala Leu Phe Tyr
            35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Val Ser
65                  70                  75                  80

Phe Glu Pro Ile Pro Ile His Tyr Cys Ala Pro Ala Gly
                85                  90

<210> SEQ ID NO 36
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
                20                  25                  30

Thr Thr Gly Ile Arg Asp Lys Met Gln Lys Glu Tyr Ala Leu Phe Tyr
            35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Ile Ser
65                  70                  75                  80

Phe Glu Pro Ile Pro Ile His Tyr Cys Ala Pro Ala Gly
                85                  90

<210> SEQ ID NO 37

```
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Ile Ser
65                  70                  75                  80

Phe Glu Pro Ile Pro Ile His Tyr Cys Ala Pro Ala Gly
                85                  90

<210> SEQ ID NO 38
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Cys Thr Asp Phe Gly Asn Asp Thr Lys Thr Asn Ser Ser Ile Glu Arg
1               5                   10                  15

Val Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Val Ser
65                  70                  75                  80

Phe Glu Pro Ile Pro Ile His Tyr Cys Ala Pro Ala Gly
                85                  90

<210> SEQ ID NO 39
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
    50                  55                  60
```

```
Ile Ser Cys Asn Thr Ser Val Ile Thr Gln Ala Cys Pro Lys Ile Ser
 65                  70                  75                  80

Phe Glu Pro Ile Pro Ile His Tyr Cys Ala Pro Ala Gly
                 85                  90

<210> SEQ ID NO 40
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Ile Ser
 65                  70                  75                  80

Phe Glu Pro Ile Pro Ile His Tyr Cys Ala Pro Ala Gly
                 85                  90

<210> SEQ ID NO 41
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Cys Thr Asp Phe Gly Asn Asp Thr Asn Thr Asn Gly Ser Phe Lys Arg
1               5                   10                  15

Thr Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Ile Ser
 65                  70                  75                  80

Phe Glu Pro Ile Pro Ile His Tyr Cys Ala Pro Ala Gly
                 85                  90

<210> SEQ ID NO 42
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
```

20                  25                  30

Thr Thr Gly Ile Arg Asp Lys Met Gln Lys Glu Tyr Ala Leu Phe Tyr
            35                  40                  45

Lys Pro Asp Ile Val Gln Ile Glu Asn Thr Ser Thr Ser Tyr Arg Leu
        50                  55                  60

Ile Ser Cys Asn Thr Ser Ile Ile Thr Gln Ala Cys Pro Lys Val Ser
65                  70                  75                  80

Phe Glu Pro Ile Pro Ile His Tyr Cys Ala Pro Ala Gly
                85                  90

<210> SEQ ID NO 43
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
                20                  25                  30

Thr Thr Gly Ile Arg Asp Lys Met Gln Lys Glu Tyr Ala Leu Phe Tyr
            35                  40                  45

Lys Pro Asp Ile Val Gln Ile Glu Asn Thr Ser Thr Ser Tyr Arg Leu
        50                  55                  60

Ile Ser Cys Asn Thr Ser Ile Ile Thr Gln Ala Cys Pro Lys Val Ser
65                  70                  75                  80

Phe Glu Pro Ile Pro Ile His Tyr Cys Ala Pro Ala Gly
                85                  90

<210> SEQ ID NO 44
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
                20                  25                  30

Thr Thr Gly Ile Arg Asp Lys Met Gln Lys Glu Tyr Ala Leu Phe Tyr
            35                  40                  45

Lys Pro Asp Ile Val Gln Ile Glu Asn Thr Ser Thr Ser Tyr Arg Leu
        50                  55                  60

Ile Ser Cys Asn Thr Ser Ile Ile Thr Gln Ala Cys Pro Lys Ile Ser
65                  70                  75                  80

Phe Glu Pro Ile Pro Ile His Tyr Cys Ala Pro Ala Gly
                85                  90

<210> SEQ ID NO 45
<211> LENGTH: 93
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 45

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Ser Thr Ser Tyr Arg Leu
    50                  55                  60

Ile Ser Cys Asn Thr Ser Ile Ile Thr Gln Ala Cys Pro Lys Ile Ser
65                  70                  75                  80

Phe Glu Pro Ile Pro Ile His Tyr Cys Ala Pro Ala Gly
                85                  90

<210> SEQ ID NO 46
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Asn Thr Ser Tyr Arg Leu
    50                  55                  60

Ile Ser Cys Asn Thr Ser Val Ile Thr Gln Ala Cys Pro Lys Ile Ser
65                  70                  75                  80

Phe Glu Pro Ile Pro Ile His Tyr Cys Ala Pro Ala Gly
                85                  90

<210> SEQ ID NO 47
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Ser Thr Ser Tyr Arg Leu
    50                  55                  60

Ile Ser Cys Asn Thr Ser Ile Ile Thr Gln Ala Cys Pro Lys Ile Ser
65                  70                  75                  80

Phe Glu Pro Ile Pro Ile His Tyr Cys Ala Pro Ala Gly
                85                  90

<210> SEQ ID NO 48
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Cys Thr Asp Phe Gly Asn Asp Thr Lys Thr Asn Ser Ser Ile Glu Arg
1               5                   10                  15

Val Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Ser Thr Ser Tyr Arg Leu
    50                  55                  60

Ile Ser Cys Asn Thr Ser Ile Ile Thr Gln Ala Cys Pro Lys Val Ser
65                  70                  75                  80

Phe Glu Pro Ile Pro Ile His Tyr Cys Ala Pro Ala Gly
                85                  90

<210> SEQ ID NO 49
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Ser Thr Ser Tyr Arg Leu
    50                  55                  60

Ile Ser Cys Asn Thr Ser Ile Ile Thr Gln Ala Cys Pro Lys Val Ser
65                  70                  75                  80

Phe Glu Pro Ile Pro Ile His Tyr Cys Ala Pro Ala Gly
                85                  90

<210> SEQ ID NO 50
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

```
Lys Pro Asp Ile Val Gln Ile Glu Asn Thr Ser Thr Ser Tyr Arg Leu
    50                  55                  60

Ile Ser Cys Asn Thr Ser Ile Ile Thr Gln Ala Cys Pro Lys Val Ser
65                  70                  75                  80

Phe Glu Pro Ile Pro Ile His Tyr Cys Ala Pro Ala Gly
                85                  90

<210> SEQ ID NO 51
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Ser Thr Ser Tyr Arg Leu
    50                  55                  60

Ile Ser Cys Asn Thr Ser Ile Ile Thr Gln Ala Cys Pro Lys Val Ser
65                  70                  75                  80

Phe Glu Pro Ile Pro Ile His Tyr Cys Ala Pro Ala Gly
                85                  90

<210> SEQ ID NO 52
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Cys Thr Asp Phe Gly Asn Asp Thr Asn Thr Asn Ser Ser Thr Glu Arg
1               5                   10                  15

Met Gly Ile Met Glu Lys Gly Glu Ile Lys Asn Cys Ser Phe Asn Ile
            20                  25                  30

Thr Thr Gly Ile Arg Asp Lys Met Gln Lys Glu Tyr Ala Leu Phe Tyr
        35                  40                  45

Lys Pro Asp Ile Val Gln Ile Glu Asn Thr Ser Thr Ser Tyr Arg Leu
    50                  55                  60

Ile Ser Cys Asn Thr Ser Ile Ile Thr Gln Ala Cys Pro Lys Ile Ser
65                  70                  75                  80

Phe Glu Pro Ile Pro Ile His Tyr Cys Ala Pro Ala Gly
                85                  90

<210> SEQ ID NO 53
<211> LENGTH: 1557
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
aagcttgtcg acaccatgcg cgtgaagggc atccgcaaga actaccagca cctgtggcgc    60
```

```
tggggcacca tgctgctggg catcctgatg atctgctccg ccgtgcccgt gtggaaggag    120
gccaccacca ccctgttctg cgcctccgac gccaaggcct acgacaccga ggtgcacaac    180
gtgtgggcca cccacgcctg cgtgcccacc gaccccaacc cccaggagct ggtgctggcc    240
aacgtgaccg agaacttcaa catgtggaac aacaccatgg tggagcagat gcacgaggac    300
atcatctccc tgtgggacca gtccctgaag ccctgcgtga agctgacccc cctgtgcgtg    360
accctgaact gcaccgacgt gaccaacgcc accaacatca cgccaccaa catcaacaac     420
tcctccggcg gcgtggagtc cggcgagatc aagaactgct ccttcaacat caccacctcc    480
gtgcgcgaca aggtgcagaa ggagtacgcc ctgttctaca gctggacat cgtgcccatc     540
accaacgagt cctccaagta ccgcctgatc tcctgcaaca cctccgtgct gacccaggcc    600
tgccccaagg tgtccttcga gcccatcccc atccactact gcgcccccgc cggcttcgcc    660
atcctgaagt gcaacaacga ccttcaac ggcaagggcc cctgcatcaa cgtgtccacc      720
gtgcagtgca cccacggcat ccgccccgtg gtgtccaccc agctgctgct gaacggctcc    780
ctggccgaga aggaggtgat catccgctcc gacaacttct ccgacaacgc caagaacatc    840
atcgtgcagc tgaaggagta cgtgaagatc aactgcaccc gccccaacaa caacacccgc    900
aagtccatcc acatcggccc cggccgcgcc ttctacgcca ccggcgagat catcggcaac    960
atccgccagg cccactgcaa catctcccgc tccaagtgga cgacacccct gaagcagatc   1020
gccgccaagc tgggcgagca gttccgcaac aagaccatcg tgttcaaccc ctcctccggc   1080
ggcgacctgg agatcgtgac ccactccttc aactgcggcg cgagttctt ctactgcaac    1140
accaccaagc tgttcaactc cacctggatt cgcgagggca caacggcac ctggaacggc    1200
accatcggcc tgaacgacac cgccggcaac gacaccatca tcctgccctg caagatcaag   1260
cagatcatca acatgtggca ggaggtgggc aaggccatgt acgccccccc catccgcggc   1320
cagatccgct gctcctccaa catcaccggc ctgatcctga cccgcgacgg cggcaaggac   1380
gactccaacg gctccgagat cctggagatc ttccgccccg gcggcggcga catgcgcgac   1440
aactggcgct ccgagctgta caagtacaag gtggtgcgca tcgagcccct gggcgtggcc   1500
cccacccgcg cccgcgagcg cgtggtgcag aaggagaagg agtagggatc ctctaga      1557
```

<210> SEQ ID NO 54
<211> LENGTH: 509
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 54

Met Arg Val Lys Gly Ile Arg Lys Asn Tyr Gln His Leu Trp Arg Trp
1               5                   10                  15

Gly Thr Met Leu Leu Gly Ile Leu Met Ile Cys Ser Ala Val Pro Val
            20                  25                  30

Trp Lys Glu Ala Thr Thr Thr Leu Phe Cys Ala Ser Asp Ala Lys Ala
        35                  40                  45

Tyr Asp Thr Glu Val His Asn Val Trp Ala Thr His Ala Cys Val Pro
    50                  55                  60

Thr Asp Pro Asn Pro Gln Glu Leu Val Leu Ala Asn Val Thr Glu Asn
65                  70                  75                  80

Phe Asn Met Trp Asn Asn Thr Met Val Glu Gln Met His Glu Asp Ile
                85                  90                  95

```
Ile Ser Leu Trp Asp Gln Ser Leu Lys Pro Cys Val Lys Leu Thr Pro
            100                 105                 110

Leu Cys Val Thr Leu Asn Cys Thr Asp Val Thr Asn Ala Thr Asn Ile
            115                 120                 125

Asn Ala Thr Asn Ile Asn Asn Ser Ser Gly Gly Val Glu Ser Gly Glu
            130                 135                 140

Ile Lys Asn Cys Ser Phe Asn Ile Thr Thr Ser Val Arg Asp Lys Val
145                 150                 155                 160

Gln Lys Glu Tyr Ala Leu Phe Tyr Lys Leu Asp Ile Val Pro Ile Thr
            165                 170                 175

Asn Glu Ser Ser Lys Tyr Arg Leu Ile Ser Cys Asn Thr Ser Val Leu
            180                 185                 190

Thr Gln Ala Cys Pro Lys Val Ser Phe Glu Pro Ile Pro Ile His Tyr
            195                 200                 205

Cys Ala Pro Ala Gly Phe Ala Ile Leu Lys Cys Asn Asn Glu Thr Phe
            210                 215                 220

Asn Gly Lys Gly Pro Cys Ile Asn Val Ser Thr Val Gln Cys Thr His
225                 230                 235                 240

Gly Ile Arg Pro Val Val Ser Thr Gln Leu Leu Leu Asn Gly Ser Leu
            245                 250                 255

Ala Glu Lys Glu Val Ile Ile Arg Ser Asp Asn Phe Ser Asp Asn Ala
            260                 265                 270

Lys Asn Ile Ile Val Gln Leu Lys Glu Tyr Val Lys Ile Asn Cys Thr
            275                 280                 285

Arg Pro Asn Asn Asn Thr Arg Lys Ser Ile His Ile Gly Pro Gly Arg
            290                 295                 300

Ala Phe Tyr Ala Thr Gly Glu Ile Ile Gly Asn Ile Arg Gln Ala His
305                 310                 315                 320

Cys Asn Ile Ser Arg Ser Lys Trp Asn Asp Thr Leu Lys Gln Ile Ala
            325                 330                 335

Ala Lys Leu Gly Glu Gln Phe Arg Asn Lys Thr Ile Val Phe Asn Pro
            340                 345                 350

Ser Ser Gly Gly Asp Leu Glu Ile Val Thr His Ser Phe Asn Cys Gly
            355                 360                 365

Gly Glu Phe Phe Tyr Cys Asn Thr Thr Lys Leu Phe Asn Ser Thr Trp
            370                 375                 380

Ile Arg Glu Gly Asn Asn Gly Thr Trp Asn Gly Thr Ile Gly Leu Asn
385                 390                 395                 400

Asp Thr Ala Gly Asn Asp Thr Ile Ile Leu Pro Cys Lys Ile Lys Gln
            405                 410                 415

Ile Ile Asn Met Trp Gln Glu Val Gly Lys Ala Met Tyr Ala Pro Pro
            420                 425                 430

Ile Arg Gly Gln Ile Arg Cys Ser Ser Asn Ile Thr Gly Leu Ile Leu
            435                 440                 445

Thr Arg Asp Gly Gly Lys Asp Ser Asn Gly Ser Glu Ile Leu Glu
            450                 455                 460

Ile Phe Arg Pro Gly Gly Gly Asp Met Arg Asp Asn Trp Arg Ser Glu
465                 470                 475                 480

Leu Tyr Lys Tyr Lys Val Val Arg Ile Glu Pro Leu Gly Val Ala Pro
            485                 490                 495

Thr Arg Ala Arg Glu Arg Val Val Gln Lys Glu Lys Glu
            500                 505
```

<210> SEQ ID NO 55
<211> LENGTH: 1557
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

| | | | | | |
|---|---|---|---|---|---|
| aagcttgtcg | acaccatgcg | cgtgaagggc | atccgcaaga | actaccagca | cctgtggcgc | 60 |
| tggggcacca | tgctgctggg | catcctgatg | atctgctccg | ccgtgcccgt | gtggaaggag | 120 |
| gccaccacca | ccctgttctg | cgcctccgac | gccaaggcct | acgacaccga | ggtgcacaac | 180 |
| gtgtgggcca | cccacgcctg | cgtgcccacc | gaccccaacc | cccaggagct | ggtgctggcc | 240 |
| aacgtgaccg | agaacttcaa | catgtggaac | aacaccatgg | tggagcagat | gcacgaggac | 300 |
| atcatctccc | tgtgggacca | gtccctgaag | ccctgcgtga | agctgacccc | cctgtgcgtg | 360 |
| accctgaact | gcaccgacgt | gaccaacgcc | accaacatca | cgccaccaa | catcaacaac | 420 |
| tcctccggcg | gcgtggagtc | cggcgagatc | aagaactgct | ccttcaacat | caccacctcc | 480 |
| gtgcgcgaca | aggtgcagaa | ggagtacgcc | ctgttctaca | agctggacat | cgtgcccatc | 540 |
| accaacgagt | cctccaagta | ccgcctgatc | tcctgcaaca | cctccgtgct | gacccaggcc | 600 |
| tgccccaagt | gtccttcga | gcccatcccc | atccactact | gcgcccccgc | cggcttcgcc | 660 |
| atcctgaagt | gcaacaacga | gaccttcaac | ggcaagggcc | cctgcatcaa | cgtgtccacc | 720 |
| gtgcagtgca | cccacggcat | ccgccccgtg | gtgtccaccc | agctgctgct | gaacggctcc | 780 |
| ctggccgaga | aggaggtgat | catccgctcc | gacaacttct | ccgacaacgc | caagaacatc | 840 |
| atcgtgcagc | tgaaggagta | cgtgaagatc | aactgcaccc | gccccaacaa | caacacccgc | 900 |
| aagtccatcc | gcatcggccc | cggccagacc | ttctacgcca | ccggcgagat | catcggcaac | 960 |
| atccgccagg | cccactgcaa | catctcccgc | tccaagtgga | cgacaccct | gaagcagatc | 1020 |
| gccgccaagc | tgggcgagca | gttccgcaac | aagaccatcg | tgttcaaccc | ctcctccggc | 1080 |
| ggcgacctgg | agatcgtgac | ccactccttc | aactgcggcg | gcgagttctt | ctactgcaac | 1140 |
| accaccaagc | tgttcaactc | cacctggatt | cgcgagggca | caacggcac | ctggaacggc | 1200 |
| accatcggcc | tgaacgacac | cgccggcaac | gacaccatca | tcctgccctg | caagatcaag | 1260 |
| cagatcatca | acatgtggca | ggaggtgggc | aaggccatgt | acgccccccc | catccgcggc | 1320 |
| cagatccgct | gctcctccaa | catcaccggc | ctgatcctga | cccgcgacgg | cggcaaggac | 1380 |
| gactccaacg | gctccgagat | cctggagatc | ttccgccccg | gcggcggcga | catgcgcgac | 1440 |
| aactggcgct | ccgagctgta | caagtacaag | gtggtgcgca | tcgagcccct | gggcgtggcc | 1500 |
| cccacccgcg | cccgcgagcg | cgtggtgcag | aaggagaagg | agtagggatc | ctctaga | 1557 |

<210> SEQ ID NO 56
<211> LENGTH: 509
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 56

Met Arg Val Lys Gly Ile Arg Lys Asn Tyr Gln His Leu Trp Arg Trp
1               5                   10                  15

Gly Thr Met Leu Leu Gly Ile Leu Met Ile Cys Ser Ala Val Pro Val
            20                  25                  30

-continued

```
Trp Lys Glu Ala Thr Thr Thr Leu Phe Cys Ala Ser Asp Ala Lys Ala
     35                  40                  45
Tyr Asp Thr Glu Val His Asn Val Trp Ala Thr His Ala Cys Val Pro
 50                  55                  60
Thr Asp Pro Asn Pro Gln Glu Leu Val Leu Ala Asn Val Thr Glu Asn
65                  70                  75                  80
Phe Asn Met Trp Asn Asn Thr Met Val Glu Gln Met His Glu Asp Ile
                 85                  90                  95
Ile Ser Leu Trp Asp Gln Ser Leu Lys Pro Cys Val Lys Leu Thr Pro
                100                 105                 110
Leu Cys Val Thr Leu Asn Cys Thr Asp Val Thr Asn Ala Thr Asn Ile
            115                 120                 125
Asn Ala Thr Asn Ile Asn Asn Ser Ser Gly Gly Val Glu Ser Gly Glu
130                 135                 140
Ile Lys Asn Cys Ser Phe Asn Ile Thr Thr Ser Val Arg Asp Lys Val
145                 150                 155                 160
Gln Lys Glu Tyr Ala Leu Phe Tyr Lys Leu Asp Ile Val Pro Ile Thr
                165                 170                 175
Asn Glu Ser Ser Lys Tyr Arg Leu Ile Ser Cys Asn Thr Ser Val Leu
            180                 185                 190
Thr Gln Ala Cys Pro Lys Val Ser Phe Glu Pro Ile Pro Ile His Tyr
        195                 200                 205
Cys Ala Pro Ala Gly Phe Ala Ile Leu Lys Cys Asn Asn Glu Thr Phe
210                 215                 220
Asn Gly Lys Gly Pro Cys Ile Asn Val Ser Thr Val Gln Cys Thr His
225                 230                 235                 240
Gly Ile Arg Pro Val Val Ser Thr Gln Leu Leu Leu Asn Gly Ser Leu
                245                 250                 255
Ala Glu Lys Glu Val Ile Ile Arg Ser Asp Asn Phe Ser Asp Asn Ala
            260                 265                 270
Lys Asn Ile Ile Val Gln Leu Lys Glu Tyr Val Lys Ile Asn Cys Thr
        275                 280                 285
Arg Pro Asn Asn Asn Thr Arg Lys Ser Ile Arg Ile Gly Pro Gly Gln
    290                 295                 300
Thr Phe Tyr Ala Thr Gly Glu Ile Ile Gly Asn Ile Arg Gln Ala His
305                 310                 315                 320
Cys Asn Ile Ser Arg Ser Lys Trp Asn Asp Thr Leu Lys Gln Ile Ala
                325                 330                 335
Ala Lys Leu Gly Glu Gln Phe Arg Asn Lys Thr Ile Val Phe Asn Pro
            340                 345                 350
Ser Ser Gly Gly Asp Leu Glu Ile Val Thr His Ser Phe Asn Cys Gly
        355                 360                 365
Gly Glu Phe Phe Tyr Cys Asn Thr Thr Lys Leu Phe Asn Ser Thr Trp
370                 375                 380
Ile Arg Glu Gly Asn Asn Gly Thr Trp Asn Gly Thr Ile Gly Leu Asn
385                 390                 395                 400
Asp Thr Ala Gly Asn Asp Thr Ile Ile Leu Pro Cys Lys Ile Lys Gln
                405                 410                 415
Ile Ile Asn Met Trp Gln Glu Val Gly Lys Ala Met Tyr Ala Pro Pro
            420                 425                 430
Ile Arg Gly Gln Ile Arg Cys Ser Ser Asn Ile Thr Gly Leu Ile Leu
        435                 440                 445
```

```
Thr Arg Asp Gly Gly Lys Asp Asp Ser Asn Gly Ser Glu Ile Leu Glu
        450                 455                 460

Ile Phe Arg Pro Gly Gly Gly Asp Met Arg Asp Asn Trp Arg Ser Glu
465                 470                 475                 480

Leu Tyr Lys Tyr Lys Val Val Arg Ile Glu Pro Leu Gly Val Ala Pro
                485                 490                 495

Thr Arg Ala Arg Glu Arg Val Val Gln Lys Glu Lys Glu
        500                 505
```

<210> SEQ ID NO 57
<211> LENGTH: 1488
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
aagcttgtcg acaccatgcg cgtgatgggc atccagcgca actacccca gtggtggatc      60
tggtccatgc tgggcttctg gatgctgatg atctgcaacg gcgtgcccgt gtggaaggag    120
gccaagacca ccctgttctg cgcctccgac gccaaggcct acgagaagga ggtgcacaac    180
gtgtgggcca cccacgcctg cgtgcccacc gaccccaacc ccaggagat ggtgctgaag     240
aacgtgaccg agaacttcaa catgtggaag aacgacatgg tggaccagat gcacgaggac    300
gtgatctccc tgtgggacca gtccctgaag ccctgcgtga agctgacccc cctgtgcgtg    360
accctgaact gcaccaacgc caccgcctcc aactcctcca tcatcgaggg catgaagaac    420
tgctccttca acatcaccac cgagctgcgc gacaagcgcg agaagaagaa cgccctgttc    480
tacaagctgg acatcgtgca gctggacggc aactcctccc agtaccgcct gatcaactgc    540
aacacctccg tgatcaccca ggcctgcccc aaggtgtcct cgaccccat ccccatccac     600
tactgcgccc ccgccggcta cgccatcctg aagtgcaaca acaagacctt caccggcacc    660
ggcccctgca caacgtgtc caccgtgcag tgcacccacg catcaagcc cgtggtgtcc      720
acccagctgc tgctgaacgg ctccctggcc gagggcgaga tcatcatccg ctccgagaac    780
atcaccaaca acgtgaagac catcatcgtg cacctgaacg agtccgtgaa gatcgagtgc    840
acccgcccca caacaagac ccgcaccctc atccgcatcg cccccggcca ggccttctac    900
gccaccggcc aggtgatcgg cgacatccgc gaggcctact gcaacatcaa cgagtccaag    960
tggaacgaga ccctgcagcg cgtgtccaag aagctgaagg agtacttccc ccacaagaac   1020
atcaccttcc agccctcctc cggcggcgac ctggagatca ccaccccactc cttcaactgc   1080
ggcggcgagt tcttctactg caacacctcc tccctgttca accgcaccta catggccaac   1140
tccaccgaca tggccaactc caccgagacc aactccaccc gcaccatcac catccactgc   1200
cgcatcaagc agatcatcaa catgtggcag gaggtgggcc gcgccatgta cgcccccccc   1260
atcgccggca acatcacctg catctccaac atcaccggcc tgctgctgac ccgcgacggc   1320
ggcaagaaca caccgagac cttccgcccc ggcggcggca acatgaagga caactggcgc   1380
tccgagctgt acaagtacaa ggtggtggag gtgaagcccc tgggcgtggc ccccaccaac   1440
gcccgcgagc gcgtggtgga gcgcgagaag gagtagggat cctctaga                1488
```

<210> SEQ ID NO 58
<211> LENGTH: 486
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 58

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Val Pro Val
            20                  25                  30

Trp Lys Glu Ala Lys Thr Thr Leu Phe Cys Ala Ser Asp Ala Lys Ala
        35                  40                  45

Tyr Glu Lys Glu Val His Asn Val Trp Ala Thr His Ala Cys Val Pro
    50                  55                  60

Thr Asp Pro Asn Pro Gln Glu Met Val Leu Lys Asn Val Thr Glu Asn
65                  70                  75                  80

Phe Asn Met Trp Lys Asn Asp Met Val Asp Gln Met His Glu Asp Val
                85                  90                  95

Ile Ser Leu Trp Asp Gln Ser Leu Lys Pro Cys Val Lys Leu Thr Pro
            100                 105                 110

Leu Cys Val Thr Leu Asn Cys Thr Asn Ala Thr Ala Ser Asn Ser Ser
        115                 120                 125

Ile Ile Glu Gly Met Lys Asn Cys Ser Phe Asn Ile Thr Thr Glu Leu
    130                 135                 140

Arg Asp Lys Arg Glu Lys Lys Asn Ala Leu Phe Tyr Lys Leu Asp Ile
145                 150                 155                 160

Val Gln Leu Asp Gly Asn Ser Ser Gln Tyr Arg Leu Ile Asn Cys Asn
                165                 170                 175

Thr Ser Val Ile Thr Gln Ala Cys Pro Lys Val Ser Phe Asp Pro Ile
            180                 185                 190

Pro Ile His Tyr Cys Ala Pro Ala Gly Tyr Ala Ile Leu Lys Cys Asn
        195                 200                 205

Asn Lys Thr Phe Thr Gly Thr Gly Pro Cys Asn Asn Val Ser Thr Val
    210                 215                 220

Gln Cys Thr His Gly Ile Lys Pro Val Val Ser Thr Gln Leu Leu Leu
225                 230                 235                 240

Asn Gly Ser Leu Ala Glu Gly Glu Ile Ile Ile Arg Ser Glu Asn Ile
                245                 250                 255

Thr Asn Asn Val Lys Thr Ile Ile Val His Leu Asn Glu Ser Val Lys
            260                 265                 270

Ile Glu Cys Thr Arg Pro Asn Asn Lys Thr Arg Thr Ser Ile Arg Ile
        275                 280                 285

Gly Pro Gly Gln Ala Phe Tyr Ala Thr Gly Gln Val Ile Gly Asp Ile
    290                 295                 300

Arg Glu Ala Tyr Cys Asn Ile Asn Glu Ser Lys Trp Asn Glu Thr Leu
305                 310                 315                 320

Gln Arg Val Ser Lys Lys Leu Lys Glu Tyr Phe Pro His Lys Asn Ile
                325                 330                 335

Thr Phe Gln Pro Ser Ser Gly Gly Asp Leu Glu Ile Thr Thr His Ser
            340                 345                 350

Phe Asn Cys Gly Gly Glu Phe Phe Tyr Cys Asn Thr Ser Ser Leu Phe
        355                 360                 365

Asn Arg Thr Tyr Met Ala Asn Ser Thr Asp Met Ala Asn Ser Thr Glu
    370                 375                 380

Thr Asn Ser Thr Arg Thr Ile Thr Ile His Cys Arg Ile Lys Gln Ile
385                 390                 395                 400

```
Ile Asn Met Trp Gln Glu Val Gly Arg Ala Met Tyr Ala Pro Pro Ile
            405                 410                 415

Ala Gly Asn Ile Thr Cys Ile Ser Asn Ile Thr Gly Leu Leu Leu Thr
        420                 425                 430

Arg Asp Gly Gly Lys Asn Asn Thr Glu Thr Phe Arg Pro Gly Gly Gly
        435                 440                 445

Asn Met Lys Asp Asn Trp Arg Ser Glu Leu Tyr Lys Tyr Lys Val Val
    450                 455                 460

Glu Val Lys Pro Leu Gly Val Ala Pro Thr Asn Ala Arg Glu Arg Val
465                 470                 475                 480

Val Glu Arg Glu Lys Glu
            485

<210> SEQ ID NO 59
<211> LENGTH: 1527
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
aagcttgtcg acaccatgcg cgtgatgggc atccagcgca actaccccca gtggtggatc      60
tggtccatgc tgggcttctg gatgctgatg atctgcaacg gcgtgcccgt gtggaaggag     120
gccaagacca ccctgttctg cgcctccgac gccaaggcct acgagaagga ggtgcacaac     180
gtgtgggcca cccacgcctg cgtgcccacc gaccccaacc ccaggagat ggtgctgaag      240 aacgtgaccg agaacttcaa catgtggaag aacgacatgg tggaccagat gcacgaggac     300
gtgatctccc tgtgggacca gtccctgaag ccctgcgtga agctgacccc cctgtgcgtg     360
accctgaact gcaccaacgc caacgccacc gcctccaact cctccatcat cgagggcatg     420
aactcctcca tcatcgaggg catgaagaac tgctccttca acatcaccac cgagctgcgc     480
gacaagcgcg agaagaagaa cgccctgttc tacaagctgg acatcgtgca gctggacggc     540
aactcctccc agtaccgcct gatcaactgc aacacctccg tgatcaccca ggcctgcccc     600
aaggtgtcct tcgaccccat ccccatccac tactgcgccc ccgcggcta cgccatcctg     660 aagtgcaaca acaagacctt caacggcacc ggccctgca acaacgtgtc caccgtgcag     720
tgcacccacg gcatcaagcc cgtggtgtcc acccagctgc tgctgaacgg ctccctggcc     780
gagggcgaga tcatcatccg ctccgagaac atcaccgaca cggcaagac catcatcgtg     840 cacctgaacg agtccgtgaa gatcgagtgc acccgcccct ccaacaacac ccgcacctcc     900
atccgcatcg gccccggcca ggccttctac gccaccggcc aggtgatcgg cgacatccgc     960
gaggcccact gcaacatctc cgagtccaag tggaacgaga ccctgcagcg cgtgtccgag    1020
aagctgaagg agtacttccc ccacaagaac atcaccttcc agccctcctc cggcggcgac    1080
ctggagatca ccacccactc cttcaactgc ggcggcgagt tcttctactg caacacctcc    1140
tccctgttca accgcaccta catggccacc tccaccgaca tggccaactc caccgagacc    1200
aactccaccc gcatcatcac catccgctgc cgcatcaagc agatcatcaa catgtggcag    1260
gaggtgggcc gcgccatgta cgccccccc atcgccggca acatcacctg catctccaac    1320
atcaccggcc tgctgctgac ccgcgacggc ggcaagaaca acaccgagac cttcagacc    1380 ttccgccccg gcggcggcaa catgaaggac aactggcgct ccgagctgta caagtacaag    1440
gtggtggagg tgaagccccct gggcgtggcc cccaccaacg cccgcgagcg cgtggtggag    1500
```
cgcgagaagg agtagggatc ctctaga 1527

<210> SEQ ID NO 60
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

```
Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Val Pro Val
            20                  25                  30

Trp Lys Glu Ala Lys Thr Thr Leu Phe Cys Ala Ser Asp Ala Lys Ala
        35                  40                  45

Tyr Glu Lys Glu Val His Asn Val Trp Ala Thr His Ala Cys Val Pro
    50                  55                  60

Thr Asp Pro Asn Pro Gln Glu Met Val Leu Lys Asn Val Thr Glu Asn
65                  70                  75                  80

Phe Asn Met Trp Lys Asn Asp Met Val Asp Gln Met His Glu Asp Val
                85                  90                  95

Ile Ser Leu Trp Asp Gln Ser Leu Lys Pro Cys Val Lys Leu Thr Pro
            100                 105                 110

Leu Cys Val Thr Leu Asn Cys Thr Asn Ala Asn Ala Thr Ala Ser Asn
        115                 120                 125

Ser Ser Ile Ile Glu Gly Met Asn Ser Ser Ile Ile Glu Gly Met Lys
    130                 135                 140

Asn Cys Ser Phe Asn Ile Thr Thr Glu Leu Arg Asp Lys Arg Glu Lys
145                 150                 155                 160

Lys Asn Ala Leu Phe Tyr Lys Leu Asp Ile Val Gln Leu Asp Gly Asn
                165                 170                 175

Ser Ser Gln Tyr Arg Leu Ile Asn Cys Asn Thr Ser Val Ile Thr Gln
            180                 185                 190

Ala Cys Pro Lys Val Ser Phe Asp Pro Ile Pro Ile His Tyr Cys Ala
        195                 200                 205

Pro Ala Gly Tyr Ala Ile Leu Lys Cys Asn Asn Lys Thr Phe Asn Gly
    210                 215                 220

Thr Gly Pro Cys Asn Asn Val Ser Thr Val Gln Cys Thr His Gly Ile
225                 230                 235                 240

Lys Pro Val Val Ser Thr Gln Leu Leu Leu Asn Gly Ser Leu Ala Glu
                245                 250                 255

Gly Glu Ile Ile Ile Arg Ser Glu Asn Ile Thr Asp Asn Gly Lys Thr
            260                 265                 270

Ile Ile Val His Leu Asn Glu Ser Val Lys Ile Glu Cys Thr Arg Pro
        275                 280                 285

Ser Asn Asn Thr Arg Thr Ser Ile Arg Ile Gly Pro Gly Gln Ala Phe
    290                 295                 300

Tyr Ala Thr Gly Gln Val Ile Gly Asp Ile Arg Glu Ala His Cys Asn
305                 310                 315                 320

Ile Ser Glu Ser Lys Trp Asn Glu Thr Leu Gln Arg Val Ser Glu Lys
                325                 330                 335

Leu Lys Glu Tyr Phe Pro His Lys Asn Ile Thr Phe Gln Pro Ser Ser
            340                 345                 350
```

```
Gly Gly Asp Leu Glu Ile Thr Thr His Ser Phe Asn Cys Gly Gly Glu
            355                 360                 365

Phe Phe Tyr Cys Asn Thr Ser Ser Leu Phe Asn Arg Thr Tyr Met Ala
    370                 375                 380

Thr Ser Thr Asp Met Ala Asn Ser Thr Glu Thr Asn Ser Thr Arg Ile
385                 390                 395                 400

Ile Thr Ile Arg Cys Arg Ile Lys Gln Ile Ile Asn Met Trp Gln Glu
                405                 410                 415

Val Gly Arg Ala Met Tyr Ala Pro Pro Ile Ala Gly Asn Ile Thr Cys
            420                 425                 430

Ile Ser Asn Ile Thr Gly Leu Leu Leu Thr Arg Asp Gly Gly Lys Asn
            435                 440                 445

Asn Thr Glu Thr Phe Glu Thr Phe Arg Pro Gly Gly Gly Asn Met Lys
    450                 455                 460

Asp Asn Trp Arg Ser Glu Leu Tyr Lys Tyr Lys Val Val Glu Val Lys
465                 470                 475                 480

Pro Leu Gly Val Ala Pro Thr Asn Ala Arg Glu Arg Val Val Glu Arg
                485                 490                 495

Glu Lys Glu

<210> SEQ ID NO 61
<211> LENGTH: 1539
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
aagcttgtcg acaccatgaa ggtgcgcggc atccagcgca actacccca gtggtggatc       60 tggtccatgc tgggcctgtg gatgctgatg atctgcaacg gcgtgcccgt gtggaaggag      120
gccaagacca cctgttctg cgcctccgac gccaaggcct acgagaagga ggtgcacaac      180
gtgtgggcca cccacgcctg cgtgcccacc gaccccaacc ccaggagat ggtgctggag      240 aacgtgaccg agaacttcaa catgtggaag aacgacatgg ccgaccagat gcacgaggac      300
gtgatctccc tgtgggacca gtccctgaag ccctgcgtga agctgacccc cctgtgcgtg      360
accctgaact gcaccgacgc caacgccacc gcctccaaca ccaacgccac cgcctccaac      420
atcaacgcca ccgcctccaa gtcctccatc atcgaggaga tgaagaactg ctccttcaac      480
atcaccaccg agctgcgcga caagcgcgag aagaagtacg ccctgttcta caagctggac      540
atcgtgcagc tggacggcaa ctcctcccag taccgcctga tcaactgcaa cacctccgtg      600
atcacccagg cctgccccaa ggtgtccttc gaccccatcc ccatccacta ctgcgcccc       660 gccggctacg ccatcctgaa gtgcaacaac aagaccttca cggcaccgg ccctgcaac       720 aacgtgtcca ccgtgcagtg cacccacggc atcaagcccg tggtgtccac ccagctgctg     780
ctgaacggct ccctggccga gggcgagatc atcatccgct ccgagaacat caccgacaac     840
tccaagacca tcatcgtgca cctgaacgag tccgtgaaga tcgagtgcac ccgccctcc     900 aacaacaccc gcacctccat ccgcatcggc cccggccagg ccttctacgc caccggccag     960
gtgatcggcg acatccgcga ggcccactgc aacatctccg agtccaagtg aacgagacc    1020 ctgcagcgcg tgtccaagaa gctgaaggag tacttccccg acaagaacat caccttccag    1080
ccctcctccg gcggcgaccc cgagatcacc acccactcct tcaactgcgg cggcgagttc    1140
```

```
ttctactgca acacctcctc cctgttcaac cgcacctaca tggccaactc caccgagacc    1200
aactccaccc gcaccatcac cctgcactgc cgcatcaagc agatcatcaa catgtggcag    1260
gaggtgggcc gcgccatgta cgccccccc  atcgccggca acatcacctg catctccaac    1320
atcaccggcc tgctgctgac ccgcgacggc ggcgagaaca cccgcgacgg cggcaacaac    1380
aacaccgaga ccttccgccc cgagggcggc aacatgaagg acaactggcg ctccgagctg    1440
tacaagtaca aggtggtgga ggtgaagccc ctgggcgtgg cccccaccaa ggcccgcgag    1500
cgcgtggtgg agcgcgagaa ggagtaggga tcctctaga                           1539
```

<210> SEQ ID NO 62
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Met Lys Val Arg Gly Ile Gln Arg Asn Tyr Pro Gln Trp Trp Ile Trp
1               5                   10                  15

Ser Met Leu Gly Leu Trp Met Leu Met Ile Cys Asn Gly Val Pro Val
            20                  25                  30

Trp Lys Glu Ala Lys Thr Thr Leu Phe Cys Ala Ser Asp Ala Lys Ala
        35                  40                  45

Tyr Glu Lys Glu Val His Asn Val Trp Ala Thr His Ala Cys Val Pro
    50                  55                  60

Thr Asp Pro Asn Pro Gln Glu Met Val Leu Glu Asn Val Thr Glu Asn
65                  70                  75                  80

Phe Asn Met Trp Lys Asn Asp Met Ala Asp Gln Met His Glu Asp Val
                85                  90                  95

Ile Ser Leu Trp Asp Gln Ser Leu Lys Pro Cys Val Lys Leu Thr Pro
            100                 105                 110

Leu Cys Val Thr Leu Asn Cys Thr Asp Ala Asn Ala Thr Ala Ser Asn
        115                 120                 125

Thr Asn Ala Thr Ala Ser Asn Ile Asn Ala Thr Ala Ser Lys Ser Ser
    130                 135                 140

Ile Ile Glu Glu Met Lys Asn Cys Ser Phe Asn Ile Thr Thr Glu Leu
145                 150                 155                 160

Arg Asp Lys Arg Glu Lys Lys Tyr Ala Leu Phe Tyr Lys Leu Asp Ile
                165                 170                 175

Val Gln Leu Asp Gly Asn Ser Ser Gln Tyr Arg Leu Ile Asn Cys Asn
            180                 185                 190

Thr Ser Val Ile Thr Gln Ala Cys Pro Lys Val Ser Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Ile Arg Ser Glu Asn Ile
            260                 265                 270

Thr Asp Asn Ser Lys Thr Ile Ile Val His Leu Asn Glu Ser Val Lys
        275                 280                 285
```

```
Ile Glu Cys Thr Arg Pro Ser Asn Asn Thr Arg Thr Ser Ile Arg Ile
    290                 295                 300

Gly Pro Gly Gln Ala Phe Tyr Ala Thr Gly Gln Val Ile Gly Asp Ile
305                 310                 315                 320

Arg Glu Ala His Cys Asn Ile Ser Glu Ser Lys Trp Asn Glu Thr Leu
                325                 330                 335

Gln Arg Val Ser Lys Lys Leu Lys Glu Tyr Phe Pro Asp Lys Asn Ile
            340                 345                 350

Thr Phe Gln Pro Ser Ser Gly Gly Asp Pro Glu Ile Thr Thr His Ser
        355                 360                 365

Phe Asn Cys Gly Gly Glu Phe Phe Tyr Cys Asn Thr Ser Ser Leu Phe
370                 375                 380

Asn Arg Thr Tyr Met Ala Asn Ser Thr Glu Thr Asn Ser Thr Arg Thr
385                 390                 395                 400

Ile Thr Leu His Cys Arg Ile Lys Gln Ile Ile Asn Met Trp Gln Glu
                405                 410                 415

Val Gly Arg Ala Met Tyr Ala Pro Pro Ile Ala Gly Asn Ile Thr Cys
            420                 425                 430

Ile Ser Asn Ile Thr Gly Leu Leu Leu Thr Arg Asp Gly Gly Glu Asn
        435                 440                 445

Thr Arg Asp Gly Gly Asn Asn Asn Thr Glu Thr Phe Arg Pro Glu Gly
    450                 455                 460

Gly Asn Met Lys Asp Asn Trp Arg Ser Glu Leu Tyr Lys Tyr Lys Val
465                 470                 475                 480

Val Glu Val Lys Pro Leu Gly Val Ala Pro Thr Lys Ala Arg Glu Arg
                485                 490                 495

Val Val Glu Arg Glu Lys Glu
            500
```

<210> SEQ ID NO 63
<211> LENGTH: 1494
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

```
aagcttgtcg acaccatgcg cgtgaccggc atccagcgca actaccccca gtggtggatc      60
tggtccatgc tgggcctgtg gatgctgatg atctgcaacg ccgtgcccgt gtggaaggag     120
gccaagacca ccctgttctg cgcctccgac gccaaggcct acgagaagga ggtgcacaac     180
gtgtgggcca cccacgcctg cgtgcccacc gaccccaacc ccaggagat ggtgctgaag      240 aacgtgaccg agaacttcaa catgtggaag aacgacatgg ccgaccagat gcacgaggac     300
gtgatctccc tgtgggacca gtccctgaag ccctgcgtga agctgacccc cctgtgcgtg     360
accctgaact gcatcgacgc caacgccacc gcctccaacg ccaccgcctc caactcctcc     420
atcatcgagg gcatgaagaa ctgctccttc aacatcacca ccgagctgcg cgacaagatc     480
gagaagaaga acgccctgtt ctacaagctg gacatcgtgc agctggacgg caactcctcc     540
cagtaccgcc tgatcaactg caacacctcc gtgatcaccc aggcctgccc caaggtgtcc     600
ttcgacccca tccccatcca ctactgcgcc cccgccggct acgccatcct gaagtgcaac     660
aacaagacct tcaacggcac cggccctcgc aacaacgtgt ccaccgtgca gtgcacccac     720
ggcatcaagc ccgtggtgtc cacccagctg ctgctgaacg ctccctggc cgagggcgag     780
```

| | |
|---|---:|
| atcatcatcc gctccgagaa catcaccaac tccgccaaga ccatcatcgt gcacctgaac | 840 |
| gagtccgtga agatcgagtg cacccgcccc tccaacaaca cccgcacctc catccgcatc | 900 |
| ggccccggcc aggccttcta cgccaccggc caggtgatcg cgacatccg caaggcccac | 960 |
| tgcaacatct ccgagtccaa gtggaacgag accctgcagc gcgtgtccaa gaagctgaag | 1020 |
| gagtacttcc cccacaagaa catcaccttc agccctcct ccggcggcga cctggagatc | 1080 |
| accacccact ccttcaactg cggcggcgag ttcttctact gcaacacctc ctccctgttc | 1140 |
| aaccgcacct acatggccaa ctccaccgag accaactcca cccgcaccat caccctgcac | 1200 |
| tgccgcatca agcagatcat caacatgtgg caggaggtgg gccgcgccat gtacgccccc | 1260 |
| cccatcgccg gcaacatcac ctgcatctcc aacatcaccg gcctgctgct gacccgcgac | 1320 |
| ggcggcaaca caacaccac cgagaccttc cgccccggcg cgcaacat gaaggacaac | 1380 |
| tggcgctccg agctgtacaa gtacaaggtg gtggagatca agccctggg cgtggccccc | 1440 |
| accaacgccc gcgagcgcgt ggtggagcgc gagaaggagt agggatcctc taga | 1494 |

<210> SEQ ID NO 64
<211> LENGTH: 488
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 64

```
Met Arg Val Thr Gly Ile Gln Arg Asn Tyr Pro Gln Trp Trp Ile Trp
1               5                   10                  15

Ser Met Leu Gly Leu Trp Met Leu Met Ile Cys Asn Gly Val Pro Val
            20                  25                  30

Trp Lys Glu Ala Lys Thr Thr Leu Phe Cys Ala Ser Asp Ala Lys Ala
        35                  40                  45

Tyr Glu Lys Glu Val His Asn Val Trp Ala Thr His Ala Cys Val Pro
    50                  55                  60

Thr Asp Pro Asn Pro Gln Glu Met Val Leu Lys Asn Val Thr Glu Asn
65                  70                  75                  80

Phe Asn Met Trp Lys Asn Asp Met Ala Asp Gln Met His Glu Asp Val
                85                  90                  95

Ile Ser Leu Trp Asp Gln Ser Leu Lys Pro Cys Val Lys Leu Thr Pro
            100                 105                 110

Leu Cys Val Thr Leu Asn Cys Ile Asp Ala Asn Ala Thr Ala Ser Asn
        115                 120                 125

Ala Thr Ala Ser Asn Ser Ser Ile Ile Glu Gly Met Lys Asn Cys Ser
    130                 135                 140

Phe Asn Ile Thr Thr Glu Leu Arg Asp Lys Ile Glu Lys Lys Asn Ala
145                 150                 155                 160

Leu Phe Tyr Lys Leu Asp Ile Val Gln Leu Asp Gly Asn Ser Ser Gln
                165                 170                 175

Tyr Arg Leu Ile Asn Cys Asn Thr Ser Val Ile Thr Gln Ala Cys Pro
            180                 185                 190

Lys Val Ser Phe Asp Pro Ile Pro Ile His Tyr Cys Ala Pro Ala Gly
        195                 200                 205

Tyr Ala Ile Leu Lys Cys Asn Asn Lys Thr Phe Asn Gly Thr Gly Pro
    210                 215                 220

Cys Asn Asn Val Ser Thr Val Gln Cys Thr His Gly Ile Lys Pro Val
225                 230                 235                 240
```

Val Ser Thr Gln Leu Leu Asn Gly Ser Leu Ala Glu Gly Glu Ile
                245                 250                 255

Ile Ile Arg Ser Glu Asn Ile Thr Asn Ser Ala Lys Thr Ile Ile Val
            260                 265                 270

His Leu Asn Glu Ser Val Lys Ile Glu Cys Thr Arg Pro Ser Asn Asn
        275                 280                 285

Thr Arg Thr Ser Ile Arg Ile Gly Pro Gly Gln Ala Phe Tyr Ala Thr
    290                 295                 300

Gly Gln Val Ile Gly Asp Ile Arg Lys Ala His Cys Asn Ile Ser Glu
305                 310                 315                 320

Ser Lys Trp Asn Glu Thr Leu Gln Arg Val Ser Lys Lys Leu Lys Glu
                325                 330                 335

Tyr Phe Pro His Lys Asn Ile Thr Phe Gln Pro Ser Ser Gly Gly Asp
            340                 345                 350

Leu Glu Ile Thr Thr His Ser Phe Asn Cys Gly Gly Glu Phe Phe Tyr
        355                 360                 365

Cys Asn Thr Ser Ser Leu Phe Asn Arg Thr Tyr Met Ala Asn Ser Thr
    370                 375                 380

Glu Thr Asn Ser Thr Arg Thr Ile Thr Leu His Cys Arg Ile Lys Gln
385                 390                 395                 400

Ile Ile Asn Met Trp Gln Glu Val Gly Arg Ala Met Tyr Ala Pro Pro
                405                 410                 415

Ile Ala Gly Asn Ile Thr Cys Ile Ser Asn Ile Thr Gly Leu Leu Leu
            420                 425                 430

Thr Arg Asp Gly Gly Asn Asn Thr Thr Glu Thr Phe Arg Pro Gly
        435                 440                 445

Gly Gly Asn Met Lys Asp Asn Trp Arg Ser Glu Leu Tyr Lys Tyr Lys
    450                 455                 460

Val Val Glu Ile Lys Pro Leu Gly Val Ala Pro Thr Asn Ala Arg Glu
465                 470                 475                 480

Arg Val Val Glu Arg Glu Lys Glu
                485

<210> SEQ ID NO 65
<211> LENGTH: 2579
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
gtcgacaaga aatgagggtc cggggaatcc agcgcaactg ccagcacctc tggaggtggg      60
gcacgctgat cctggggatg ctgatgatct gcagcgcggc tgagaacctg tgggtgacag     120
tgtactacgg cgtgcctgtg tggaaggagg ccaacaccac cctgttctgc gcctcggacg     180
ccaaggccta cgacacggag gtccacaacg tgtgggctac ccacgcctgc gtgcccaccg     240 acccccaatcc tcaggagatc gtcctggaga cgtgaccga gaacttcaac atgtggaaga     300
acaacatggt ggagcagatg cacgaggaca tcatcagcct gtgggaccag agcctgaagc     360
cctgcgtgaa gctgaccccc ctgtgcgtga ccctgaactg cacgaacgtg aacgtgacca     420
acaccacgaa caacacggag gagaaggggg agatcaagaa ctgcagcttc aacatcacca     480
ccgagatccg ggacaagaag cagaaggtgt acgccctgtt ctaccggctg acgtcgtgc      540 cgatcgacga caacaacaac aactccagca actacaggct gatcaactgc aacaccagcg     600

```
cgatcaccca ggcctgccct aaggtgtcgt tcgagcccat ccccatccac tactgcgcgc      660
ctgccggctt cgccatcctg aagtgcaacg acaagaagtt caacggcacc ggccctgca       720
agaacgtcag caccgtccag tgcacccacg gcatcaagcc tgtggtgtcc acccagctgc      780
tcctgaacgg cagcctggcc gaggaggaga tcatcatcag gagcgagaac atcaccaaca      840
acgccaagac gatcatcgtg cagctgaacg agtcggtgga gatcaactgc acccggccca      900
acaacaacac gcggaagagc atccggatcg ccctggaca gcgttctac gccacgggcg        960
acatcatcgg cgacatcagg caggcccact gcaacatctc ggggacgaag tggaacaaga     1020
ccctgcagca ggtcgcgaag aagctgaggg agcacttcaa caacaagacc atcatcttca     1080
agccgagcag cggcggagac ctggagatca ccacgcactc gttcaactgc cggggcgagt     1140
tcttctactg taacacgtcg ggcctgttca cagcacctg gatcggcaac ggcacgaaga      1200
acaacaacaa cactaacgac accatcaccc tgccctgccg gatcaagcag atcatcaaca     1260
tgtggcaggg cgtgggccag gctatgtacg cccctcccat cgagggcaag atcacgtgca    1320
agagcaacat caccggcctg ctgctgacca gggacggcgg aacaacaac acgaacgaga     1380
ccgagatctt cagacctggc ggcggagaca tgagagacaa ctggcggagc gagctgtaca     1440
agtacaaggt cgtgaagatc gagcccctgg gcgtcgcacc caccaaggcc aagcgcaggg     1500
tggtggagcg ggagaagcgc gcggtcggca tcggcgccgt gttcctgggc ttcctgggag     1560
cagccggcag caccatggga gccgcctcga tcaccctgac cgtgcaggcg aggcagctgc     1620
tgtccggcat cgtgcagcag cagtcgaacc tgctgagggc catcgaggcc agcagcacc     1680
tgctccagct gaccgtgtgg ggcatcaagc agctccaggc cagggtgctg gccgtcgagc     1740
gctacctgaa ggaccagcag ctgctcggca tctggggctg cagcggcaag ctgatctgca     1800
ccaccaccgt gcccctggaac agcagctgga gcaacaagag ccaggacgag atctgggaca     1860
acatgacctg gatggagtgg gagcgggaga tcaacaacta caccgacatc atctacagcc     1920
tgatcgagga gagccagaac cagcaggaga agaacgagca ggagctgctg gcgctggaca     1980
agtgggcgtc gctgtggaac tggttcgaca tcaccaactg gctgtggtac atcaagatct     2040
tcatcatgat cgtcggcggc ctgatcggtc tgagaatcgt cttcgccgtg ctgtccatcg     2100
tgaaccgcgt gaggcagggc tacagccccc tgagcttcca gaccctgatc cctaacccga     2160
gaggcccga cagaccggag ggcatcgagg aggaggagg agagcaggac agggacaggt       2220
ccatcaggct cgtaaacggc ttcctggcac tcgcctggga cgacctgagg agcctgtgcc     2280
tgttcagcta ccaccggctg cgcgacttca tcctgatcgc ggccagaacc gtcgagctgc     2340
tgggcaggaa gggtctcagg cggggctggg aggccctgaa gtacctgtgg aacctgctcc     2400
agtactgggg tcaggagctg aagaacagcc catctccct gctggacacg acggccatcg     2460
cggtggccga gggaaccgac cgcgtcatcg aggtggtgca gagggcctgc cgcgcgatcc     2520
tgaacatccc ccggagaatc cgccagggcc tggagcgcgc cctgctctga tgaggatcc     2579
```

<210> SEQ ID NO 66
<211> LENGTH: 852
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

Met Arg Val Arg Gly Ile Gln Arg Asn Cys Gln His Leu Trp Arg Trp

-continued

```
1               5                   10                  15
Gly Thr Leu Ile Leu Gly Met Leu Met Ile Cys Ser Ala Ala Glu Asn
            20                  25                  30

Leu Trp Val Thr Val Tyr Tyr Gly Val Pro Val Trp Lys Glu Ala Asn
            35                  40                  45

Thr Thr Leu Phe Cys Ala Ser Asp Ala Lys Ala Tyr Asp Thr Glu Val
            50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
            115                 120                 125

Asn Cys Thr Asn Val Asn Val Thr Asn Thr Thr Asn Asn Thr Glu Glu
            130                 135                 140

Lys Gly Glu Ile Lys Asn Cys Ser Phe Asn Ile Thr Thr Glu Ile Arg
145                 150                 155                 160

Asp Lys Lys Gln Lys Val Tyr Ala Leu Phe Tyr Arg Leu Asp Val Val
                165                 170                 175

Pro Ile Asp Asp Asn Asn Asn Ser Ser Asn Tyr Arg Leu Ile Asn
                180                 185                 190

Cys Asn Thr Ser Ala Ile Thr Gln Ala Cys Pro Lys Val Ser Phe Glu
            195                 200                 205

Pro Ile Pro Ile His Tyr Cys Ala Pro Ala Gly Phe Ala Ile Leu Lys
210                 215                 220

Cys Asn Asp Lys Lys Phe Asn Gly Thr Gly Pro Cys Lys Asn Val Ser
225                 230                 235                 240

Thr Val Gln Cys Thr His Gly Ile Lys Pro Val Val Ser Thr Gln Leu
                245                 250                 255

Leu Leu Asn Gly Ser Leu Ala Glu Glu Ile Ile Arg Ser Glu
            260                 265                 270

Asn Ile Thr Asn Asn Ala Lys Thr Ile Ile Val Gln Leu Asn Glu Ser
            275                 280                 285

Val Glu Ile Asn Cys Thr Arg Pro Asn Asn Thr Arg Lys Ser Ile
            290                 295                 300

Arg Ile Gly Pro Gly Gln Ala Phe Tyr Ala Thr Gly Asp Ile Ile Gly
305                 310                 315                 320

Asp Ile Arg Gln Ala His Cys Asn Ile Ser Gly Thr Lys Trp Asn Lys
                325                 330                 335

Thr Leu Gln Gln Val Ala Lys Lys Leu Arg Glu His Phe Asn Asn Lys
            340                 345                 350

Thr Ile Ile Phe Lys Pro Ser Ser Gly Gly Asp Leu Glu Ile Thr Thr
            355                 360                 365

His Ser Phe Asn Cys Arg Gly Glu Phe Phe Tyr Cys Asn Thr Ser Gly
            370                 375                 380

Leu Phe Asn Ser Thr Trp Ile Gly Asn Gly Thr Lys Asn Asn Asn
385                 390                 395                 400

Thr Asn Asp Thr Ile Thr Leu Pro Cys Arg Ile Lys Gln Ile Ile Asn
                405                 410                 415

Met Trp Gln Gly Val Gly Gln Ala Met Tyr Ala Pro Pro Ile Glu Gly
            420                 425                 430
```

```
Lys Ile Thr Cys Lys Ser Asn Ile Thr Gly Leu Leu Leu Thr Arg Asp
            435                 440                 445

Gly Gly Asn Asn Thr Asn Glu Thr Glu Ile Phe Arg Pro Gly Gly
    450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Lys Ala Lys Arg Arg
                485                 490                 495

Val Val Glu Arg Glu Lys Arg Ala Val Gly Ile Gly Ala Val Phe Leu
                500                 505                 510

Gly Phe Leu Gly Ala Ala Gly Ser Thr Met Gly Ala Ala Ser Ile Thr
            515                 520                 525

Leu Thr Val Gln Ala Arg Gln Leu Leu Ser Gly Ile Val Gln Gln Gln
            530                 535                 540

Ser Asn Leu Leu Arg Ala Ile Glu Ala Gln Gln His Leu Leu Gln Leu
545                 550                 555                 560

Thr Val Trp Gly Ile Lys Gln Leu Gln Ala Arg Val Leu Ala Val Glu
                565                 570                 575

Arg Tyr Leu Lys Asp Gln Gln Leu Leu Gly Ile Trp Gly Cys Ser Gly
            580                 585                 590

Lys Leu Ile Cys Thr Thr Thr Val Pro Trp Asn Ser Ser Trp Ser Asn
            595                 600                 605

Lys Ser Gln Asp Glu Ile Trp Asp Asn Met Thr Trp Met Glu Trp
            610                 615                 620

Arg Glu Ile Asn Asn Tyr Thr Asp Ile Ile Tyr Ser Leu Ile Glu Glu
625                 630                 635                 640

Ser Gln Asn Gln Gln Glu Lys Asn Glu Gln Glu Leu Leu Ala Leu Asp
                645                 650                 655

Lys Trp Ala Ser Leu Trp Asn Trp Phe Asp Ile Thr Asn Trp Leu Trp
            660                 665                 670

Tyr Ile Lys Ile Phe Ile Met Ile Val Gly Gly Leu Ile Gly Leu Arg
            675                 680                 685

Ile Val Phe Ala Val Leu Ser Ile Val Asn Arg Val Arg Gln Gly Tyr
            690                 695                 700

Ser Pro Leu Ser Phe Gln Thr Leu Ile Pro Asn Pro Arg Gly Pro Asp
705                 710                 715                 720

Arg Pro Glu Gly Ile Glu Glu Gly Gly Glu Gln Asp Arg Asp Arg
                725                 730                 735

Ser Ile Arg Leu Val Asn Gly Phe Leu Ala Leu Ala Trp Asp Asp Leu
            740                 745                 750

Arg Ser Leu Cys Leu Phe Ser Tyr His Arg Leu Arg Asp Phe Ile Leu
            755                 760                 765

Ile Ala Ala Arg Thr Val Glu Leu Leu Gly Arg Lys Gly Leu Arg Arg
            770                 775                 780

Gly Trp Glu Ala Leu Lys Tyr Leu Trp Asn Leu Gln Tyr Trp Gly
785                 790                 795                 800

Gln Glu Leu Lys Asn Ser Ala Ile Ser Leu Leu Asp Thr Thr Ala Ile
                805                 810                 815

Ala Val Ala Glu Gly Thr Asp Arg Val Ile Glu Val Gln Arg Ala
                820                 825                 830

Cys Arg Ala Ile Leu Asn Ile Pro Arg Arg Ile Arg Gln Gly Leu Glu
            835                 840                 845
```

Arg Ala Leu Leu
    850

<210> SEQ ID NO 67
<211> LENGTH: 2037
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

| | | | | |
|---|---|---|---|---|
| aagcttgtcg | acgaaatgag | ggtcaaggag | acgcagatga | actggccgaa | cctctggaag | 60 |
| tggggcaccc | tgatcctggg | cctcgtgatc | atctgctccg | cgagcgacaa | cctgtgggtg | 120 |
| acggtgtact | acggcgtgcc | tgtgtggaag | gaggccacca | ccaccctgtt | ctgcgcctcg | 180 |
| gacgccaagg | cctacgacac | ggaggtccac | aacgtgtggg | ctacctacgc | ctgtgtgccc | 240 |
| accgatccca | accctcagga | ggtcgtgctg | ggcaacgtga | ccgagaactt | caacatgtgg | 300 |
| aagaacaaca | tggtggagca | gatgcacgag | gacatcatca | gcctgtggga | ccagagcctg | 360 |
| aagccctgcg | tgcgcctgac | cccgctgtgc | gtgaccctga | actgctccaa | cgccaacacc | 420 |
| acgaacacca | actcgacgga | ggagatcaag | aactgcagct | tcaacatcac | caccagcatc | 480 |
| cgggacaagg | tgcagaagga | gtacgccctg | ttctacaagc | tggacgtcgt | gccgatcgac | 540 |
| aacgacaaca | ccagctacag | gctgatctcg | tgcaacacca | cgtcatcac | ccaggcctgc | 600 |
| cccaaagtta | gcttcgagcc | catccccatc | cactactgcg | cgcctgccgg | cttcgccatc | 660 |
| ctgaagtgca | aggacaagaa | gttcaacggc | accggcccct | gcacgaacgt | cagcaccgtc | 720 |
| cagtgcaccc | acggcatcag | gcctgtggtg | tccacccagc | tgctcctgaa | cggcagcctg | 780 |
| gccgaggagg | aggtcgtgat | caggagcgag | aacttcacca | acaacgccaa | gacgatcatc | 840 |
| gtgcacctga | acaagtcggt | ggagatcaac | tgcacccggc | ccaacaacaa | cacccggaag | 900 |
| agcatccaca | tcggccctgg | acgggcgttc | tacgctacgg | gggagatcat | cggcgacatc | 960 |
| aggcaggccc | actgcaacat | ctcgcgggcc | aagtggaaca | cacccctgaa | gcagatcgtg | 1020 |
| aagaagctga | aggagcagtt | caacaagacc | atcatcttca | accagagcag | cggcggagac | 1080 |
| ccggagatca | ccacgcactc | gttcaactgt | ggtggcgagt | tcttctactg | taacacgtcc | 1140 |
| gggctgttca | acagcacctg | gaactcgacc | gcgacgcagg | agtctaacaa | caccgagctg | 1200 |
| aacggcaaca | tcaccctgcc | cgtgccggat | caagcagatcg | tcaacatgtg | gcaggaggtg | 1260 |
| ggcaaggcta | tgtacgcccc | tcccatccgc | ggccagatcc | ggtgcagctc | gaacatcacc | 1320 |
| ggcctgatcc | tgaccaggga | cggcggcaac | aacaactcga | cgaacgagac | cttcagacct | 1380 |
| ggcggcggag | acatgcggga | caactggcgg | agcgagctgt | acaagtacaa | ggtcgtgaag | 1440 |
| atcgagcccc | tgggcgtcgc | acccaccaag | gccaaggaga | gagtggtgca | gcgggagaag | 1500 |
| gaggcggtgg | gaacgatcgg | cgccatgttc | ctgggcttcc | tgggagcggc | cggaagcacg | 1560 |
| atgggagccg | cctcgctgac | cctgaccgtg | caggcgagc | tcctgctgtc | cggcatcgtg | 1620 |
| cagcagcaga | acaacctgct | gagggccatc | gaggcccagc | agcacctgct | ccagctgaca | 1680 |
| gtgtggggca | tcaagcagct | ccaggcgagg | gtgctggccg | tcgagagata | cctgaaggac | 1740 |
| cagcaactgc | tcggcatctg | gggctgtagc | ggcaagctga | tctgtaccac | caccgtgccc | 1800 |
| tggaacacca | gctggagcaa | caagagcctc | aacgagatct | gggacaacat | gacctggatg | 1860 |
| gagtgggagc | gggagatcga | caactacaca | gggctcatct | acacgctgct | ggaggagagc | 1920 |
| cagaaccagc | aggagaagaa | cgagcaggag | ctgctggagc | tggacaagtg | ggcgtcgctg | 1980 | tggaactggt tcgacatcac caagtggctg tggtacatca agtgaggatc ctctaga    2037

<210> SEQ ID NO 68
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Glu Asn
            20                  25                  30

Leu Trp Val Thr Val Tyr Tyr Gly Val Pro Val Trp Lys Glu Ala Asn
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Val Asn Val Thr Asn Thr Thr Asn Asn Thr Glu Glu
    130                 135                 140

Lys Gly Glu Ile Lys Asn Cys Ser Phe Asn Ile Thr Thr Glu Ile Arg
145                 150                 155                 160

Asp Lys Lys Gln Lys Val Tyr Ala Leu Phe Tyr Arg Leu Asp Val Val
                165                 170                 175

Pro Ile Asp Asp Asn Asn Asn Ser Ser Asn Tyr Arg Leu Ile Asn
            180                 185                 190

Cys Asn Thr Ser Ala Ile Thr Gln Ala Cys Pro Lys Val Ser Phe Glu
        195                 200                 205

Pro Ile Pro Ile His Tyr Cys Ala Pro Ala Gly Phe Ala Ile Leu Lys
    210                 215                 220

Cys Asn Asp Lys Lys Phe Asn Gly Thr Gly Pro Cys Lys Asn Val Ser
225                 230                 235                 240

Thr Val Gln Cys Thr His Gly Ile Lys Pro Val Val Ser Thr Gln Leu
                245                 250                 255

Leu Leu Asn Gly Ser Leu Ala Glu Glu Ile Ile Arg Ser Glu
            260                 265                 270

Asn Ile Thr Asn Asn Ala Lys Thr Ile Ile Val Gln Leu Asn Glu Ser
        275                 280                 285

Val Glu Ile Asn Cys Thr Arg Pro Asn Asn Asn Thr Arg Lys Ser Ile
    290                 295                 300

Arg Ile Gly Pro Gly Gln Ala Phe Tyr Ala Thr Gly Asp Ile Ile Gly
305                 310                 315                 320

Asp Ile Arg Gln Ala His Cys Asn Ile Ser Gly Thr Lys Trp Asn Lys
                325                 330                 335

Thr Leu Gln Gln Val Ala Lys Lys Leu Arg Glu His Phe Asn Asn Lys
            340                 345                 350
```

```
Thr Ile Ile Phe Lys Pro Ser Ser Gly Gly Asp Leu Glu Ile Thr Thr
            355                 360                 365
His Ser Phe Asn Cys Arg Gly Glu Phe Phe Tyr Cys Asn Thr Ser Gly
        370                 375                 380
Leu Phe Asn Ser Thr Trp Ile Gly Asn Gly Thr Lys Asn Asn Asn Asn
385                 390                 395                 400
Thr Asn Asp Thr Ile Thr Leu Pro Cys Arg Ile Lys Gln Ile Ile Asn
                405                 410                 415
Met Trp Gln Gly Val Gly Gln Ala Met Tyr Ala Pro Pro Ile Glu Gly
            420                 425                 430
Lys Ile Thr Cys Lys Ser Asn Ile Thr Gly Leu Leu Leu Thr Arg Asp
        435                 440                 445
Gly Gly Asn Asn Asn Thr Asn Glu Thr Glu Ile Phe Arg Pro Gly Gly
    450                 455                 460
Gly Asp Met Arg Asp Asn Trp Arg Ser Glu Leu Tyr Lys Tyr Lys Val
465                 470                 475                 480
Val Lys Ile Glu Pro Leu Gly Val Ala Pro Thr Lys Ala Lys Glu Arg
                485                 490                 495
Val Val Glu Arg Glu Lys Glu
            500

<210> SEQ ID NO 69
<211> LENGTH: 1860
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
aagcttgtcg acgaaatgcg cgtgcgcggc atccagcgca actgccagca cctgtggcgc        60
tggggcaccc tgatcctggg catgctgatg atctgctccg ccgccgagaa cctgggggtg       120
accgtgtact acggcgtgcc cgtgtggaag gaggccaaca ccaccctgtt ctgcgcctcc       180
gacgccaagg cctacgacac cgaggtgcac aacgtgtggg ccacccacgc tgccgtgccc       240
accgacccca ccccccagga gatcgtgctg agaacgtga ccgagaactt caacatgtgg        300
aagaacaaca tggtggagca gatgcacgag gacatcatct ccctgtggga ccagtccctg       360
aagccctgcg tgaagctgac cccctgtgc gtgaccctga actgcaccaa cgtgaacgtg        420
accaacacca ccaacaacac cgaggagaag ggcgagatca gaactgctc cttcaacatc       480 accaccgaga tccgcgacaa gaagcagaag gtgtacgccc tgttctaccg cctggacgtg       540
gtgcccatcg acgacaacaa caacaactcc tccaactacc gcctgatcaa ctgcaacacc       600
tccgccatca cccaggcctg ccccaaggtg tccttcgagc ccatccccat ccactactgc       660 gccccgccg gcttcgccat cctgaagtgc aacgacaaga agttcaacgg caccggcccc       720
tgcaagaacg tgtccaccgt gcagtgcacc cacggcatca gcccgtggt gtccacccag       780 ctgctgctga acggctccct ggccgaggag gagatcatca tccgctccga aacatcacc       840 aacaacgcca gaccatcat cgtgcagctg aacgagtccg tggagatcaa ctgcacccgc       900
cccaacaaca cacccgcaa gtccatccgc atcggccccg gccaggcctt ctacgccacc       960
ggcgacatca tcggcgacat ccgccaggcc cactgcaaca tctccggcac caagtggaac      1020
aagaccctgc agcaggtggc caagaagctg cgcgagcact tcaacaacaa gaccatcatc      1080
ttcaagcccc tctccggcgg cgacctggag atcaccaccc actccttcaa ctgccgcggc      1140
```

```
gagttcttct actgcaacac ctccggcctg ttcaactcca cctggatcgg caacggcacc    1200
aagaacaaca acaacaccaa cgacaccatc accctgccct gccgcatcaa gcagatcatc    1260
aacatgtggc agggcgtggg ccaggccatg tacgccccc ccatcgaggg caagatcacc     1320
tgcaagtcca acatcaccgg cctgctgctg acccgcgacg gcggcaacaa caacaccaac    1380
gagaccgaga tcttccgccc cggcggcggc gacatgcgcg acaactggcg ctccgagctg    1440
tacaagtaca aggtggtgaa gatcgagccc tgggcgtgg ccccaccaa ggccaagctg      1500 accgtgcagg cccgccagct gctgtccggc atcgtgcagc agcagtccaa cctgctgcgc    1560
gccatcgagg cccagcagca cctgctgcag ctgaccgtgt ggggcatcaa gcagctgcag    1620
gcccgcgtgc tggccgtgga cgctacctg aaggaccagc agctggagat ctgggacaac     1680
atgacctgga tggagtggga cgcgagatc aacaactaca ccgacatcat ctactccctg     1740
atcgaggagt cccagaacca gcaggagaag aacgagcagg agctgctggc cctggacaag    1800
tgggcctccc tgtggaactg gttcgacatc accaactggc tgtggtgagg atcctctaga   1860
```

<210> SEQ ID NO 70
<211> LENGTH: 610
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Glu Asn
            20                  25                  30

Leu Trp Val Thr Val Tyr Tyr Gly Val Pro Val Trp Lys Glu Ala Asn
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Val Asn Val Thr Asn Thr Thr Asn Asn Thr Glu Glu
    130                 135                 140

Lys Gly Glu Ile Lys Asn Cys Ser Phe Asn Ile Thr Thr Glu Ile Arg
145                 150                 155                 160

Asp Lys Lys Gln Lys Val Tyr Ala Leu Phe Tyr Arg Leu Asp Val Val
                165                 170                 175

Pro Ile Asp Asp Asn Asn Asn Ser Ser Asn Tyr Arg Leu Ile Asn
            180                 185                 190

Cys Asn Thr Ser Ala Ile Thr Gln Ala Cys Pro Lys Val Ser Phe Glu
        195                 200                 205

Pro Ile Pro Ile His Tyr Cys Ala Pro Ala Gly Phe Ala Ile Leu Lys
    210                 215                 220

Cys Asn Asp Lys Lys Phe Asn Gly Thr Gly Pro Cys Lys Asn Val Ser
```

```
            225                 230                 235                 240
        Thr Val Gln Cys Thr His Gly Ile Lys Pro Val Val Ser Thr Gln Leu
                        245                 250                 255

Leu Leu Asn Gly Ser Leu Ala Glu Glu Ile Ile Ile Arg Ser Glu
                        260                 265                 270

Asn Ile Thr Asn Asn Ala Lys Thr Ile Ile Val Gln Leu Asn Glu Ser
                        275                 280                 285

Val Glu Ile Asn Cys Thr Arg Pro Asn Asn Thr Arg Lys Ser Ile
                290                 295                 300

Arg Ile Gly Pro Gly Gln Ala Phe Tyr Ala Thr Gly Asp Ile Ile Gly
        305                 310                 315                 320

Asp Ile Arg Gln Ala His Cys Asn Ile Ser Gly Thr Lys Trp Asn Lys
                        325                 330                 335

Thr Leu Gln Gln Val Ala Lys Lys Leu Arg Glu His Phe Asn Asn Lys
                        340                 345                 350

Thr Ile Ile Phe Lys Pro Ser Ser Gly Gly Asp Leu Glu Ile Thr Thr
                        355                 360                 365

His Ser Phe Asn Cys Arg Gly Glu Phe Phe Tyr Cys Asn Thr Ser Gly
                        370                 375                 380

Leu Phe Asn Ser Thr Trp Ile Gly Asn Gly Thr Lys Asn Asn Asn
        385                 390                 395                 400

Thr Asn Asp Thr Ile Thr Leu Pro Cys Arg Ile Lys Gln Ile Ile Asn
                        405                 410                 415

Met Trp Gln Gly Val Gly Gln Ala Met Tyr Ala Pro Pro Ile Glu Gly
                        420                 425                 430

Lys Ile Thr Cys Lys Ser Asn Ile Thr Gly Leu Leu Leu Thr Arg Asp
                        435                 440                 445

Gly Gly Asn Asn Asn Thr Asn Glu Thr Glu Ile Phe Arg Pro Gly Gly
                        450                 455                 460

Gly Asp Met Arg Asp Asn Trp Arg Ser Glu Leu Tyr Lys Tyr Lys Val
        465                 470                 475                 480

Val Lys Ile Glu Pro Leu Gly Val Ala Pro Thr Lys Ala Lys Leu Thr
                        485                 490                 495

Val Gln Ala Arg Gln Leu Leu Ser Gly Ile Val Gln Gln Ser Asn
                        500                 505                 510

Leu Leu Arg Ala Ile Glu Ala Gln Gln His Leu Leu Gln Leu Thr Val
                        515                 520                 525

Trp Gly Ile Lys Gln Leu Gln Ala Arg Val Leu Ala Val Glu Arg Tyr
                        530                 535                 540

Leu Lys Asp Gln Gln Leu Glu Ile Trp Asp Asn Met Thr Trp Met Glu
        545                 550                 555                 560

Trp Glu Arg Glu Ile Asn Asn Tyr Thr Asp Ile Ile Tyr Ser Leu Ile
                        565                 570                 575

Glu Glu Ser Gln Asn Gln Gln Glu Lys Asn Glu Gln Glu Leu Leu Ala
                        580                 585                 590

Leu Asp Lys Trp Ala Ser Leu Trp Asn Trp Phe Asp Ile Thr Asn Trp
                        595                 600                 605

Leu Trp
            610

<210> SEQ ID NO 71
<211> LENGTH: 1539
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 71

```
aagcttgtcg acgaaatgcg cgtgcgcggc atccagcgca actgccagca cctgtggcgc      60
tggggcaccc tgatcctggg catgctgatg atctgctccg ccgccgagaa cctgtgggtg     120
accgtgtact acggcgtgcc cgtgtggaag gaggccaaca ccaccctgtt ctgcgcctcc     180
gacgccaagg cctacgacac cgaggtgcac aacgtgtggg ccacccacgc cctgcgtgccc    240
accgacccca accccagga gatcgtgctg gagaacgtga ccgagaactt caacatgtgg     300
aagaacaaca tggtggagca gatgcacgag gacatcatct ccctgtggga ccagtccctg    360
aagccctgcg tgaagctgac cccctgtgc gtgaccctga actgcaccaa cgtgaacgtg      420
accaacacca ccaacaacac cgaggagaag ggcgagatca agaactgctc cttcaacatc    480
accaccgaga tccgcgacaa gaagcagaag gtgtacgccc tgttctaccg cctggacgtg    540
gtgcccatcg acgacaacaa caacaactcc tccaactacc gcctgatcaa ctgcaacacc    600
tccgccatca cccaggcctg ccccaaggtg tccttcgagc ccatccccat ccactactgc    660
gcccccgccg gcttcgccat cctgaagtgc aacgacaaga agttcaacgg caccggcccc    720
tgcaagaacg tgtccaccgt gcagtgcacc cacggcatca agcccgtggt gtccacccag    780
ctgctgctga acggctccct ggccgaggag gagatcatca tccgctccga gaacatcacc    840
aacaacgcca gaccatcat cgtgcagctg aacgagtccg tggagatcaa ctgcacccgc    900
cccaacaaca cacccgcaa gtccatccgc atcggccccg ccaggccctt ctacgccacc    960
ggcgacatca tcggcgacat ccgccaggcc cactgcaaca tctccggcac caagtggaac   1020
aagaccctgc agcaggtggc caagaagctg cgcgagcact tcaacaacaa gaccatcatc   1080
ttcaagccct cctccggcgg cgacctggag atcaccaccc actccttcaa ctgccgcggc   1140
gagttcttct actgcaacac ctccggcctg ttcaactcca cctggatcgg caacggcacc   1200
aagaacaaca caacaccaa cgacaccatc accctgccct gccgcatcaa gcagatcatc   1260
aacatgtggc agggcgtggg ccaggccatg tacgcccccc ccatcgaggg caagatcacc   1320
tgcaagtcca acatcaccgg cctgctgctg acccgcgacg gcggcaacaa caacaccaac   1380
gagaccgaga tcttccgccc cggcggcggc gacatgcgcg acaactggcg ctccgagctg   1440
tacaagtaca aggtggtgaa gatcgagccc ctgggcgtgg cccccaccaa ggccaaggag   1500
cgcgtggtgg agcgcgagaa ggagtgagga tcctctaga                          1539
```

<210> SEQ ID NO 72
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Glu Asn
                20                  25                  30

Leu Trp Val Thr Val Tyr Tyr Gly Val Pro Val Trp Lys Glu Ala Asn
            35                  40                  45

Thr Thr Leu Phe Cys Ala Ser Asp Ala Lys Ala Tyr Asp Thr Glu Val
```

```
                50                  55                  60
His Asn Val Trp Ala Thr His Ala Cys Val Pro Thr Asp Pro Asn Pro
 65                  70                  75                  80

Gln Glu Ile Val Leu Glu Asn Val Thr Glu Asn Phe Asn Met Trp Lys
                     85                  90                  95

Asn Asn Met Val Glu Gln Met His Glu Asp Ile Ile Ser Leu Trp Asp
                    100                 105                 110

Gln Ser Leu Lys Pro Cys Val Lys Leu Thr Pro Leu Cys Val Thr Leu
                115                 120                 125

Asn Cys Thr Asn Val Asn Val Thr Asn Thr Thr Asn Asn Thr Glu Glu
            130                 135                 140

Lys Gly Glu Ile Lys Asn Cys Ser Phe Asn Ile Thr Thr Glu Ile Arg
145                 150                 155                 160

Asp Lys Lys Gln Lys Val Tyr Ala Leu Phe Tyr Arg Leu Asp Val Val
                165                 170                 175

Pro Ile Asp Asp Asn Asn Asn Ser Ser Asn Tyr Arg Leu Ile Asn
                180                 185                 190

Cys Asn Thr Ser Ala Ile Thr Gln Ala Cys Pro Lys Val Ser Phe Glu
                195                 200                 205

Pro Ile Pro Ile His Tyr Cys Ala Pro Ala Gly Phe Ala Ile Leu Lys
                210                 215                 220

Cys Asn Asp Lys Lys Phe Asn Gly Thr Gly Pro Cys Lys Asn Val Ser
225                 230                 235                 240

Thr Val Gln Cys Thr His Gly Ile Lys Pro Val Val Ser Thr Gln Leu
                245                 250                 255

Leu Leu Asn Gly Ser Leu Ala Glu Glu Ile Ile Arg Ser Glu
                260                 265                 270

Asn Ile Thr Asn Asn Ala Lys Thr Ile Ile Val Gln Leu Asn Glu Ser
                275                 280                 285

Val Glu Ile Asn Cys Thr Arg Pro Asn Asn Asn Thr Arg Lys Ser Ile
                290                 295                 300

Arg Ile Gly Pro Gly Gln Ala Phe Tyr Ala Thr Gly Asp Ile Ile Gly
305                 310                 315                 320

Asp Ile Arg Gln Ala His Cys Asn Ile Ser Gly Thr Lys Trp Asn Lys
                325                 330                 335

Thr Leu Gln Gln Val Ala Lys Lys Leu Arg Glu His Phe Asn Asn Lys
                340                 345                 350

Thr Ile Ile Phe Lys Pro Ser Ser Gly Gly Asp Leu Glu Ile Thr Thr
                355                 360                 365

His Ser Phe Asn Cys Arg Gly Glu Phe Phe Tyr Cys Asn Thr Ser Gly
                370                 375                 380

Leu Phe Asn Ser Thr Trp Ile Gly Asn Gly Thr Lys Asn Asn Asn
385                 390                 395                 400

Thr Asn Asp Thr Ile Thr Leu Pro Cys Arg Ile Lys Gln Ile Ile Asn
                405                 410                 415

Met Trp Gln Gly Val Gly Gln Ala Met Tyr Ala Pro Pro Ile Glu Gly
                420                 425                 430

Lys Ile Thr Cys Lys Ser Asn Ile Thr Gly Leu Leu Leu Thr Arg Asp
                435                 440                 445

Gly Gly Asn Asn Asn Thr Asn Glu Thr Glu Ile Phe Arg Pro Gly Gly
                450                 455                 460

Gly Asp Met Arg Asp Asn Trp Arg Ser Glu Leu Tyr Lys Tyr Lys Val
465                 470                 475                 480
```

```
Val Lys Ile Glu Pro Leu Gly Val Ala Pro Thr Lys Ala Lys Glu Arg
            485                 490                 495
Val Val Glu Arg Glu Lys Glu
            500
```

METHODS FOR REDUCING HIV-1
MOTHER-TO-CHILD TRANSMISSION BY
INDUCING V3-SPECIFIC OR CD4 BINDING
SITE-SPECIFIC ANTIBODIES

This application is a National Stage Application under 35 U.S.C. section 371 of PCT/US2014/057809 filed Sep. 26, 2014, which claims priority from and the benefit of U.S. application Ser. No.: 61/884,024 filed Sep. 28, 2013, U.S. application Ser. No.: 61/883,220 filed Sep. 27, 2013, U.S. application Ser. No.: 61/954,340 filed Mar. 17, 2014, and U.S. application Ser. No.: 61/968,560 filed Mar. 21, 2014, the entire contents of each application are hereby incorporated by reference in their entireties.

This invention was made with government support under the following grants: a Center for HIV/AIDS Vaccine Immunology-Immunogen Design grant Nos. UM1-AI100645, U19 AI067854 from the NIH, NIAID, Division of AIDS. The government has certain rights in the invention.

SEQUENCE LISTING

The instant application contains a Sequence Listing which has been submitted electronically in ASCII format and is hereby incorporated by reference in its entirety. Said ASCII copy, created on Jul. 11, 2016, is named 2933311-032-US4_SL.txt and is 113,905 bytes in size.

TECHNICAL FIELD

The invention is directed to methods and composition to induce and boost HIV-1 antibodies which can neutralize difficult-to-neutralize autologous HIV-1 strains, such as is required for protection in HIV-1 mother-to-child transmission (MTCT). The invention is related to methods and HIV-1 reagents suitable for use in methods of predicting risk of maternal to child transmission of HIV-1, analyzing immune responses of vaccinees so as to assess the efficacy of candidate vaccines.

BACKGROUND

Prevention of maternal to child transmission (MTCT) of HIV continues to be a global health challenge. In 2011, approximately 330,000 infants and children were infected with HIV, the majority of these in the developing world. In the absence of antiretroviral therapy (ARV), around 15-45% of HIV positive mothers will transmit the virus to their infants. The development of ARV's has allowed for effective prevention of MTCT in resource rich settings. Approximately only 50% of HIV-infected women in Sub-Saharan Africa even receive the ARV's necessary to prevent transmission. In addition to their implementation and adherence challenges, ARV therapy presents a myriad of challenges. ARV therapy often interacts with treatments for co-infections such as HBV or tuberculosis and causes toxicities such as pancreatitis or peripheral neuropathy that make adherence to ARV regimens difficult. Infant HIV acquisition still occurs at a low rate in the setting of optimal ARV prophylaxis. For these reasons, it is important to continue to focus on the development of other methods to prevent MTCT, such as vaccination. Despite availability of effective antiretroviral prophylaxis, >250,000 infants acquire HIV-1 annually, emphasizing the need for immunologic interventions to reduce pediatric infections.

SUMMARY

In certain aspects the inventions are based on the discovery that easy-to-induce, tier 1 virus-neutralizing antibodies potently neutralize autologous tier 2 HIV-1 isolates. In other aspects the invention is based on the discovery of tier 1 virus-neutralizing antibodies as a correlate of infection risk in MTCT. In certain aspects the invention provides methods to determine infection risk in HIV-1 MTCT. In other aspects the invention provides a vaccine for HIV-1 infected pregnant women, wherein the vaccine boosts easy-to-induce, tier 1 virus-neutralizing antibodies potently neutralize autologous tier 2 HIV-1 isolates.

In certain aspects the invention is directed to compositions and methods to induce and boost commonly induced HIV-1 antibodies which in certain embodiments can neutralize difficult-to-neutralize autologous HIV-1 strains, such as is required for protection in HIV-1 mother-to-child transmission.

To investigate humoral immune correlates of risk of mother-to-child transmission (MTCT), we studied untreated, HIV-1-transmitting mothers (n=83) and clinically-matched non-transmitting mothers (n=165) from the Women and Infant Transmission Study (WITS) of U.S. non-breastfeeding HIV-1-infected mother-infant pairs. We employed a multivariable logistic regression model to define antibody responses that predicted the risk of MTCT. The magnitude of the maternal Envelope third variable (V3)-specific IgG responses predicted reduced risk of MTCT (OR=0.64, p=0.04). Secondary analyses revealed that neutralizing antibody responses against easy-to-neutralize (tier 1) HIV-1 strains predicted reduced risk of peripartum transmission (OR=0.54, p=0.005). Moreover, ten recombinant maternal V3-specific IgG monoclonal antibodies mediated neutralization of multiple autologous HIV isolates, suggesting that inducing or boosting autologous neutralizing antibodies through vaccination might decrease HIV-1 MTCT.

In certain aspects the invention provides methods to define maternal humoral immune correlates of protection against intrauterine/peripartum mother to child transmission (MTCT) of HIV-1. In certain aspects, the invention provides that maternal IgG response against V3 from HIV-1 envelope is correlated with MTCT risk. In one embodiment, the V3 correlate comprises the peptide of sequence KKKNN-TRKSIHIGPGRAFYATGDIIGDIRQAHC (SEQ ID NO: 1). In one embodiment, the V3 correlate is Bio-KKKNN-TRKSIHIGPGRAFYATGDIIGDIRQAHC (SEQ ID NO: 2) (V3B). In other embodiments the V3 correlate is any one of the V3 correlates described herein, for example but not limited to V3_BioV3B, V3_BioV3M, V3_gp70MNV3, V3_gp70MNV3auc. In certain embodiments, the correlate is V3_BioV3B, V3_BioV3B is the same as V3B. In other embodiments the correlate is V3M: Bio-KKKNNTRKSI-HIGPGQAFYATGDIIGDIRQAHC (SEQ ID NO: 3)

In certain aspects, the invention provides that neutralization of clade-matched tier 1 variants is correlated with risk of peripartum HIV-1 transmission.

In certain aspects, the invention provides that the magnitude of the plasma sCD4 blocking response (for example but not limited against B.JFRL, E) and tier 1 neutralization (for example but not limited to SF162, F) was associated with reduced MTCT risk.

In certain aspects, the invention provides that avidity is an important characteristic of potentially-protective maternal IgG antibodies.

In certain aspects, the invention provides that there is no mitigating effect of IgA responses on potentially protective IgG responses in MTCT.

In certain embodiments, the combination of correlation of V3 score, neutralization of clade-matched tier 1 variants score, avidity of maternal IgG antibodies score, magnitude of the plasma sCD4 blocking response, as described herein, or a combination thereof is correlated with MTCT risk.

In certain embodiments, the invention provides that there is a synergistic effect of neutralizing antibody responses and gp41 antibody responses on risk of MTCT.

In certain aspects, the invention provides methods of determining risk of maternal to child transmission/protection of HIV-1, comprising obtaining a sample from a subject, analyzing the sample for IgG response against HIV-1 V3, including but not limited to a V3 reagent/peptide as described herein, optionally analyzing the sample for HIV-1 virus neutralization, determining the avidity of IgG antibodies, or a combination thereof, wherein significant positive correlation of IgG binding to HIV-1 V3, including but not limited to the V3 peptide and V3 reagents described herein referred as "V3 correlate", is associated with increased protection/decreased risk of maternal to child transmission, wherein neutralization of tier-1 clade matched HIV-1 variants is associated with increased protection/decreased risk of maternal to child transmission, and wherein increased avidity of the maternal IgG antibodies is further associated with increased protection/reduced risk of MTCT of HIV-1.

In certain aspects, the invention provides a method of determining risk of transmission/likelihood of protection against HIV-1, comprising: obtaining a sample from a subject, analyzing the sample: (a) for IgG response against HIV-1 V3 (plasma anti V-3 IgG concentration), (b) for HIV-1 virus neutralization, (c) for the avidity of IgG antibodies, (d) plasma blocking of soluble CD4 (sCD4) binding to envelope (CD4 binding site antibody response), or any combination of (a), (b), (c) and (d), wherein significant positive correlation of IgG binding to HIV-1 V3 is associated with increased protection/decreased risk of transmission, wherein neutralization of tier-1 clade matched HIV-1 variants is associated with increased protection/decreased risk of transmission, wherein increased avidity of the IgG antibodies is further associated with increased protection/reduced risk of transmission, or wherein CD4 binding site antibody response is associated with increased protection/decreased risk of transmission.

In certain embodiments, a significant positive correlation of IgG binding to HIV-1 V3 is associated with increased protection/decreased risk of transmission, wherein neutralization of tier-1 clade matched HIV-1 variants is associated with increased protection/decreased risk of transmission, and/or plasma blocking of soluble CD4 (sCD4) binding to envelope (CD4 binding site antibody response) is associated with increased protection/reduced risk of transmission, thereby indicating that the HIV-1 immunogen is eliciting protective immune response.

In certain embodiments, the transmission is maternal to child transmission/protection of HIV-1.

In certain embodiments, the IgG response against HIV-1 V3 is determined using a V3 binding reagent as described herein.

In certain embodiments, IgG response against HIV-1 V3 in the bottom tenth percentile of the V3 response score is associated with risk of transmission (transmission rate of 56%), and wherein IgG response against HIV-1 V3 in the top ninety percentile of the V3 response score is associated with protection (transmission rate of 31%).

In certain embodiments, plasma anti V-3 IgG concentration higher than or equal to about 38 microgram/ml is associated with protection. In certain embodiments, plasma anti V-3 IgG concentration higher than or equal to 37 microgram/ml is associated with protection.

In certain embodiments, the combination of plasma anti V-3 IgG concentration higher than or equal to 38 microgram/ml and high levels of plasma blocking of soluble CD4 (sCD4) binding to envelope (CD4 binding site antibody response) is associated with protection. In certain embodiments, the plasma anti V-3 IgG concentration higher than or equal to 37 microgram/ml.

In certain embodiments, the subject is chronically or acutely infected with HIV-1 or the subject is vaccinated with an anti-HIV-1 immunogen, for example as a participant in an HIV-1 vaccine trial.

A composition comprising a nucleic acid encoding B63521 HIV-1 envelope and a nucleic acid encoding CH505 T/F HIV-1 envelope (or CH505 w004.03 HIV-1 envelope).

The composition of claim 1, further comprising a nucleic acid sequence encoding HIV-1 clade M envelope CON-S.

A composition comprising a first protein sequence comprising B63521 HIV-1 envelope and a second protein sequence comprising CH505 T/F HIV-1 envelope (or CH505 w004.03 HIV-1 envelope).

In certain embodiments the composition further comprises a third protein sequence comprising HIV-1 clade M envelope CON-S.

In certain embodiments the first protein sequence is a gp120 B63521 envelope, the second protein sequence is a gp120 CH505 T/F envelope (or CH505 w004.03 envelope) and the third protein sequence is a gp120 CON-S envelope. The protein is recombinantly produced. In certain embodiments the protein includes modifications described as N-terminal deletions. In other embodiments the protein includes V3 loop modifications.

In certain embodiments the compositions of further comprise an adjuvant. The adjuvant is alum, or any other suitable adjuvant.

A method of inducing V3 and/or CD4 binding site [IgG] antibody responses in a subject in need thereof comprising administering to the subject an immunogenic composition comprising an HIV-1 envelope in an amount sufficient to effect such induction. Any suitable immunogenic HIV-1 envelope could be used, including but not limited to a Transmitted Founder envelope, mosaic envelope and/or consensus envelope. In certain embodiments, the immunogenic envelope is selected from any one of HIV-1 subtypes, for example but not limited to subtype C envelopes, for example CH0505 envelopes; 1086C; The immunogenic composition could comprise the envelope as a DNA, protein and/or a combination thereof.

In certain embodiments of the methods boost the V3 and/or CD4 binding site [IgG] antibody responses in a subject in need thereof.

A method of inducing V3 and/or CD4 binding site IgG responses in a subject in need thereof comprising administering to the subject a composition of any one of claims 1 to 5 in an amount sufficient to effect such induction.

In certain embodiments the subject is infected with HIV-1. The subject is acutely or chronically infected with HIV-1.

In certain embodiments the subject is a female subject. In certain embodiments the subject is a female subject who is expecting to become pregnant, or is pregnant.

In certain embodiments administering boosts a V3 and/or CD4 binding site IgG responses.

In certain embodiments the induced/boosted plasma level of the V3 and/or CD4 binding site IgG responses is over a threshold level associated with reduced risk of MTCT. In certain embodiments, the threshold is 39 microgram/ml. In certain embodiments, the threshold is 38 microgram/ml. In certain embodiments, the threshold is 37 microgram/ml.

In certain embodiments the over the threshold plasma levels of binding IgG responses and high avidity is correlated with reduced MTCT transmission risk.

In certain embodiments the V3 and/or CD4 binding site IgG responses are V3 and/or CD4 binding site neutralizing antibodies.

In certain embodiments the neutralizing antibodies are V3-specific mAbs able to neutralize tier 1 and tier 2 autologous maternal HIV-1 strains. In certain embodiments the neutralizing antibodies are V3-specific mAbs able to neutralize tier 1 and tier 2 autologous HIV-1 strains.

In certain embodiments the neutralizing antibodies are CD4 binding site mAbs able to neutralize tier 1 and tier 2 autologous maternal HIV-1 strains. In certain embodiments wherein the neutralizing antibodies are CD4 binding site mAbs able to neutralize tier 1 and tier 2 autologous HIV-1 strains.

BRIEF DESCRIPTION OF THE FIGURES

FIG. 1. Comparison of the humoral immune responses measured in HIV-1-infected transmitting and nontransmitting mothers. Neither the maternal MN gp120-specific IgG binding (A), MN gp41-specific IgG (B) or IgA (C) responses predicted MTCT risk, however maternal V3 IgG-binding score predicted reduced risk of MTCT (D, OR: 0.64, p=0.04, q=0.15). The magnitude of the plasma sCD4 blocking response (against B.JFRL, E) and tier 1 neutralization (SF162, F) was associated with reduced MTCT risk in exploratory analyses. 3D plot of maternal plasma sCD4 blocking of B.JFRL Env, neutralization potency of B.SF162, and B.V3 IgG binding of transmitting and nontransmitting women (G), showing a high degree of correlation between these three measurements, as well as higher density of nontransmitters relative to transmitters at a higher response level for all three assays. Nontransmitting women are shown in blue and transmitting women are shown in red.

FIG. 2. Heat map of the neutralization sensitivity ($IC_{50}$) of env pseudovirus variants isolated from the plasma of a nontransmitting mother against autologous V3-specific IgG mAbs. Env pseudoviruses (5426.1-5426.47) were divided into two groups by their neutralization sensitivity to the autologous V3-specific mAbs (DH290-299), based on hierarchical clustering of neutralization sensitivity, as indicated on the heat map (A). A single env pseudovirus from the resistant group (5426.31) was selected for insertion of the mutations associated with neutralization sensitivity to the autologous V3-specific mAbs, V200I and N188S (FIG. 7), both alone and in combination. The mutant env variants were found to gain sensitivity to the autologous V3-specific mAbs (DH290-299) when both mutations were present (B). According to the legend, darker color indicates greater neutralization sensitivity (lower $IC_{50}$).

FIG. 3. Comparison of the primary RV144 clade B-modified humoral immune responses in HIV-infected transmitting and nontransmitting women. Neither the maternal V1V2-specific IgG response (A), the clade B-modified Env-binding IgA score (B), clade B neutralizing antibody score (C), clade B gp140 avidity (D) or the ADCC response (E) correlated with the risk of MTCT. Nontransmitting women are shown on the left (blue) and transmitting women are shown on the right (red) of each graph.

FIG. 4. Gating scheme for isolation of Env V3-specific IgG-producing memory B cells for recombinant V3-specific mAb production. PBMCs from a nontransmitting mother were stained for B cell markers and dually labeled Env Con.B V3 peptide tetramer. The gating scheme was as follows: generous lymphocyte gate on forward scatter/side scatter plot, selection for singlet events by side scatter and forward scatter, selection of live, aqua vital-dye negative cells, selection of CD14/CD16 negative cells, selection of CD19 positive, CD3/CD235a negative cells, selection of IgG-expressing cells, then sorting of CD19+IgG+Con.B V3 tetramer (AF647 vs BV421) double positive (DP) cells (diagonal stripe).

FIG. 5. Phylogenetic tree analysis of complete env gene sequences isolated from plasma collected at two months postpartum of a nontransmitting, HIV-1-infected mother and tested for neutralization sensitivity against autologous Env V3-specific monoclonal antibodies. The phylogenetic tree was constructed with the nucleotide sequences of complete env gene using the neighbor-joining method. The tree was midpoint rooted. Horizontal branch lengths are drawn to scale (the scale bar represents 0.001 nucleotide substitution per site). Vertical separation is for clarity only. All sequenced, full length env genes are included, though three env variants yielded very low titer or no functional virus and were unable to be used in neutralization assays (FIG. 2).

FIG. 6. Env V3-specific, heterologous tier 1 virus-neutralizing antibodies isolated from a nontransmitting woman can neutralize all autologous plasma HIV-1 env variants isolated from maternal plasma. Neutralization potency ($IC_{50}$) of heterologous V3-specific mAbs (19B and CH48) (FIG. 6A) and 10 autologous) FIG. 6B) maternal V3-specific IgG mAbs (DH290-299) against tier 1 and 2 heterologous and autologous SGA-derived env pseudovirus variants. Polyclonal anti-HIV antibody, HIVIG-C, and two serum samples from HIV-infected individuals (S455 and H243) is included to assess the neutralization-sensitivity of the env pseudovirus variants.

FIG. 7. Alignment of variable loop 1 and 2 (V1,V2) and constant region 2 (C2) sequences from Env variants isolated from a nontransmitting mother grouped by neutralization sensitivity to autologous V3-specific mAbs (FIG. 6). While the sequence in the V3 loop was uniform among the Env sequences of the nontransmitting mother, two unique mutations were identified in the V2 loop and C2 region of the Env sequences from the group of the most neutralization-sensitive pseudovirus variants (Sensitive group). The V2 loop mutation (N188S) moves a potential N-liked glycosylation site by three amino acids (www.lanl.gov/content/sequence/GLYCOSITE/glycosite.html). Figure discloses SEQ ID NOS 14-52, respectively, in order of appearance.

FIG. 8. Clonal lineages derived from participant 0457. A: PBMC were stained with a panel of antibodies to identify B-cell-specific markers, non-B-cell markers, and with antigen-specific reagents ($gp120_{ConC}$). Cells shown are memory B cells; the kite-shaped gate was sorted as single cells into 96-well plates, with a diagonal of $gp120_{ConC}$ core+/+ isolated. The frequency of antigen-specific cells was similar in both sorted samples, representative data from the week 8 sample shown. B: Two IgG1 gp120 V3 mAbs (CH14, CH48) were isolated and were not related to other isolated mAbs. Clonal lineage CH13 consisted of six IgG1 mAbs that used $V_H1$~69*01/$J_H3$*02 and $V_K1$~39*01/$J_K4$*01, and had a mean heavy chain mutation frequency of 9.8%. Lineage CH27 consisted of three mAbs, two IgA2 (CH27, CH28) and one IgG1 (CH44); this lineage used $V_H3$~66*02/$J_H2$*01 and $V_K3$~20*01/$J_K1$*01, and had a mean heavy chain mutation frequency of 15.7%. All trees are plotted on the same scale. C: Clonal lineage CH13 mAbs were tested for sensitivity to amino acid substitution in binding and neutralization assays (Example 2 Tables S2 and S3) Residues found to be critical for mAb binding are highlighted in the crystal structure of gp120 C.YU2 complexed with mAb 17b and CD4 (72). Antibody 17b removed for clarity; CD4 is shown in light gray and gp120 in light blue. Mapped residues are largely located within the CD4-gp120 contact surface. Residues in the V1/V2 loop are not shown; the gp120 used for this crystal structure lacked that feature. D. Antibodies CH14 and CH48 were tested for binding to an array of peptides reflective of multiple HIV-1 clades. Both antibodies bound to peptides reflective of the V3 loop (residues 301-325) across multiple clades; no binding was observed for other epitopes within gp120 or gp41

Figure 9A:
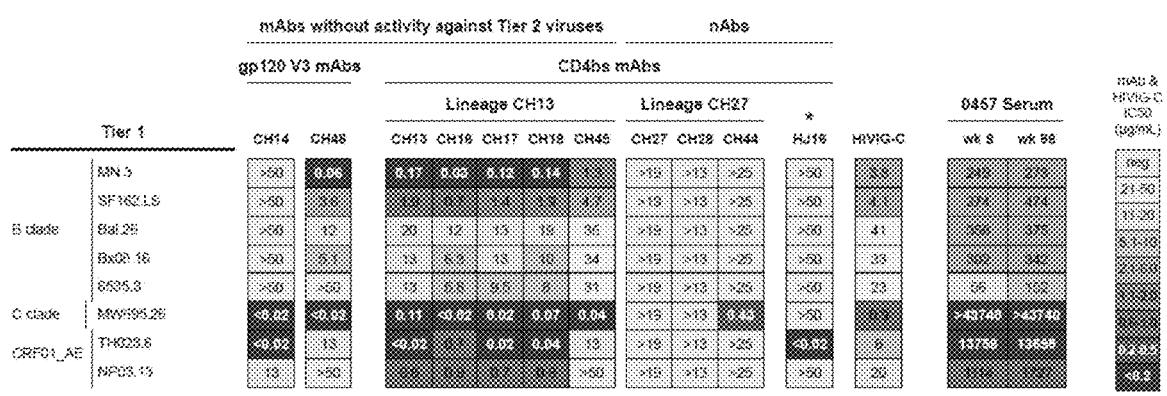
Figure 9B:
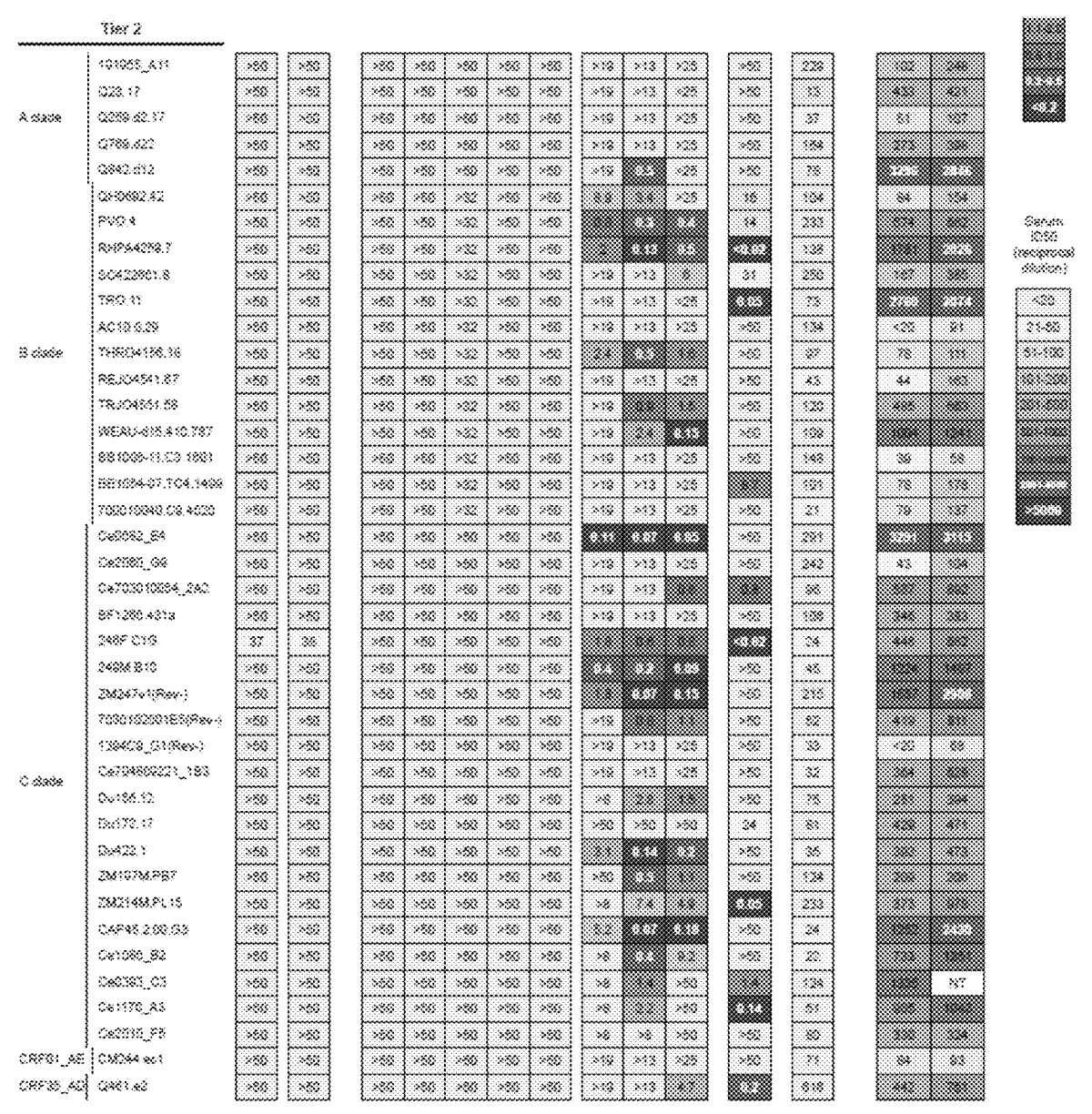

FIGS. 9A and 9B. Heterologous neutralization by mAbs from participant CH0457. Antibodies were tested against a panel of tier 1 (9A) and tier 2 (9B) viruses from diverse clades. Antibodies with detectable neutralization are shown in colored boxes with the EC50 concentration. Control polyclonal antibody preparation HIVIG-C is shown to the right of the mAbs. Serum from participant 0457 at the week 8 and week 96 time points is shown on the right, also in colored boxes with the EC50 reciprocal dilution values. Lineage CH13 mAbs and the non-lineage mAbs CH14, CH15, and CH48 potently neutralized tier 1 viruses but only weakly neutralized a single tier 2 virus (C.246F_C1G). In contrast, lineage CH27 neutralized a single tier 1 virus but neutralized 23/40 (58%) of tier 2 viruses. Antibody HJ16 neutralization data include published reports (25, 73) and additional data. The participant serum neutralized all tier 1 viruses at >1:20, and 37/40 (93%) and 31/40 (78%) of tier 2 viruses at week 8 and week 96, respectively.

Figure 10:
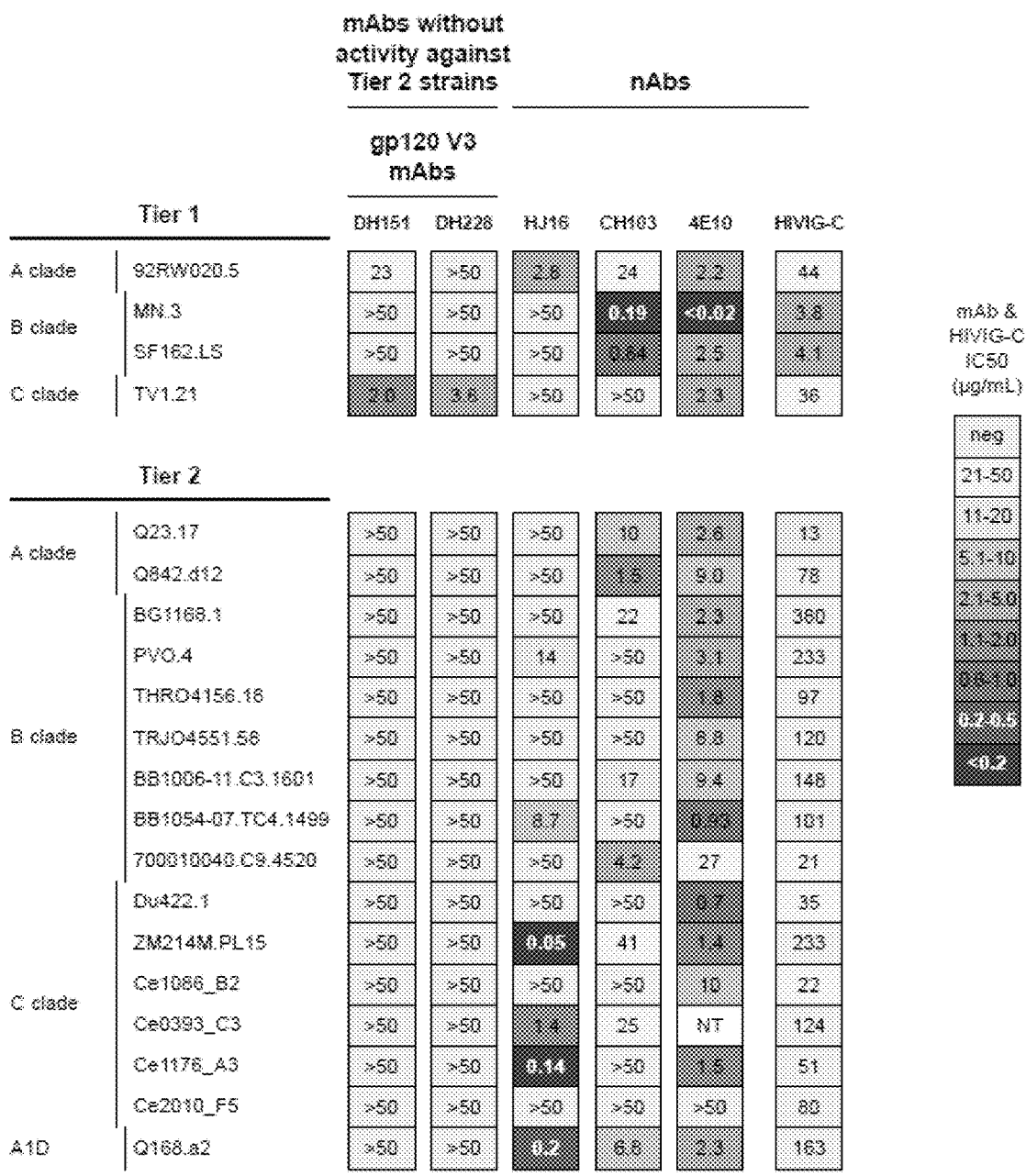

FIG. 10. Neutralization of heterologous viruses by mAbs from participant CH505. V3 loop mAbs DH151 and DH228 from participant CH505 were tested against a heterologous HIV isolate panel. Two of four tier 1 isolates were neutralized by the mAbs; none of the 16 tier 2 isolates were neutralized by the mAbs.

Figure 11:
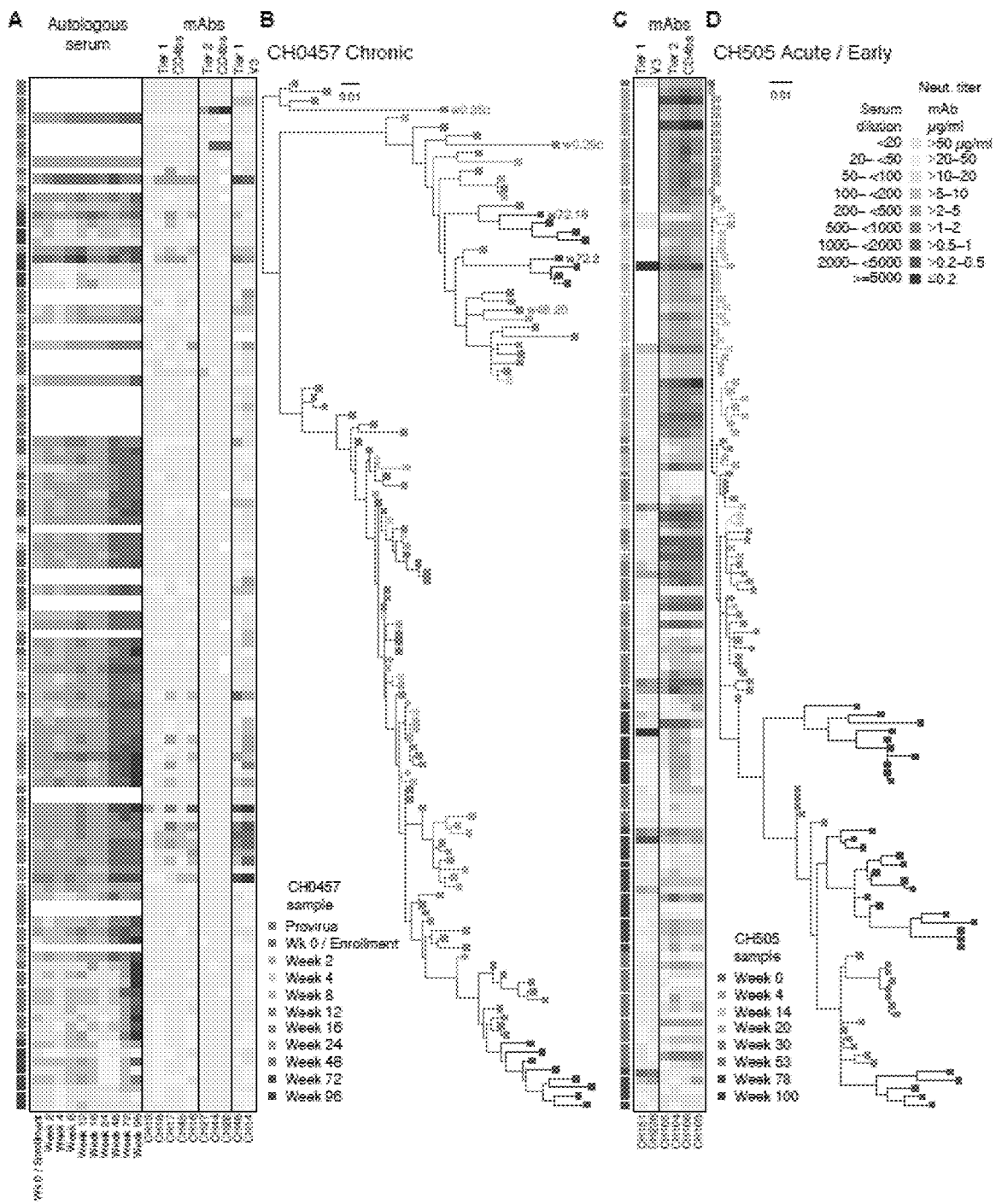

FIG. 11. Neutralization of mAbs against autologous viruses and Env sequence phylogenies. Data from CH0457 shown in A and B; data from CH505 shown in C and D. Neutralization by autologous serum and isolated mAbs shown as a heat map (A and C). A panel of 84 pseudoviruses amplified from participant CH0457 that spanned the study period was tested. Each row in the neutralization panel (A) and phylogeny tree (B) depicts a distinct Env isolate from longitudinal sampling, spanning week 0 (enrollment; red) to week 96 after enrollment (purple). Provirus sequences isolated from PBMC are also shown in grey. The phylogeny only shows those Envs for which neutralization data was obtained; the full phylogeny for CH0457 is in FIG. 14. Neutralization of autologous serum (reciprocal dilution) and isolated mAbs (concentration in μg/mL) shown. Antibody data (A) are shown for lineage CH13 mAbs (Tier 1 CD4bs), lineage CH27 mAbs (Tier 2 CD4bs), and CH14 and CH48 (Tier 1 V3). For CH505, neutralization data (C) and phylogeny (D) are shown; Env sequences span transmission (week 0, red) through week 100 (purple). Antibody data for DH151 and DH228 (Tier 1 V3) and lineage CH103 mAbs (Tier 2 CD4bs) are shown.

Figure 12:
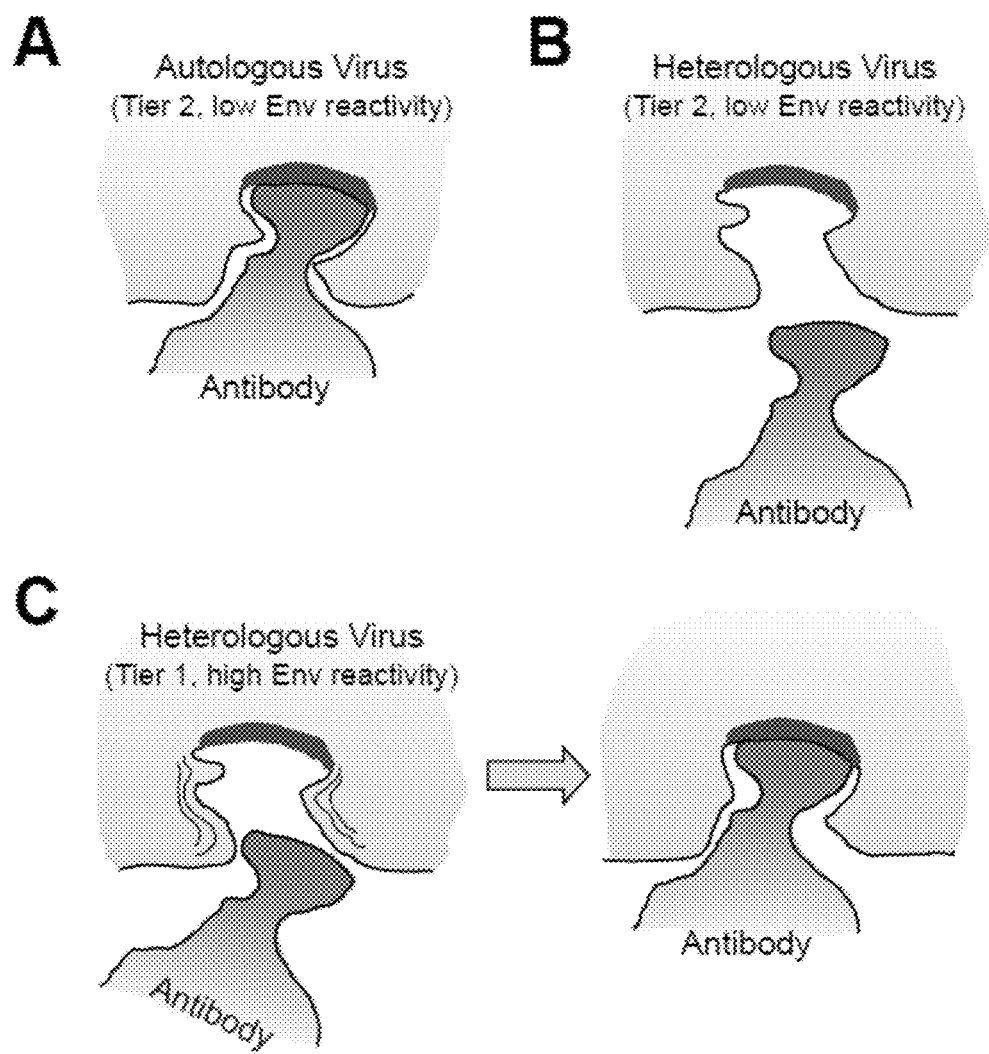

FIG. 12. Recognition of Env epitopes by antibodies without neutralization breadth. The dark blue region in the interior of the binding pocket represents conserved gp120 epitopes targeted by CD4bs or V3 mAbs. In CH0457 and CH505, these antibodies evolved to accommodate and bypass the variable gp120 regions on autologous viruses that potentially limit access to the epitope. This results in a good fit by autologous antibodies for Envs with low reactivity (ie, tier 1B or tier 2 virus Envs) (A). On heterologous tier 2, low-reactivity Envs (B), conformational change is resisted (34, 35), thus the antibodies fail to bind and neutralize. In contrast, on heterologous tier 1 A viruses, Env reactivity is high, thus Env can undergo conformational change more readily (C). Therefore, even though the antibody surface complements only the epitope and not the surrounding variable gp120 structures, the variable structures are conformationally flexible on tier 1A and some tier 1B virus high-reactivity Envs, allowing the antibody to bind and neutralize.

Figures 13A, 13B:
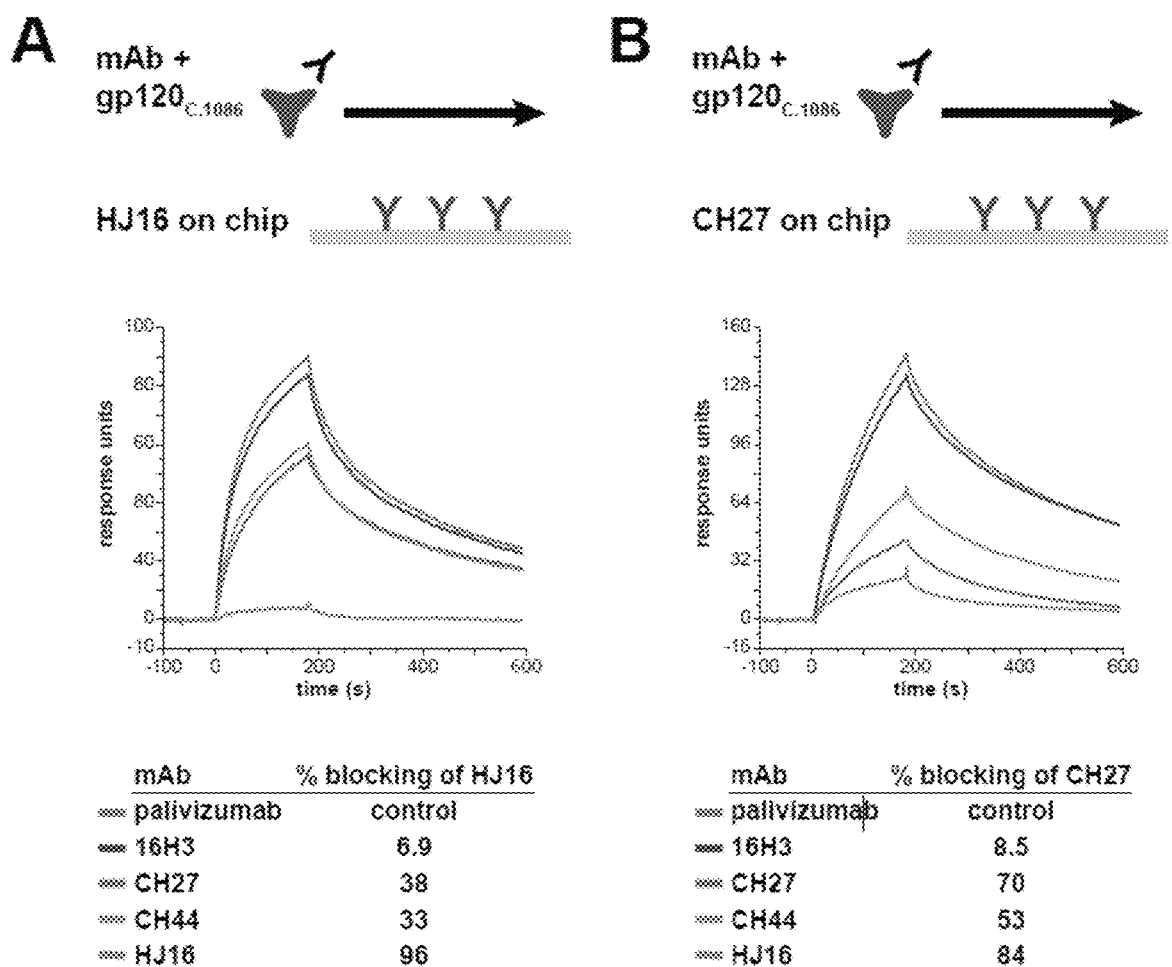
Figure 13C:
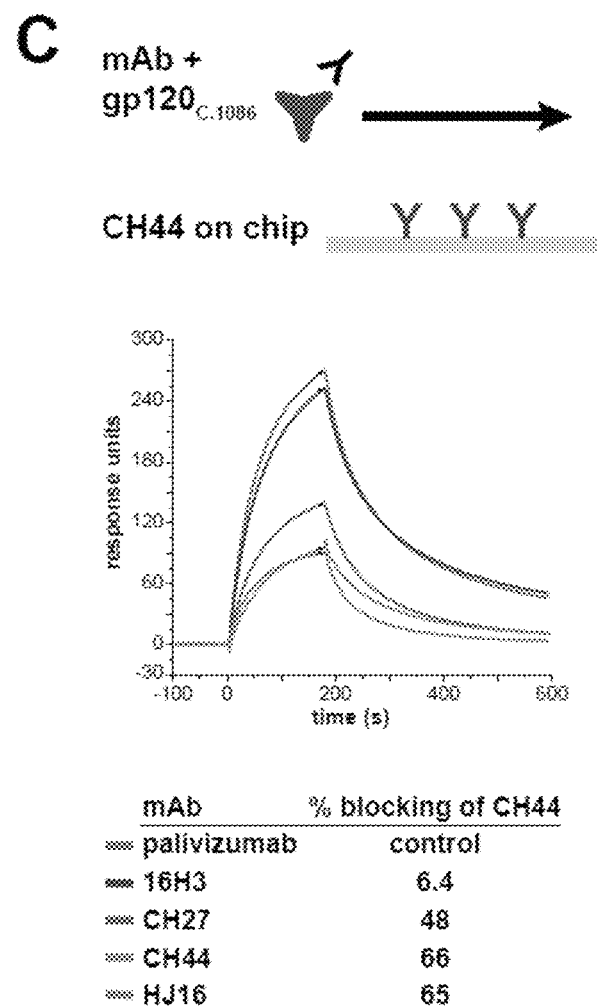

FIG. 13. Cross blocking of HJ16 and lineage CH27 mAbs. Antibodies from lineage CH27 were tested for cross-blocking against HJ16. Taken together, the data suggest that the binding sites for the lineage CH27 mAbs and HJ16 overlap but are not identical. A. HJ16 was immobilized on a surface plasmon resonance chip and antibody-Env mixtures were flowed over the chip to determine if the antibody-Env complex bound to HJ16. Control mAb palivizumab was the control; non-neutralizing anti-HIV-1 mAb 16H3 did not significantly block binding to HJ16. In contrast, HJ16 blocked to 96% as expected, while CH27 and CH44 blocked about ⅓ of binding to HJ16. B. CH27 immobilized on a chip was able to bind to Env mixed with palivizumab or 16H3, but binding was partially blocked when Env was mixed with CH27, CH44, or HJ16. C. CH44 immobilized on a chip was able to bind to Env mixed with palivizumab or 16H3, but binding was blocked when Env was mixed with CH27, CH44, or HJ16.

Figure 14:
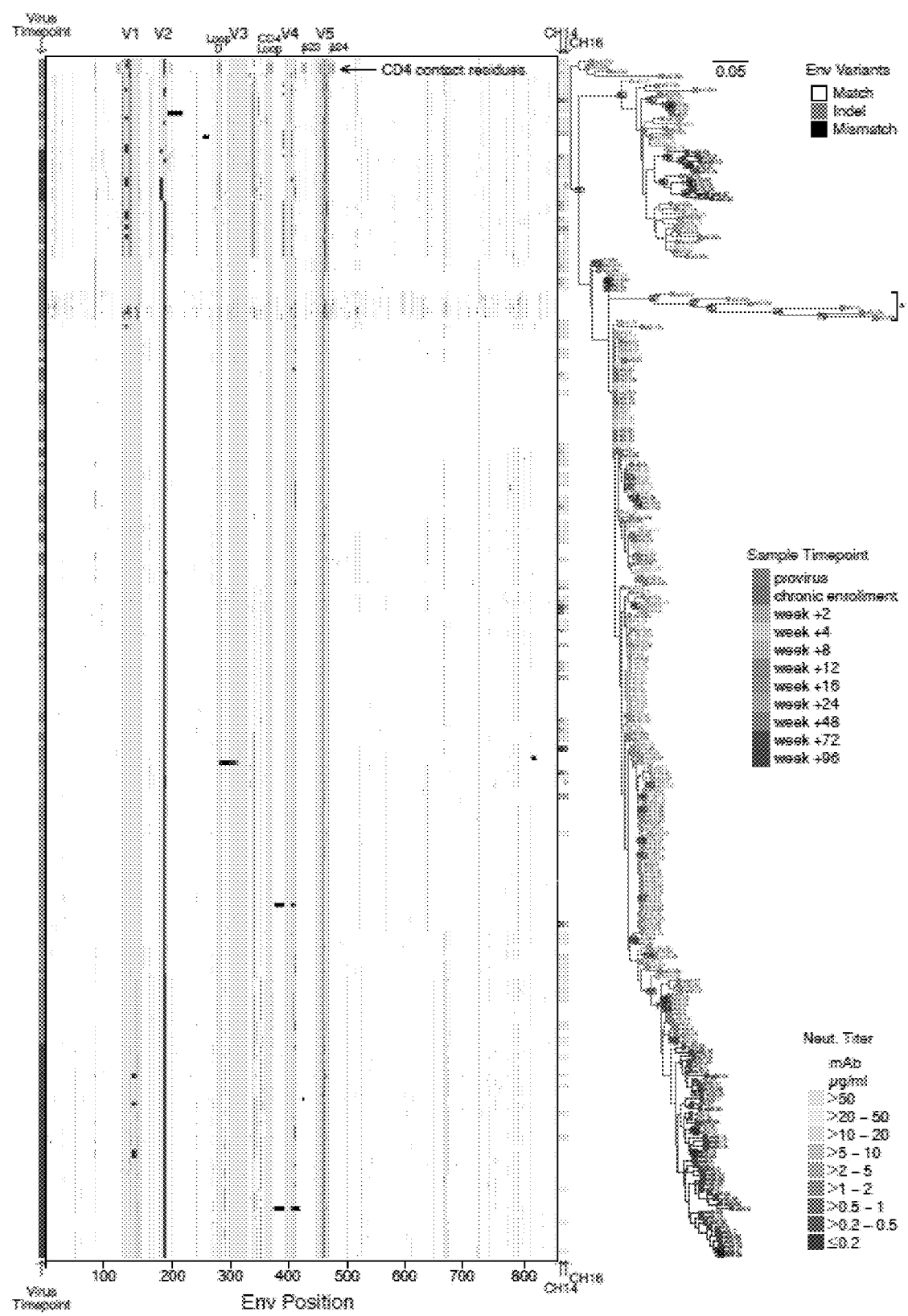

FIG. 14. HIV-1 env gene evolution in participant CH0457. Env phylogeny from CH0457 during chronic infection is shown. A pixel map (left) depicts mutations where each site differs from the consensus of earliest plasma Envs, whether mutations (red) or insertions/deletions (black). Each row in the tree and the pixel map depicts a distinct Env isolated from longitudinal samples; i.e., week 0 (enrollment; red) through week 96 post-enrollment (purple). Env provirus sequenced from PBMCs in the enrollment sample are also shown (grey). The phylogeny was inferred from protein sequences by PhyML (5) with the HIVw substitution model (6). Node labels indicate at least 60% bootstrap support. Root placement was chosen to minimize the sum of variances among within-timepoint distances (7, 8). A group of six provirus-derived Envs was enriched for APOBEC3G hypermutations (4), as identified by a square bracket and asterisk. Neutralization titers (μg/mL) from two representative mAbs (CH14, CH16) are shown in two columns between the pixel map and the tree for the subset of Envs assayed. Locations of V1-V5 and other Env landmarks are shown by (faint grey boxes) and sites that contact CD4 are shown near the top of the pixel map (pink tic marks).

Figure 15A:
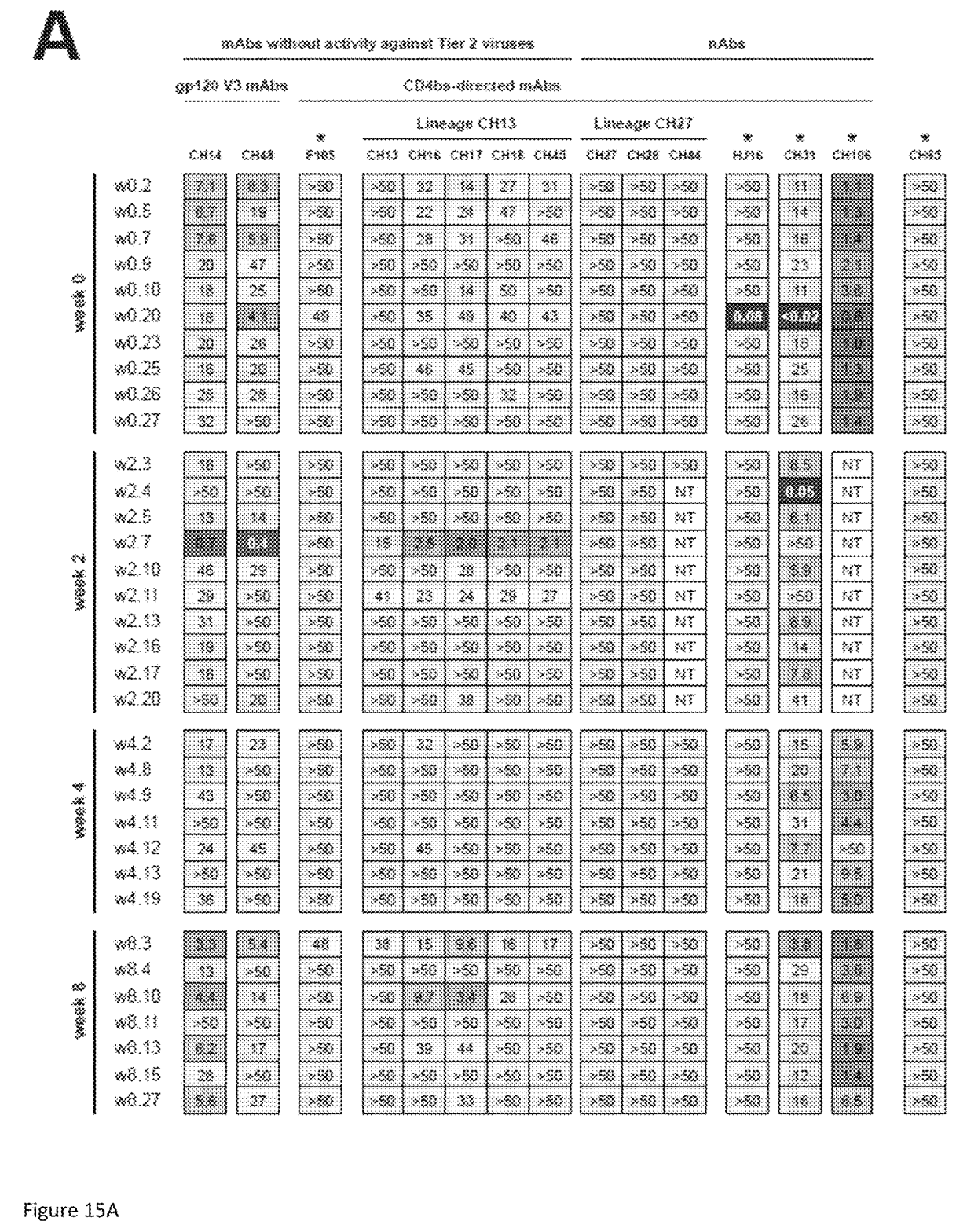
Figure 15A:
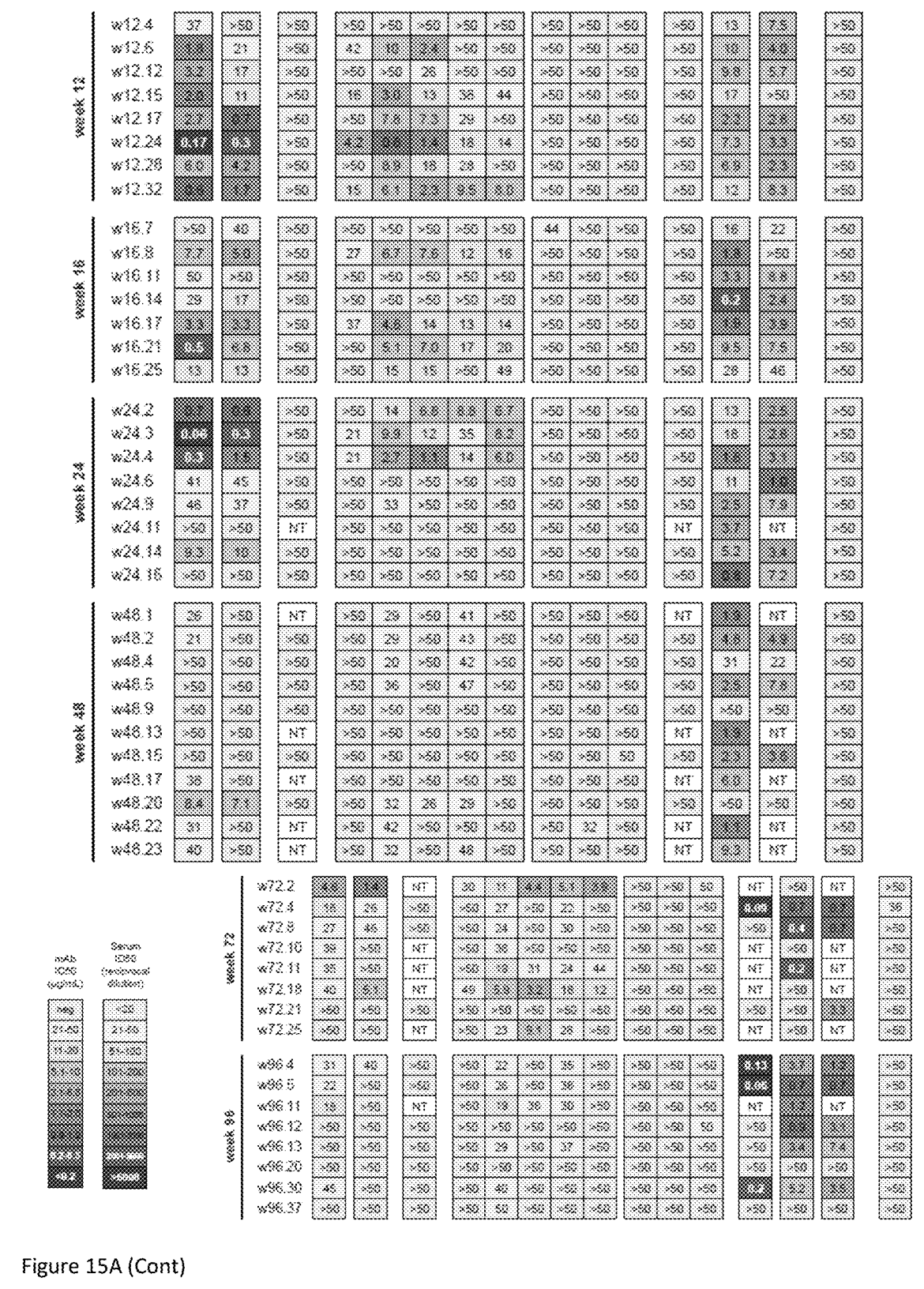

FIG. 15. Neutralization of autologous viruses from CH0457 by mAbs. A: Antibodies were tested against a panel of 84 pseudoviruses amplified from plasma from participant CH0457 that spanned the study period. Antibodies from lineage CH13 neutralized 52/84 (62%) of isolates tested and mAbs from this lineage were active against at least one isolate from each of the time points tested. For mAbs from lineage CH13, neutralization titers ranged from 0.8-50 μg/mL. In contrast, mAbs from lineage CH27 neutralized only 5/84 (6%) of isolates; neutralization titers ranged from 44-50 μg/mL. Control mAbs are shown with asterisks above their names; narrow neutralizing CD4bs mAb F105 (9) weakly neutralized 2/72 (2.8%) while bnAb HJ16 (10) potently neutralized 5/72 (6.9%) of pseudoviruses. Anti-HIV-1 bnAbs CH31 (11) and CH106 (2) neutralized 73/84 (87%) and 55/62 (89%) respectively with titers ranging from <0.02 to 46 μg/mL, while anti-influenza bnAb CH65 (12) weakly neutralized a single isolate (w72.4). Testing of the autologous viruses by these and additional samples (FIG. 18) was used to classify the viruses for neutralization sensitivity (Tier Classification). B: HIV-1 Env sequences were amplified by single genome amplification from week 0 PBMC. Env sequences from plasma are indicated by a "p"; cell derived sequences are indicated by a "c". Pseudoviruses made from these Env sequences were tested against the panel of mAbs isolated from CH0457. Of the 34 pseudoviruses tested, 28/34 (82%) were sensitive to the V3 mAbs CH14 and CH48 and 11/34 (32%) were sensitive to the CD4bs-directed lineage CH13 mAbs. Only 5/34 (15%) of pseudoviruses were sensitive to the nAb lineage CH27 mAbs; of these, the two Envs most distant in the phylogenetic tree from the week 0 plasma Envs, w0.29c and w0.35c, were the most sensitive to neutralization (IC50 range 0.1-2.0 µg/mL).

Figure 16:
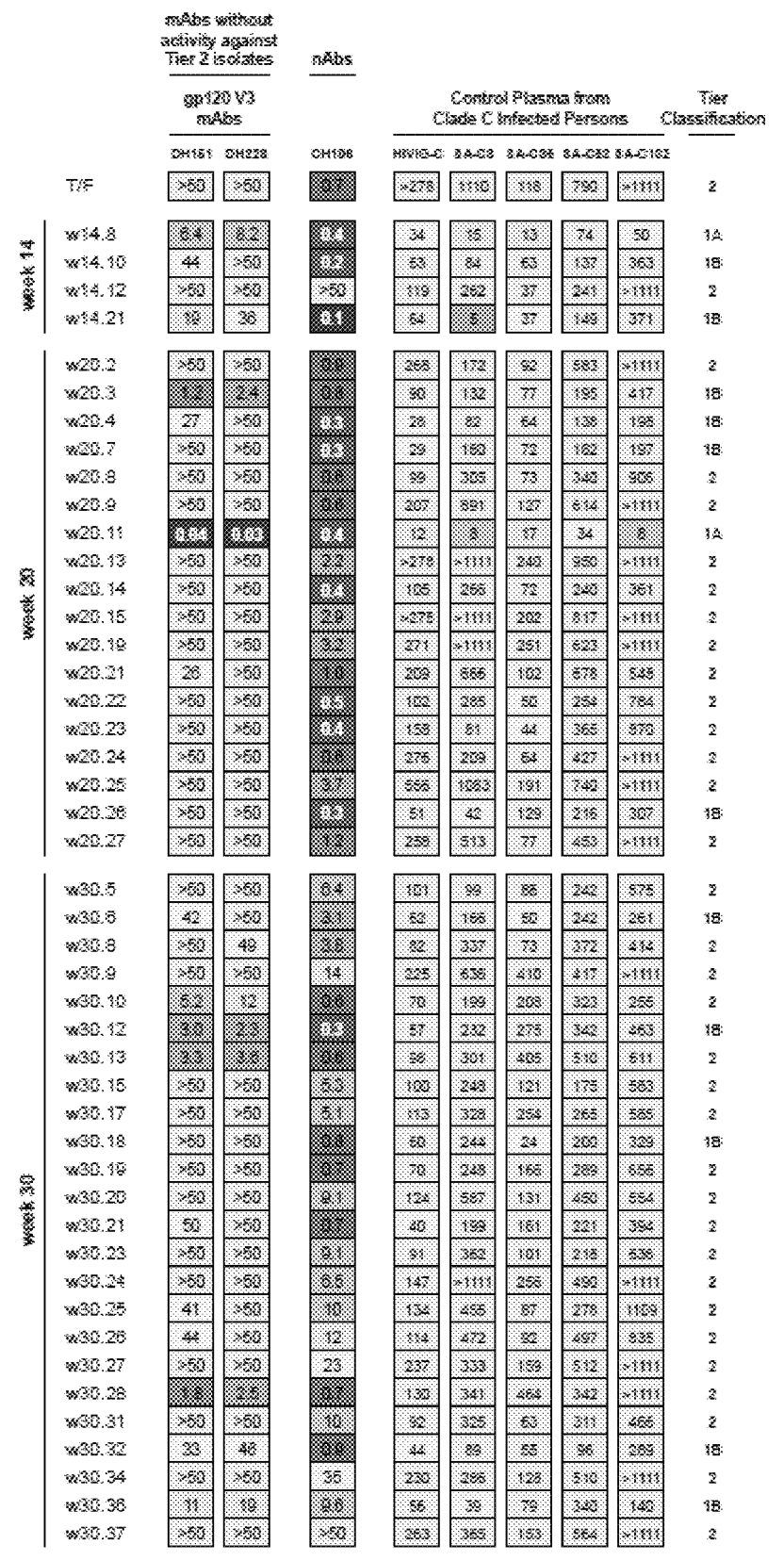
Figure 16:
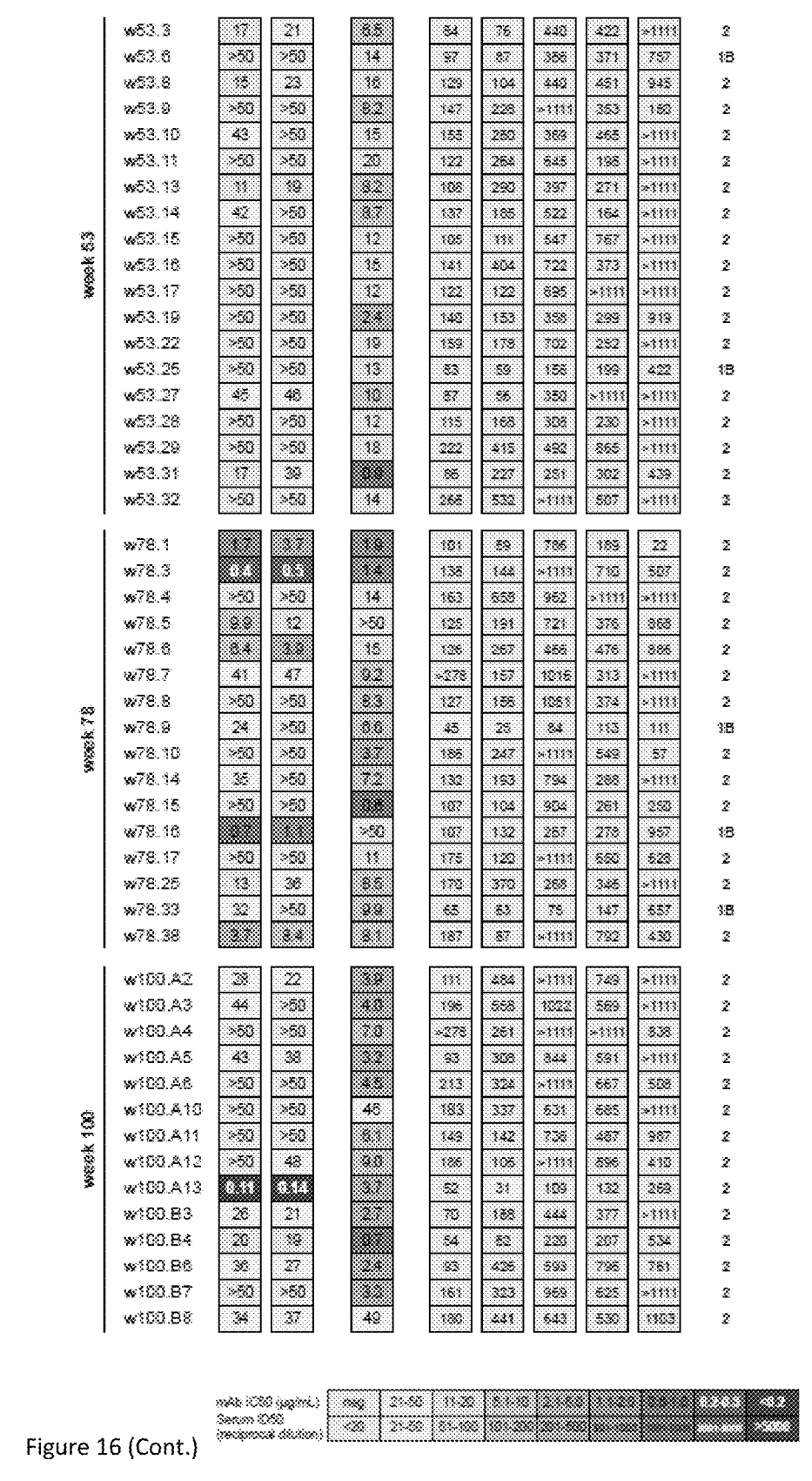

FIG. 16. Neutralization of autologous viruses from CH505 by mAbs. Antibodies DH151 and DH228 were tested against a panel of 96 autologous pseudoviruses from participant CH505. Tier 1 V3 mAbs neutralized 45/96 (47%, range 50-0.03 µg/mL) of the autologous viruses. Like CH0457 tier 1 V3 abs, mAbs DH151 and DH228 neutralized 7/96 (7.3%) viruses at ≤2 µg/mL. Testing of the autologous viruses against HIVIG-C and a panel of well characterized sera from clade C infected participants (SA-C8, SA-C36, SA-C82, SA-C102) (FIG. 20) was used to classify the viruses for neutralization sensitivity (Tier Classification).

Figure 17:
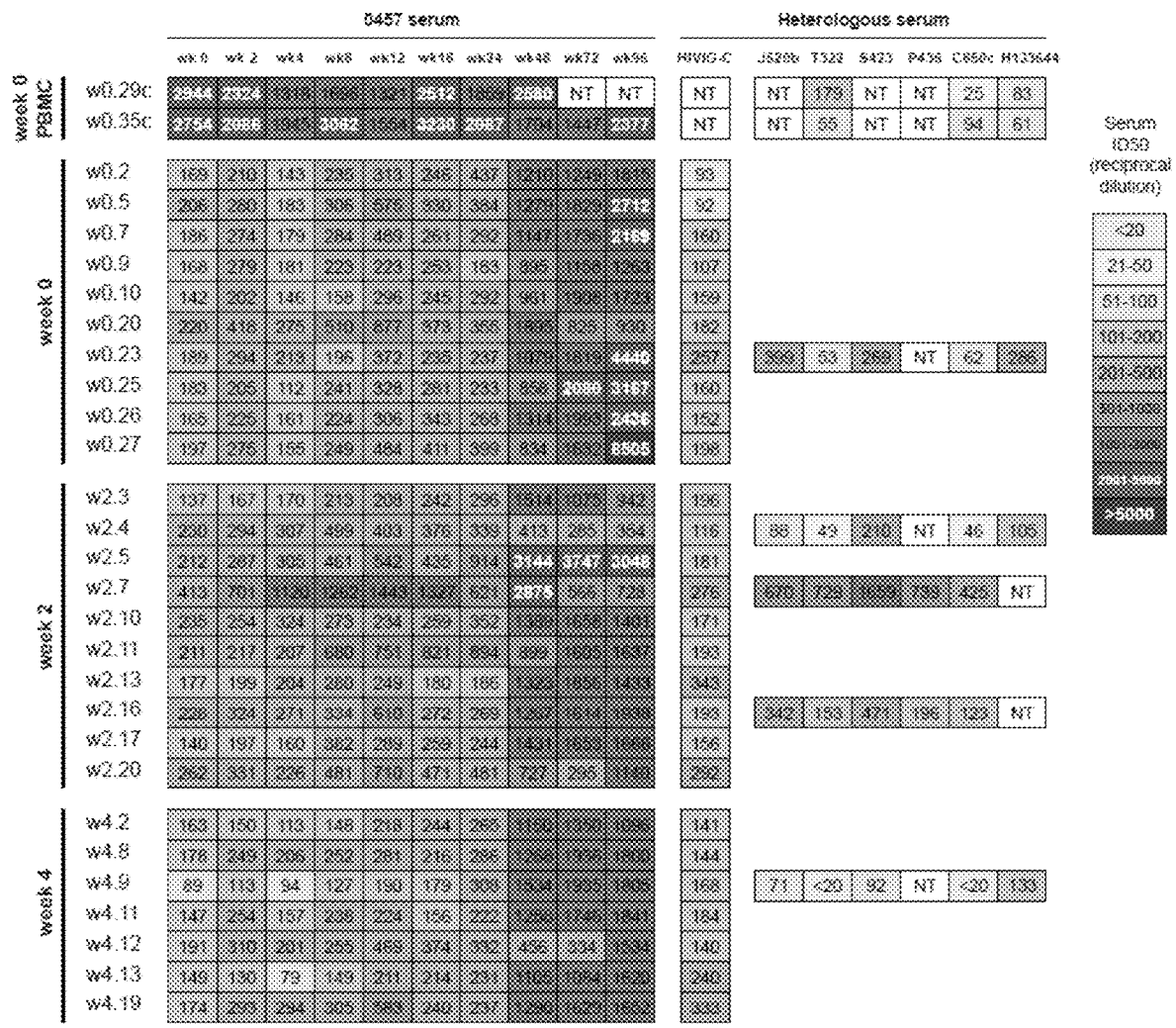

FIG. 17. Autologous neutralization by serum from participant CH0457. Serum from participant CH0457 spanning the study period was tested against 84 autologous virus isolates from the same time period and two autologous viruses isolated from PBMC. Control HIVIG-C pooled antibodies are shown on the right. Serum antibodies from CH0457 neutralized autologous viruses from all early time points, and serum from weeks 48, 72, and 96 showed greater potency against autologous viruses. Virus isolates from week 96 were resistant to plasma from all time points, suggesting that a new escape event may have occurred during the later study period. Six viruses were tested for sensitivity to a panel of five well characterized serum samples; these viruses demonstrated an intermediate sensitivity to these sera, consistent with an intermediate phenotype (tier 1b). Companion data for these sera against other HIV-1 strains is shown in FIG. 19.

Figure 18:
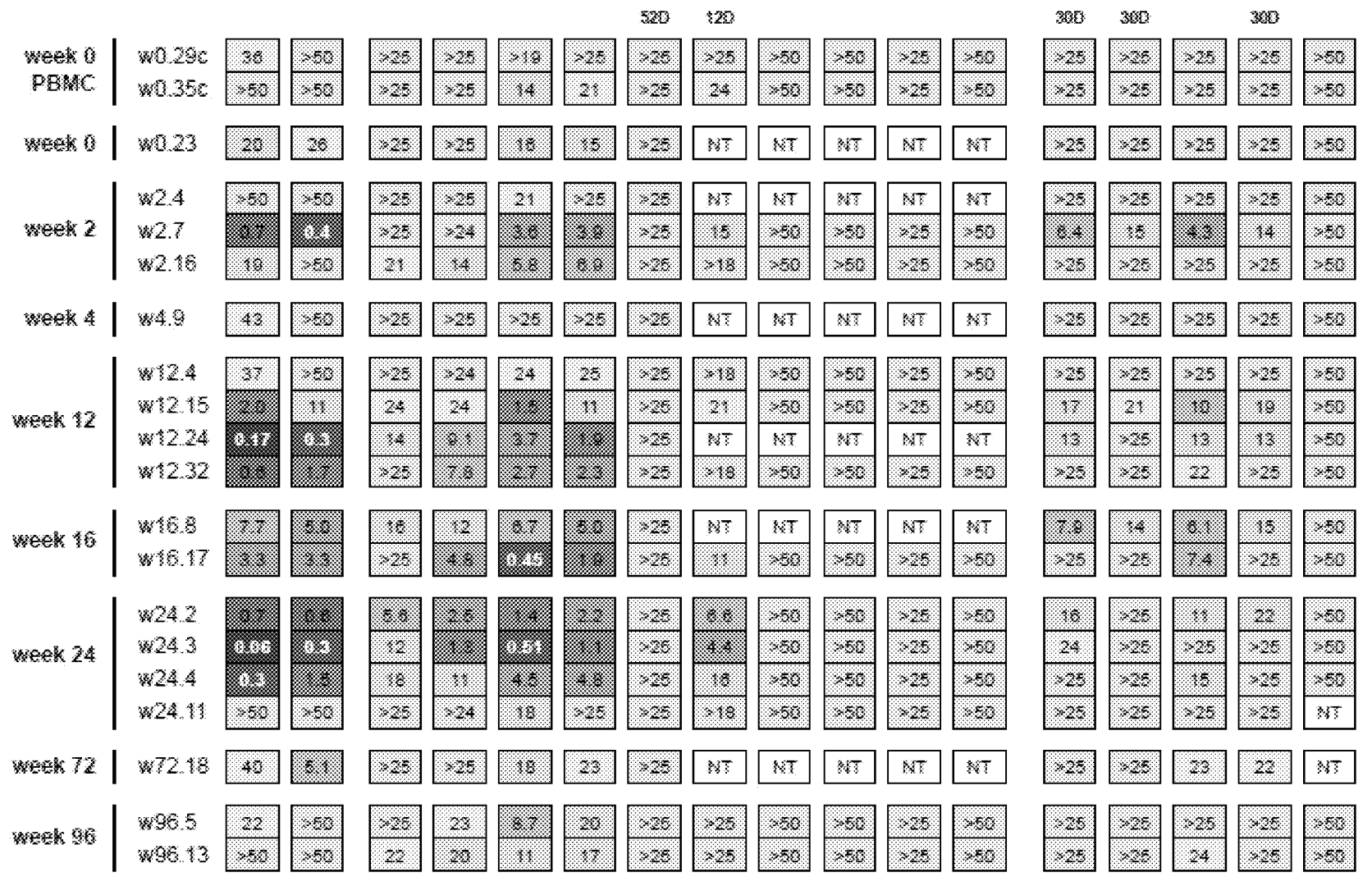
Figure 18:
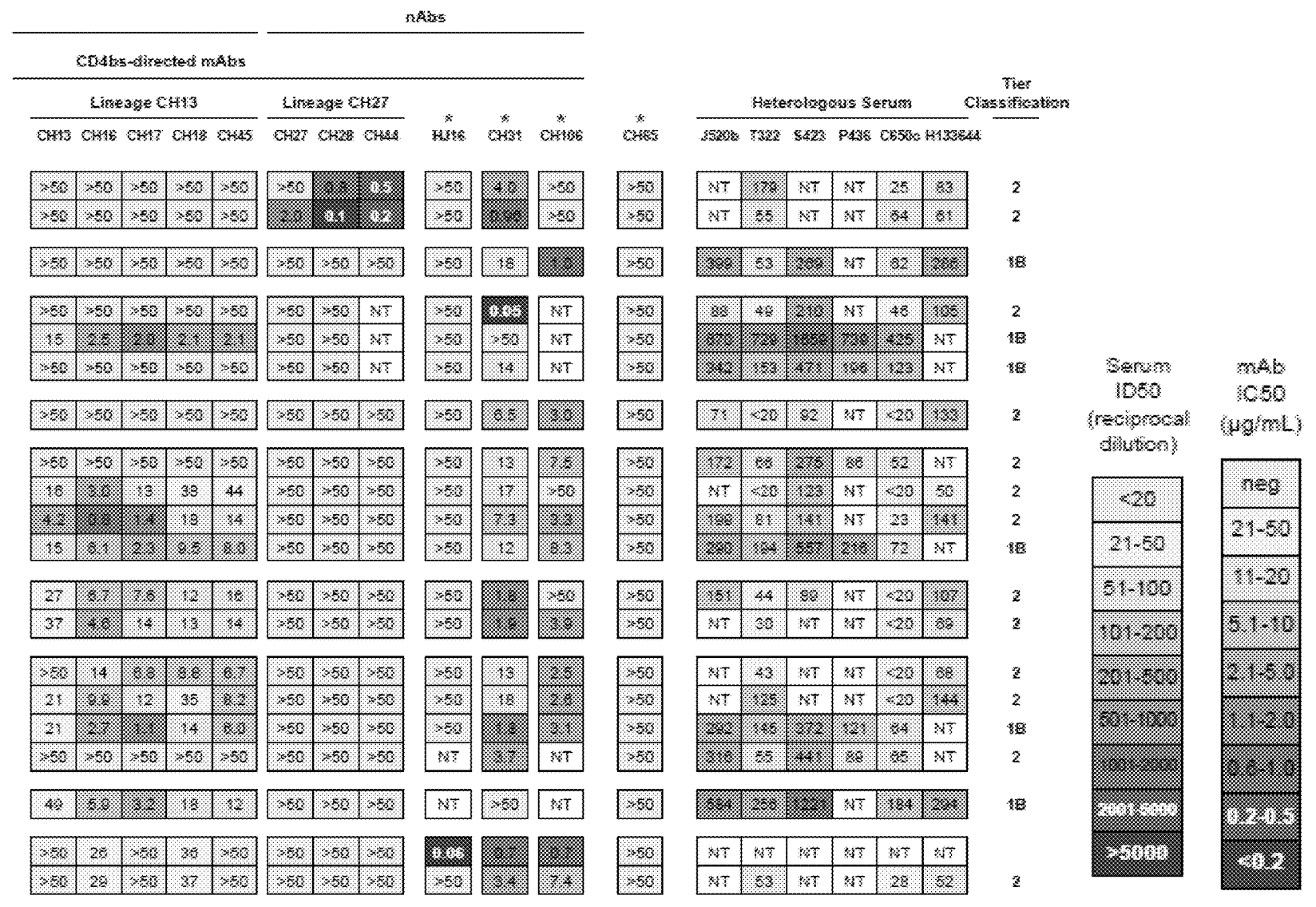

FIG. 18. Neutralization of mAbs against autologous viruses from CH0457: extended panel. Data shown here include some neutralization data shown in FIG. 11A and FIG. 15. Twenty of the viruses were tested against a panel of V3 and CD4bs mAbs with restricted neutralization profiles (13-19) and a panel of well-characterized HIV-1-infected patient serum samples. These neutralization profiles were used to classify the pseudoviruses for neutralization sensitivity.

Figure 19:
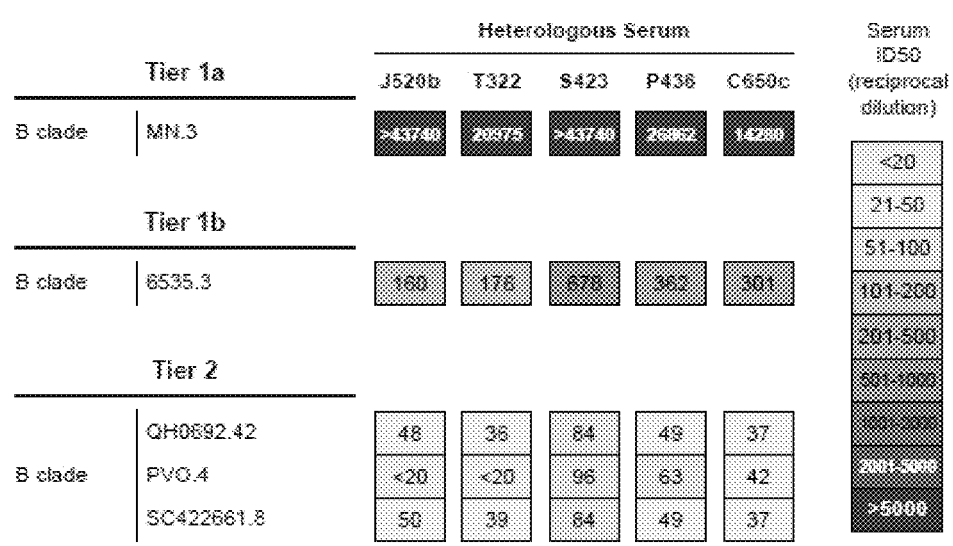

FIG. 19. Neutralization of a panel of HIV-1 isolates by well characterized serum samples. Five HIV-1 isolates were tested against five well characterized serum samples. The canonical tier 1 virus MN.3 was very sensitive to the serum samples. The intermediate sensitive virus 6535.3 was more resistant than MN.3 but not as resistant as the three tier 2 viruses.

Figure 20:
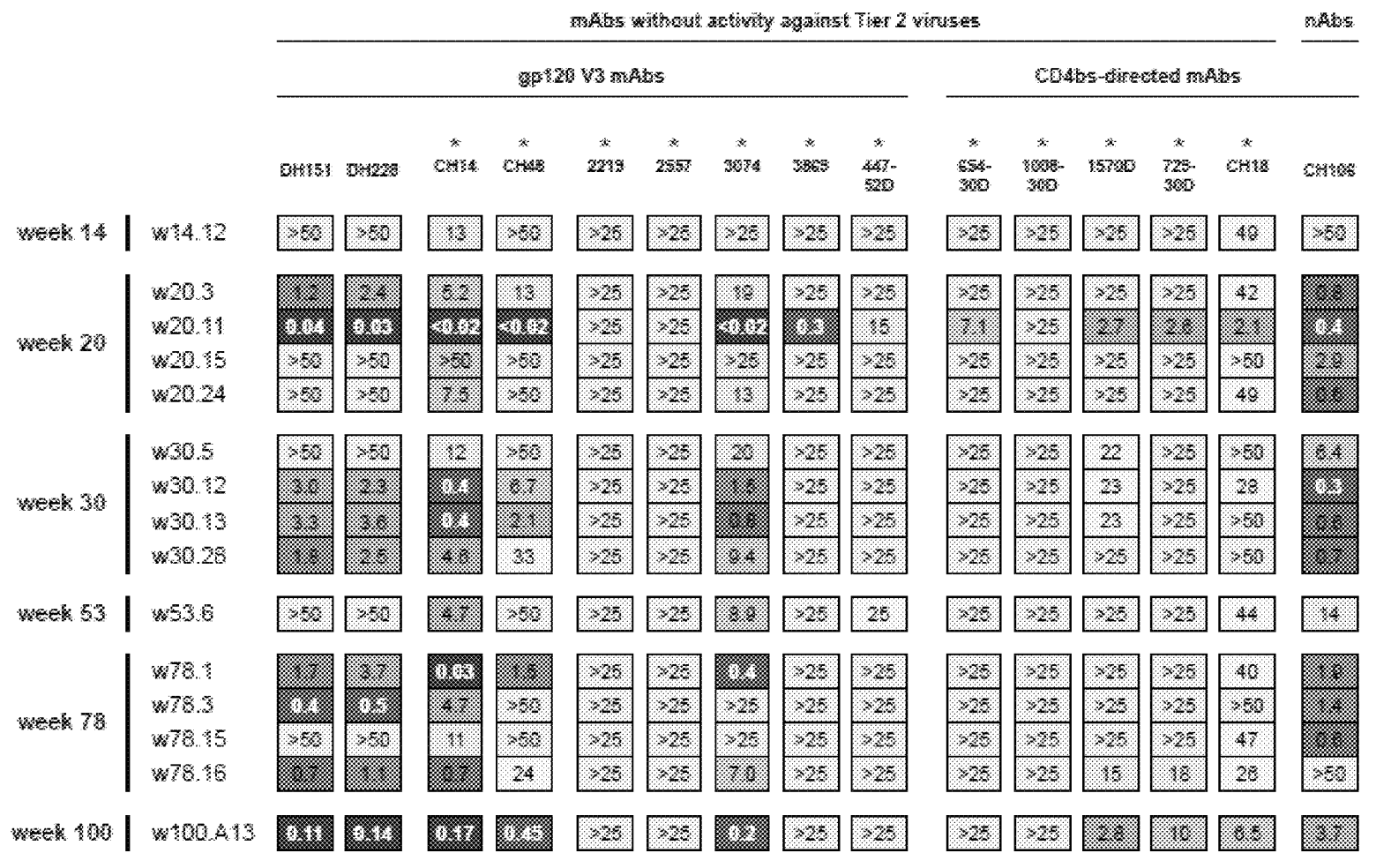
Figure 20:
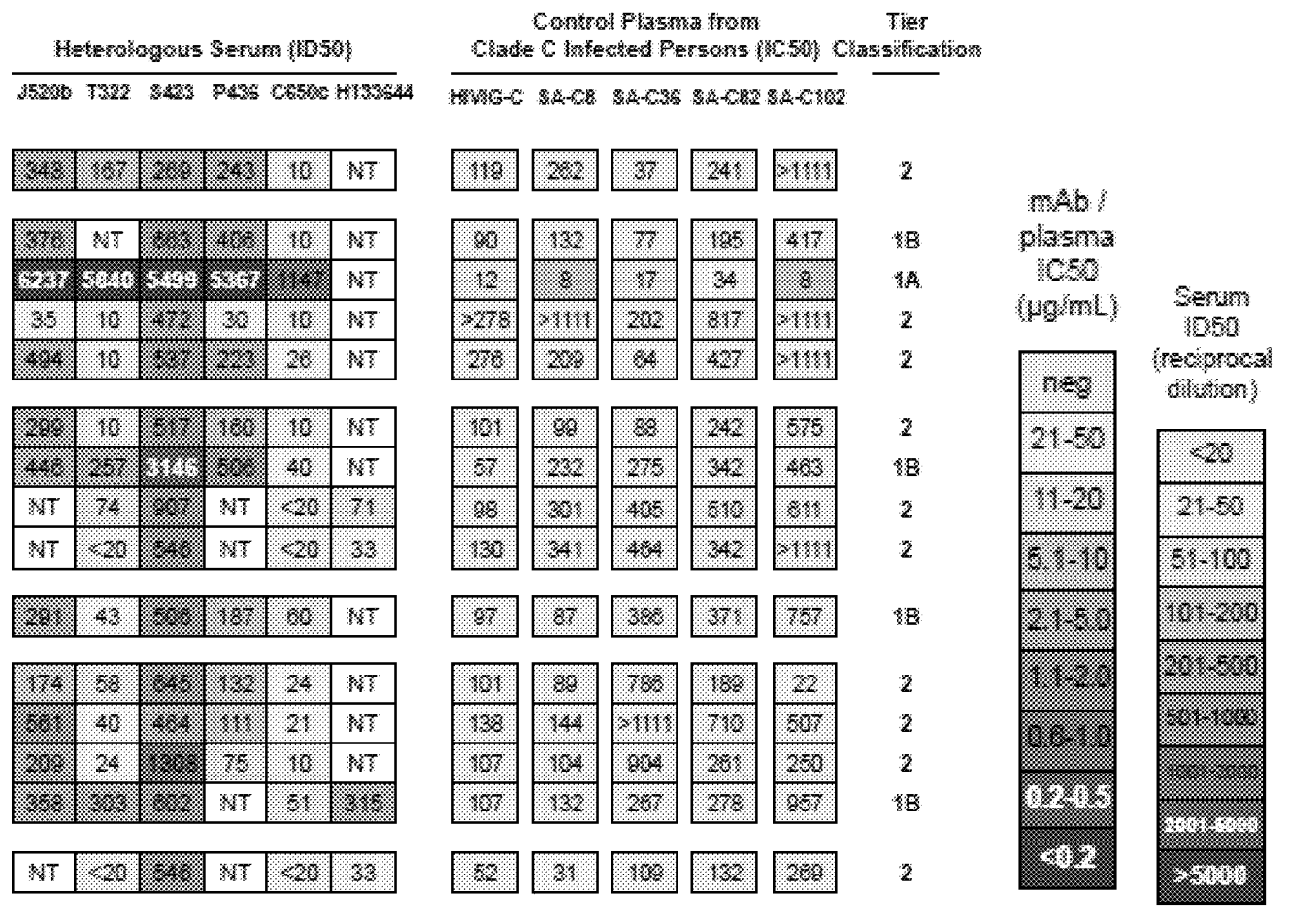

FIG. 20. Neutralization of mAbs against autologous viruses from CH505, tabular format. Data shown in FIG. 11C are here supplemented with additional neutralization data. Fifteen pseudoviruses were tested against a panel of mAbs and well characterized HIV-1-infected patient serum samples. Isolates that were sensitive to the autologous V3 mAbs DH151 and CH228 were also mostly sensitive to heterologous mAbs. Sensitivity to the mAbs and sera were used to refine the tier classification shown in the rightmost column.

FIG. 21 shows B.63521, CH505 T/F and CON-S envelopes. B.63521 D11gp120mutC is a mutant of B.63521 D11gp120 with mutations at the V3 loop to minimize the V3 cleavage. (opt. indicates optimized sequence). Figure discloses SEQ ID NOS 53-72, respectively, in order of appearance.

Figure 22:
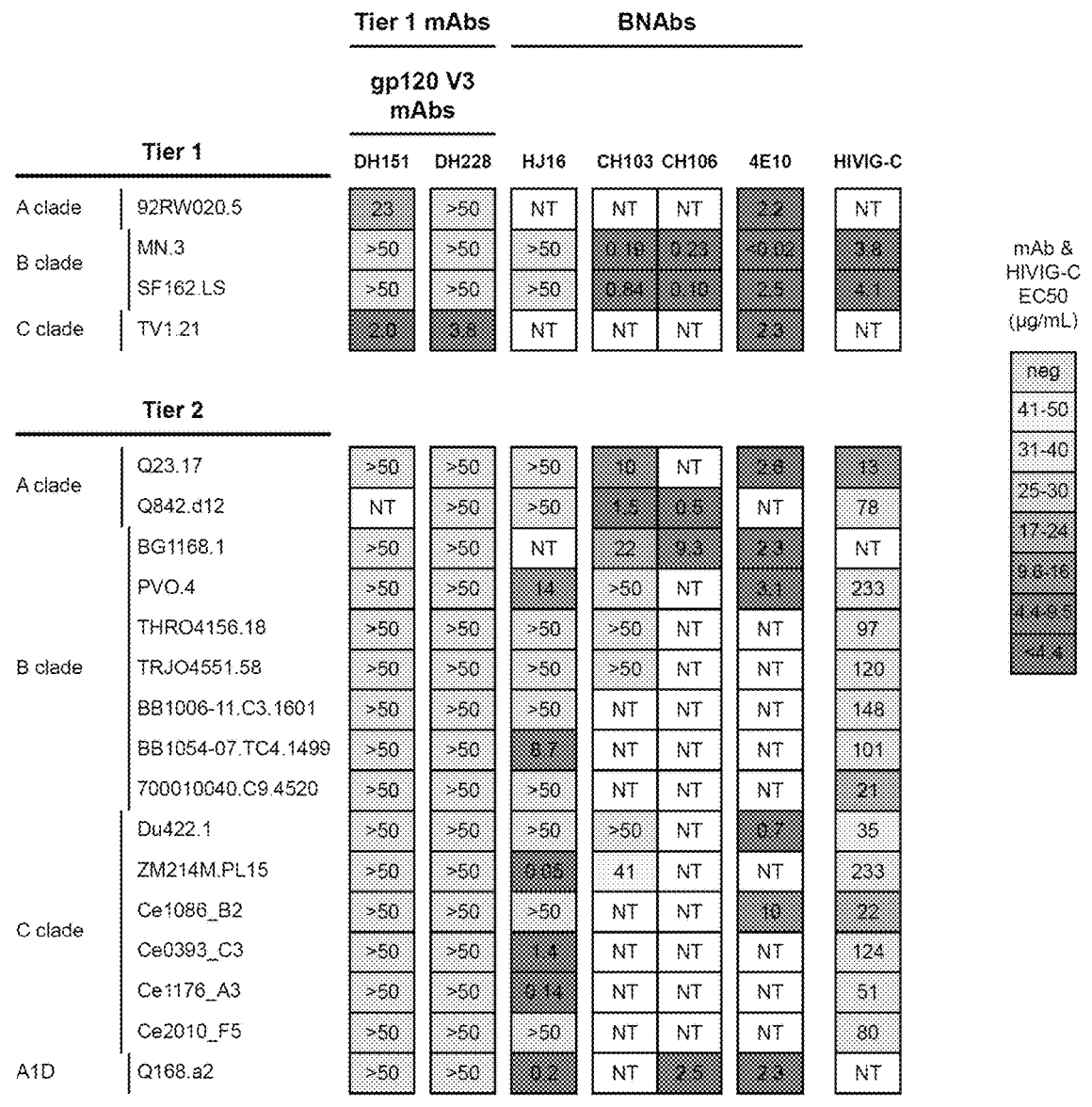

FIG. 22 Neutralization of Tier 1 heterologous viruses by common V3 Nabs (DH151, DH228) but not neutralization of heterologous Tier 2 viruses by common Nabs. In contrast, CD4 bs bnAbs potently neutralize ~50% of heterologous Tier 2 HIV strains. (See Liao et al. (2013) Nature 496:469, 2013).

Figure 23A:
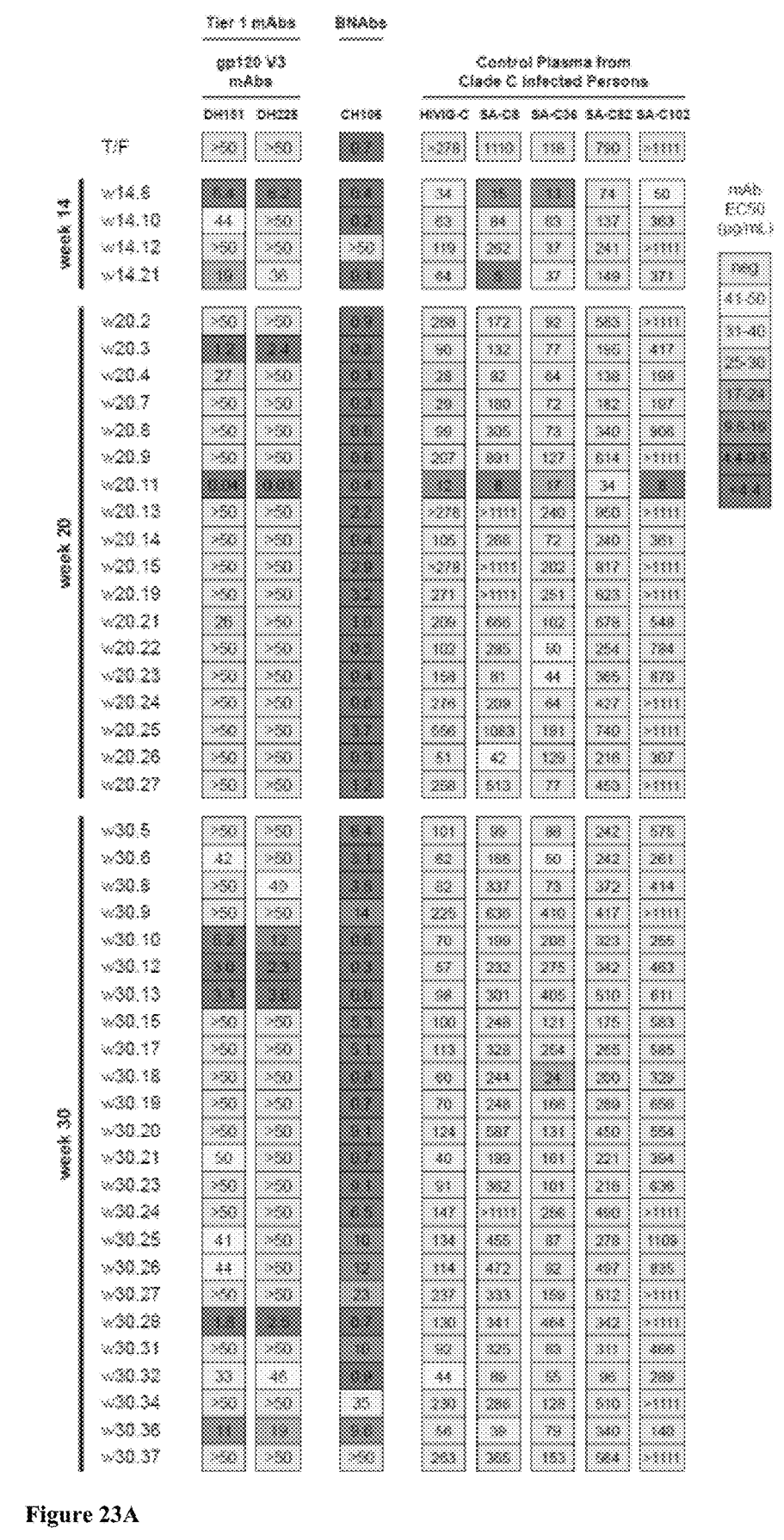
Figure 23B:
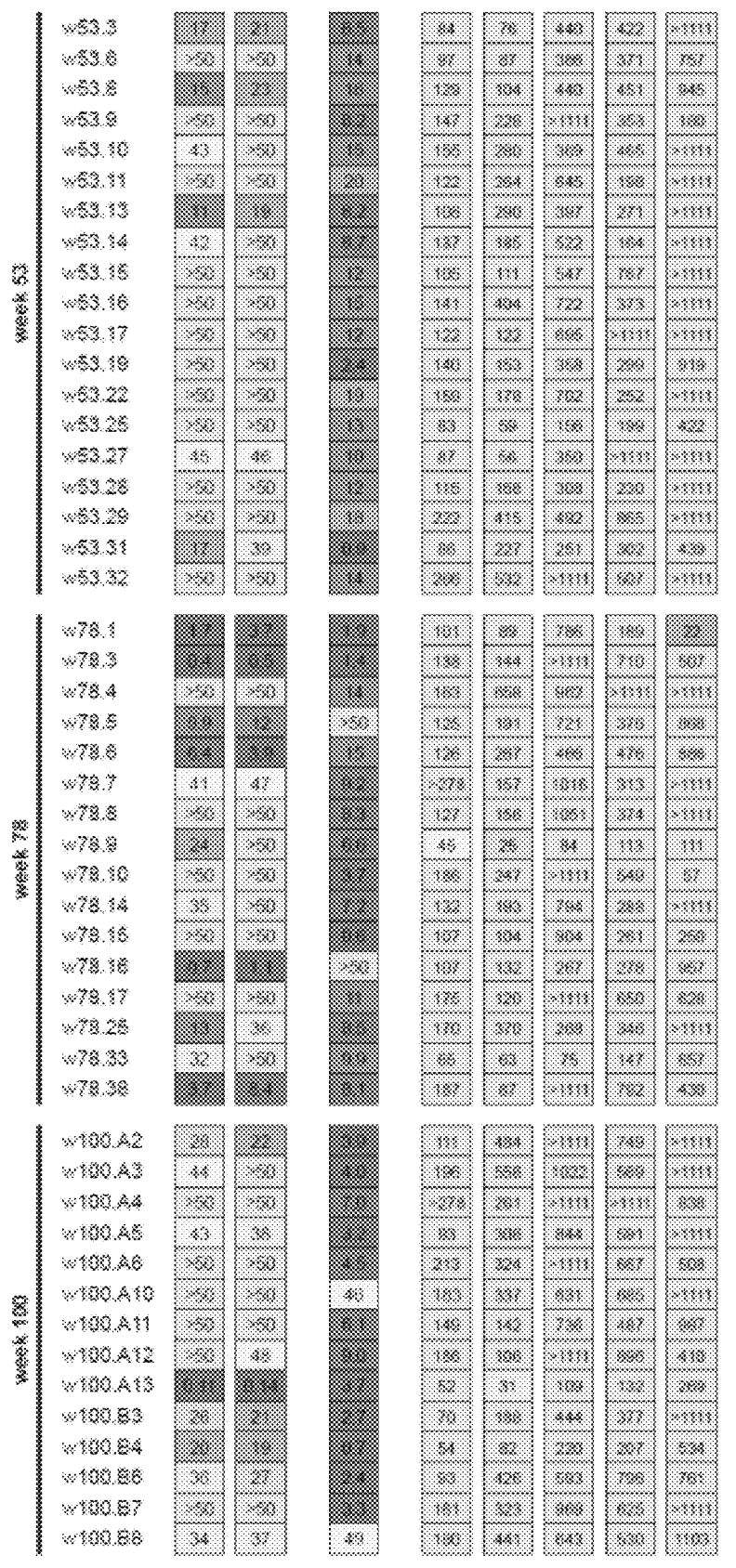

FIGS. 23A and 23 B. Neutralization of Tier autologous viruses by common V3 Nabs (DH151, DH228). The CD4 bs bnAb CH106 from CH505 also potently neutralizes these autologous viruses because they are much earlier autologous mutants compared to the autologous strains from CH0457 that had escaped from the CH0457 bnAbs. The key here however, is that the CH505 V3 abs are able to robustly neutralize a subset of autologous tier 2 viruses.

DETAILED DESCRIPTION

Described herein are nucleic and amino acids sequences of HIV-1 envelopes. In certain embodiments, the described HIV-1 envelope sequences are gp160s. In certain embodiments, the described HIV-1 envelope sequences are gp120s. Other sequences, for example but not limited to gp140s, both cleaved and uncleaved, gp150s, gp41s, which are readily derived from the nucleic acid and amino acid gp160 sequences. In certain embodiments the nucleic acid sequences are codon optimized for optimal expression in a host cell, for example a mammalian cell, a rBCG cell or any other suitable expression system.

In certain embodiments, the envelope design in accordance with the present invention involves deletion of residues (e.g., 5-11, 5, 6, 7, 8, 9, 10, or 11 amino acids) at the N-terminus. For delta N-terminal design, amino acid residues ranging from 4 residues or even fewer to 14 residues or even more are deleted. These residues are between the maturation (signal peptide, usually ending with CX, X can be any amino acid) and "VPVXXXX . . . ". In case of CH505 T/F Env as an example, 8 amino acids (italicized and underlined in the below sequence) were deleted:

MRVMGIQRNYPQWWIWSMLGFWMLMICNG*MWVTVYYG*VPVWKEAKTTLFC

ASDAKAYEKEVHNVWATHACVPTDPNPQE

. . . (rest of envelope sequence is indicated as ". . . ") (SEQ ID NO: 4). In other embodiments, the delta N-design described for CH505 T/F envelope can be used to make delta N-designs of other CH505 envelopes. In certain embodiments, the invention relates generally to an immunogen, gp160, gp120 or gp140, without an N-terminal Herpes Simplex gD tag substituted for amino acids of the N-terminus of gp120, with an HIV leader sequence (or other leader sequence), and without the original about 4 to about 25, for example 11, amino acids of the N-terminus of the envelope (e.g. gp120). See WO2013/006688, e.g. at pages 10-12, the contents of which publication is hereby incorporated by reference in its entirety.

The general strategy of deletion of N-terminal amino acids of envelopes results in proteins, for example gp120s, expressed in mammalian cells that are primarily monomeric, as opposed to dimeric, and, therefore, solves the production and scalability problem of commercial gp120 Env vaccine production. In other embodiments, the amino acid deletions at the N-terminus result in increased immunogenicity of the envelopes.

In certain embodiments, the invention provides envelope sequences, amino acid sequences and the corresponding nucleic acids, and in which the V3 loop is substituted with the following V3 loop sequence TRPNNNTRK-SIRIGPGQTFY ATGDIIGNIRQAH (SEQ ID NO: 5). This substitution of the V3 loop reduced product cleavage and improves protein yield during recombinant protein production in CHO cells.

In certain embodiments, the CH505 envelopes will have added certain amino acids to enhance binding of various broad neutralizing antibodies. Such modifications could include but not limited to, mutations at W680G or modification of glycan sites for enhanced neutralization.

In certain aspects the invention contemplates using immunogenic compositions wherein immunogens are delivered as recombinant proteins. Various methods for production and purification of recombinant proteins suitable for use in immunization are known in the art.

The immunogenic envelopes can also be administered as a protein boost in combination with a variety of nucleic acid envelope primes (e.g., HIV-1 Envs delivered as DNA expressed in viral or bacterial vectors).

Dosing of proteins and nucleic acids can be readily determined by a skilled artisan. A single dose of nucleic acid can range from a few nanograms (ng) to a few micrograms (μg) or milligram of a single immunogenic nucleic acid. Recombinant protein dose can range from a few μg micrograms to a few hundred micrograms, or milligrams of a single immunogenic polypeptide.

Administration: The compositions can be formulated with appropriate carriers using known techniques to yield compositions suitable for various routes of administration. In certain embodiments the compositions are delivered via intramascular (IM), via subcutaneous, via intravenous, via nasal, via mucosal routes.

The compositions can be formulated with appropriate carriers and adjuvants using techniques to yield compositions suitable for immunization. The compositions can include an adjuvant, such as, for example but not limited to, alum, poly IC, MF-59 or other squalene-based adjuvant, ASOIB, or other liposomal based adjuvant suitable for protein or nucleic acid immunization. In certain embodiments, TLR agonists are used as adjuvants. In other embodiment, adjuvants which break immune tolerance are included in the immunogenic compositions.

Over half of mothers, even without ARV, will not transmit the virus to their infants. This demonstrates that maternal defenses such as humoral immunity modulate HIV infection and transmission. Such defenses include maternal IgG antibodies that can bind and neutralize the HIV envelope (Env). Levels of IgG against the V1V2 region of the HIV Env were correlated with greater protection following vaccination in the RV-144 trial in Thailand, which produced an overall 31% vaccine efficacy. Thus, we hypothesized that certain maternal IgG antibodies against HIV Env may prevent MTCT.

A cohort of HIV-infected pregnant U.S. women in the preARV era (Women and Infant Transmission Study) was analyzed. The invention provides that a maternal plasma IgG response against the HIV Env V3 region was associated with protection against infant HIV transmission. Thus, we further hypothesized that founder HIV variants that escape antibody binding and result in infant infection contain mutations in the V3 Env region that renders these antibodies ineffective. Understanding candidate antibody responses that effectively prevent MTCT provides specific targets for design and evaluation of an effective maternal HIV vaccine.

In certain aspects, the invention provides methods to define transmitted/founder (T/F) HIV virus variants in HIV infected infants from the WITS cohort.

In other aspects, the invention provides methods to compare infant T/F and maternal Env sequences to identify signature in the V3 region associated with transmission risk In other aspects, the invention provides methods to define the susceptibility of maternal and infant T/F Env variants to neutralization by maternal and infant plasma.

Characterizing the humoral immune response required for protection against HIV transmission continues to be a crucial area of research as an effective HIV vaccine is still not available. The invention provides two areas of effective vaccination to prevent MTCT. In certain aspects the invention provides methods to define V3 immunogens, and V3 immunogens comprised in a maternal vaccine to prevent infant HIV transmission. In certain aspects, the invention provides methods to establish the V3-specific IgG response that can be used to determine the potential efficacy of candidate maternal HIV vaccines.

MTCT Immune Correlate Study:

In certain aspects, the invention provides methods to define the maternal humoral immune correlates of protection against intrauterine/peripartum mother to child transmission in the absence of antiretroviral therapy, including the potentially-protective HIV Env-specific antibody responses identified in the RV144 HIV vaccine trial. The invention further provides methods to define immune correlates of protection against distinct modes of mother to child transmission (intrauterine vs peripartum). The subjects for this study come from the Woman and Infants Transmission Study (WITS), a cohort of HIV-infected pregnant women in the U.S. that was enrolled between 1990 and 1996, many before the availability of antiretroviral prophylaxis. Placental or peripartum-transmitting women were selected, who were reported to have no ART exposure and a viral load >400 at the time of delivery (n=83). A nontransmitting group of women was matched for plasma viral load, CD4 count, infant gestational age and delivery mode at a 1:2 case:control ratio (n=166). Plasma or serum samples available from this cohort of women were collected between 25 weeks gestation and 2 months postpartum.

Non-limiting examples of humoral immune assays, to determine correlation between immune variable and transmission risk, include: HIV Env-binding IgG ELISA focusing on V1V2, and/or V3, HIV Env-binding IgA measured by luminex ELISA to determine the breadth of the IgA response, HIV Env IgG avidity measured by SPR, ADCC of two clade B variants, and tier 1 and 2 neutralization of a panel of clade variants, example clade B variants, screened for their ability to be neutralized by the broadly-neutralizing monoclonal antibodies.

EXAMPLES

Example 1

Maternal HIV-1 Envelope Variable Region 3-Specific IgG and Neutralization Response Predicts Reduced Risk of Perinatal HIV-1 Transmission Despite availability of effective antiretroviral prophylaxis, >250,000 infants acquire HIV-1 annually, emphasizing the need for immunologic interventions to reduce pediatric infections. To investigate humoral immune correlates of risk of mother-to-child transmission (MTCT), we studied untreated, HIV-1-transmitting mothers (n=83) and clinically-matched non-transmitting mothers (n=165) from the Women and Infant Transmission Study (WITS) of U.S. non-breastfeeding HIV-1-infected mother-infant pairs. The magnitude of the maternal envelope third variable loop (V3)-specific IgG responses predicted reduced risk of MTCT (OR=0.64, 95% CI: 0.42-0.97, p=0.04). Secondary analyses revealed that neutralizing antibody responses against easy-to-neutralize (tier 1) HIV-1 strains predicted reduced risk of peripartum transmission (OR=0.54, 95% CI: 0.35-0.84, p=0.005). Moreover, recombinant maternal V3-specific IgG monoclonal antibodies mediated neutralization of autologous HIV-1 isolates, suggesting that boosting V3-specific autologous neutralizing antibodies through vaccination might decrease HIV-1 MTCT.

While antiretroviral prophylaxis administered to mothers or infants can reduce the risk of mother-to-child transmission (MTCT) (1), implementation barriers, adherence challenges, drug toxicities, and antiretroviral drug-resistant HIV-1 strains continue to limit the effectiveness of these interventions. Thus, immunologic interventions, such as maternal or infant vaccines, may be required to achieve the goal of an HIV-1-free generation(2, 3).

The role of maternal envelope (Env)-specific antibody responses in protection against MTCT remains an area of controversy. Early work investigating the role of maternal antibody responses in protection against infant HIV-1 acquisition suggested that high levels of maternal IgG antibodies directed against the Env gp120 protein, including the variable region 3 (V3) loop, correlated with protection against MTCT (4, 5). However, other studies were unable to find a similar correlation between protection and maternal Env-specific antibody responses (6-8). Additional work suggested that antibody responses against the gp41 Env protein were associated with protection of infants (9, 10). Several studies observed more potent HIV-1-neutralizing antibody responses in non-transmitting mothers compared to transmitting mothers (11, 12) as well as the transmission of neutralization-escape variants (13-15), yet other studies did not observe this phenomenon (12, 16-19). Thus, a critical question remains whether maternal humoral immunity contributes to the risk of vertical HIV-1 transmission.

Analysis of the immune correlates of risk of HIV-1 acquisition in the RV144 adult HIV-1 vaccine efficacy trial revealed that a vaccine-elicited IgG response against the variable 1 and variable 2 regions (V1 V2) of the HIV-1 Env predicted lower risk of HIV-1 acquisition (20). Further analysis revealed that binding IgG responses against the linear variable 3 (V3) region also correlated with reduced infection risk in vaccine recipients with low levels of other types of Env-specific antibody responses, including Env-specific IgA (21). In addition, specific plasma Env-binding IgA responses correlated with decreased vaccine efficacy in RV144 vaccinees (20), and one potential mechanism for this effect is IgA blocking of IgG antibody dependent cellular cytotoxicity (ADCC) effector functions (22).

The potential for identified immune correlates of risk of transmission to be true immune correlates of protection against HIV-1 acquisition is strengthened if the same responses are found to be protective against a distinct mode of natural HIV-1 transmission (23). MTCT of HIV-1 provides an ideal setting to investigate whether the humoral immune correlates of infection risk identified in the RV144 vaccine trial similarly predicted infection risk in a distinct natural transmission setting where infants are passively-immunized with maternal antibody in utero. To investigate the humoral immune correlates of risk of MTCT, we utilized a natural history cohort of U.S. HIV-1-infected mother-infant pairs enrolled in an observational study (Women and Infants Transmission Study, WITS; Table 1) prior to the availability of antiretroviral prophylaxis (24).

A primary humoral immune variable model adapted from that applied to the RV144 study (20) (i.e., RV144 clade B-modified model) was used to determine if the identified antibody correlates of risk of HIV-1 acquisition were predictive of the risk of MTCT. In contrast to the RV144 adult vaccine trial, the Env V1V2 IgG binding response did not predict the risk of MTCT (OR: 1.06, p=0.67). Furthermore, a clade B-modified Env IgA binding score, clade B Env IgG avidity, and clade B ADCC responses also did not predict the risk of MTCT (Table 2, FIG. 3). The composite maternal plasma neutralization score had a low odds ratio for the risk of MTCT (0.76), however this association with reduced risk of MTCT did not reach significance (p=0.1, q=0.48).

To account for the differences in biology of adult heterosexual transmission and MTCT, we also applied a pre-specified second humoral immune response model that included Env binding IgG and IgA responses previously implicated to be important in MTCT (defined here as the MTCT model). Neither IgG responses against gp120 or gp41, nor IgA responses against gp41 were associated with the risk of MTCT. However, in the MTCT model, IgG binding responses against V3 antigens (V3 score) predicted reduced MTCT risk, with an odds ratio of 0.64 (p=0.04, q=0.15, Table 2, FIG. 1A-D).

We next determined the threshold (change-point) in the level of V3 antibodies associated with MTCT using a single predictor logistic model (p=0.04). This analysis revealed an estimated threshold at the $10^{th}$ percentile of the V3 IgG response score associated with an odds ratio of MTCT risk of 0.31. The transmission rate of mothers with a V3 IgG response below the estimated $10^{th}$ percentile threshold was 56% (14 of 25 transmitting women), whereas the transmission rate of mothers above the threshold was 31% (69 of 223 transmitting women). The median anti-clade B V3 IgG concentration in transmitting mothers' plasma was 23.8 µg/ml (interquartile range: 8.5-55.3 µg/ml), whereas the median V3-specific IgG concentration was 39.4 µg/ml (interquartile range: 12.5-72.6 µg/ml) in non-transmitting women.

We next performed a series of hypothesis-generating exploratory analyses of the entire panel of Env-specific humoral immune responses and their association with MTCT risk. Performing the analysis on the entire maternal cohort, a neutralization response against the clade B easy-to-neutralize (tier 1) HIV-1 variants B.SF162 (OR: 0.67, p=0.006, FIG. 1E) and B.MN.3 (OR: 0.71, p=0.02) best predicted reduced MTCT risk, though their false discovery rate did not fall below the preset criteria of <0.2 (q=0.25 and 0.4, respectively, Table S2). However, when a secondary analysis restricted to peripartum-transmitting mothers and their clinically-matched non-transmitting counterparts (52% of the transmitting cohort) was performed, neutralization response against both tier 1 HIV strains, B.SF162 and B.MN.3 predicted reduced peripartum transmission risk (OR: 0.54, p=0.005, q=0.1 for both) (Table S3).

We next assessed interactions between the primary maternal Env-specific antibody responses and the risk of MTCT to generate hypotheses about the characteristics of potentially-protective maternal antibody responses. Interestingly, even though the avidity of IgG to clade B gp140 did not predict the risk of MTCT alone, it interacted with IgG binding to MN gp41 (p=0.01, q=0.17), MN gp120 (p=0.014, q=0.17), and the V3 binding score (p=0.015, q=0.17) to predict the risk of MTCT. High levels of Env-binding IgG and avidity more strongly predicted reduced MTCT risk than low levels of each response (Table S4).

Figures 1E, 1F:
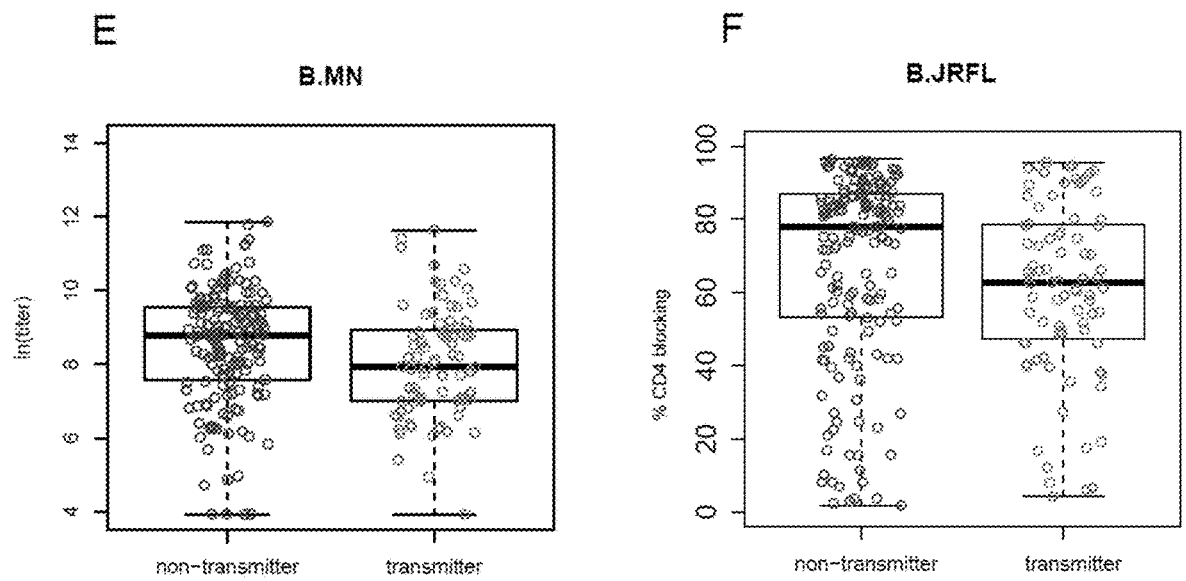
Figure 1G:
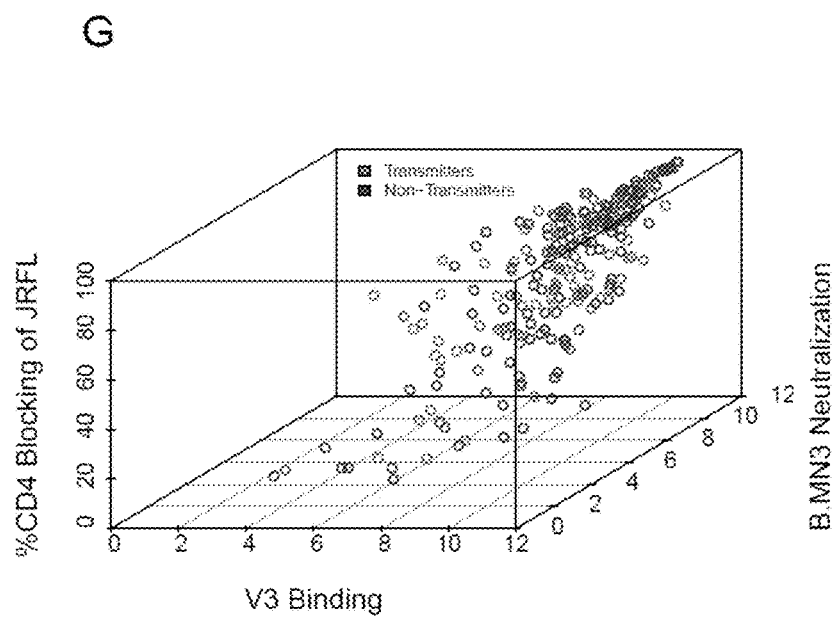

Because of the association with neutralization of tier 1 neutralization-sensitive viruses and the risk of peripartum transmission, we performed a post-hoc secondary analysis of the ability of maternal plasma to block soluble CD4 (sCD4) binding to three clade B HIV Env proteins (FIG. 1F and Table S5). A standard deviation increase in sCD4 blocking was a significant predictor of transmission risk with B.JRFL (FIG. 1F, OR: 0.70, p=0.014) and B.63521 (OR: 0.74, p=0.036). Interestingly, measures of sCD4 blocking, tier 1 virus neutralization (B.SF162), and B.V3 IgG binding in maternal plasma were highly correlated (FIG. 1G and Table S6). Moreover, these responses were co-linear in the prediction of MTCT risk, suggesting that the three activities tracked together in the HIV-infected pregnant women and may have contributed to or be a surrogate for the same underlying biologic mechanism that influences transmission outcome.

Figure 2A:
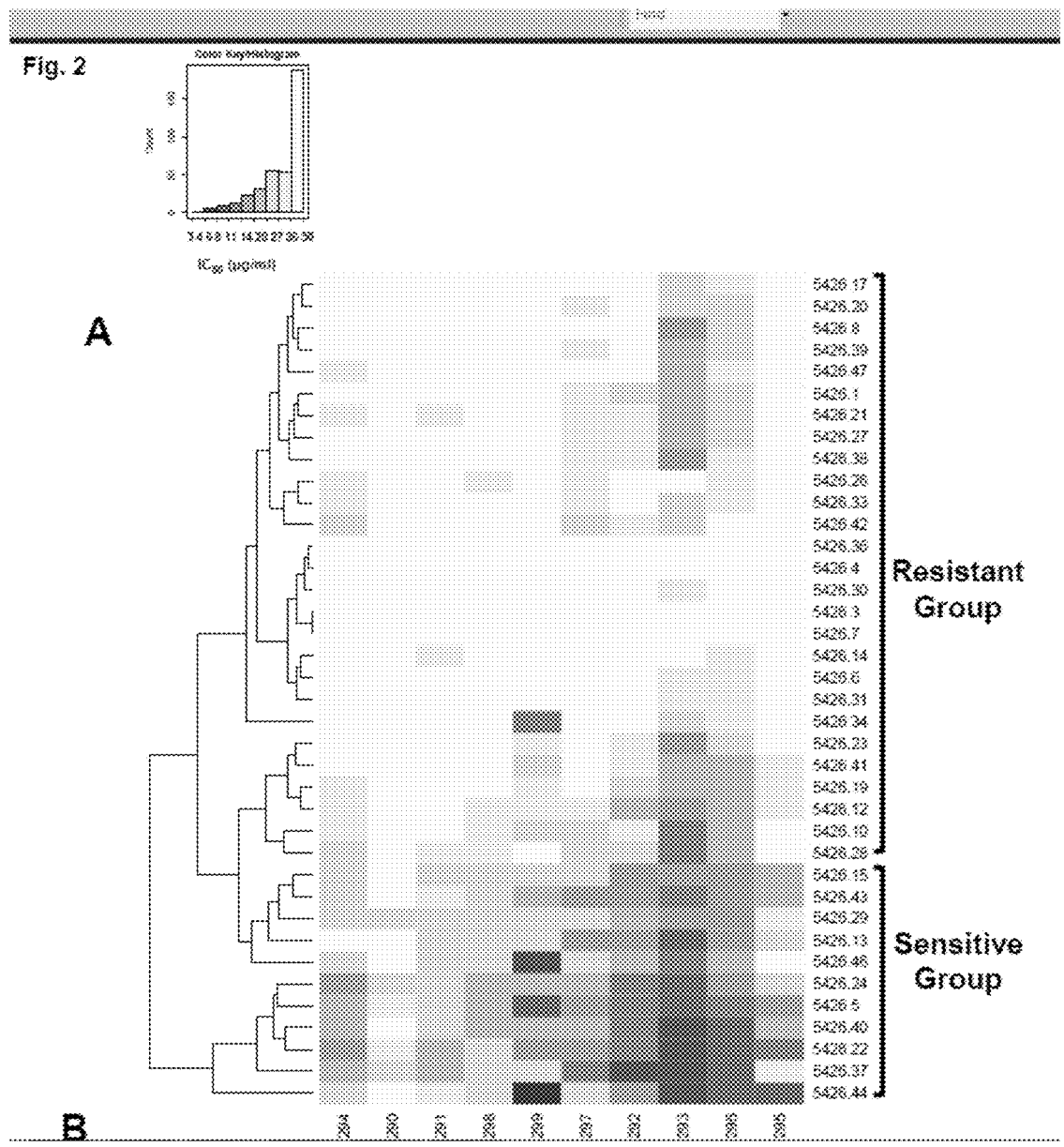
Figure 4:
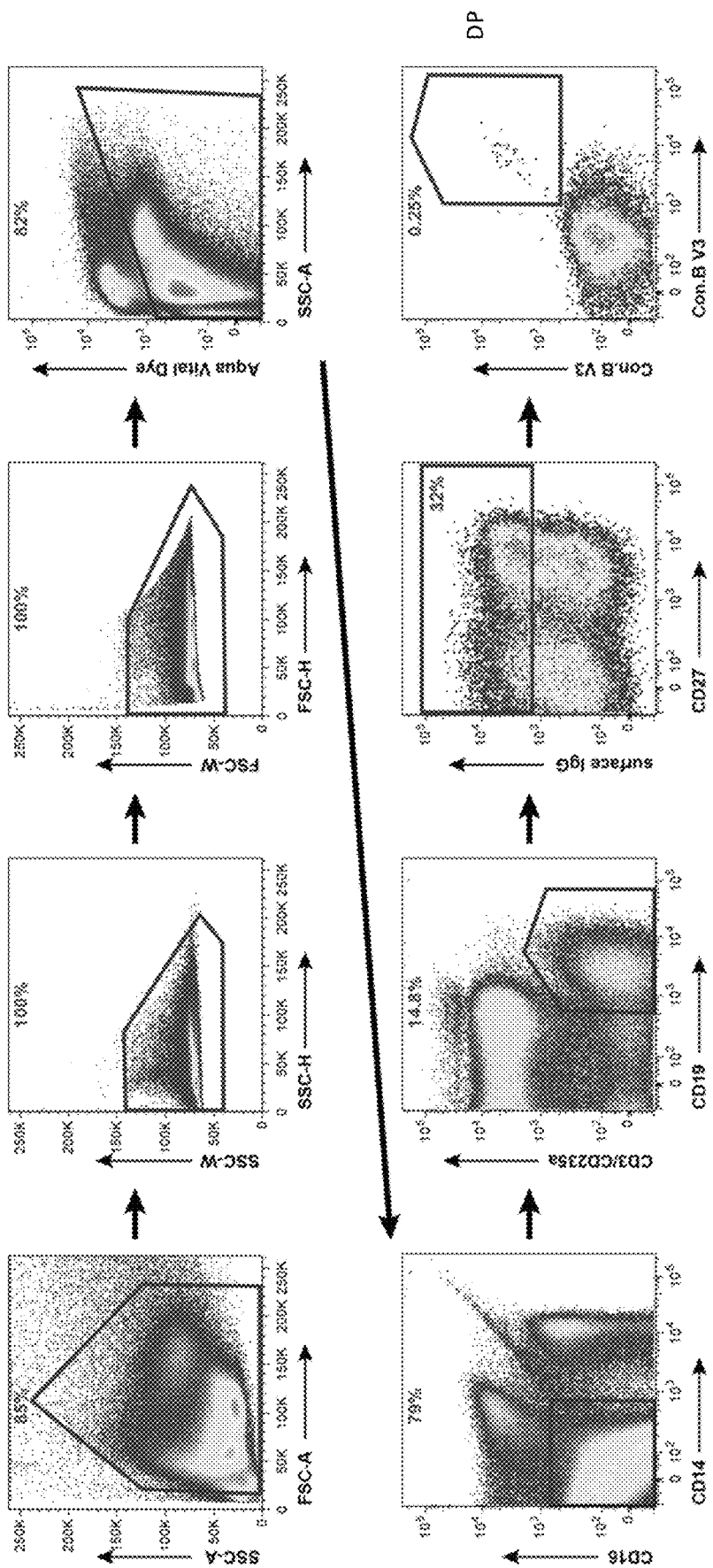
Figure 5:
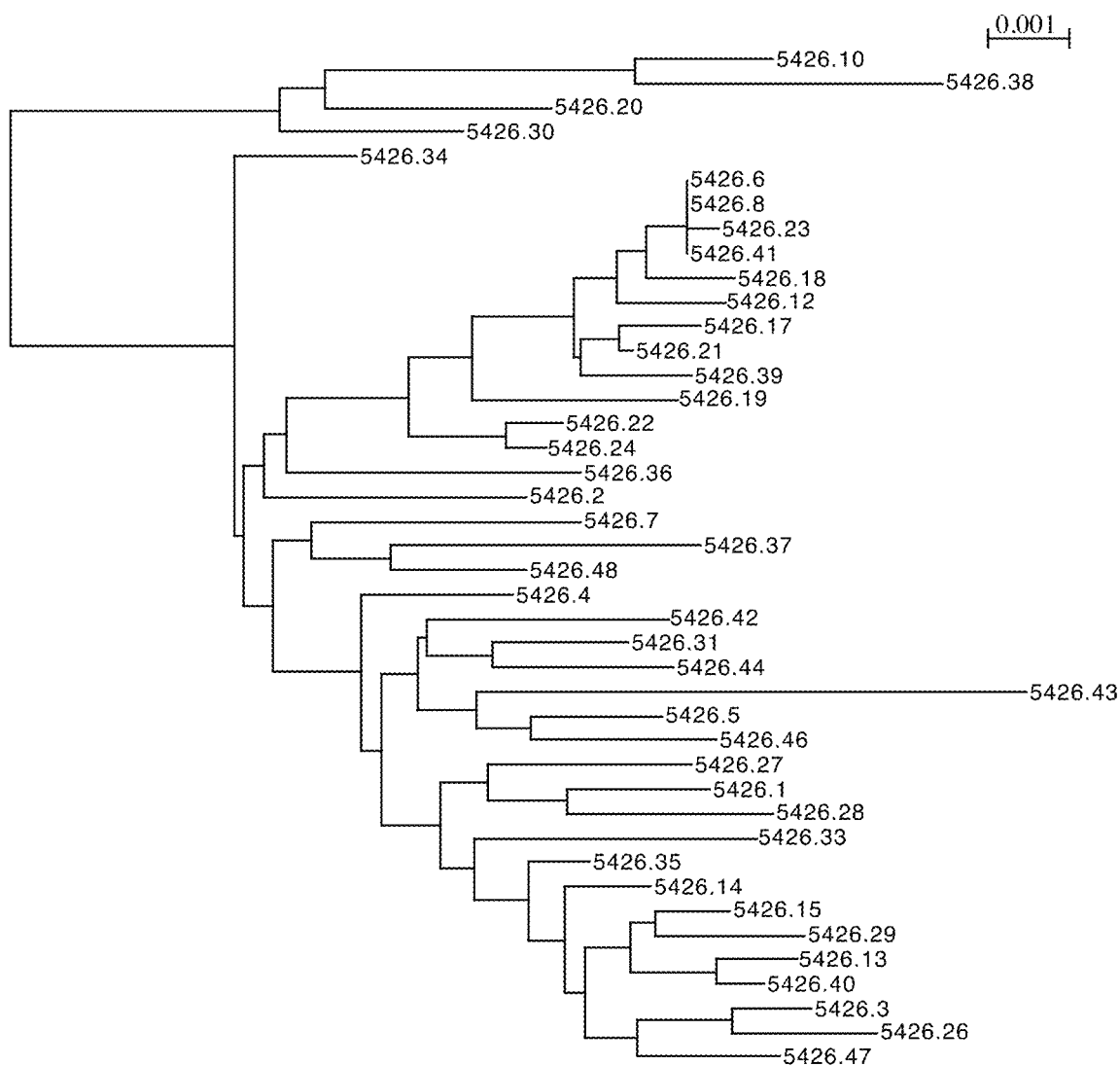
Figure 6A:
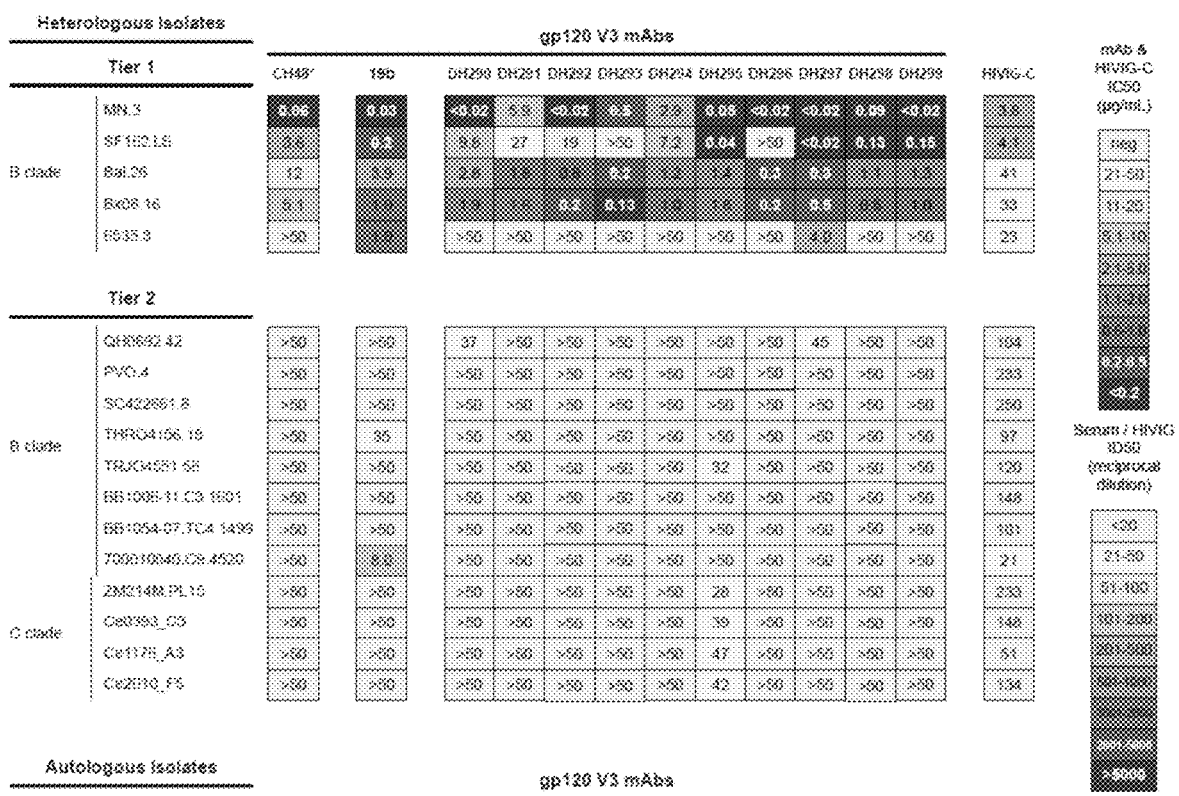
Figure 6B:
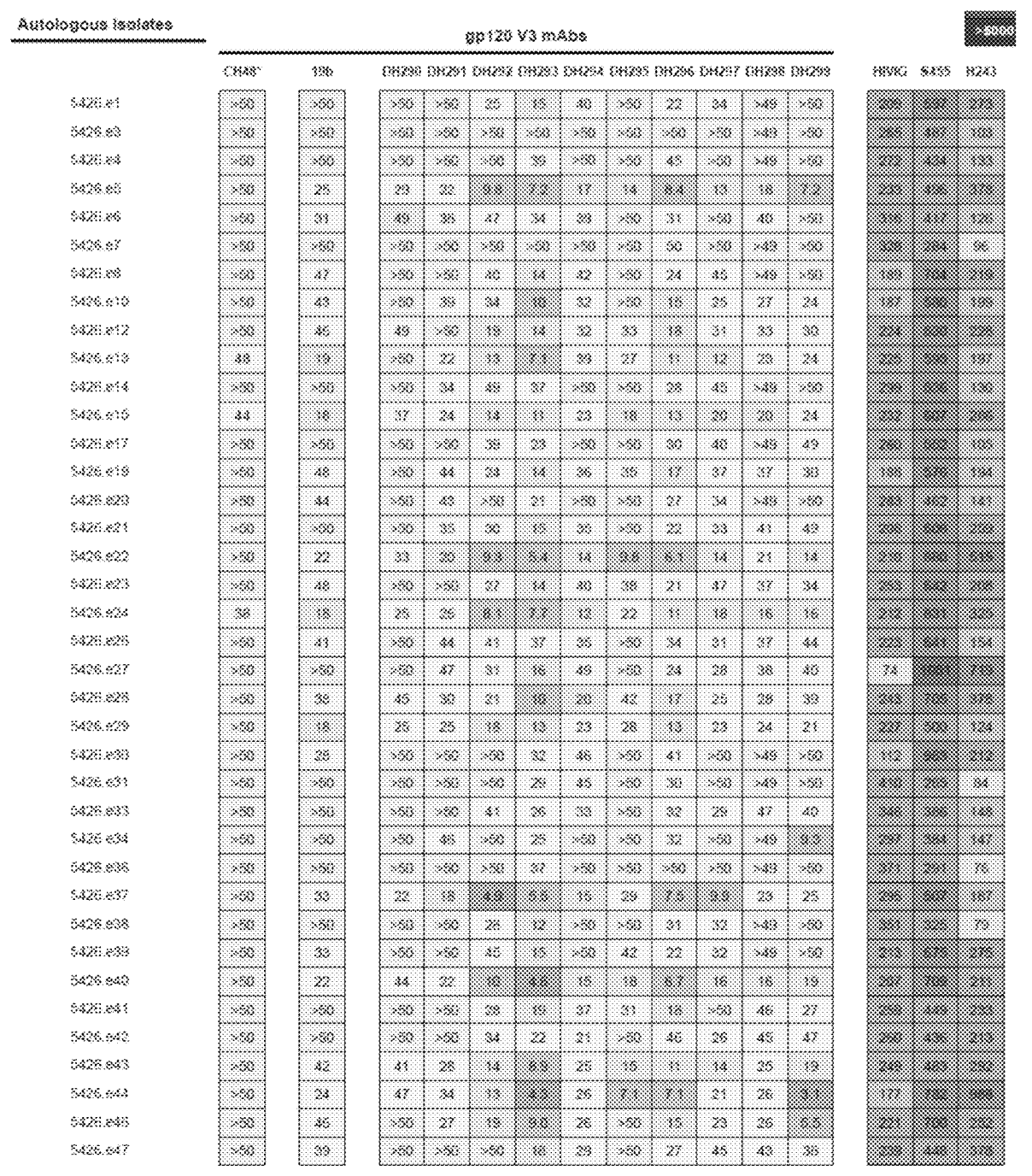
Figure 7:
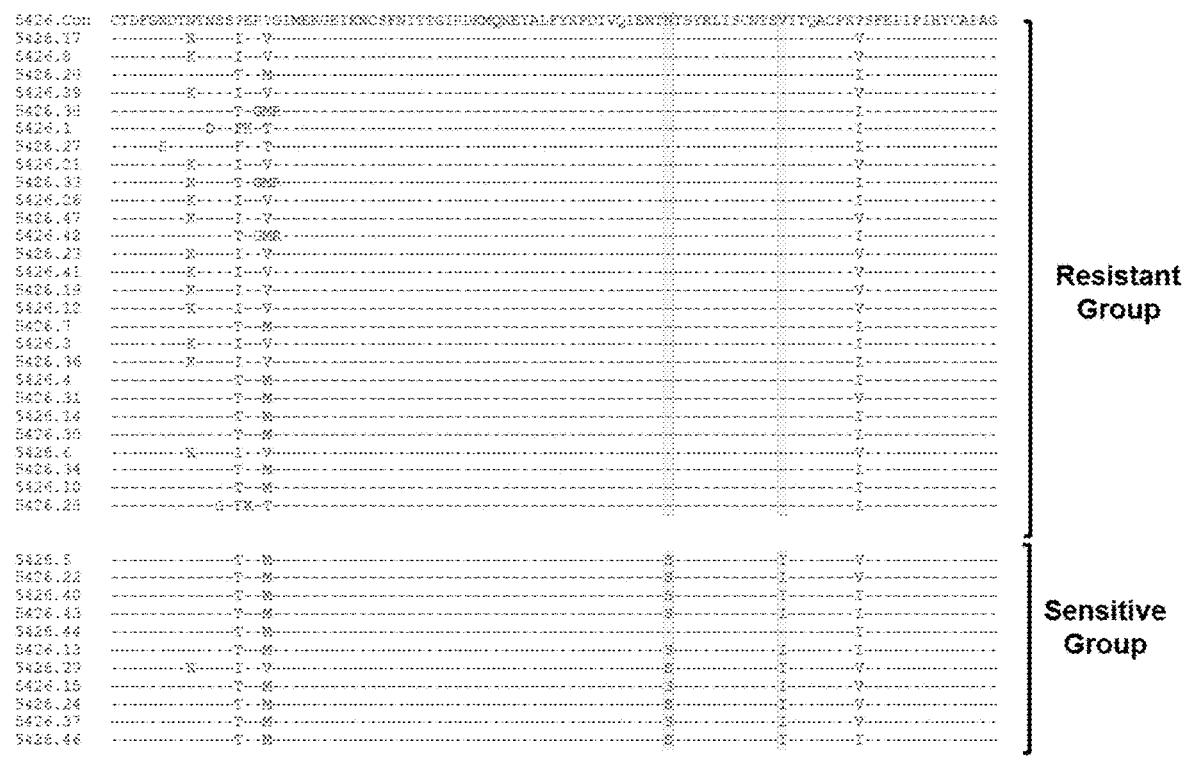

Finally, to directly ask if maternal V3-specific IgG antibodies can neutralize circulating autologous virus strains, we isolated and produced 10 recombinant V3-specific IgG monoclonal antibodies (mAbs) from blood memory B cells from a nontransmitting, HIV-1-infected mother (Table S7 and S8 and FIG. 4), and determined their ability in the TZM-bl pseudovirus neutralization assay to neutralize 38 single genome amplification-generated autologous HIV-1 env pseudoviruses from the same mother (FIG. 5). While the recombinant V3-specific IgG mAbs were able to neutralize only tier 1 (easy-to-neutralize) and not tier 2 (difficult-to-neutralize) heterologous HIV-1 strains, they were able to neutralize autologous maternal HIV-1 strains (FIG. 2), with 10 of 38 viruses neutralized by all 10 V3-specific autologous mAbs. The average number of isolated autologous viruses neutralized by the V3-specific mAbs was 25.6 (SD=7.8, 67.4%) with the mean $IC_{50}$ of 26.4 μg/ml (SD=12.1 μg/ml, $IC_{50}$ range of the V3-specific mAbs: 3.1-49.6 μg/ml). The neutralization sensitivity phenotype of all 38 autologous viruses was classified as an intermediate level of neutralization sensitivity (tier 1B) based on neutralization sensitivity to polyclonal heterologous HIVIG and serum of HIV-infected individuals (FIG. 6) (25). Yet, the neutralization sensitivity of the 38 viruses to autologous V3-specific antibodies fell into two distinct groups (FIG. 2), despite uniform V3 loop sequences among all the viruses. Interestingly, the group of viruses that was most sensitive to neutralization by the anti-V3 antibodies (FIG. 2A) shared two unique amino acid signatures: Ser188 in the V2 loop and Ile200 in the C2 region (FIG. 7). In fact, the Ser188 resulted in a move of a potential N-linked glycosylation site by three amino acids, potentially achieving better exposure of the V3 epitope. To test the hypothesis that these two unique amino acids altered neutralization sensitivity of the virus to the autologous V3-specific IgG mAbs, we generated three env mutants by introducing Ser and Ile at positions 188 and 200, individually or in combination, in a V3 mAb resistant env clone (5426.31). The N188S mutant remained resistant to maternal-derived V3-specific mAbs, while the V200I maternal viral mutant was slightly more sensitive to V3-specific mAbs than the wildtype maternal virus, 5426.31. However, the double env mutant with both N188S and V200I mutations was as sensitive to the V3-specific mAb as the sensitive viruses, directly demonstrating selection pressure on those two sites exerted by the autologous V3-specific antibodies (FIG. 2B).

For 21.5% of the mAb-virus combinations from this non-transmitting mother, the $IC_{50}$ of V3-specific mAbs against the autologous HIV-1 strains was $ID_{50} \leq 15$ μg/ml and for 78% of the combinations, the $IC_{50}$ was ≤37 μg/ml. A plasma anti-V3 IgG concentration of 37 μg/ml was the threshold that best correlated with transmission risk by the change point analysis; above this threshold, the risk of MTCT was 24%, whereas below this threshold, the risk of MTCT was 41%. Although, this particular threshold analysis did not reach statistical significance (p=0.1).

Thus, in this study, we have demonstrated that levels of IgG against the HIV-1 Env gp120 V3 loop inversely correlated with decreased MTCT risk. Our exploratory analyses also raised the hypotheses that antibodies targeted to the CD4 binding site and tier 1 virus neutralizing antibodies correlated as well with decreased MTCT risk, suggesting the hypothesis that these common HIV-specific antibody types can prevent MTCT.

It is well-established that commonly-induced antibodies that only neutralize tier 1 HIV-1 strains do not neutralize the majority of heterologous HIV-1 variants and do not protect in the setting of HIV-1 transmission (26, 27). Therefore, it was initially surprising that our primary and exploratory MTCT correlates analyses revealed that tier 1 virus-neutralizing and V3 and CD4 binding site-specific IgG antibodies were correlates of decreased MTCT risk. However, it is highly relevant to the MTCT setting that Moody et al. have demonstrated neutralizing capacity of both V3 and CD4 binding site-specific antibodies for concomitant autologous virus strains (Moody et al, co-submitted with this manuscript). Moreover, supporting this hypothesis, in this current paper, our isolated maternal V3-specific IgG antibodies exerted selection pressure and neutralized circulating autologous maternal virus strains at $IC_{50}$s compatible with concentrations associated with decreased MTCT risk. Nonetheless, it is important to caution that measuring maternal V3-binding IgG responses may be a surrogate for multiple antibodies of distinct effector functions competing for overlapping epitopes or for an as yet unmeasured anti-viral function.

Notably, our study of humoral immune correlates of MTCT did not identify that Env V1V2-specific IgG responses as a correlate of risk in MTCT, in spite of this response being associated with a reduced risk of infection in the RV144 HIV-1 vaccine efficacy trial (20). Differences in the type of viruses transmitted (autologous vs heterologous) and the infection routes between the RV144 and MTCT cohorts likely contributed to the observed differences in correlates of risk. As expected, we did not find a correlation with infant infection risk and the maternal clade B-modified Env IgA score, because infants acquire maternal IgG via the placenta in utero, but do not other antibody isotypes by this route (28). Thus, the lack of both a correlation of maternal Env plasma IgA responses with MTCT risk and lack of an interaction between maternal Env-specific IgA and IgG responses in the prediction of MTCT may be explained by the absence of maternally-acquired plasma IgA in the infant.

Finally, it is likely that immunologic interventions will be required to bolster the current antiretroviral-based MTCT prevention methods and achieve a generation free of HIV-1(2, 3). We have previously shown that immunization of HIV-1-infected individuals with a V3 peptide immunogen can boost tier 1 virus neutralizing antibodies (29) although the ability of pregnant HIV-1-infected women to respond to Env vaccination remains to be shown (30). Our current study raises the hypothesis that augmentation of V3 and CD4 binding site-specific neutralizing antibodies by Env vaccination of HIV-1-infected pregnant women is a plausible strategy to effectively reduce the risk of MTCT of HIV-1.

REFERENCES

1. C. S. Chasela et al., *N Engl J Med* 362, 2271 (Jun. 17, 2010).
2. G. G. Fouda et al., *J Infect Dis*, (Aug. 27, 2014).
3. G. E. Gray, L. Corey, *J Infect Dis*, (Aug. 27, 2014).
4. P. Rossi et al., *Proc Natl Acad Sci USA* 86, 8055 (October, 1989).
5. P. A. Broliden et al., *Aids* 3, 577 (September, 1989).
6. G. Pancino et al., *J Infect Dis* 177, 1737 (June, 1998).
7. H. Guevara et al., *J Acquir Immune Defic Syndr* 29, 435 (Apr. 15, 2002).
8. R. B. Markham et al., *Lancet* 343, 390 (Feb. 12, 1994).
9. K. E. Ugen et al., *J Clin Invest* 89, 1923 (June, 1992).
10. L. Diomede et al., *J Virol* 86, 4129 (April, 2012).
11. G. Scarlatti et al., *Aids* 7 Suppl 2, S45 (November, 1993).
12. E. Baan et al., *PLoS One* 8, e69274 (2013).
13. R. Dickover et al., *J Virol* 80, 6525 (July, 2006).
14. X. Wu et al., *J Virol* 80, 835 (January, 2006).
15. S. M. Rainwater et al., *Curr HIV Res* 5, 189 (March, 2007).
16. E. S. Russell et al., *J Virol* 85, 8253 (August, 2011).
17. S. Thenin et al., *Virology* 426, 12 (Apr. 25, 2012).
18. A. Chaillon et al., *J Virol* 86, 10540 (October, 2012).
19. J. B. Lynch et al., *J Virol* 85, 5252 (June, 2011).
20. B. F. Haynes et al., *N Engl J Med* 366, 1275 (Apr. 5, 2012).
21. R. Gottardo et al., *PLoS One* 8, e75665 (2013).
22. G. D. Tomaras et al., *Proc Natl Acad Sci USA* 110, 9019 (May 28, 2013).
23. S. A. Plotkin, *Clin Infect Dis* 47, 401 (Aug. 1, 2008).
24. K. C. Rich et al., *Pediatrics* 105, e8 (January, 2000).
25. M. S. Seaman et al., *J Virol* 84, 1439 (February, 2010).
26. P. Gilbert et al., *J Infect Dis* 202, 595 (Aug. 15, 2010).
27. P. Pitisuttithum et al., *J Infect Dis* 194, 1661 (Dec. 15, 2006).
28. A. Malek, R. Sager, P. Kuhn, K. H. Nicolaides, H. Schneider, *Am J Reprod Immunol* 36, 248 (November, 1996).
29. J. A. Bartlett et al., *Aids* 12, 1291 (Jul. 30, 1998).
30. P. F. Wright et al., *J Infect Dis* 180, 1080 (October, 1999).

Study Design

Inclusion criteria for the selection of HIV-1-infected women from the WITS cohort included: no documented antiretroviral treatment during pregnancy/delivery, detectable plasma virus load during pregnancy (>50 copies/ml), and non-heparin plasma and serum samples available for immune assays collected between 25 weeks of gestation and two months postpartum. Eighty-five HIV-transmitting mothers were eligible. The control, non-transmitting group of HIV-infected mothers were selected at a 1:2 case:control ratio (n=170) using propensity score matching (1, 2) for the following parameters: maternal plasma virus load, peripheral CD4+ T cell count at delivery (or the pregnancy timepoint closest to delivery), mode of delivery (caesarian section vs vaginal delivery), and infant gestational age (based on estimated delivery date) (3, 4). The post-matching clinical characteristics of the continuous variables (plasma viral load, CD4 count, gestational age) were compared by student's t test and birth type was compared by Chi squared test (Table 1). Four non-transmitting and 3 transmitting subjects were removed following matching due to lack of adequate sample, and one non-transmitting subject was removed due to the detection of antiretroviral drug in the plasma. As no breastfeeding occurred in this population, all transmission events were in utero or peripartum (5). Thirteen percent of the infected infants in the HIV-transmitting group were infected in utero and 52% were infected peripartum, the remaining 35% did not have a perinatal transmission mode retrospectively defined due to lack of infant birth sample availability.

Selection of Humoral Immune Response Variables

The five types of primary humoral immune assays that were selected for the RV144 immune correlate analysis ("clade B modified RV144 model"): Env V1V2 IgG binding, Env IgA binding breadth, Env IgG avidity, ADCC, neutralization (6) were tailored to focus on clade B Env antigens/viruses and analyzed together in an RV144 clade B-modified humoral immune response model. We also selected additional humoral immune assays to assess antibody responses that had previously been implicated to play a role in MTCT ("MTCT model") including gp120 IgG binding, gp41 IgG binding, V3 IgG binding, and gp41 IgA binding (7-16) and analyzed them in parallel.

Statistical Analysis

The statistical analysis plan was finalized prior to data analysis. We used multivariable logistic regression with transmission status as the dependent variable (17). All continuous immune response variables were mean-centered and scaled to one so that the estimated odds ratios were all per one standard deviation increment. All regression analyses were adjusted for delivery mode, log maternal plasma viral load, infant gestational age, and peripheral CD4+ T cell count. In primary analyses, we applied multivariable logistic regression models for both the primary analysis of the six RV144-adapted humoral immune variables and four MTCT-related humoral immune variables in parallel. Combined immune variable scores (Env-binding IgA, neutralization, V3 binding IgG) were defined as a weighted combination of multiple immune response variables (18). We also used change point models to model the threshold of the association between identified immune correlates of risk and the transmission status (Fong, Yet al 2013, Fred Hutchison Technical Report, works.bepress dot com/yfong/ID. In secondary analyses, each individual humoral immune response measured in this cohort was studied in logistic regression models. To correct for multiplicity, we applied a false discovery rate (q value) (19), setting a significance threshold of p<0.05, and q<0.2 (6). This approach optimizes the hypothesis-generating discovery of immune correlates at the expense of a 20% false positivity rate. In light of the results from this study and in Moody et al, a post-hoc analysis was performed using CD4 blocking assay results for the antigens B.JRFL, B.63521 and B.6240 as predictors in multivariable logistic regression models predicting transmission status adjusting for delivery mode, log maternal plasma viral load, infant gestational age, and peripheral CD4+ T cell count. No multiple comparison adjustments were performed.

Definition of Score Variables

Each score was defined similarly as a weighted combination of multiple immune response variables. For example, to define the Env IgA score, we first scaled each IgA binding variable to have standard deviation of one. Then we computed a weight designed to maximize the diversity of the signals contained in all the Env-binding IgA variables (6, 18).

Missing Data

Neutralization score was missing in six subjects due to limited sample volume. Missing clinical variables included: 8 subjects did not have delivery mode, 11 subjects did not have viral load and 1 subject did not have infant gestational age. We took a multiple imputation approach to handle the missing data in the primary analysis. Twenty imputation datasets were carried out (20) and the regression results across the 20 datasets were combined with the help of the R package mitools from the Comprehensive R Archive Network (CRAN) to properly account for the uncertainty in the regression coefficient estimates (21). Comparing multiple imputation results with single imputation results, we saw that the two results were nearly identical except for the odds ratio and p value for the neutralization score, which needed to be imputed. As such, in the secondary analysis, we used a single dataset with imputed clinical variables and, when studying the impact of the neutralization variables, excluded subjects with missing neutralization variables.

Post-Matching Cohort Characteristics

Analysis of the post-matching transmitting and non-transmitting cohort revealed no significant differences in the peripheral CD4+ T cell count, plasma virus load, mode of delivery or gestational age (Table 1). Moreover, the year in which the case and control subjects were enrolled was equally distributed. While the available plasma sample that was closest to delivery was selected in all subjects, the distribution of the peripartum visit at which maternal plasma was available differed between the transmitting and non-transmitting subjects (Table 1), with 46% of transmitting mothers with plasma available from the delivery time point, and only 10% of non-transmitting women with plasma available from delivery. Thus, we performed a pilot study that assessed Env IgG and IgA binding, Env-specific IgG avidity, ADCC, and neutralization score in 24 HIV-infected pregnant women with two samples available during the study window. The humoral Env-specific antibody responses were then compared between the earlier and later timepoints by student's t test. The overwhelming majority of antibody responses were not statistically different between peripartum timepoints (Table S1). However, we detected slightly higher IgG responses against the clade B scaffolded V1V2 antigens in the $2^{nd}$ trimester compared to $3^{rd}$ trimester (fold difference in mean OD: 0.18, p=0.04 for gp70 case A2 V1V2 and 0.15, p=0.01 for gp70 case A2 V1V2 V169K) and more potent neutralization of the tier 1 strain SF162 (fold difference in mean $ID_{50}$: 1.45, p<0.001 for NAb SF162) between $3^{rd}$ trimester and delivery, but these differences did not persist when comparing across other visit windows (Table S1 and FIG. 3). Thus, we selected the maternal plasma sample that was closest for delivery for all subjects for the main study.

Humoral Env-Specific Response Assays

All assays were performed blinded to transmission status. Maternal samples were aliquoted for each assay in an observed, quality-controlled manner (Duke CFAR GCLP-Compliant AIDS Program) to avoid aliquoting mistakes.

Env and V1V2 Binding IgG ELISA

Plate-based binding IgG ELISA to scaffolded (gp70) and avi-tagged V1V2 proteins and MN gp41 and gp120 were performed as follows. Direct binding ELISAs were conducted in 384 well ELISA plates (Costar) coated with 2 ug/ml antigen in 0.1M sodium bicarbonate and blocked with assay diluent (PBS containing 4% (w/v) whey protein/15% Normal Goat Serum/0.5% Tween-20/0.05% Sodium Azide). Duplicate sera were incubated for 90 min in three fold serial dilutions beginning at 1:33.3 followed by washing with PBS/0.1% Tween-20. 10 ul HRP conjugated goat anti-human secondary antibody (Jackson ImmunoResearch C:109-035-008) was diluted to 1:10,000 in assay diluent without azide, incubated at for 1 hour, washed and detected with 20 ul SureBlue Reserve (KPL 53-00-03) for 15 minutes. Reaction was stopped with the addition of 20 ul HCL stop solution. Plates were read at 450 nm. The plasma dilution with the majority of samples in the linear range (optical density (OD) between 0.5 and 3.5) was determined for each antigen in the pilot study (1:100 for V1V2 antigens, 1:72900 for MN gp41, and 1:8100 for MN gp120) and the OD at the selected dilution was analyzed. To improve the precision of the summary measure, a five-parameter logistic curve was fitted to the dilution series for each subject using the R package nCal from the Comprehensive R Archive Network (CRAN) (21), the fitted OD at the selected dilution was taken to be the readout for the subject. The IgG response against the MuLV gp70 scaffold control was determined and the variance of the V1V2 IgG response was similar with and without subtraction of the gp70 response; therefore, the gp70 response was not subtracted from the gp70 V1V2 IgG responses, similar to the analysis that was done for the RV144 immune correlate analysis (6). A panel of negative control sera was included for each antigen.

Env IgA and V3 IgG Binding Antibody Multiplex Assays (BAMA)

BAMA for IgA were performed as previously described (6, 22-24) after IgG depletion from maternal plasma/sera. The multiclade panel of consensus and primary Env gp120 and gp140 antigens, MN gp41, consensus C1 and V3 peptides were covalently coupled to carboxylated fluorescent beads and incubated with the plasma/sera at predetermined dilutions of 1:30 (used for analysis of gp120 and C1 antigens), 1:90 (used for analysis of gp41 and gp140 antigens), 1:2500 (V3 peptides), and 1:500 (MLV gp70-scaffolded B. MN V3 protein) and was detected with a PE-conjugated goat anti-human IgA antibody (Jackson Immunoresearch) at 4 µg/ml, or with a PE-conjugated goat anti-human IgG (Southern Biotech) at 2 µg/ml. Antibody measurements were acquired on the Bio-Plex instrument (Bio-Rad) and the readout was expressed in median fluorescent intensity (MFI). Positive control polyclonal (HIVIG) and/or monoclonal antibodies were included in each assay to ensure specificity, consistency and reproducibility between assays. Negative controls included in every assay were blank beads and HIV-1 negative sera. The preset assay criteria for sample reporting were: coefficient of variation (CV) for duplicate values ≤20% for the IgA and ≤15% for the V3 assays and >100 beads counted per sample. To control for reproducibility and Env protein performance, we used a preset criteria that the positive control titer (HIVIG) included in each assay had to be +/− three standard deviations of the mean for each antigen, tracked with Levy Jennings plot calculated with a four-parameter logistic equation (Sigma plot, Systat Software). We then assessed the concentration of the V3-specific IgG antibodies by measuring the response the against the clade B V3 linear peptide, sequence: Bio-V3.B Bio-KKKNNTRKSI-HIGPGRAFYATGDIIGDIRQAHC_ (SEQ ID NO: 2) at an optimized plasma dilution of 1:31,250 to the known concentration of a serial diluted anti-V3 specific monoclonal antibody standard that was isolated from an RV144 vaccine recipient, CH22 mAb (25). The concentration was calculated by nonlinear calibration using the five parameter logistic model using the R package nCal (21).

Surface Plasmon Resonance (SPR) Measurements of Plasma IgG Avidity

Using the multiplex array format, purified plasma IgG avidity was measured on a BIAcore 4000 instrument (BIAcore/GE Healthcare). Using a Series S CM5 chip (BIAcore/GE Healthcare) 6000-16000 RU of gp120 and gp140 envelope proteins were immobilized through amine coupled directly on the chip surface. For biotinylated V1V2 proteins (C.1086.V1V2, B.caseA2.V1V2, B.CaseA2 V1V2N156QN160Q), the Series S CM5 chip first had 1400-2500 RU of Streptavidin immobilized onto the surface, then the biotinylated V1V2 proteins were then immobilized through Streptavidin/Biotin interaction and immobilized between 1350-1600 RU. All proteins were immobilized in duplicate spots on the chip. Purified plasma IgG at 200 ug/mL was flowed over the chip at 30 uL/min for 150 s and allowed to dissociate for 600 s. Regeneration of the surface was performed using Glycine pH 2.0 flowing over the surface for 30 s two times. Non-specific interactions were subtracted out using the negative control respiratory syncytial virus (RSV) mAb palivizumab flowed over each surface. Antigen surface activity was monitored by flowing the positive control mAbs CH58 and A32 at 10 µg/mL. Antigen surface decay was monitored by running CH58 and A32 every 20 cycles throughout the entire run and was used to normalize the purified plasma IgG response. Data analysis was performed using BIAcore 4000 evaluation and BIAcore evaluation 4.1 software (BIAcore/GE Helathcare). Data analysis and Avidity score calculation was done as previously described (6). In order to primarily assess avidity to epitopes of broadly neutralizing antibodies, avidity against the clade B Env B.6420 gp140 was selected as the primary avidity variable based on the ability of the B.6420 gp120 to bind to broadly HIV-neutralizing mAbs, including the V2-specific monoclonal antibody PG9 (32.1 nM), but not the nonbroadly-neutralizing V2-specific monoclonal antibody CH58 (26).

ADCC

HIV-1 reporter viruses used in ADCC assays were replication-competent infectious molecular clones (IMC) designed to encode the SF162.LS (accession number EU123924) or the transmitted/founder WITO.c (accession number JN944948) subtype B env genes in cis within an isogenic backbone that also expresses the Renilla luciferase reporter gene and preserves all viral orfs. The Env-IMC-LucR viruses used were NL-LucR.T2A-SF162.ecto (IMC$_{SF162}$) and NL-LucR.T2A-WITO.ecto (IMC$_{WITO}$) (27). IMCs were titrated in order to achieve maximum expression within 72 hours post-infection by detection of Luciferase activity and intra-cellular p24 expression. We infected CEM.NKR$_{CCR5}$ cells (NIH AIDS Research and Reference Reagent Repository) with IMC$_{SF162}$ and IMC$_{WITO}$ by incubation with the appropriate TCID$_{50}$/cell dose of IMC for 0.5 hour at 37° C. and 5% CO$_2$ in presence of DEAE-Dextran (7.5 µg/ml). The cells were subsequently resuspended at 0.5×10$^6$/ml and cultured for 72 hours in complete medium containing 7.5 µg/ml DEAE-Dextran. The infection was monitored by measuring the frequency of cells expressing intracellular p24. Assays performed using the IMC-infected target cells were considered reliable if the percentage of viable p24$^+$ target cells was ≥20% on assay day.

A luciferase-based ADCC assay was performed as previously described (26). Briefly, HIV-1 IMC$_{SF162}$ and IMC$_{WITO}$ infected CEM.NKR$_{CCR5}$ cells were used as targets. Whole PBMC obtained from a HIV seronegative donor with the F/V Fc-gamma Receptor (FcRγ) IIIa phenotype were used as the source of NK effector cells. After overnight resting, the PBMC were used as effector cells at an effector to target ratio of 30:1. The target and effector cells were incubated in the presence of 5-fold serial concentrations of plasma starting at 1:50 dilution for 6 hours at 37° C. in 5% CO$_2$. The final read-out was the luminescence intensity generated by the presence of residual intact target cells that have not been lysed by the effector population in presence of ADCC-mediating mAb. The % of killing was calculated using the formula:

$$\% \text{ killing} = \frac{(RLU \text{ of Target} + \text{Effector well}) - (RLU \text{ of test well})}{RLU \text{ of Target} + \text{Effector well}} \times 100$$

In this analysis, the RLU of the target plus effector wells represents spontaneous lysis in absence of any source of Ab. Plasma samples collected from a HIV-1 seronegative and seropositive donor were used as negative and positive control samples, respectively, in each assay.

Neutralization

Neutralization was performed with heat-inactivated plasma or sera or recombinantly-produced monoclonal antibodies as previously described (28) using Tat-regulated Luc reporter gene expression to quantify reductions in virus infection in TZM-bl cells (NIH AIDS Reagent Program, contributed by John Kappes and Xiaoyn Wu). For the MTCT immune correlate study, two clade B tier 1A (B.MN.3, B.SF162.LS), four tier 1B (B.Bal.26, B.SS1196.1, B.6535.3, B.1012.11TC21), four tier 2 (B.AC10.0.29, B.REJO4541.67, B.RHPA4259.7, B.WITO4160.33) Env pseudovirions produced in 293T cells were selected for the neutralization panel. The tier 1 and 2 variants were selected based on their ability to be differentially neutralized by a panel of HIV-neutralizing sera (29), potentially representing distinct neutralization epitope targets. Twelve three fold dilutions of plasma starting at 1:40 were included, yet target cell toxicity of some of the samples limited detection of neutralization below 1:100, and thus our cut off of detection was set at 1:100 for all plasma samples and viruses. Autologous V3-specific IgG antibodies were tested for neutralization against autologous env pseudovirus variants starting at a concentration of 50 µg/ml. The neutralization titer is reported as the dilution or concentration at which the relative luminescence units were reduced by 50% (inhibitory dose or concentration 50%, ID$_{50}$ or IC$_{50}$) compared to the RLU in virus control wells. Any sample with an ID$_{50}$<100 was set to 50. Plasma samples that had neutralizing activity against a nonspecific retrovirus (Murine Leukemia Virus, SVA.MLV) were tested for the presence of antiretroviral drugs and if detected, the subject was removed from the study (n=1 nontransmitter). Inadequate plasma volume was available for the neutralization panel in 6 subjects, so these subjects did not have a neutralization score assigned. All other assays were performed on all study subjects.

Soluble CD4 Plasma Blocking Assays

Similar to the previously-described soluble CD4 (sCD4) blocking assay (30), 384 well ELISA plates (Costar #3700) were coated with 30 ng/well of each HIV-1 Env (B.JRFL, B.6240, B.63521) overnight at 4° C. and blocked with assay diluent (PBS containing 4% (w/v) whey protein/15% Normal Goat Serum/0.5% Tween20/0.05% Sodium Azide) for 1 hour at room temperature. All assay steps were conducted in assay diluent (except substrate) and incubated for 1.5 hours at room temperature followed by washing with PBS/0.1% Tween-20. Plasma samples were diluted 1:50 and incubated in triplicate wells. To measure plasma antibody sCD4 binding site blocking, 10 µl of a predetermined saturating concentration of sCD4 (Progenics Pharm Inc., 0.64 µg/ml) was added following the plasma incubation step. sCD4 binding was detected by 1 hour incubations with biotinylated anti-CD4 mAb OKT4 (0.015 µg/ml) and streptavidin-HRP at 1:30,000 dilution followed by TMB substrate. Plates were read with a plate reader at 450 nm. Triplicate wells were background subtracted and averaged. Percent inhibition was calculated as follows: 100−(plasma triplicate mean/no plasma control mean)*100.

Generation of Full Length Env Sequences and Env Pseudovirion Production from Maternal Plasma Viral RNA (vRNA) was prepared from plasma samples (500 µL) using the EZ1Virus Mini Kit V2.0 on BIO ROBOT EZ1 (Qiagen; Valencia, Calif.). Reverse transcription was performed with 20 µL of vRNA and 80 pmol primer 1.R3.B3R (5'-ACTACTTGAAGCACTCAAGGCAAGC-TTTATTG-3' (SEQ ID NO: 6); HXB2 nt9611-9642) in 50 µL using Superscript III (Invitrogen; Carlsbad, Calif.). The complete env genome was amplified by single genome amplification (SGA) using OFM19 (5'-GCACTCAAGG-CAAGCTTTATTGAGGCTTA-3' (SEQ ID NO: 7); nt9604-9632) and VIF1 (5'-GGGTTTATTACAGGGACAG-CAGAG -3' (SEQ ID NO: 8); nt4900-4923) as first round primers, and env1A (5'-GGCTTAGGCATCTCCTAT-GGCAGGAAGAA-3' (SEQ ID NO: 9); nt5954-5982) and envN (5'-CTGCCAATCAGGGAAGTAGCCTTGTGT3'-(SEQ ID NO: 10); nt9145-9171) as the second round primers. The PCR thermocycling conditions were as follows: one cycle at 94° C. for 2 minutes; 35 cycles of a denaturing step at 94° C. for 15 seconds, an annealing step at 55° C. for 30 second, an extension step at 68° C. for 4 minutes; and one cycle of an additional extension at 68° C. for 10 minutes. The PCR products were purified with the QiaQuick PCR Purification kit (Qiagen; Valencia, Calif.). The SGA amplicons were directly sequenced by the cycle sequencing and dye terminator methods on an ABI 3730xl genetic analyzer (Applied Biosystems, Foster City, Calif.). Individual sequences were assembled and edited using Sequencher 4.7 (Gene Codes, Ann Arbor, Mich.). The sequences were aligned and the manual adjusted for optimal alignment using Seaview. The Neighbor-joining (NJ) tree was constructed using the Kimura 2-parameter model. The CMV promoter was added to the 5' end of each env gene amplified by SGA using the promoter addition PCR (pPCR) method as described (31). Env mutants containing single or double mutants that were associated with neutralization susceptibility changes were constructed using the Quick Change 11 Site-Directed Mutagenesis kit (Agilent Technologies, Santa Clara, Calif.). All final env mutants were confirmed by sequencing. The Env pPCR products and mutant were used for generation of pseudoviruses by cotransfecting with the env-deficient HIV-1 backbone pSG3Δenv into 293T cells in a 6-well tissue culture plate using FuGENE6 transfection reagent (Roche Diagnostics; Indianapolis, Ind.). The pPCR product was used for generation of pseudoviruses by cotransfecting with the env-deficient HIV-1 backbone pSG3Δenv into 293T cells in a 6-well tissue culture plate using FuGENE6 transfection reagent (Roche Diagnostics; Indianapolis, Ind.). Transfected cells were maintained in DMEM with 10% FBS at 37° C. with 5% CO2. Forty-eight hours after transfection, supernatants were harvested and stored in 20% FBS medium at −80° C. Neutralization sensitivity (tier designation) of the env pseudoviruses was determined by assessing neutralization potency by HIVIG and plasma samples from HIV-infected individuals with established neutralization potency (H243 and S455) against the panel of autologous viruses in the TZM-bl neutralization assay. The heat map demonstrating the hierarchical neutralization sensitivity of the virus variants was produced using tools available from www.lanl.gov/content/sequence/HEAT-MAP/heatmap.html.

Isolation of B.Con V3 Tetramer-Specific B Cells and Monoclonal Antibody Production Peripheral Env V3-specific IgG-expressing memory B cell isolation from a nontransmitting mother at six months postpartum was performed as described (32-34) with the following modifications. Thawed PBMCs were stained with a viability marker (Aqua Vital Dye-Life technologies-L34957), SAV-AF647 (Life technologies-S21374), SAV-BV421 (BioLegend-405225) labeled-tetramers and the following antibodies: CD27 PE-Cy7 (eBioscience), anti-IgG FITC (Jackson Immuno Research), IgD PE, CD19 APC-Cy7, CD3 PE-Cy5, CD235a PE-Cy5 (BD Pharmingen), CD14 BV605, CD16 BV570 (Sony/iCyt), CD10 ECD, CD38 APC AF700 (Beckman Coulter). Total B cells were gated as viable (Aqua Vital Dye negative) CD14/CD16 and CD3/CD235a negative, and CD19+. Env V3-specific, IgG-expressing memory B cells were further selected by gating for IgG+ and Con.B V3 peptide tetramer +/+ cells using dual color antigen-specific labeling (SAV-AF647 and SAV-BV421). Flow cytometric data was acquired on a BD FACS Arian (BD Biosciences) at the time of sorting and the data analyzed using FlowJo (Tree Star Inc). The double positive tetramer stained cell. Cell sorting of this population was performed using a FACSAria2 (BD Biosciences) as single-cells into 96-well plates precharged with an RNA stabilization cocktail and subjected to immunoglobulin gene RNA amplification, as previously described (35). Immunoglobulin gene analysis was performed as previously described (36). Overlapping PCR was used to construct full length IgG1 (for heavy chain) and kappa or lambda (for light chain) cassettes for expression of recombinant antibodies (35). Transiently-transfected antibodies were tested for Env V3 binding against a panel of consensus V3 peptides and MLVgp70-scaffolded V3 antigens by ELISA (26). Selected antibodies were cloned into pcDNA 3.3 (Invitrogen) and co-transfected into 293T cells using polyethylenimine (37) for large-scale production of the V3-specific antibodies for neutralization assays.

TABLE 1

Clinical characteristics of the post-matching cohort of transmitting and nontransmitting HIV-1 infected, untreated mothers

| Variable | Transmission status | N[1] | Mean (Range) | SD | P value[2] |
|---|---|---|---|---|---|
| Plasma viral load (copies/ml) | Nontransmitters | 160 | 62,906 (167-1,031,250) | 139,273 | |
| | Transmitters | 83 | 112,235 (699-3,101,258) | 347,778 | 0.22 |

TABLE 1-continued

Clinical characteristics of the post-matching cohort of transmitting and nontransmitting HIV-1 infected, untreated mothers

| | | | | | |
|---|---|---|---|---|---|
| CD4 Count (cells/µl) | Nontransmitters | 170 | 553.3 (32-2330) | 333.3 | |
| | Transmitters | 83 | 488.5 (16-1792) | 285.3 | 0.08 |
| Gestational Age (weeks) | Nontransmitters | 170 | 37.8 (28-43) | 2.8 | |
| | Transmitters | 84 | 37.3 (26-42) | 3.2 | 0.18 |

| Variable | Transmission status | N | Percent | P value[3] |
|---|---|---|---|---|
| Birth type | | | | |
| Vaginal birth | Nontransmitters | 125/170 | 74% | 0.74 |
| | Transmitters | 64/85 | 75% | |
| Cesarean section | Nontransmitters | 40/170 | 24% | |
| | Transmitters | 17/85 | 20% | |
| Birth year | | | | |
| 1990 | Nontransmitters | 37/166 | 22% | |
| | Transmitters | 14/83 | 17% | |
| 1991 | Nontransmitters | 53/166 | 32% | |
| | Transmitters | 23/83 | 28% | |
| 1992 | Nontransmitters | 32/166 | 19% | |
| | Transmitters | 20/83 | 24% | |
| 1993 | Nontransmitters | 28/166 | 17% | |
| | Transmitters | 18/83 | 22% | |
| 1994-1998 | Nontransmitters | 16/83 | 9% | |
| | Transmitters | 8/83 | 10% | |
| Visit | | | | |
| 25 weeks gestation | Nontransmitters | 58/166 | 35% | |
| | Transmitters | 8/83 | 10% | |
| 34 weeks gestation | Nontransmitters | 41/166 | 25% | |
| | Transmitters | 33/166 | 40% | |
| Delivery | Nontransmitters | 16/166 | 10% | |
| | Transmitters | 38/83 | 46% | |
| 2 months postpartum | Nontransmitters | 51/166 | 31% | |
| | Transmitters | 4/83 | 5% | |

[1] Missing data from 85 transmitters and 170 clinically-matched nontransmitters included: 10 nontransmitters and 2 transmitters plasma virus load, and 1 transmitter infant gestational age. Two transmitters and 4 nontransmitters were removed from the study following matching due to lack of adequate sample availability.
[2] P value calculated by student's t test
[3] P value calculated by Chi squared test

TABLE 2

Odds ratios of perinatal HIV-1 transmission in multivariable analyses of the primary RV144-adapted and MTCT humoral immune correlate models

| Humoral immune variables | Multivariate Logistic Regression | | |
|---|---|---|---|
| | Odds Ratio (95% CI) | P[1] Value | Q[1] Value |
| RV144-clade B modified model | | | |
| IgG binding to B.case A2 V1V2 | 1.06 (0.80-1.42) | 0.67 | 0.76 |
| Env IgA binding (score) | 0.96 (0.72-1.27) | 0.76 | 0.76 |
| Neutralizing antibodies (clade B tier 1 and 2) | 0.76 (0.55-1.05) | 0.1 | 0.48 |
| Avidity (B.6240) | 1.12 (0.83-1.51) | 0.45 | 0.76 |
| ADCC (B.SF162) | 0.94 (0.71-1.24) | 0.65 | 0.76 |
| MTCT model | | | |
| IgG binding to B.MN gp120 | 1.18 (0.69-2.03) | 0.55 | 0.91 |
| IgG binding to B.MN gp41 | 1.09 (0.72-1.65) | 0.69 | 0.91 |
| IgA binding to B.MN gp41 | 1.02 (0.76-1.36) | 0.91 | 0.91 |
| IgG binding to V3 (score) | 0.64 (0.42-0.97) | 0.04 | 0.15 |

[1] immune variable interactions with p < 0.05 and q < 0.2 are bolded

TABLE S1

Comparison of maternal plasma Env-specific IgG/IgA responses collected prepartum and peripartum (Pilot study)

| Humoral assay type (units) | Env antigen/virus | 25 wks vs 34 wks | p | 34 wks vs delivery | p | 25 wks vs delivery | p |
|---|---|---|---|---|---|---|---|
| Env-specific IgG (difference in mean OD) | AE.A244 V1V2 | 0.15 | 0.09 | 0.1 | 0.06 | 0.14 | 0.36 |
| | C.1086 V1V2 | 0.12 | 0.08 | 0.14 | 0.19 | 0.19 | 0.19 |
| | B.CaseA V1V2 gp70 | 0.18 | 0.04 | 0.13 | 0.09 | 0.17 | 0.19 |
| | B.CaseA2V1V2169K gp70 | 0.15 | 0.01 | 0.15 | 0.09 | 0.12 | 0.31 |
| | B.MN gp120 | −0.02 | 0.48 | 0.2 | 0.26 | 0.18 | 0.08 |
| | B.MN gp41 | −0.03 | 0.45 | 0.16 | 0.16 | 0.16 | 0.06 |
| Env-specific IgA (fold change in MFI) | 00MSA4076 gp140 | 0.94 | 0.58 | 0.8 | 0.24 | 1.11 | 0.51 |
| | A1con03140CF gp140 | 0.93 | 0.37 | 0.81 | 0.39 | 1.33 | 0.26 |
| | AE.A244gp120 | 0.75 | 0.32 | 1.47 | 0.73 | 0.26 | 0.18 |
| | B.Con gp120 | 0.93 | 0.13 | 0.94 | 0.42 | 1.18 | 0.17 |
| | B.C.C1 peptide IgA | 0.92 | 0.26 | 0.92 | 0.6 | 0.99 | 0.96 |
| | Con6 gp120 | 1 | 0.99 | 1.06 | 0.66 | 1.12 | 0.54 |
| | ConS gp140 | 0.9 | 0.63 | 0.59 | 0.46 | 1 | 1 |
| | B.MN gp41 | 0.95 | 0.57 | 0.98 | 0.84 | 1.1 | 0.49 |
| | B.MN gp120 | 0.92 | 0.35 | 1.23 | 0.34 | 0.87 | 0.5 |
| | B.VRC gp140 | 1.36 | 0.16 | 0.43 | 0.41 | 2.9 | 0.3 |
| Neutralization (fold change in $ID_{50}$) | B.101211TC21 NAb | 1.4 | 0.43 | 1.64 | 0.45 | 1 | NA |
| | B.65353 NAb | 1.04 | 0.9 | 1.66 | 0.13 | 1.93 | 0.14 |
| | B.AC10029 NAb | 1.13 | 0.57 | 1.73 | 0.16 | 1 | NA |
| | B.BaL26 NAb | 1.02 | 0.91 | 1.19 | 0.15 | 1.48 | 0.13 |
| | B.MN3 NAb | 1.04 | 0.89 | 1.74 | 0.2 | 1.21 | 0.19 |
| | B.REJO454167 NAb | 1.39 | 0.5 | 1.67 | 0.38 | 1.62 | 0.25 |
| | B.RHPA42597 NAb | 1.16 | 0.24 | 1.26 | 0.17 | 1 | NA |
| | B.SF162LS NAb | 0.78 | 0.08 | 1.45 | <0.01 | 0.98 | 0.82 |
| | B.SS11961 NAb | 1.14 | 0.7 | 1.52 | 0.18 | 1.53 | 0.18 |
| | B.WITO416033 NAb | 1.34 | 0.35 | 1.51 | 0.36 | 1 | NA |
| IgG avidity (fold change in avidity score) | B.MN gp120 | 0.97 | 0.56 | 1.06 | 0.35 | 1.12 | 0.47 |
| | B.6240 gp140 | 0.96 | 0.42 | 1.01 | 0.87 | 0.99 | 0.89 |
| | AE.A244 V1V2K169V | 0.93 | 0.27 | 1.22 | 0.39 | 0.68 | 0.33 |
| | B.CaseA2 V1V2K169V | 1.05 | 0.47 | 1.05 | 0.67 | 0.76 | 0.23 |
| | C.1086 V1V2 | 1.09 | 0.46 | 1.09 | 0.26 | 0.79 | 0.44 |
| | B.63521 V1V2 | 1.19 | 0.38 | 0.92 | 0.53 | 0.92 | 0.7 |
| | AE.A244 V1V2 | 1.1 | 0.27 | 1.11 | 0.52 | 0.84 | 0.59 |
| | B.CaseA2 V1V2 | 1.06 | 0.66 | 0.95 | 0.47 | 0.74 | 0.24 |
| ADCC (difference in mean % specific lysis) | B.SF162 | −1.14 | 0.68 | 5.66 | 0.07 | 7.33 | 0.09 |

TABLE S2

Odds ratios of HIV-1 MTCT for each measured Env-specific humoral immune responses (secondary analysis)

| | Odds Ratio (95% CI) | P value | Q value |
|---|---|---|---|
| B.SF162 Nab | 0.67 (0.50-0.90) | 0.006 | 0.25 |
| B.MN3 Nab | 0.71 (0.54-0.95) | 0.02 | 0.4 |
| B.V3 IgG | 0.75 (0.58-0.98) | 0.035 | 0.47 |
| B.MN V3 gp70 IgG | 0.78 (0.59-1.01) | 0.061 | 0.49 |
| M.V3 IgG | 0.78 (0.59-1.01) | 0.061 | 0.49 |
| B.WITO ADCC | 1.26 (0.96-1.65) | 0.088 | 0.57 |
| B.BaL26 Nab | 0.79 (0.60-1.05) | 0.106 | 0.57 |
| B.RHPA42597 Nab | 0.78 (0.57-1.07) | 0.117 | 0.57 |
| B.SS11961 Nab | 0.80 (0.60-1.08) | 0.141 | 0.57 |
| B.CaseA2 V1V2 IgG avidity | 0.81 (0.61-1.07) | 0.142 | 0.57 |
| B.AC10029 Nab | 0.80 (0.59-1.09) | 0.158 | 0.57 |
| B.65353 Nab | 0.82 (0.61-1.10) | 0.177 | 0.59 |
| B.REJO454167 Nab | 0.83 (0.62-1.11) | 0.204 | 0.6 |
| A.00MSA4076 gp140 IgA | 0.84 (0.64-1.10) | 0.211 | 0.6 |
| B.MN gp120 avidity | 0.85 (0.65-1.11) | 0.23 | 0.61 |
| Con6 gp120 IgA | 0.86 (0.66-1.13) | 0.275 | 0.69 |
| A1con03 gp140 IgA | 0.88 (0.67-1.14) | 0.329 | 0.7 |
| AE.A244 gp120K169V IgG avidity | 0.89 (0.68-1.16) | 0.382 | 0.7 |
| ConS gp140 IgA | 0.89 (0.68-1.17) | 0.395 | 0.7 |
| C.1086 V1V2 IgG avidity | 0.89 (0.67-1.18) | 0.411 | 0.7 |
| AE.A244 V1V2 IgG | 0.89 (0.68-1.17) | 0.413 | 0.7 |
| B.C.C1 peptide IgA | 1.12 (0.85-1.48) | 0.415 | 0.7 |
| B.MN gp120 IgG | 0.89 (0.68-1.17) | 0.415 | 0.7 |
| B.CaseA2 V1V2N156QN160Q IgG avidity | 1.11 (0.86-1.44) | 0.419 | 0.7 |
| B.6240 gp120mutC IgG avidity | 0.90 (0.69-1.17) | 0.435 | 0.7 |
| AE.A244gp120 IgG | 0.90 (0.69-1.19) | 0.466 | 0.72 |
| AE.C1peptide IgA | 1.10 (0.83-1.44) | 0.513 | 0.76 |
| B.101211TC213257 Nab | 1.08 (0.82-1.42) | 0.576 | 0.8 |
| B.SF162 ADCC | 0.93 (0.70-1.22) | 0.58 | 0.8 |
| B.con03 gp140 IgA | 0.93 (0.71-1.22) | 0.6 | 0.8 |
| B.CaseA2V1V2169K gp70 IgG | 0.95 (0.73-1.25) | 0.728 | 0.9 |
| B.WITO416033 Nab | 1.05 (0.79-1.38) | 0.75 | 0.9 |
| B.MN gp41 IgA | 0.96 (0.73-1.26) | 0.761 | 0.9 |
| AE.A244 gp120 monomer | 0.97 (0.73-1.28) | 0.817 | 0.9 |
| B.6240 gp140 IgG avidity | 1.03 (0.78-1.36) | 0.838 | 0.9 |
| AE.A244 gp120 IgA | 0.97 (0.74-1.28) | 0.853 | 0.9 |
| B.MN gp41 IgG | 0.98 (0.74-1.28) | 0.858 | 0.9 |
| B.CaseA V1V2 gp70 IgG | 1.02 (0.78-1.34) | 0.879 | 0.9 |
| C.1086 V1V2 IgG | 0.98 (0.75-1.29) | 0.88 | 0.9 |
| B.MN gp120 IgG | 1.00 (0.76-1.31) | 0.999 | 1 |

TABLE S3

Odds ratios of peripartum HIV-1 MTCT for each measured Env-specific humoral immune responses (secondary analysis)

| | Odds Ratio (95% CI) | P-value | Q-value |
|---|---|---|---|
| B.MN3 Nab | 0.54 (0.35-0.83) | 0.005 | 0.1 |
| B.SF162LS Nab | 0.54 (0.35-0.84) | 0.005 | 0.1 |
| B.BaL26 Nab | 0.65 (0.43-0.98) | 0.037 | 0.38 |
| B.V3 IgG | 0.67 (0.46-0.99) | 0.042 | 0.38 |
| A1con03 gp140 IgA | 0.69 (0.47-1.01) | 0.057 | 0.38 |
| M.V3 IgG | 0.69 (0.47-1.03) | 0.064 | 0.38 |
| B.SS11961 Nab | 0.68 (0.44-1.04) | 0.07 | 0.38 |
| B.MN V3 gp70 IgG | 0.71 (0.49-1.05) | 0.082 | 0.38 |
| B.AC10029 Nab | 0.68 (0.44-1.06) | 0.087 | 0.38 |
| A.00MSA4076 gp140 IgA | 0.74 (0.50-1.09) | 0.125 | 0.5 |
| ConS gp140 IgA | 0.78 (0.53-1.13) | 0.186 | 0.64 |
| B.65353 Nab | 0.76 (0.50-1.16) | 0.193 | 0.64 |
| B.RHPA42597 Nab | 0.77 (0.50-1.19) | 0.237 | 0.71 |
| B.REJO454167 Nab | 0.79 (0.52-1.19) | 0.256 | 0.71 |
| B.MN gp120 IgG avidity | 0.81 (0.55-1.18) | 0.267 | 0.71 |
| B.MN gp120 IgG | 0.81 (0.54-1.20) | 0.284 | 0.71 |
| B.conenv03 gp140 IgA | 0.83 (0.57-1.20) | 0.318 | 0.74 |
| Con6 gp120 IgA | 0.83 (0.56-1.22) | 0.333 | 0.74 |
| B.MN gp41 IgG | 0.84 (0.56-1.24) | 0.369 | 0.74 |
| B.CaseA2 V1V2 IgG | 0.84 (0.56-1.24) | 0.372 | 0.74 |
| B.WITO ADCC | 1.17 (0.80-1.71) | 0.419 | 0.77 |
| B.6240 gp120mutC IgG avidity | 0.85 (0.57-1.27) | 0.423 | 0.77 |
| B.WITO416033 Nab | 0.86 (0.57-1.28) | 0.45 | 0.78 |
| B.MN gp41 IgA | 0.88 (0.60-1.28) | 0.491 | 0.82 |
| C.1086C V1V2 IgG | 1.13 (0.77-1.67) | 0.53 | 0.82 |
| B.CaseA2 V1V2 IgG | 1.11 (0.75-1.65) | 0.587 | 0.82 |
| AE.A244 V1V2 IgG | 0.90 (0.60-1.34) | 0.594 | 0.82 |
| AE.A244 gp120 IgA | 0.90 (0.61-1.34) | 0.603 | 0.82 |
| B.MN gp120 IgA | 0.90 (0.61-1.33) | 0.609 | 0.82 |
| B.CaseA2 V1V2N156QN160Q IgG avidity | 0.91 (0.61-1.34) | 0.618 | 0.82 |
| B.C.C1 peptide IgA | 1.08 (0.73-1.60) | 0.696 | 0.9 |
| AE.A244 gp120K169V IgG avidity | 0.93 (0.64-1.36) | 0.723 | 0.9 |
| B.101211TC213257 Nab | 1.06 (0.72-1.56) | 0.754 | 0.9 |
| ADCC SF162 | 1.06 (0.72-1.57) | 0.765 | 0.9 |
| AE.C1 peptide IgA | 1.05 (0.71-1.57) | 0.798 | 0.91 |
| B.CaseA2V1V2169K gp70 IgG | 1.03 (0.70-1.52) | 0.89 | 0.96 |
| B.6240 gp140C IgG avidity | 0.97 (0.66-1.44) | 0.89 | 0.96 |
| C.1086 V1V2 IgG avidity | 1.00 (0.67-1.47) | 0.983 | 0.98 |
| AE.A244 gp120 IgG avidity | 1.00 (0.69-1.47) | 0.983 | 0.98 |
| AE.A244 gp120 IgA | 1.00 (0.67-1.49) | 0.985 | 0.98 |

TABLE S4

Interpretation of significant interactions between maternal HIV-1 Env-specific humoral immune responses and their association with MTCT risk

| Percentile | Odds Ratio[1] | Lower CI[2] | Upper CI[3] | P value[4] |
|---|---|---|---|---|
| \multicolumn{5}{c}{Effect of increasing IgG MNgp120 at selected percentiles of IgG B.6240 gp140 avidity} | | | | |
| 20% | 1.085 | 0.786 | 1.497 | 0.62 |
| 50% | 0.812 | 0.609 | 1.085 | 0.159 |
| 80% | 0.606 | 0.4 | 0.917 | 0.018 |
| \multicolumn{5}{c}{Effect of increasing IgG MN gp41 at selected percentiles of IgG B.6240 gp140 avidity} | | | | |
| 20% | 1.257 | 0.89 | 1.775 | 0.193 |
| 50% | 0.916 | 0.686 | 1.223 | 0.551 |
| 80% | 0.663 | 0.44 | 1 | 0.05 |
| \multicolumn{5}{c}{Effect of increasing IgG V3 score at selected percentiles of IgG 6240 gp140 avidity} | | | | |
| 20% | 0.845 | 0.621 | 1.151 | 0.286 |
| 50% | 0.646 | 0.474 | 0.88 | 0.006 |
| 80% | 0.492 | 0.317 | 0.761 | 0.001 |
| \multicolumn{5}{c}{Effect of increasing NAb score at selected percentiles of IgG MN gp41} | | | | |
| 20% | 1.119 | 0.722 | 1.735 | 0.616 |
| 50% | 0.807 | 0.581 | 1.122 | 0.203 |
| 80% | 0.508 | 0.308 | 0.84 | 0.008 |
| \multicolumn{5}{c}{Effect of increasing NAb response against SF162 at selected percentiles of IgG MN gp41} | | | | |
| 20% | 0.804 | 0.535 | 1.207 | 0.293 |
| 50% | 0.552 | 0.381 | 0.8 | 0.002 |
| 80% | 0.324 | 0.179 | 0.583 | <0.0001 |

[1] Odds ratio per increasing one standard deviation for each humoral immune variable
[2] Lower confidence interval
[3] Upper confidence interval
[4] immune variable interactions with p < 0.05 are bolded

TABLE S5

Odds ratios of HIV-1 MTCT in multivariable analyses of the post-hoc analysis of maternal plasma CD4 blocking activity and the risk of MTCT.

| HIV Envelope proteins | Odds Ratio (95% CI[1]) | P[1] value |
|---|---|---|
| Entire MTCT cohort | | |
| B.63521 gp120 | 0.70 (0.52-0.93) | 0.014 |
| B.6240 gp120 | 0.75 (0.56-1.01) | 0.058 |
| B.JRFL gp120 | 0.74 (0.56-0.98) | 0.036 |

[1]immune variable ORs at $p < 0.05$ are in bold

TABLE S6

Correlations of percent sCD4 blocking for B.JFRL Env neutralization potency against B.SF162, and IgG binding to B.V3 in plasma of HIV-1-infected mothers.

| | % CD4 blocking (B.JRFL) | B.MN Nab | B.V3 IgG |
|---|---|---|---|
| Entire MTCT cohort | | | |
| % CD4 blocking (B.JRFL gp120) | 1 | | |
| B.MN Nab | 0.72 | 1 | |
| B.V3 IgG | 0.66 | 0.78 | 1 |

TABLE S7

The variable gene usage and binding-specificity (area under the curve) of the autologous Env V3-specific IgG1 mAbs isolated from a nontransmitting HIV-1-infected, untreated mother at six months postpartum

| Ig ID | $V_H$ | $V_H$ Mutation | $V_L$ | Con B.V3 | Con C.V3 | ConS V3 | MN gp120 | gp70 ConAG. V3 | gp70 ConA. V3 | gp70 ConC. V3 | gp70 MN. V3 | gp70 A244 92TH23 V3 |
|---|---|---|---|---|---|---|---|---|---|---|---|---|
| DH290 | 3~7*01 | 3.6% | K 1~9*01 | 14.5[1] | 0 | 1.6 | 16.2 | 3.8 | 3.0 | 3.1 | 14.3 | 0.6 |
| DH291 | 1~46*02 | 4.3% | K 4~1*01 | 15.9 | 0 | 1.8 | 14.3 | 0 | 1.7 | 0.2 | 3.5 | 0.3 |
| DH292 | 1~24*01 | 3.4% | L 3~1*01 | 16.4 | 6.7 | 9.7 | 16.5 | 11.4 | 11.3 | 13.1 | 16.5 | 0.2 |
| DH293 | 1~f*01 | 2.5% | K 4~1*01 | 15.8 | 11.1 | 13 | 15.4 | 12.5 | 16.5 | 16.9 | 9.6 | 0.3 |
| DH294 | 1~8*01 | 2.8% | L 1~40*01,02 | 15.6 | 0 | 1.6 | 12.3 | 0 | 0 | 0 | 9.4 | 0.6 |
| DH295 | 5~51*03 | 2.3% | L 3~1*01 | 14.3 | 14.4 | 15.3 | 15.6 | 16.5 | 17.4 | 16.2 | 15.8 | 1.7 |
| DH296 | 3~66*01 | 3.8% | K 2D~29*01 | 17 | 0 | 1.9 | 15.6 | 0 | 0 | 0 | 16 | 1 |
| DH297 | 1~f*01 | 4.8% | L 1~51*01 | 13.1 | 12.7 | 12.6 | 16.1 | 15.4 | 16.9 | 16 | 15.7 | 0.2 |
| DH298 | 3~30*04 | 3.2% | K 2D~29*02 | 16.7 | 0 | 2.4 | 15.5 | 0 | 5.8 | 0 | 10.4 | 0.4 |
| DH299 | 5~51*03 | 2.0% | L 1~51*01 | 14 | 10.3 | 14.1 | 16.3 | 10.8 | 16.2 | 16.1 | 16.2 | 0.2 |

[1]Each value indicates area under the curve (AUC) of mAb binding to each V3 peptide, gp120, or gp70-scaffolded V3 antigens antigen, grey shading indicates binding.

TABLE S8

Flow cytometry antigen-specific B cell sort setup configuration details

| Detector Array (Laser) | PMT | LP Mirror | BP Filter | Intended Fluor | Voltage |
|---|---|---|---|---|---|
| Octagon | | | | | |
| 488 nm Blue laser | A | 755 | 780/60 | | |
| Coherent Sapphire | B | 635 | 710/50 | | |
| 100 mW | C | 600 | 610/20 | | |
| | D | 550 | 575/25 | | |
| | E | 505 | 525/50 | FITC | 550 |
| | F | — | 488/10 | Side Scatter (SSC) | 275 |
| Octagon | | | | | |
| 532 nm Green laser | A | 755 | 780/60 | PE-Cy7 | 585 |
| Compass | B | 685 | 710/50 | | |
| 150 mW | C | 635 | 660/20 | PE-CY5 | 530 |
| | D | 600 | 610/20 | ECD | 500 |
| | E | 550 | 575/25 | PE | 370 |
| Octagon | | | | | |
| 406 nm Violet laser | A | 755 | 780/60 | | |
| Cube | B | 685 | 705/70 | | |
| 100 mW | C | 630 | 670/30 | | |
| | D | 595 | 605/40 | BV605 | 490 |
| | E | 570 | 585/42 | BV570 | 485 |
| | F | 557 | 560/40 | | |
| | G | 505 | 525/50 | Aqua Vital Dye | 555 |
| | H | — | 450/50 | BV421 | 505 |

TABLE S8-continued

Flow cytometry antigen-specific B cell sort setup configuration details

| Detector Array (Laser) | PMT | LP Mirror | BP Filter | Intended Fluor | Voltage |
|---|---|---|---|---|---|
| Trigon | | | | | |
| 639 nm Red laser | A | 755 | 780/60 | APC-Cy7 | 640 |
| 40 mW | B | 690 | 730/45 | APC-AF700 | 600 |
| | C | — | 670/30 | AF647 | 560 |
| | | | | | Gain |
| Diode | | | | Forward Scatter (FSC) | 175 |

Example 2

HIV Neutralizing Antibodies without Heterologous Breadth can Potently Neutralize Autologous Viruses Example 2 shows that antibodies with neutralization restricted to heterologous tier 1 HIV-1 isolates can neutralize autologous HIV-1 strains, a phenomenon predicted to be protective in mother-to-child transmission.

Broadly neutralizing antibodies (bnAbs) against HIV-1 have activity in vitro against difficult-to-neutralize (tier 2) viruses while antibodies that arise following vaccination or early in HIV-1 infection have activity only against easy-to-neutralize (tier 1) viruses. The capacity for antibodies that neutralize only heterologous tier 1 viruses to exert selection pressure on HIV-1 is not known. To study this question, we isolated tier 1 virus-nAbs that bind to the third variable loop (V3) or the CD4 binding site (CD4bs) from two HIV-1-infected individuals and determined the antibody sensitivity of autologous HIV-1 strains sampled over time. We found functional autologous viruses could be neutralized by these V3 and CD4bs antibodies, and found that resistant forms of HIV-1 accumulated over time, suggesting Ab-mediated viral selection pressure. One clinical setting where transfer of both autologous nAbs and virus can occur is that of mother-to-child transmission (MTCT). In this setting, high levels of maternal V3 and CD4bs autologous nAbs may be able to reduce transmission, regardless of autologous nAb breadth and potency against heterologous viruses.

Induction of antibodies with neutralization breadth is a primary goal of HIV-1 vaccine development (1). All current HIV-1 envelope (Env) immunogens frequently induce neutralizing antibodies (nAbs) that inhibit only easy-to-neutralize (tier 1) HIV-1 strains (2). In contrast, broadly neutralizing antibodies (bnAbs) that can potently neutralize a variety of difficult-to-neutralize (tier 2) HIV-1 strains that have been associated with HIV-1 transmission (3) are not induced by current vaccines (1, 2, 4, 5).

The initial autologous nAb response in HIV-1-infected subjects is generally restricted to neutralizing the infecting transmitted/founder virus (6-13). Epitopes frequently targeted by the initial autologous nAbs are the third constant region-variable loop 4 (C3-V4) domain (8, 10, 13), the base of the third variable (V3) loop (11, 12, 14), the first and second variable loop (V1V2) regions (9, 10, 12, 15), and the CD4 binding site (CD4bs) (16, 17). In chronic HIV-1 infection, virus escape mutants are selected that repopulate the plasma virus pool, and neutralization breadth accrues to varying degrees in different individuals (18). In addition, antibodies to V3 and the CD4bs arise that can neutralize heterologous tier 1 but not tier 2 HIV-1 isolates (2, 19-24). However, the neutralization sensitivity of the autologous repopulated plasma virus pool to this type of V3 and CD4bs nAbs has not been studied. Here, we have isolated from two chronically HIV-1-infected individuals V3 and CD4bs nAbs with breadth only for tier 1 but not tier 2 heterologous viruses, and for comparison, CD4bs bnAbs with tier 2 neutralization breadth; and determined the ability of these Abs to neutralize a large pane of autologous viruses as well as to select virus escape mutants.

Isolation of nAbs with Restricted or Broad Neutralizing Activity from Chronically Infected Individuals.

Figures 8A, 8B:
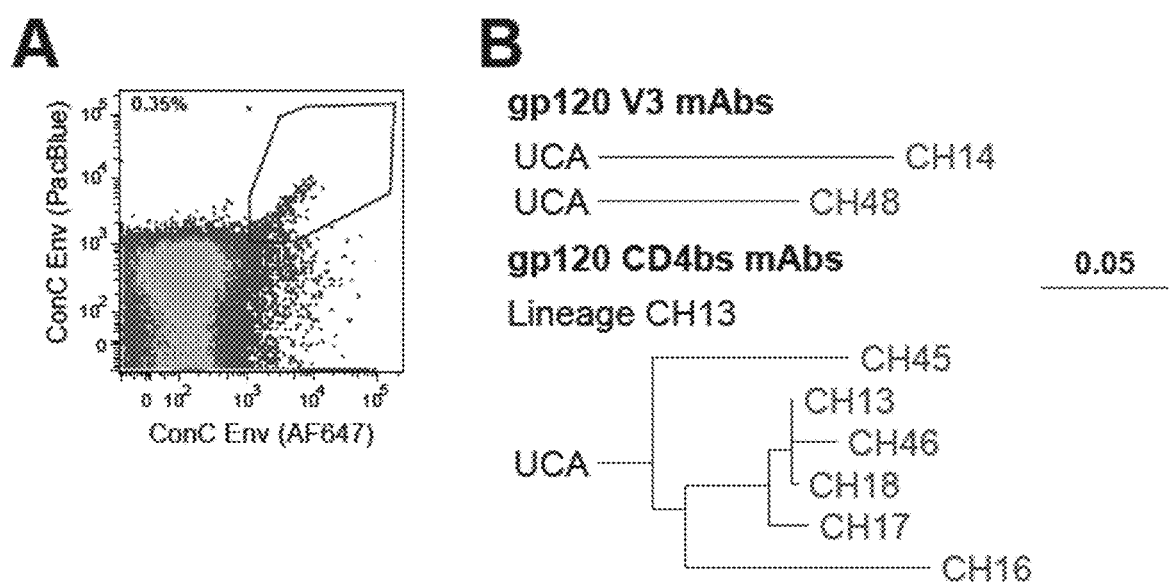
Figures 8C, 8D:
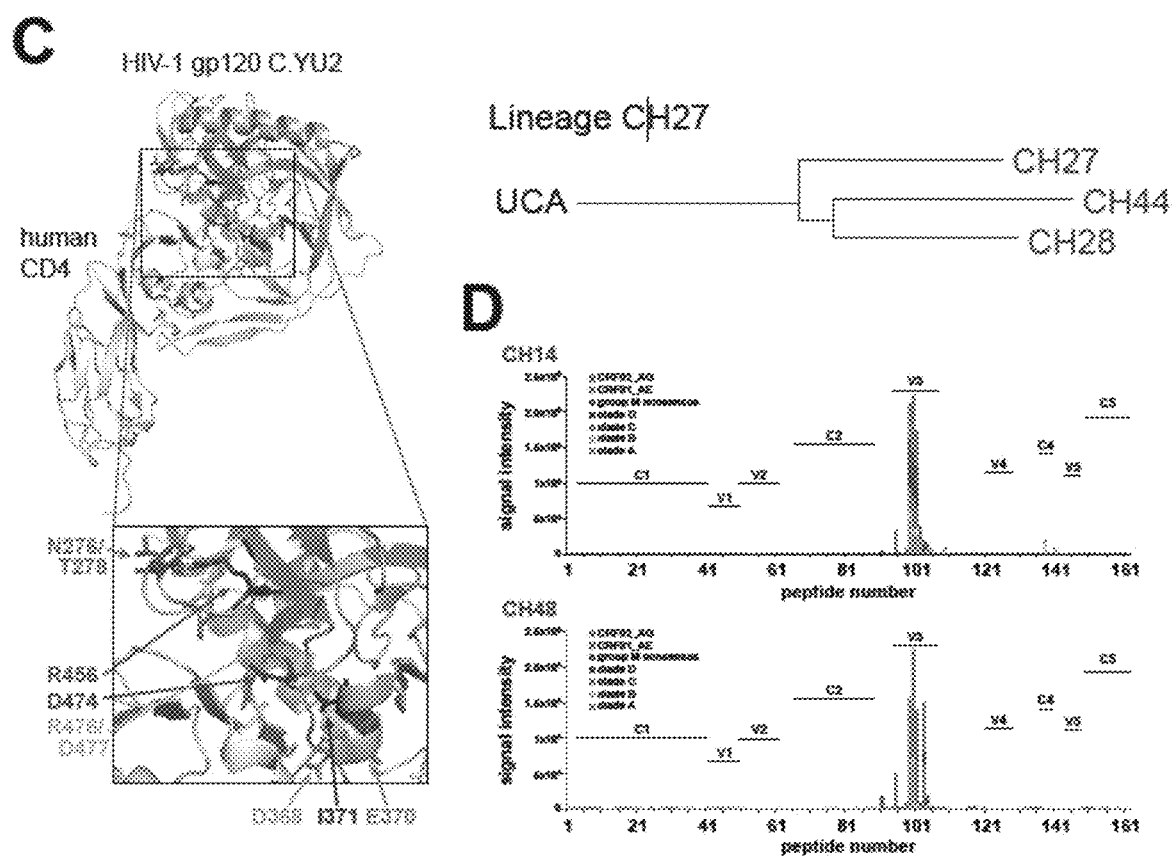

From chronically HIV-1 infected individual CH0457, we isolated two clonal lineages as well as single monoclonal antibodies (mAbs) using antigen-specific memory B cell flow cytometry sorting (FIG. 8a, 8b; Ex. 2 Table S1). Epitope mapping with virus mutants demonstrated that the CH13 lineage mAbs (CH13, CH16, CH17, CH18, CH45) bound to the CD4bs (FIG. 8c; Ex. 2 Tables S2 and S3), and neutralization assays demonstrated that members of the lineage neutralized 8/8 tier 1 heterologous HIV-1 Env pseudoviruses, but did not neutralize any of 26-40 tier 2 heterologous HIV-1 Env pseudoviruses (FIG. 9). Two additional mAbs, CH14 and CH48, were not clonally related, and both mAbs mapped to the HIV-1 Env V3 loop (FIG. 8d; Ex. 2 Table S4). Like the CD4bs clonal lineage CH13, V3 mAbs CH14 and CH48 neutralized tier 1 but not tier 2 heterologous HIV-1 strains (FIG. 9).

The second clonal lineage of mAbs from CH0457, CH27 (FIG. 8b), had two members (CH27 and CH28) that were IgA2 while the third (CH44) was IgG1 (Ex. 2 Table S1). Neutralization assays with clonal lineage CH27 mAbs showed that all three lineage members (CH27, CH28, CH44) neutralized 40% (range 25-48%) of 40 tier 2 heterologous HIV-1 strains (FIG. 9). The CH27 lineage mAbs preferentially neutralized tier 2 but not tier 1 heterologous viruses. HJ16 is a CD4bs bnAb isolated from another infected individual (25) and like the CH27 lineage mAbs, HJ16 neutralizes multiple tier 2 but not tier 1 viruses. Mutation of Env at N276 conferred resistance to HJ16 (26), and mAbs of the CH27 lineage were similarly sensitive to mutations at N276 and T278 (Ex. 2 Table S5). CH27, CH44, and CD4bs nAb HJ16 (26) cross-blocked each other in Env binding assays (FIG. 13), demonstrating that the CH27 lineage antibodies were similar to HJ16 (FIG. 9). Serum from chronically-infected individual CH0457 taken from weeks 8 and 96 of observation were tested against the same panel of heterologous viruses (FIG. 9). Neutralization titers and breadth against heterologous viruses were very similar at the two chronic infection time points ($R^2=0.95$, Pearson's correlation $p<22\times10^{-16}$).

From a second individual, CH505, previously described to have a CD4bs bnAb lineage (represented by CH103 in FIG. 10) (16), we isolated two V3 nAbs (DH151 and DH228; Ex. 2 Table S6) from 41 weeks after transmission (FIG. 10). The neutralization patterns exhibited by nAbs DH151 and DH228 were similarly restricted to a subset of tier 1 heterologous viruses, and they did not neutralize any of 16 tier 2 heterologous viruses (FIG. 10).

Virus Evolution in Chronically Infected Individual CH0457.

We amplified a total of 209 CH0457 env gene sequences by single genome amplification (SGA) from 10 time points over a two year period during chronic infection (weeks 0, 2, 4, 8, 12, 16, 24, 48, 72, and 96 post-enrollment). An average of 21 (range 12-35) SGA env sequences were analyzed for each time point. Phylogenetic analysis showed that the Env sequences continuously evolved over time (FIG. 14). The Env sequences from weeks 48, 72 and 96 were more divergent compared with the earlier viruses (0 to week 16) (FIG. 14). Furthermore, within-subject phylogeny maintained a persistent minority clade that represented a small fraction (average 14%) of Envs sampled at any given time point (FIG. 11; FIG. 14) throughout the study period. The consensus of this clade differed at 85/888 (9.6%) aligned Env amino acid positions from the consensus of the main clade. Phylogenetic analysis and BLAST searching of sequences from CH0457 relative to the database indicated that despite the genetic distance, the sequences from this minor persistant clade were more closely related other sequences from CH0457 than to other strains, and validated that this clade was not a contamination event, nor was it evidence of super-infection with two distinct viruses. Rather the major and minor clades emerged from a common founder in CH0457.

Neutralization of Autologous Viruses by bnAbs and Tier 1 Virus-Neutralizing mAbs.

We made 84 pseudoviruses from these env sequences (FIG. 11B; average 8 per time point; range 7-11) for neutralization assays against CH0457 serum samples (FIG. 11A). The serum from later time points (weeks 72 and 96) potently neutralized the early viruses (week 48 or earlier) but not the later viruses, indicating that autologous nAbs were continuously elicited during chronic infection in CH0457 (FIGS. 11A and 11B).

We next determined the neutralization activities of the CH27 CD4bs lineage bnAbs against the panel of 84 autologous pseudoviruses derived from viral RNA from plasma samples. Five autologous viruses were weakly neutralized by one of three lineage CH27 bnAbs (range 32-50 µg/mL), while the other 79 pseudoviruses (94%) were resistant to the CH27 lineage bnAbs (FIG. 11A; FIG. 15A). These data suggested that the autologous virus population in this individual by the time of enrollment had already escaped from pressure exerted by the CH27 lineage of bnAbs, with viral escape occurring during chronic infection prior to study enrollment.

Thus, to seek definitive evidence of evolutionary selection exerted by the CH27 bnAb lineage, we amplified proviral env genes archived in peripheral blood mononuclear cells (PBMC) from the earliest time point (termed week 0) in this study. Like plasma-derived Env pseudoviruses, the majority of the PBMC-derived Env pseudoviruses were resistant to the lineage CH27 bnAbs (FIGS. 11A and 11B). However, two cell-derived Env pseudoviruses (w0.35c and w0.29c) were found to be highly sensitive to the lineage CH27 bnAbs, thus documenting CH27 bnAb lineage-mediated escape (FIG. 11A; FIG. 15B). Remarkably, both of these viruses sensitive to the CH27 lineage were members of the persistent minority clade (FIG. 11B; FIG. 14). Of note, the archived proviral DNA sequences recapitulated evolutionary intermediates reconstructed from the sequence data that represented transition forms between the two CH0457 viral clades.

Next, we asked if 7 of the CH0457 tier 1 virus-nAbs (5 CH13 lineage CD4bs mAbs, and 2 V3 mAbs CH14 and CH48) could neutralize autologous HIV-1 pseudoviruses. We found that the V3 and CD4bs mAbs were able to neutralize autologous viruses throughout the 2-year study period, including PBMC-archived viruses (FIGS. 11A and 11B; FIG. 15). Remarkably, the tier 1 virus-neutralizing CD4bs clonal lineage CH13 mAbs neutralized 52/84 (62%) autologous plasma viruses and 11/34 (32%) of autologous PBMC viruses, while the V3 tier 1 virus-neutralizing mAbs (CH14 and CH48) neutralized 67/84 (80%) autologous plasma viruses and 28/34 (82%) of autologous PBMC viruses. Neutralization potency ranged from 50 µg/mL to 0.06 µg/mL, with 21/257 (8%) neutralization assays of tier 1 virus-neutralizing antibodies demonstrating neutralization of autologous viruses at ≤2 µg/mL.

Sensitivity to the CH13 lineage and to the two V3 mAbs peaked at week 24 after enrollment; by week 48 of follow-up, most viruses were resistant to the V3 mAbs (FIG. 11A; FIG. 15A online) suggesting selection of escape mutants by these nAbs. Of note, among the viruses sampled between weeks 48 and 96, only three viruses were still moderately sensitive to these nAbs (w48.20, w72.2, and w72.18), with the rest only weakly sensitivy or completely resistant.

The 3 CH0457 viruses sensitive to the CD4bs CH13 lineage (w48.20, w72.2, and w72.18) were all located within the persistent minor clade (3/10 in the minor clade vs. 0/17 in the dominant clade; Fisher's exact test p=0.04). The fact that both in the CDbs CH27 lineage and in the CH13 lineage the sensitive viruses persisted longest in the minor clade but not in the dominant clade raises the possibility that the viruses in the minor clade may be emerging from an immunologically protected site (eg, brain or the CD4 T cell latent pool) where antibody pressure would be limited (27). Across all time points, 32/84 (38%) of autologous pseudoviruses were resistant to the CD4bs nAbs while 17/84 (20%) were resistant to the V3 loop mAbs. Analysis of CH0457 Env sequences did not demonstrate an accumulation of Env mutations at the putative nAb contact sites suggested by epitope mapping (Ex. 2 Tables S2, S3, S4).

To determine if autologous virus neutralization by autologous tier-1 virus nAbs was a phenomenon unique to individual CH0457, we studied two V3 nAbs (DH151 and DH228; Ex. 2 Table S6) isolated from a second HIV-1-infected African individual, CH505, 41 weeks after transmission (16). CH505 also developed a CD4bs clonal lineage (termed CH103) at 136 weeks after transmission (16). CH505 was studied earlier during infection compared with CH0457, thus Env selection by bnAbs was ongoing in individual CH505 at the time of study and many autologous Env pseudoviruses were only partially resistant to the CH103 bnAb lineage (FIG. 16) (28). Whereas both CH505 V3 mAbs neutralized a subset of tier 1 heterologous viruses, they did not neutralize any of 16 tier 2 heterologous viruses (FIG. 10). However, V3 mAbs DH151 and DH228 neutralized 45/96 (47%, $IC_{50}$ range 50-0.03 µg/mL) autologous CH505 viruses (FIG. 11C; FIG. 16), and potently neutralized 7/96 (7.3%) viruses at ≤2 µg/mL. Interestingly, the transmitted/founder virus from CH505 was resistant to both V3 nAbs but became sensitive by week 14 after infection (FIGS. 11C and 11D; FIG. 16), suggesting that an escape mutant of the transmitted/founder elicited these V3 nAbs. Moreover, these data demonstrated viral Env V3 loop epitope exposure by week 14 after infection. As with the CH0457 individual, CH505 viruses sensitive to the V3 mAbs were present throughout all time points studied. Thus, CH505 V3 mAbs DH151 and DH228 had no neutralizing activity against heterologous tier 2 viruses but were able to neutralize autologous CH505 viruses, indicating that this phenomenon was not limited to the chronically HIV-1-infected individual CH0457.

Autologous Virus Neutralization Sensitivity.

To assess the susceptibility of autologous viruses to heterologous nAbs, we performed neutralization assays with a panel of tier 1 virus-neutralizing antibodies and bnAbs. Of 84 CH0457 autologous pseudoviruses, 73 (87%) were sensitive to the heterologous VRC01-like CD4bs bnAb CH31 (29) (FIG. 15A). Similarly 55/62 (89%) of viruses were sensitive to the loop binding CD4bs bnAb CH106 (16) (FIG. 15A). Glycan-dependent bnAb HJ16 (25) neutralized only 5/72 (7%) of viruses, consistent with escape of these autologous viruses from the clonal lineage CH27 nAbs (FIG. 13, Ex. 2 Table S5).

Next, we tested each of the 84 CH0457 Env pseudoviruses against the pooled serum product HIVIG-C and a subset of Env pseudoviruses against well-characterized HIV-1 patient serum samples (FIG. 17). The neutralization data suggested that CH0457 viruses sensitive to the autologous mAbs (CH13 lineage, CH14, and CH48) had exposed V3 and CD4bs epitopes. Thus, we analyzed a subset of Env pseudoviruses (10 sensitive and 10 resistant to autologous V3 and CD4bs nAbs) against a large panel of heterologous V3 and CD4bs mAbs previously shown to lack the ability to neutralize tier 2 virus isolates (2, 19-24) (FIG. 18). The 10 viruses sensitive to autologous nAbs were neutralized by this panel of heterologous V3 and CD4bs nAbs, suggesting that the V3 loop and CD4bs epitopes were indeed trimer-surface exposed. The 10 viruses resistant to autologous nAbs were also resistant to the heterologous nAb panel (FIG. 18). Testing of the same viruses using a panel of neutralization typing sera from HIV-1 infected persons showed that viruses with sensitivity to heterologous nAbs had an intermediate sensitivity to the typing sera (FIG. 18) consistent with an intermediate (tier 1B) (30) neutralization sensitivity phenotype (FIG. 19). Testing of autologous viruses from CH505 using a similar panel demonstrated predominant tier 1B neutralization sensitivity as well (FIG. 20). These data demonstrated that viruses arose in chronic infection in African individuals CH0457 and CH505 that could be neutralized by autologous V3 and CD4bs nAbs that themselves lacked tier 2 virus neutralization activity.

The initial autologous neutralizing antibody response that arises in acute HIV-1 infection is specific for the autologous virus with little tier 1 autologous virus breadth (31-33). This response differs from the autologous nAb response in chronic infection where breadth for heterologous tier 1 viruses can develop. When autologous neutralizing antibodies begin to show heterologous tier 1 breath, it is possible that such antibodies may be enroute to developing some degree of bnAb activity as occurred in the CH103 CD4bs lineage (16).

The CD4bs and V3 antibody lineages studied here were able to neutralize tier 1B and select tier 2 autologous HIV-1 isolates. We speculate that this was possible because the mAbs and viruses isolated in the present study co-evolved in the same HIV-1-infected individuals. During HIV-1 infection, virus quasispecies evolve that have different degrees of Env reactivity; viruses with high intrinsic activity (ie, tier 1A viruses) (30) are more reactive with both soluble CD4 and neutralizing antibodies (34). Thus, in these individuals, autologous viruses with low Env reactivity (ie, tier 1B or tier 2 viruses) (34, 35) can act as templates for antibody evolution, giving rise to antibodies that bind and neutralize autologous virus Envs with low reactivity (FIG. 12A). Such antibodies could broadly react with heterologous tier 1 A Envs that have high reactivity (FIG. 12B), but would be expected to bind poorly to heterologous tier 2 Envs with low reactivity (FIG. 12C).

The ability of autologous neutralizing antibodies that arise in acute HIV-1 infection to exert immune pressure has been demonstrated by studies of the evolution of transmitted/founder viruses and plasma antibodies (31, 33, 36). In particular, the initial autologous-specific neutralizing antibody response to HIV-1 appears within the first year of infection and is associated with the development of resistant viruses in virtually all infected individuals (31, 33). A critical question is why neutralization of autologous viruses by tier 1 heterologous virus-neutralizing antibodies like the CH13 lineage from CH0457 and DH151 and DH228 V3 mAbs from CH505 has not been previously observed? The simplest answer is that testing of a large series of autologous Envs isolated in the setting of a chronically infected individual from whom multiple specificities of recombinantly-produced neutralizing mAbs have also been isolated has not been performed.

To date, HIV-1 vaccine efficacy trials have not convincingly demonstrated a protective effect of vaccine-elicited tier 1 virus-neutralizing antibodies (37, 38). In particular, the only vaccine study to date that demonstrated a degree of protection, the RV144 trial, did not elicit bnAbs (2, 39) and has been postulated to have as correlates of protection antibody dependent cellular cytotoxicity (ADCC)-mediating antibodies (37, 40-42) and V3 antibodies (43). The present study reaffirms that tier 1 virus-neutralizing antibodies would be of limited benefit in protection from infection against heterologous tier 2 viruses. However, in our study we show that such antibodies could neutralize autologous tier 1B and tier 2 HIV-1 Envs with which they co-evolved (FIG. 11; FIGS. 15, 16) with which they co-evolved. It is important to note that there is one clinical setting where restricted tier 1 autologous virus-neutralizing antibodies could be potentially protective—that of mother-to-child transmission (MTCT) (44). Maternal IgG antibodies are actively transferred to the developing fetus over the second half of gestation (45), and the presence of maternally-derived antibodies could plausibly prevent newborn infection. Thus, V3- or CD4bs-directed antibodies of the type described here could correlate with decreased transmission risk for MTCT. Example 1, a study of the correlates of transmission risk in the Women and Infants Transmission Study (WITS) has indeed demonstrated that the correlates of transmission risk are plasma tier 1 virus-neutralizing antibodies. Thus, induction of high levels of V3 and CD4bs autologous neutralizing antibodies by an Env vaccine in pregnant women might be expected to reduce intrapartum and peripartum HIV-1 transmission to infants that occurs in mothers that arrive late to antenatal care or despite peripartum treatment with antiretroviral drugs (46)

Materials and Methods:

The clinical material used for the present study was obtained as a part of the CHAVI 001 observational study. The participants studied here were identified during the screening of CHAVI 001 and CHAVI 008 subjects for the presence of neutralization breadth (47). The present work was performed under a protocol approved by the Duke University Health System Institutional Review Board for Clinical Investigations. These original studies with human subjects from which we obtained the clinical material herein studied were approved by the Kilimanjaro Christian Medical Centre Research Ethics Committee, the Tanzania National Institutes for Medical Research Ethics Coordinating Committee, and the Institutional Review Boards of the London School of Hygiene and Tropical Medicine and Duke University as well as by the NIH Human Subject Review Committee.

Clinical Material.

The participants in this study (CH0457 and CH505) were recruited in 2008 in Tanzania and Malawi, respectively. At the time of recruitment, CH0457 had been chronically infected with a subtype C virus for an unknown period. This participant did not receive antiretroviral drug therapy during the study period. Peripheral blood collections were performed at weeks 0, 2, 4, 8, 12, 16, 24, 48, 72, and 96 of observation. Blood was processed for peripheral blood mononuclear cells (PBMC), plasma, and serum, all of which were cryopreserved for transport to the research laboratories. Participant CH505 was recruited early following infection and has been described previously (16).

Flow Cytometry Panel Antibodies, Recombinant Proteins, and Assay Control Antibodies.

The gp120$_{ConC}$ core protein was produced as described (48) and labeled with Pacific Blue and Alexa Fluor (AF) 647 using fluorochrome labeling kits (Invitrogen, Carlsbad, Calif.). The protein batches were confirmed to bind to CD4 expressed on the surface of the H9 T cell line as a quality control after conjugation. Setup for flow cytometry was performed as described (49). Sorting was performed using antibodies reactive with surface IgM (FITC), surface IgD (phycoerythrin [PE]), CD3 (PE-Cy5), CD16 (PE-Cy5), CD235a (PE-Cy5), and CD19 (allophycocyanin [APC]-Cy7) (BD Biosciences, San Jose, Calif.); CD14 (PE-Cy5) (Invitrogen, Carlsbad, Calif.); CD27 (PE-Cy7) and CD38 (APC-Alexa Fluor 700) (Beckman Coulter, Brea, Calif.).

Hyperimmune HIV-1 globulin subtype C (HIVIG-C) is a mixture of purified IgG from 5 subtype C HIV-1-infected plasma donors in South Africa (Johannesburg blood bank). (50). Genetic subtype was confirmed by SGA sequencing of the plasma Envs. The 5 IgG samples included in HIVIG-C were selected among 35 IgG samples for having the greatest magnitude and breadth of neutralizing activity against a panel of 6 tier 2 viruses. Palivizumab, a humanized monoclonal antibody against the F protein of respiratory syncytial virus, was purchased from MedImmune, LLC (Gaithersburg, Md.). Negative control CH65 is a mAb directed against the sialic acid binding site of hemagglutinin (51, 52). Positive control CH31 is a bnAb directed against the CD4bs (29, 53), as is positive control CH106 (16). Positive control was CD4bs-directed BNAb HJ16 (25).

Antibody Reactivity by Binding Antibody Multiplex Assay and Enzyme-Linked Immunosorbent Assay (ELISA).

Expressed mAbs were studied for reactivity to HIV-1 antigens using a standardized custom binding antibody multiplex assay using Luminex (54). All assays were run under conditions compliant with Good Clinical Laboratory Practice, including tracking of positive controls by Levy-Jennings charts. FDA-compliant software, Bio-Plex Manager, version 5.0 (Bio-Rad, Hercules, Calif.), was utilized for the analysis of specimens. Screening by binding antibody multiplex assays was performed against a panel of HIV-1 antigens (gp140$_{ConC}$, gp120$_{ConC}$ full length, gp140$_{ConB}$, gp140$_{CconG}$, gp140$_{JR.FL}$); mAbs that had a blank-bead-subtracted value greater than 2000 units and greater than 1000 times the mAb IgG concentration in µg/mL were evaluated further. Binding of all mAbs was confirmed by subsequent assays on mAbs prepared from transfected cells at large scales.

ELISA testing of mAbs was performed as described (55); testing was considered positive if the optical density reading at 405 nm was above 0.3 units and greater than 4-fold over background.

Flow Cytometric Analysis and Single-Cell Sorting.

We previously reported that CH0457 had broad neutralizing activity in plasma that could be absorbed by a subtype C consensus (ConC) gp120 protein that lacked V1V2 and V3 loops (gp120$_{ConC}$ core) (47). To isolate neutralizing antibody-producing memory B cells, we used antigen-specific sorting. Fluorescently-labeled gp120$_{ConC}$ core protein was used to isolate Env-reactive memory B cells using a dual-color technique (13, 56). We sorted samples from the week 8 and week 12 time points, and in both cases we isolated antigen-specific B cells from which immunoglobulin (Ig) genes were recovered (FIG. 13). In total, we isolated 19 heavy chains with paired light chains and found that when expressed as mAbs, 12/19 (63%) were reactive with one or more consensus Env proteins from clades A, B, C, G and CRF01_AE; 11 of these mAbs were carried forward for further study (Ex. 2 Table S1).

Single-cell sorting was performed using a BD FACSAria II (BD Biosciences, San Jose, Calif.) and the flow cytometry data were analyzed using FlowJo (Treestar, Ashland, Oreg.). Antigen-specific memory B cells were identified by using gp120$_{ConC}$ core labeled with Alexa Fluor 647 and Pacific Blue; cells were gated on CD3− CD14− CD16− CD235a− CD19+ surface IgD− gp120$_{ConC}$ core+/+. Single cells were directly sorted into 96-well plates containing 20 µL per well of reverse transcription (RT) reaction buffer (5 µL of 5′ first-strand cDNA buffer, 0.5 µL of RNaseOUT [Invitrogen, Carlsbad, Calif.], 1.25 µL of dithiothreitol, 0.0625 µL Igepal CA-630 [Sigma, St. Louis, Mo.], 13.25 µL of distilled H$_2$O [dH$_2$O; Invitrogen, Carlsbad, Calif.]); plates were stored at −80° C. until use and after sorting were again stored at −80° C. until PCR was performed.

PCR Isolation and Analysis of Immunoglobulin (Ig) V$_H$, V$_κ$, and V$_λ$ Genes.

Single-cell PCR was performed as described (49, 57, 58). PCR amplicons were sequenced in forward and reverse directions using a BigDye sequencing kit on an ABI 3730XL (Applied Biosystems, Foster City, Calif.). Sequence base calling was performed using Phred (59, 60), forward and reverse strands were assembled using an algorithm based on the quality scores at each position (61). Local alignment with known sequences was used to determine Ig isotype (62); V, D, and J region genes, complementarity-determining region 3 (CDR3) lengths, and mutation frequencies were determined using SoDA (63). Clonal lineages of antibodies were determined as described (51, 56) and were confirmed by alignment of complete V(D)J sequences. Maximum-likelihood trees for clonal lineages were generated using V(D)J regions (excluding constant region sequences); trees were constructed (dnaml), reorganized (retree), and plotted (drawgram) with the PHYLIP package, version 3.69 (64).

Expression of V$_H$ and V$_{κ/λ}$ as Full-Length IgG1 mAbs.

PCR was used to assemble isolated Ig V$_H$ and V$_{κ/λ}$ gene pairs into linear full-length Ig heavy- and light-chain gene expression cassettes as described (57). Human embryonic kidney cell line 293T (ATCC, Manassas, Va.) was grown to near confluence in six-well tissue culture plates (Becton Dickinson, Franklin Lakes, N.J.) and transfected with 2 µg per well of both IgH and Igκ/λ, purified PCR-produced cassettes using Effectene (Qiagen, Valencia, Calif.). Culture supernatants were harvested 3 days after transfection and concentrated 4-fold using centrifugal concentrators; expressed IgG was quantitated by ELISA (65); tested mAbs were expressed at 10 µg/mL up to 20 mg/mL. Larger-scale production of mAbs was performed using synthesized linear IgH and Igκ/λ gene constructs (GeneScript, Piscataway, N.J.).

Amplification of full-length env genes. Viral RNA (vRNA) was prepared from plasma samples (400 µL) using the EZ1Virus Mini Kit V2.0 on BIO ROBOT EZ1 (Qiagen; Valencia, Calif.). Reverse transcription was performed with 20 µL of vRNA and 80 pmol primer 1.R3.B3R (5'-ACT-ACTTGAAGCACTCAAGGCAAGCTTTATTG-3' (SEQ ID NO: 6)) in 50 µL using Superscript III (Invitrogen; Carlsbad, Calif.). The 3' half genomes were amplified by single genome amplication (SGA) as previous described (66, 67), using 07For7 (5'CAAATTAYAAAAATT-CAAAATTTTCGGGTTTATTACAG-3' (SEQ ID NO: 11)) and 2.R3.B6R (5'-TGAAGCACTCAAGGCAAGCTTTAT-TGAGGC-3' (SEQ ID NO: 12)) as first round primers, and VIF1 (5'-GGGTTTATTACAGGGACAGCAGAG-3' (SEQ ID NO: 8)) and Low2c (5'-TGAGGCT-TAAGCAGTGGGTTCC-3' (SEQ ID NO: 13)) as the second round primers. The PCR products were purified with the QiaQuick PCR Purification kit (Qiagen; Valencia, Calif.). The env gene sequences were obtained by cycle-sequencing and dye terminator methods with an ABI 3730XL genetic analyzer (Applied Biosystems; Foster City, Calif.). Individual sequence contigs from each env SGA were assembled and edited using the Sequencher program 4.7 (Gene Codes; Ann Arbor, Mich.).

Amplification of HIV-1 Env Genes from PBMCs by SGA.

Proviral DNA was extracted from $3\times10^6$ PBMCs at the enrollment (week 0) time point using the QIAamp DNA Blood and Tissue kit (Qiagen; Valencia, Calif.). The HIV-1 rev/env cassette was amplified from the genomic DNA using the single genome amplification (SGA) method. The PCR primers and conditions were the same as those used for viral RNA templates extracted from plasma.

Generation of Pseudoviruses.

The CMV promoter was added to the 5' end of each env gene amplified by SGA using the promoter addition PCR (pPCR) method as described (68). The pPCR product was used for generation of pseudoviruses by cotransfecting with the env-deficient HIV-1 backbone pSG3Δenv into 293T cells in a 6-well tissue culture plate using FuGENE6 transfection reagent (Roche Diagnostics; Indianapolis, Ind.) according to manufacturer instructions. Transfected cells were maintained in DMEM with 10% FBS at 37° C. with 5% $CO_2$. Forty-eight hours after transfection, supernatants were harvested and stored in 20% FBS medium at −80° C.

Neutralization Assay in TZM-bl Cells.

Neutralizing antibody assays in TZM-bl cells were performed as described (69). Antibodies were tested at concentrations up to 50 µg/mL using eight serial 3-fold dilutions. Control antibodies include HJ16 which was generously provided by D. Corti (Institute for Research in Biomedicine, Università della Svizzera Italiana, Bellinzona, Switzerland). Env-pseudotyped viruses were added to the antibody dilutions at a predetermined titer to produce measurable infection and incubated for 1 h. TZM-bl cells were added and incubated for 48 h. Firefly luciferase (Luc) activity was measured as a function of relative luminescence units (RLU) using a Britelite Luminescence Reporter Gene Assay System as described by the supplier (Perkin-Elmer Life Sciences, Waltham, Mass.). Neutralization was calculated as the reduction in RLU in test wells compared with control wells after subtraction of background RLU in cell control wells and reported as mAb 50% inhibitory concentration (IC50) in µg/mL. Env-pseudotyped viruses were prepared in 293T cells and titrated in TZM-bl cells as described (69).

Mapping of mAb Specificities by Neutralization.

Single amino acid substitutions were introduced into the consensus C (ConC) or B.RHPA Env by oligonucleotide-directed PCR mutagenesis using the QuickChange site-directed mutagenesis kit (Stratagene, La Jolla, Calif.). Alanine or conserved mutations were introduced in C1 (L125A), V1 (R132A/T), C2 (S256A, N289K), C3 (T372V, T373M, S375M), C5 (G471E), the β23 sheet of C4 (R456W), as well as the CD4bs (D-loop: N276A/Q, T278A, N279D and α5: D474A, M475A, R476A). The ability of antibodies to neutralize pseudoviruses containing Env point mutations was assessed and compared to the wild-type pseudovirus neutralization. A fifteen-fold or higher increase in $IC_{50}$ titer from the wild-type to the mutant was considered positive.

Statistical Analysis.

Graphs of the data were created using GraphPad Prism (GraphPad Software, La Jolla, Calif.) with layout in Illustrator CS5 (Adobe, San Jose, Calif.). Statistical tests were performed in SAS, version 9.2 (SAS Institute, Cary, N.C.) or in R, version 2.15.2 (R Foundation for Statistical Computing, Vienna, Austria). The statistical test used is noted when p values are presented. Env sequence phylogenies were inferred using PhyML (70) with the HIVw substitution model (71).

REFERENCES

1. J. R. Mascola, B. F. Haynes, HIV-1 neutralizing antibodies: understanding nature's pathways. *Immunol Rev* 254, 225-244 (2013).
2. D. C. Montefiori et al., Magnitude and breadth of the neutralizing antibody response in the RV144 and Vax003 HIV-1 vaccine efficacy trials. *Journal of Infectious Diseases* 206, 431-441 (2012).
3. B. F. Keele et al., Identification and characterization of transmitted and early founder virus envelopes in primary HIV-1 infection. *Proceedings of the National Academy of Sciences* 105, 7552-7557 (2008).
4. J. R. Mascola, D. C. Montefiori, The role of antibodies in HIV vaccines. *Annu Rev Immunol* 28, 413-444 (2010).
5. P. Gilbert et al., Magnitude and breadth of a nonprotective neutralizing antibody response in an efficacy trial of a candidate HIV-1 gp120 vaccine. *Journal of Infectious Diseases* 202, 595-605 (2010).
6. J. Albert et al., Rapid development of isolate-specific neutralizing antibodies after primary HIV-1 infection and consequent emergence of virus variants which resist neutralization by autologous sera. *AIDS* 4, 107-112 (1990).
7. T. Igarashi et al., Emergence of a highly pathogenic simian/human immunodeficiency virus in a rhesus macaque treated with anti-CD8 mAb during a primary infection with a nonpathogenic virus. *Proc Natl Acad Sci USA* 96, 14049-14054 (1999).
8. P. L. Moore et al., The c3-v4 region is a major target of autologous neutralizing antibodies in human immunodeficiency virus type 1 subtype C infection. *J Virol* 82, 1860-1869 (2008).
9. M. E. Laird, T. Igarashi, M. A. Martin, R. C. Desrosiers, Importance of the V1N2 loop region of simian-human immunodeficiency virus envelope glycoprotein gp120 in determining the strain specificity of the neutralizing antibody response. *J Virol* 82, 11054-11065 (2008).

10. P. L. Moore, E. S. Gray, L. Morris, Specificity of the autologous neutralizing antibody response. *Curr Opin HIV AIDS* 4, 358-363 (2009).
11. H. Tang et al., Epitopes immediately below the base of the V3 loop of gp120 as targets for the initial autologous neutralizing antibody response in two HIV-1 subtype B-infected individuals. *J Virol* 85, 9286-9299 (2011).
12. K. J. Bar et al., A. Trkola, Ed. Early low-titer neutralizing antibodies impede HIV-1 replication and select for virus escape. *PLoS Pathog* 8, e1002721 (2012).
13. E. S. Gray et al., Isolation of a monoclonal antibody that targets the alpha-2 helix of gp120 and represents the initial autologous neutralizing-antibody response in an HIV-1 subtype C-infected individual. *J Virol* 85, 7719-7729 (2011).
14. P. L. Moore et al., Evolution of an HIV glycan-dependent broadly neutralizing antibody epitope through immune escape. *Nat Med* 18, 1688-1692 (2012).
15. P. L. Moore et al., Multiple pathways of escape from HIV broadly cross-neutralizing V2-dependent antibodies. *J Virol* 87, 4882-4894 (2013).
16. H.-X. Liao et al., Co-evolution of a broadly neutralizing HIV-1 antibody and founder virus. *Nature* 496, 469-476 (2013).
17. C. K. Wibmer et al., A. Trkola, Ed. Viral escape from HIV-1 neutralizing antibodies drives increased plasma neutralization breadth through sequential recognition of multiple epitopes and immunotypes. *PLoS Pathog* 9, e1003738 (2013).
18. P. Hraber et al., Prevalence of broadly neutralizing antibody responses during chronic HIV-1 infection. *AIDS* 28, 163-169 (2014).
19. J. Swetnam, E. Shmelkov, S. Zolla-Pazner, T. Cardozo, Comparative magnitude of cross-strain conservation of HIV variable loop neutralization epitopes. *PLoS ONE* 5, e15994 (2010).
20. M. K. Gorny et al., Preferential use of the VH5-51 gene segment by the human immune response to code for antibodies against the V3 domain of HIV-1. *Mol Immunol* 46, 917-926 (2009).
21. M. K. Gorny et al., Human monoclonal antibodies to the V3 loop of HIV-1 with intra- and interclade cross-reactivity. *J Immunol* 159, 5114-5122 (1997).
22. S. A. Jeffs et al., Characterization of human monoclonal antibodies selected with a hypervariable loop-deleted recombinant HIV-1(IIIB) gp120. *Immunol. Lett.* 79, 209-213 (2001).
23. J. P. Moore, Q. J. Sattentau, R. Wyatt, J. Sodroski, Probing the structure of the human immunodeficiency virus surface glycoprotein gp120 with a panel of monoclonal antibodies. *J Virol* 68, 469-484 (1994).
24. R. Pantophlet, T. Wrin, L. A. Cavacini, J. E. Robinson, D. R. Burton, Neutralizing activity of antibodies to the V3 loop region of HIV-1 gp120 relative to their epitope fine specificity. *Virology* 381, 251-260 (2008).
25. D. Corti et al., D. Unutmaz, Ed. Analysis of Memory B Cell Responses and Isolation of Novel Monoclonal Antibodies with Neutralizing Breadth from HIV-1-Infected Individuals. *PLoS ONE* 5, e8805 (2010).
26. S. S. Balla-Jhagjhoorsingh et al., C. M. Gray, Ed. The N276 glycosylation site is required for HIV-1 neutralization by the CD4 binding site specific HJ16 monoclonal antibody. *PLoS ONE* 8, e68863 (2013).
27. D. S. Ruelas, W. C. Greene, An integrated overview of HIV-1 latency. *Cell* 155, 519-529 (2013).
28. F. Gao et al., Cooperation of B Cell Lineages in Induction of HIV-1-Broadly Neutralizing Antibodies. *Cell* 158, 481-491 (2014).
29. X. Wu et al., Focused evolution of HIV-1 neutralizing antibodies revealed by structures and deep sequencing. *Science* 333, 1593-1602 (2011).
30. M. S. Seaman et al., Tiered categorization of a diverse panel of HIV-1 Env pseudoviruses for assessment of neutralizing antibodies. *J Virol* 84, 1439-1452 (2010).
31. X. Wei et al., Antibody neutralization and escape by HIV-1. *Nature* 422, 307-312 (2003).
32. D. C. Montefiori et al., Viremia control despite escape from a rapid and potent autologous neutralizing antibody response after therapy cessation in an HIV-1-infected individual. *J Immunol* 170, 3906-3914 (2003).
33. D. D. Richman, T. Wrin, S. J. Little, C. J. Petropoulos, Rapid evolution of the neutralizing antibody response to HIV type 1 infection. *Proceedings of the National Academy of Sciences* 100, 4144-4149 (2003).
34. H. Haim et al., A. Trkola, Ed. Contribution of intrinsic reactivity of the HIV-1 envelope glycoproteins to CD4-independent infection and global inhibitor sensitivity. *PLoS Pathog* 7, e1002101 (2011).
35. H. Haim et al., Modeling virus- and antibody-specific factors to predict human immunodeficiency virus neutralization efficiency. *Cell Host Microbe* 14, 547-558 (2013).
36. S. D. W. Frost et al., Neutralizing antibody responses drive the evolution of human immunodeficiency virus type 1 envelope during recent HIV infection. *Proc Natl Acad Sci USA* 102, 18514-18519 (2005).
37. B. F. Haynes et al., Immune-correlates analysis of an HIV-1 vaccine efficacy trial. *N Engl J Med* 366, 1275-1286 (2012).
38. S. M. Hammer et al., Efficacy trial of a DNA/rAd5 HIV-1 preventive vaccine. *N Engl J Med* 369, 2083-2092 (2013).
39. S. Rerks-Ngarm et al., Vaccination with ALVAC and AIDSVAX to Prevent HIV-1 Infection in Thailand. *N Engl J Med* 361, 2209-2220 (2009).
40. M. Bonsignori et al., Antibody-dependent cellular cytotoxicity-mediating antibodies from an HIV-1 vaccine efficacy trial target multiple epitopes and preferentially use the VH1 gene family. *J Virol* 86, 11521-11532 (2012).
41. G. D. Tomaras et al., Vaccine-induced plasma IgA specific for the C1 region of the HIV-1 envelope blocks binding and effector function of IgG. *Proceedings of the National Academy of Sciences* 110, 9019-9024 (2013).
42. H.-X. Liao et al., Vaccine induction of antibodies against a structurally heterogeneous site of immune pressure within HIV-1 envelope protein variable regions 1 and 2. *Immunity* 38, 176-186 (2013).
43. R. Gottardo et al., Z. Chen, Ed. Plasma IgG to linear epitopes in the V2 and V3 regions of HIV-1 gp120 correlate with a reduced risk of infection in the RV144 vaccine efficacy trial. *PLoS ONE* 8, e75665 (2013).
44. C. Wettstein et al., Missed opportunities to prevent mother-to-child-transmission: systematic review and meta-analysis. *AIDS* 26, 2361-2373 (2012).
45. A. Malek, R. Sager, P. Kuhn, K. H. Nicolaides, H. Schneider, Evolution of maternofetal transport of immunoglobulins during human pregnancy. *Am. J Reprod. Immunol,* 36, 248-255 (1996).
46. C. S. Chasela et al., Maternal or Infant Antiretroviral Drugs to Reduce HIV-1 Transmission. *N Engl J Med* 362, 2271-2281 (2010).
47. G. D. Tomaras et al., Polyclonal B cell responses to conserved neutralization epitopes in a subset of HIV-1-infected individuals. *J Virol* 85, 11502-11519 (2011).

48. E. S. Gray et al., The Neutralization Breadth of HIV-1 Develops Incrementally over Four Years and Is Associated with CD4+ T Cell Decline and High Viral Load during Acute Infection. *J Virol* 85, 4828-4840 (2011).

49. M. A. Moody et al., HIV-1 gp120 vaccine induces affinity maturation in both new and persistent antibody clonal lineages. *J Virol* 86, 7496-7507 (2012).

50. L. Morris et al., Isolation of a human anti-HIV gp41 membrane proximal region neutralizing antibody by antigen-specific single B cell sorting. *PLoS ONE* 6, e23532 (2011).

51. M. A. Moody et al., H3N2 influenza infection elicits more cross-reactive and less clonally expanded anti-hemagglutinin antibodies than influenza vaccination. *PLoS ONE* 6, e25797 (2011).

52. J. R. R. Whittle et al., Broadly neutralizing human antibody that recognizes the receptor-binding pocket of influenza virus hemagglutinin. *Proceedings of the National Academy of Sciences* 108, 14216-14221 (2011).

53. M. Bonsignori et al., Two distinct broadly neutralizing antibody specificities of different clonal lineages in a single HIV-1-infected donor: implications for vaccine design. *J Virol* 86, 4688-4692 (2012).

54. G. D. Tomaras et al., Initial B-cell responses to transmitted human immunodeficiency virus type 1: virion-binding immunoglobulin M (IgM) and IgG antibodies followed by plasma anti-gp41 antibodies with ineffective control of initial viremia. *J Virol* 82, 12449-12463 (2008).

55. S. M. Alam et al., Human immunodeficiency virus type 1 gp41 antibodies that mask membrane proximal region epitopes: antibody binding kinetics, induction, and potential for regulation in acute infection. *J Virol* 82, 115-125 (2008).

56. M. Moody et al., Antibody lineages with evidence of somatic hypermutation persisting for >4 years in a South African subject with broad neutralizing activity. *Retrovirology* 9, P85 (2012).

57. H.-X. Liao et al., High-throughput isolation of immunoglobulin genes from single human B cells and expression as monoclonal antibodies. *Journal of Virological Methods* 158, 171-179 (2009).

58. J. Wrammert et al., Rapid cloning of high-affinity human monoclonal antibodies against influenza virus. *Nature* 453, 667-671 (2008).

59. B. Ewing, L. Hillier, M. C. Wendl, P. Green, Base-calling of automated sequencer traces using phred. I. Accuracy assessment. *Genome Res.* 8, 175-185 (1998).

60. B. Ewing, P. Green, Base-calling of automated sequencer traces using phred. II. Error probabilities. *Genome Res.* 8, 186-194 (1998).

61. T. B. Kepler et al., Chiropteran types I and II interferon genes inferred from genome sequencing traces by a statistical gene-family assembler. *BMC Genomics* 11, 444 (2010).

62. T. F. Smith, M. S. Waterman, Identification of common molecular subsequences. *J Mol Biol* 147, 195-197 (1981).

63. J. M. Volpe, L. G. Cowell, T. B. Kepler, SoDA: implementation of a 3D alignment algorithm for inference of antigen receptor recombinations. *Bioinformatics* 22, 438-444 (2006).

64. J. Felsenstein, PHYLIP (Phylogeny Inference Package) (2009).

65. E. S. Gray et al., Antibody specificities associated with neutralization breadth in plasma from human immunodeficiency virus type 1 subtype C-infected blood donors. *J Virol* 83, 8925-8937 (2009).

66. J. F. Salazar-Gonzalez et al., Genetic identity, biological phenotype, and evolutionary pathways of transmitted/founder viruses in acute and early HIV-1 infection. *J Exp Med* 206, 1273-1289 (2009).

67. C. Jiang et al., Primary infection by a human immunodeficiency virus with atypical coreceptor tropism. *J Virol* 85, 10669-10681 (2011).

68. J. L. Kirchherr et al., High throughput functional analysis of HIV-1 env genes without cloning. *Journal of Virological Methods* 143, 104-111 (2007).

69. D. C. Montefiori, Evaluating neutralizing antibodies against HIV, SIV, and SHIV in luciferase reporter gene assays. *Curr Protoc Immunol* Chapter 12, Unit 12.11 (2005).

70. S. Guindon, O. Gascuel, A simple, fast, and accurate algorithm to estimate large phylogenies by maximum likelihood. *Syst. Biol.* 52, 696-704 (2003).

71. D. C. Nickle et al., O. Pybus, Ed. HIV-specific probabilistic models of protein evolution. *PLoS ONE* 2, e503 (2007).

72. P. D. Kwong et al., Structures of HIV-1 gp120 envelope glycoproteins from laboratory-adapted and primary isolates. *Structure* 8, 1329-1339 (2000).

73. S. S. Balla-Jhagjhoorsingh et al., L. N. F. Poh, Ed. Characterization of neutralizing profiles in HIV-1 infected patients from whom the HJ16, HGN194 and HK20 mAbs were obtained. *PLoS ONE* 6, e25488 (2011).

Isolation of nAbs.

Antibodies from CH0457 were isolated by antigen-specific B cell sorting using a clade C consensus Env protein. Clonal lineage CH13 consisted of six monoclonal antibodies (mAbs) of IgG1 isotype (CH13, CH16, CH17, CH18, CH45, CH46) that used $V_H1$~69*01/$J_H3$*02 and $V_K1$~39*01/$J_K4$*01 genes. Epitope mapping with binding and neutralization assays demonstrated that the CH13 lineage antibody bound to the CD4bs and were sensitive to mutations at D386, E370, I371, S375, and K421 (FIG. 8c; Ex. 2 Tables S2 and S3). Two additional mAbs, CH14 and CH48, were not clonally related to any other mAbs isolated nor to each other, and both mAbs mapped in Env peptide binding assays to the HIV-1 Env third variable (V3) loop (FIG. 8d; Ex. 2 Table S4). Like clonal lineage CH13, mAbs CH14 and CH48 neutralized only tier 1 but not tier 2 heterologous HIV-1 strains (FIG. 9).

The second group of mAbs, clonal lineage CH27 (FIG. 8b), consisted of three mAbs that used $V_H3$~66*02/$J_H2$*01 and $V_K3$~20*01/$J_K1$*01 (CH27, CH28, CH44). Two members of this clonal lineage (CH27 and CH28) were found to be isotype IgA2 while the third was IgG1 (Ex. 2 Table S1). All were expressed as IgG1 mAbs. Testing of this group of mAbs using HIV-1 strain B.RHPA mutants demonstrated that they were sensitive to changes at N276 and T278, suggesting that the CH27 lineage consisted of HJ16-like CD4bs-directed bnAbs (1) (Ex. 2 Table S5). Surface plasmon resonance studies of mAbs from the CH27 lineage and HJ16 showed that they cross-blocked each other for binding to HIV-1 Env (FIG. 13).

Plasma samples from CH0457 taken from weeks 8 and 96 were tested against the same panel of heterologous viruses (FIG. 9). Neutralization titers against heterologous viruses were similar at the two chronic infection time points, despite the fact that the samples were collected nearly two years apart. Plasma antibodies neutralized all tier 1 isolates, consistent with the clonal lineage CH13 mAbs and V3 mAbs CH14 and CH48 neutralization patterns. Of the 10 heterologous HIV isolates neutralized by plasma at >1:1000 dilution, nine viruses were neutralized by lineage CH27 mAbs at <2 μg/mL (FIG. 9). Thus, the isolated mAbs accounted for the majority of CH0457 plasma heterologous virus neutralization.

We isolated restricted V3 neutralizing antibodies from a second HIV-1-infected African individual, CH505, 41 weeks after transmission (2). This individual eventually developed a CD4bs clonal lineage (termed CH103) at 136 weeks after transmission (2).

Validation of CH0457 Sequence Integrity.

To determine if there was any evidence for multiple infection or contamination, particularly given that there were two distinctive clades in the CH0457 sample, we did the following tests using the tools at the Los Alamos HIV database (www.hiv.lanl.gov). First we made a DNA consensus of the sequences from the persistent minor clade and the major lineage in CH0457. We then used HIV-BLAST to these compare the two consensus sequences against the HIV database. Both consensus sequences are closest to natural sequences from CH0457 in already GenBank, supporting that they came from the same quasispecies, and same individual. At the DNA level, the consensus from the persistent minor clade shared between 94 and 97% identity in Blast searches with other CH0457 sequences from the cominant clade. In contrast, the next closest match shared only 87%; it was a C clade isolate from Malawi. We then extracted all full length Env sequences from Tanzania; there were 388 of them. We combined these with the HIV subtyping reference set, and the consensus sequences from CH0457, and made a neighbor joining phylogeny based on these 435 reference and Tanzanian sequences. The two consensus sequences from the 2 distinctive within-subject CH0457 lineages always clustered together, among natural sequences from CH0457, forming a monophyletic group with high bootstrap support in a neighbor joining tree (data not shown, as this was a quality control check). This again indicates that the unusual clade is not a recurrent contamination, or independent infecting strain, and that both lineages evolved from a single infecting strain within CH0457, and had diverged prior to the first sample in taken during chronic infection.

This view is was further supported by the addition of the PBMC proviral DNA sequences from the enrollment time point, that were considered to be biologically "archived" in the host representing virus that had been replicating prior to the time of enrollment. These sequences revealed intermediate steps between the two distinctive lineages found in the CH0457 SGA sequences (FIG. 14). Among the proviral sequences, there were 6 that were highly significantly enriched for G-to-A hypermutated in Apobec motifs (Hypermut, www.hiv.lanl.gov) (3, 4) giving rise to multiple stop codons in Env resulting in clearly inactive virus. These are evident as a hypermutated cluster in the fully phylogenetic tree shown in FIG. 14 (w0.41c, w0.40c, w0.19c, w0.c, w0.13c, w0.48c; highlighted by an asterisk). There were no other significantly hypermutated sequences in the proviral set, and none among the SGA viral sequences.

TABLE S1

Ex. 2: HIV-1 Env-reactive antibodies isolated from CH0457.

| | | | heavy chain | | | | light chain | | | |
|---|---|---|---|---|---|---|---|---|---|---|
| | week | isotype | $V_H$ | $J_H$ | CDR3 length | mutation frequency | V | J | CDR3 length | mutation frequency |
| non-lineage | | | | | | | | | | |
| CH14 | 12 | IgG1 | 1~69*04 | 3*02 | 17 | 14.8% | κ 4~1*01 | 3*01 | 9 | 8.2% |
| CH18 | 12 | IgG1 | 4~30-4*01 | 4~02 | 19 | 9.5% | λ 2~14*03 | 3*02 | 9 | 6.2% |
| Lineage CH13 | | | | | | | | | | |
| CH13 | 8 | IgG1 | 1~69*01 | 4*01 | 17 | 9.1% | κ 1~39*01 | 4*01 | 9 | 4.0% |
| CH16 | 12 | IgG1 | 1~69*01 | 4*01 | 17 | 12.9% | κ 1~39*01 | 4*01 | 9 | 9.0% |
| CH17 | 12 | IgG1 | 1~69*01 | 4*01 | 17 | 9.9% | κ 1~39*01 | 4*01 | 9 | 5.3% |
| CH18 | 12 | IgG1 | 1~69*01 | 4*01 | 17 | 9.4% | κ 1~39*01 | 4*01 | 9 | 4.3% |
| CH45 | 8 | IgG1 | 1~69*01 | 4*01 | 17 | 8.3% | κ 1~39*01 | 4*01 | 9 | 9.6% |
| CH46 | 8 | IgG1 | 1~69*01 | 4*01 | 17 | 9.1% | κ 1~39*01 | 4*01 | 9 | 8.7% |
| average | | | | | | 9.8% | | | | 6.8% |
| Lineage CH27 | | | | | | | | | | |
| CH27 | 8 | IgA2 | 3~66*02 | 2*01 | 10 | 15.3% | κ 3~20*01 | 1*01 | 11 | 15.6% |
| CH28 | 12 | IgA2 | 3~66*02 | 2*01 | 10 | 14.0% | κ 3~20*01 | 1*01 | 11 | 15.6% |
| CH44 | 8 | IgG1 | 3~66*02 | 2*01 | 10 | 17.7% | κ 3~20*01 | 1*01 | 11 | 16.5% |
| average | | | | | | 15.7% | | | | 15.9% |

TABLE S2

Ex. 2: Mapping of mAbs by binding to gp120 mutants.

mAb binding assay to gp120*

| Lineage CH13 | B.HXBc2[†] | | | | B.YU2 | | | |
|---|---|---|---|---|---|---|---|---|
| | E370K | K421A | R476A | D477A | D368A | E370A | I371A | S375W |
| CH13 | 0.04 | 0.31 | 0.79 | 1.08 | 0.18 | 0.23 | 0.31 | 0.29 |
| CH16 | 0.27 | 0.73 | 1.34 | 1.10 | 0.79 | 0.48 | 0.71 | 0.41 |
| CH17 | 0.07 | 0.68 | 0.91 | 1.23 | 0.78 | 0.46 | 0.60 | 0.37 |

*Data normalized vs. binding to wild type gp120 protein.
[†]Additional mutants tested for which no binding change was observed: B.HXBc2 K429E, D474V, M475S; B.YU2 G473A, M475A, ΔV1/V2/V3.
[‡]NR = not reactive to B.HXB2c or B.YU2 gp120 proteins.
Lineage members CH18, CH45, and CH46 not tested.

TABLE S3

Ex. 2: Mapping of mAbs by neutralization of clade C consensus variants.

Neutralization* clade C consensus[†]

| | R132A | R132T | T372V T373M | S375M | D474A |
|---|---|---|---|---|---|
| Lineage CH13 | | | | | |
| CH13 | >100 | 1.8 | >50 | >100 | 16 |
| CH16 | 0.5 | 0.5 | 7.3 | >32 | 1.3 |
| CH17 | 91 | >55 | 19 | >100 | 10 |
| CH18 | 0.4 | >15 | >9 | >15 | 2 |
| CH45 | >20 | >20 | 9 | >36 | 8.1 |
| CH46 | — | — | — | — | — |
| Lineage CH27 | | | | | |
| CH27 | 0.7 | 1 | 2.1 | 2.3 | 0.4 |
| CH28 | 0.8 | 0.9 | 2.8 | 1.7 | 0.8 |
| CH44 | 1.5 | 3.2 | 2.5 | 2.6 | 0.6 |

*Data shown is fold increase in concentration required to produce 50% neutralization (increase in IC$_{50}$ in μg/mL of mAb).
[†]Other mutants of clade C consensus tested that did not show changes >20 fold for any tested mAb: L125A, S256A, N289K, G471E, M475A, R476A.
[‡]NR = no neutralization of clade C consensus.
[§]— = not tested.

TABLE S4

Ex. 2: Mapping of V3-directed mAbs from CH0457 by ELISA.

EC50*

| | V3 loop peptides | | | scaffolded V3 loop antigens | | Env constructs | |
|---|---|---|---|---|---|---|---|
| non-lineage | ConB[†] | ConC | ConS | gp70 B.MN3 | gp70 AE.92TH023 | RSC3 | ΔRSC3 |
| CH14 | 0.05 | 0.03 | 0.02 | NB[‡] | 0.004 | NB | NB |
| CH48 | 0.05 | 0.03 | 0.005 | 1.0 | 6.1 | NB | NB |

*Data shown is half maximal effective concentration (EC$_{50}$) in μg/mL of mAb.
[†]ConB = clade B consensus; ConC = clade C consensus; ConS = group M consensus.
[‡]NB = no binding observed.

TABLE S5

Ex. 2: Mapping of lineage CH27 mAbs by neutralization of B.RHPA mutants.

neutralization* B.RHPA

| | N160K | N276A | T278A | T278A R456W |
|---|---|---|---|---|
| Lineage CH27 | | | | |
| CH27 | 0.1 | 7.6 | 7.1 | 7 |
| CH28 | 0.3 | >333 | >333 | >307 |
| CH44 | 0.2 | >106 | >106 | >1000 |
| HJ16 | 0.5 | >10 | >10 | >1000 |

*Data shown is fold increase in concentration required to produce 50% neutralization (increase in IC$_{50}$ in μg/mL of mAb).

TABLE S6

Ex. 2: Mapping of V3 mAbs from CH505 by ELISA.

EC50*

| | V3 loop peptides | | | scaffolded V3 loop antigens | | | | Env constructs | |
|---|---|---|---|---|---|---|---|---|---|
| non-lineage | ConB[†] | ConC | ConS | gp70 B.MN3 | gp70 AE.92TH023 | gp70 ConAG | gp70 ConC | RSC3 | ΔRSC3 |
| DH151 | 0.15 | 0.009 | 0.008 | NB[‡] | 0.003 | 0.002 | 0.002 | NB | NB |
| DH228 | NB | NB | 0.008 | NB | NB | 1.50 | 2.52 | NB | NB |

*Data shown is half maximal effective concentration (EC$_{50}$) in μg/mL of mAb.
[†]ConB = clade B consensus; ConC = clade C consensus; ConS = group M consensus.
[‡]NB = no binding observed.

1. S. S. Balla-Jhagjhoorsingh et al., C. M. Gray, Ed. The N276 glycosylation site is required for HIV-1 neutralization by the CD4 binding site specific HJ16 monoclonal antibody. *PLoS ONE* 8, e68863 (2013).
2. H.-X. Liao et al., Co-evolution of a broadly neutralizing HIV-1 antibody and founder virus. *Nature* 496, 469-476 (2013).
3. R. S. Harris, M. T. Liddament, Retroviral restriction by APOBEC proteins. *Nat Rev Immunol* 4, 868-877 (2004).
4. P. P. Rose, B. T. Korber, Detecting hypermutations in viral sequences with an emphasis on G->A hypermutation. *Bioinformatics* 16, 400-401 (2000).
5. S. Guindon, O. Gascuel, A simple, fast, and accurate algorithm to estimate large phylogenies by maximum likelihood. *Syst. Biol.* 52, 696-704 (2003).
6. D. C. Nickle et al., O. Pybus, Ed. HIV-specific probabilistic models of protein evolution. *PLoS ONE* 2, e503 (2007).
7. I. Maljkovic Berry et al., Unequal evolutionary rates in the human immunodeficiency virus type 1 (HIV-1) pandemic: the evolutionary rate of HIV-1 slows down when the epidemic rate increases. *J Virol* 81, 10625-10635 (2007).
8. I. Maljkovic Berry et al., The evolutionary rate dynamically tracks changes in HIV-1 epidemics: application of a simple method for optimizing the evolutionary rate in phylogenetic trees with longitudinal data. *Epidemics* 1, 230-239 (2009).
9. M. R. Posner et al., An IgG human monoclonal antibody that reacts with HIV-1/GP120, inhibits virus binding to cells, and neutralizes infection. *J Immunol* 146, 4325-4332 (1991).
10. D. Corti et al., D. Unutmaz, Ed. Analysis of Memory B Cell Responses and Isolation of Novel Monoclonal Antibodies with Neutralizing Breadth from HIV-1-Infected Individuals. *PLoS ONE* 5, e8805 (2010).
11. X. Wu et al., Focused evolution of HIV-1 neutralizing antibodies revealed by structures and deep sequencing. *Science* 333, 1593-1602 (2011).
12. J. R. R. Whittle et al., Broadly neutralizing human antibody that recognizes the receptor-binding pocket of influenza virus hemagglutinin. *Proceedings of the National Academy of Sciences* 108, 14216-14221 (2011).
13. J. Swetnam, E. Shmelkov, S. Zolla-Pazner, T. Cardozo, Comparative magnitude of cross-strain conservation of HIV variable loop neutralization epitopes. *PLoS ONE* 5, e15994 (2010).
14. M. K. Gorny et al., Preferential use of the VH5-51 gene segment by the human immune response to code for antibodies against the V3 domain of HIV-1. *Mol Immunol* 46, 917-926 (2009).
15. M. K. Gorny et al., Human monoclonal antibodies to the V3 loop of HIV-1 with intra- and interclade cross-reactivity. *J Immunol* 159, 5114-5122 (1997).
16. S. A. Jeffs et al., Characterization of human monoclonal antibodies selected with a hypervariable loop-deleted recombinant HIV-1(IIIB) gp120. *Immunol. Lett.* 79, 209-213 (2001).
17. J. P. Moore, Q. J. Sattentau, R. Wyatt, J. Sodroski, Probing the structure of the human immunodeficiency virus surface glycoprotein gp120 with a panel of monoclonal antibodies. *J Virol* 68, 469-484 (1994).
18. D. C. Montefiori et al., Magnitude and breadth of the neutralizing antibody response in the RV144 and Vax003 HIV-1 vaccine efficacy trials. *Journal of Infectious Diseases* 206, 431-441 (2012).
19. R. Pantophlet, T. Wrin, L. A. Cavacini, J. E. Robinson, D. R. Burton, Neutralizing activity of antibodies to the V3 loop region of HIV-1 gp120 relative to their epitope fine specificity. *Virology* 381, 251-260 (2008).

Example 3

Therapeutic Vaccine for Prevention of MTCT

Example 1 shows that autologous antibodies in maternal humoral immune responses contribute to protection against perinatal HIV transmission. Example 1 shows that maternal IgG responses against the V3 loop of HIV Env is correlated with MTCT risk; Neutralization of clade-matched tier 1 variants is correlated with risk of peripartum HIV-1 transmission; and that CD4bs, V3, and tier 1 virus-neutralizing ab responses are co-linear in a model of MTCT risk.

This example provides the rationale for a vaccine strategy to prevent MTCT HIV transmission. In the biology of mother to child transmission of HIV, tt is the mother's virus that infects the baby. Because of placental transfer of maternal IgG, it is also the mother's antibody that will protect the baby from the maternal autologous virus. As Examples 1 and 2 show, common V3 and CD4 bs non-bnAb NAbs may be correlates of decreased transmission risk, which raises the question whether they are they biologically relevant Nabs. That is, can these autologous tier 1-virus neutralizing antibodies neutralize tier 2 autologous viruses? If so, then the possibility is that maternal tier 1 virus-neutralizing antibodies may plausibly be correlates of protection in MTCT. If not, then these tier1-virus Nabs may only be a surrogate marker for some other immune function. To address this question, common V3 and CD4 bs antibodies as well as CD4 bs bnAbs from two chronically infected individuals, CH0457 and CH505 were isolated and tested for their ability to neutralize both heterologous tier 1 and tier 2 viruses as well as autologous tier 2 viruses.

From the CH0457 individual, the N276 (HJ16-like) CD4bs bnAbs neutralized tier 2 heterologous viruses but not tier 1 viruses. From CH0457 the common CD4bs and V3 loop Nabs neutralized only heterologous tier 1 HIV but not tier 2 viruses.

From CH0457, we isolated ~80 autologous viruses that were typed as tier 2 viruses. From CH0457, the N276 (HJ16-like) CD4bs bnAbs neutralized no tier 2 autologous viruses—they had all escaped from the CD4bs bnAbs.

From CH0457 the common CD4bs and V3 loop Nabs robustly neutralized autologous tier 2 strains-65% of isolates neutralized by CD4 bs non-bnAbs, and ~80% of isolates by V3 NAbs. (FIGS. 9-11, 15-20 from Example 2).

From CH505 individual, we isolated common tier 1 virus-neutralizing V3 Nabs and the CH505 V3 neutralizing antibodies also neutralized the CH505 tier 2 autologous viruses well. (FIG. 22).

Thus, common non-bnAb neutralizing antibodies that only neutralize tier 1 heterologous HIV strains, potently neutralize a majority of autologous HIV strains. Thus, the correlates of transmission risk found in the MTCT correlates analysis are indeed plausible correlates of protection, i.e. the maternal V3 and CD4 bs antibodies may be able to neutralize maternal primary viruses.

Common non-bnAb CD4 bs and V3 Nabs robustly neutralized subsets of autologous Tier 2 viruses. Those they didn't neutralized likely were selected by the CD4bs and V3 Nabs as escape mutants. While this ability of commonly induced CD4bs and V3 Nabs to neutralize autologous viruses is not relevant for their ability to protect in the setting of challenge with heterologous HIV challenge, it is relevant to the one clinical setting where autologous virus and autologous Nabs are present, that of maternal to child HIV transmission.

Example 1 shows that that V3 and CD4 bs common Nabs are correlates of protection in MTCT setting. Example 1 also shows that common V3 Nabs and 38 autologous primary virus strains were isolated from a non-transmitting WITS mother. These autologous V3 Nabs were tested for their ability to neutralize the autologous viruses. Example 1 (FIGS. 2, 4-7) shows that the maternal V3 Abs could indeed neutralize the autologous virus strains. Thus, commonly induced Nabs can be protective in the setting of MTCT.

Examples 1 and 2 show that common CD4 bs and V3 Nabs while not neutralizing heterologous HIV tier 2 strains, robustly neutralize autologous tier 2 strains. These examples show isolation of both hundreds of autologous viruses and clones of common Nabs from chronically infected individuals, and neutralization against each other in the autologous setting.

These data demonstrate that common CD4 bs and V3 abs are not recognizing Env "junk" but are recognizing native trimers on autologous Env but not on heterologous Env. How these antibodies recognize autologous Env will be determined by structural studies. The MTCT case control study demonstrated that those who had above a certain threshold levels of (e.g. >38 ug/ml) of maternal plasma V3 antibody had 21% transmission while those who had, e.g. 38 ug/ml of V3 antibody had 41% transmission rate.

These data show that a therapeutic vaccine administered to pregnant HIV+ women that can boost existing V3 and CD4 bs neutralizing antibodies to well beyond the ~38 ug/ml level, could dramatically reduce MTCT that still occurs in spite of prenatal ART.

In certain aspects the invention provide an immunogenic composition comprising an HIV-1 envelope or a combination of several HIV-1 envelopes. In certain embodiments, the composition can be bivalent comprising clade B/C Env gp120 vaccine comprised of the founder virus clade B Env 63521 and the founder virus clade C Env CH505. The envelopes could be included as DNAs or proteins.

The compositions comprising Envs would be formulated in Alum, or any other adjuvant. In certain embodiments, durability of the antibody response is only needed for ~6 months. In certain embodiments, pregnant HIV+ women would be on ART, their immune systems would be intact and V3 and CD4 bs responses would be intact. Some of the considerations are whether: a bivalent B/C gp120 vaccine would be sufficiently broadly antigenic in order to be able to be a global inducer of CD4 bs and V3 antibodies; a bivalent B/C gp120 vaccine given in the therapeutic vaccine setting boost existing V3 or CD4 bs antibodies; such a vaccine be safe in HIV-infected pregnant women?

NHP studies are underway with both B.63521 and C.CH505 Envs to test the breadth of V3 and CD4 bs recognition induced by the Envs. Second, we have previously shown that priming with one V3 and boosting with a second V3 leads to original antigenic sin, with boosting of the first V3 by the second (Haynes, B F et al. AIDS Res. Hum. Retrovirol. 11: 211, 1995). Thus, a combination of Env B/C breadth and original antigenic sin make the B/C Env concept as a boost for antibodies induced by HIV-1 infection tractable. Third, Phase I studies could be performed with many clades of infection to determine if the B/C was adequate for use with non-B/C clades or rather if additional Envs added would be needed. In certain embodiments, one additional Env that could be added is the group M consensus Env CON-S, which is the best inducer of broad tier 1 Nabs (Liao H X et al. Virology 353: 268, 2006, J. Virol. 87: 4185, 2013).

There are data from a trial in HIV-infected individuals using polyvalent V3 peptide, i.e. an immunogen which is a less immunogenic than bivalent B/C En, showing the ability to boost V3 binding antibodies and tier 1 neutralizing antibodies in 50% of vaccinees (Bartlett J A, et al., AIDS 12: 1291, 1998). Thus, boosting V3 and tier 1 Nabs in HIV-infected with an immunogen such as an envelope or a combination thereof as described herein is achievable.

In certain embodiments, the immunogenic composition for use in the vaccination schedules contemplated herein can be formulated with any suitable adjuvant. In a non-limiting embodiment this adjuvant is Alum. The immunogenic composition would be tested for safety first in uninfected individuals.

In certain embodiments, the immunogenic compositions described herein are contemplated for use in prenatal care of all HIV infected women world-wide.

What is claimed is:

1. A method for reducing maternal to child HIV-1 transmission by inducing or boosting V3-specific or CD4 binding site-specific HIV-1 antibody responses in a pregnant female subject infected with HIV-1 comprising administering to the subject an immunogenic composition comprising an HIV-1 envelope in an amount sufficient to effect such induction, wherein the composition comprises clade B gp120 HIV-1 envelope and clade C gp120 HIV-1 envelope and wherein the subject's anti-V3 IgG concentration above 37 micorgram/ml in plasma is correlated with reduced risk of maternal to child transmission.

2. The method of claim 1, wherein the HIV-1 antibody responses are V3-specific antibodies able to neutralize tier 1 and tier 2 autologous HIV-1 strains.

3. The method of claim 1, wherein the composition comprises clade B gp120 HIV-1 envelope B.63521 and clade C gp120 envelope CH505 T/F.

4. The method of claim 1, wherein the composition comprises clade B gp120 HIV-1 envelope B.63521 and clade C gp120 envelope 1086.C.

5. The method of claim 1, wherein the HIV-1 antibody response is CD4 binding_site antibodies able to neutralize tier 1 and tier 2 autologous HIV-1 strains.

6. The method of claim 1, further comprising administering HIV-1 Clade M envelope CON-S.

7. The method of claim 1, wherein each Clade B HIV-1 envelope and Clade C HIV-1 envelope is administered as a recombinant protein.

8. The method of claim 1, where wherein each Clade B HIV-1 envelope and Clade C HIV-1 envelope is administered as a nucleic acid encoding the envelope.

9. The method of claim 6, wherein the HIV-1 Clade M envelope CON-S is administered as a recombinant protein.

10. The method of claim 6, wherein the HIV-1 Clade M envelope CON-S is administered as a nucleic acid encoding the envelope.

11. The method of claim 1, further comprising administering an adjuvant.

12. The method of claim 1, wherein the composition comprises an adjuvant.

13. The method of claim 3, wherein the composition comprises an adjuvant.

14. The method of claim 4, wherein the composition comprises an adjuvant.

15. The method of claim 6, wherein the composition comprises an adjuvant.

16. The method of claim 7, wherein the composition comprises an adjuvant.

17. The method of claim 9, wherein the composition comprises an adjuvant.

* * * * *